US008063091B2

(12) United States Patent
Dai et al.

(10) Patent No.: US 8,063,091 B2
(45) Date of Patent: *Nov. 22, 2011

(54) INDAZOLE, BENZISOXAZOLE, AND BENZISOTHIAZOLE KINASE INHIBITORS

(75) Inventors: Yujia Dai, Gurnee, IL (US); Steven K. Davidsen, Libertyville, IL (US); Anna M. Ericsson, Shrewsbury, MA (US); Kresna Hartandi, Los Angeles, CA (US); Zhiqin Ji, Libertyville, IL (US); Michael R. Michaelides, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/507,575

(22) Filed: Jul. 22, 2009

(65) Prior Publication Data

US 2009/0286784 A1  Nov. 19, 2009

Related U.S. Application Data

(60) Continuation of application No. 11/867,887, filed on Oct. 5, 2007, now Pat. No. 7,598,283, which is a division of application No. 10/842,292, filed on May 10, 2004, now Pat. No. 7,297,709.

(60) Provisional application No. 60/472,810, filed on May 22, 2003.

(51) Int. Cl.
*A61K 31/415* (2006.01)
*C07D 231/56* (2006.01)
(52) U.S. Cl. ..................... 514/405; 548/360.1
(58) Field of Classification Search .......... None
See application file for complete search history.

(56) References Cited

U.S. PATENT DOCUMENTS

| | | | |
|---|---|---|---|
| 5,773,459 A | 6/1998 | Tang et al. | |
| 6,177,401 B1 | 1/2001 | Ullrich et al. | |
| 6,262,040 B1 | 7/2001 | Marfat | |
| 6,277,847 B1 | 8/2001 | Theodoridis et al. | |
| 6,524,832 B1 | 2/2003 | Kufe et al. | |
| 7,070,968 B2 | 7/2006 | Kufe et al. | |
| 7,297,709 B2 * | 11/2007 | Dai et al. ............ | 514/406 |
| 2003/0207870 A1 | 11/2003 | Dumas et al. | |
| 2006/0251734 A1 | 11/2006 | Kufe et al. | |
| 2008/0227827 A1 | 9/2008 | Kawabe et al. | |

FOREIGN PATENT DOCUMENTS

| | | |
|---|---|---|
| EP | 136745 A2 | 4/1985 |
| GB | 816382 A | 7/1959 |
| WO | WO9521613 A1 | 8/1995 |
| WO | WO9623783 A1 | 8/1996 |
| WO | WO9640637 | 12/1996 |
| WO | WO9640673 A1 | 12/1996 |
| WO | WO9737989 A1 | 10/1997 |
| WO | WO9742187 A1 | 11/1997 |
| WO | WO9900357 A1 | 1/1999 |
| WO | WO9932463 A1 | 7/1999 |
| WO | WO0027627 A1 | 5/2000 |
| WO | WO0042012 A1 | 7/2000 |
| WO | WO0119788 A2 | 3/2001 |
| WO | WO0119828 A2 | 3/2001 |
| WO | WO0214311 A2 | 2/2002 |
| WO | WO02055517 A2 | 7/2002 |
| WO | WO02062763 A2 | 8/2002 |
| WO | WO02070494 A1 | 9/2002 |
| WO | WO03051366 A2 | 6/2003 |
| WO | WO03051847 A1 | 6/2003 |
| WO | WO03068228 A1 | 8/2003 |
| WO | WO03087072 A1 | 10/2003 |
| WO | WO03097610 A1 | 11/2003 |
| WO | WO2004010995 A1 | 2/2004 |
| WO | WO2004022544 A | 3/2004 |
| WO | WO2004062662 A1 | 7/2004 |

OTHER PUBLICATIONS

Adams, et al., "A strategy, for the design of multiplex inhibitors for kinase-mediated signaling in angiogenesis," Current Opinion in Chemical Biology, 2002, 6 (4), 486-492.
Cullinan-Bove et al., "Vascular endothelial growth factor/vascular permeability factor expression in the rat uterus: rapid stimulation by estrogen correlates with estrogen-inuced increases in uterine capillary permeability and growth," Endrocinology, 1993, 133 (2), pp. 829-837.
Derbyshire, et al., "Anti-tumor and anti-angiogenic effects in mice of heparin conjugated to angiostatic steroids," Int. J. Cancer, 1995, 63 (5), 694-701.
Mongin et al., "Regioselective ortho-lithiation of chloro and bromo substituted fluoroarenes," Tetrahedron Letters, 1996, 37 (36), 6551-6554.
Passaniti, A. et al., "Methods in Laboratory Investigation/A Simple, Quantitative Method for Assessing Angiogenesis and Antiangiogenic Agents Using Reconstituted Basement Membrane, Heparin, and Fibroblast Growth Factor," Lab. Invest, 1992, 67 (4), 519-528.
PCT International search report for application No. PCT/US2004/016166 mailed on Nov. 8, 2004, 2 pages.
Rupert, et al., "Suzuki Couplings with Phthalimidines—An Efficient Route to Staurosporinone analogs," Heterocycles, 1997, 45 (11), 2217-2221.

(Continued)

Primary Examiner — Kamal Saeed
(74) Attorney, Agent, or Firm — Glen Gesicki

(57) ABSTRACT

Compounds having the formula

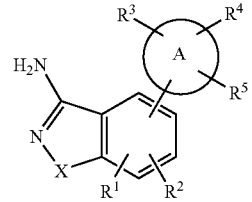

are useful for inhibiting protein tyrosine kinases. The present invention also discloses methods of making the compounds, compositions containing the compounds, and methods of treatment using the compounds.

21 Claims, No Drawings

OTHER PUBLICATIONS

Silvagno et al., "In Vivo Activation of met Tyrosine Kinase by Heterodimeric Hepatocyte Growth Factor Molecule Promotes Angiogenesis," Arterioselerosis, Thrombosis, and Vascular Biology, 1995, 15 (11), 1857-1865.

Songyang et al., "Catalytic specificity of protein-tyrosine kinases is critical for selective signalling," Nature, 1995, 373, 536-539.

Thistlethwaite et al., "Human angiopoietin gene expression is a marker for severity of pulmonary hypertension in patients undergoing pulmonary thromboendarterectomy," Journal of Thoracic and Cardiovascular Surgery, 2001, 122 (1), pp. 65-73.

Tyle, "Iontophoretic Devices for Drug Delivery," Pharmaceutical Research, 1986, 3 (6), pp. 318-326.

Voller et al., "Enzyme-Linked Immunosorbent Assay," in: Manual of clinical immunology, Rose N.R. & Friedman H., eds., American Society of Microbiology, 1980, 2nd ed., pp. 359-371.

Wilson et al., "Human prostate tumor angiogenesis in nude mice: metalloprtoease and plasminogen activator activities during tumor growth and neovasularization of subcutaneously injected matrigel impregnated with human prostate tumor cells," Anat. Rec., 1997, 249 (1), pp. 63-73.

* cited by examiner

INDAZOLE, BENZISOXAZOLE, AND BENZISOTHIAZOLE KINASE INHIBITORS

This application is a continuation of U.S. patent application No. 11/867,887 filed Oct. 5, 2007, which is a divisional of U.S. patent application No. 10/842,292, filed May 22, 2004, now U.S. Pat. No. 7,297,709, which claims priority to U.S. patent application No. 60/472,810, filed May 22, 2003, each of which is herein incorporated by reference.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment the present invention provides a compound of formula (I)

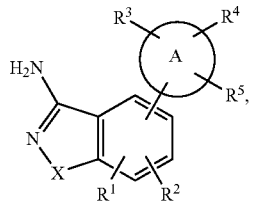

(I)

or a therapeutically acceptable salt thereof, wherein

A is selected from the group consisting of indolyl, phenyl, pyrazinyl, pyridazinyl, pyridinyl, pyrimidinyl, and thienyl;

X is selected from the group consisting of O, S, and $NR^9$;

$R^1$ and $R^2$ are independently selected from the group consisting of hydrogen, alkoxy, alkoxyalkoxy, alkoxyalkyl, alkyl, aryl, arylalkyl, aryloxy, aryloxyalkyl, halo, haloalkoxy, haloalkyl, heterocyclyl, heterocyclylalkenyl, heterocyclylalkoxy, heterocyclylalkyl, heterocyclyloxyalkyl, hydroxy, hydroxyalkoxy, hydroxyalkyl, $(NR^aR^b)$alkoxy, $(NR^aR^b)$alkenyl, $(NR^aR^b)$alkyl, $(NR^aR^b)$alkynyl, $(NR^aR^b)$carbonylalkenyl, and $(NR^aR^b)$carbonylalkyl;

$R^3$, $R^4$, and $R^5$ are each independently selected from the group consisting of hydrogen, alkoxy, alkoxyalkyl, alkyl, halo, haloalkoxy, haloalkyl, hydroxy, and $LR^6$; provided that at least two of $R^3$, $R^4$, and $R^5$ are other than $LR^6$;

L is selected from the group consisting of $(CH_2)_mN(R^7)C(O)N(R^3)(CH_2)_n$ and $CH_2C(O)NR^7$, wherein m and n are independently 0 or 1, and wherein each group is drawn with its left end attached to A;

$R^6$ is selected from the group consisting of hydrogen, aryl, cycloalkyl, heterocyclyl, and 1,3-benzodioxolyl wherein the 1,3-benzodioxolyl can be optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, $-NR^cR^d$, and $(NR^cR^d)$alkyl;

$R^7$ and $R^8$ are independently selected from the group consisting of hydrogen and alkyl;

$R^9$ is selected from the group consisting of hydrogen, alkenyl, alkoxyalkyl, alkyl, alkylcarbonyl, aryl, heterocyclylalkyl, hydroxyalkyl, and $(NR^aR^b)$alkyl;

$R^a$ and $R^b$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, cycloalkyl, heterocyclyl, heterocyclylalkyl, and heterocyclylsulfonyl; and $R^c$ and $R^d$ are independently selected from the group consisting of hydrogen, alkyl, alkylcarbonyl, aryl, arylalkyl, cycloalkyl, cycloalkylalkyl, heterocyclyl, and heterocyclylalkyl.

In another embodiment the present invention provides a compound of formula (II)

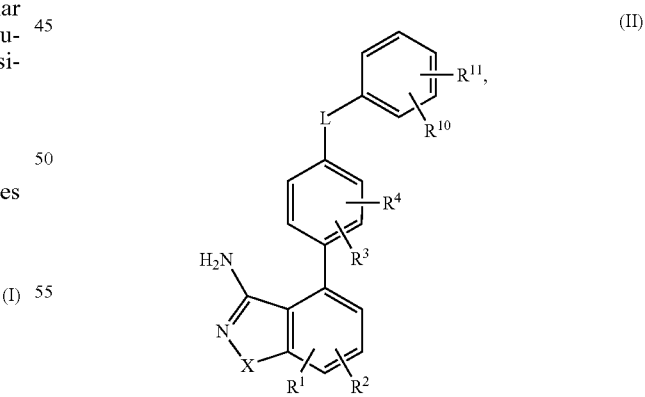

(II)

or a therapeutically acceptable salt thereof, wherein

X is selected from the group consisting of O, S, and $NR^9$;

$R^1$ and $R^2$ are independently selected from the group consisting of hydrogen, alkoxy, alkoxyalkoxy, alkoxyalkyl, alkyl, aryloxy, aryloxyalkyl, halo, haloalkoxy, haloalkyl, heterocyclyl, heterocyclylalkenyl, heterocyclylalkoxy, heterocyclylalkyl, heterocyclyloxyalkyl, hydroxy, hydroxyalkoxy, hydroxyalkyl, (NR$^a$R$^b$)alkoxy, (NR$^a$R$^b$)alkenyl, (NR$^a$R$^b$)alkyl, (NR$^a$R$^b$)carbonylalkenyl, and (NR$^a$R$^b$)carbonylalkyl;

R$^3$ and R$^4$ are independently selected from the group consisting of hydrogen, alkoxy, alkyl, halo, haloalkoxy, haloalkyl, and hydroxy;

L is selected from the group consisting of (CH$_2$)$_m$N(R$^7$)C(O)N(R$^8$)(CH$_2$)$_n$ and CH$_2$C(O)NR$^7$, wherein m and n are independently 0 or 1, and wherein each group is drawn with its left end attached to the ring substituted with R$^3$ and R$^4$;

R$^7$ and R$^8$ are independently selected from the group consisting of hydrogen and alkyl;

R$^9$ is selected from the group consisting of hydrogen, alkenyl, alkoxyalkyl, alkyl, alkylcarbonyl, aryl, heterocyclylalkyl, hydroxyalkyl, and (NR$^a$R$^b$)alkyl;

R$^{10}$ and R$^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —NR$^c$R$^d$;

R$^a$ and R$^b$ are independently selected from the group consisting of hydrogen, alkyl, alkylcarbonyl, alkylsulfonyl, arylsulfonyl, haloalkylsulfonyl, and heterocyclylsulfonyl; and R$^c$ and R$^d$ are independently selected from the group consisting of hydrogen, alkyl, alkylcarbonyl, aryl, arylalkyl, cycloalkyl, cycloalkylalkyl, heterocyclyl, and heterocyclylalkyl.

In another embodiment, the present invention provides a compound of formula (I) wherein X is O and A, R$^1$, R$^2$, R$^3$, R$^4$, and R$^5$ are as defined in formula (I).

In another embodiment, the present invention provides a compound of formula (I) wherein A is phenyl; X is O; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and R$^c$R$^d$)alkyl; L is (CH$_2$)$_m$N(R$^7$)C(O)N(R$^8$)(CH$_2$)$_n$; and m, n, R$^c$, R$^d$, R$^1$, R$^2$, R$^3$, R$^4$R$^7$, and R$^8$ are as defined in formula (I).

In another embodiment, the present invention provides a compound of formula (I) wherein A is phenyl; X is O; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and (NR$^c$R$^d$)alkyl; L is (CH$_2$)$_m$N(R$^7$)C(O)N(R$^8$)(CH$_2$)$_n$; m and n are 0; R$^1$ and R$^2$ are independently selected from the group consisting of hydrogen and alkoxy; R$^3$, R$^4$, R$^7$, and R$^8$ are hydrogen; and R$^c$ and R$^d$ are selected from the group consisting of hydrogen and alkyl.

In another embodiment, the present invention provides a compound of formula (I) wherein A is phenyl; X is O; R$^5$ is LR$^6$; R$^6$ is 1,3-benzodioxolyl; L is (CH$_2$)$_m$N(R$^7$)C(O)N(R$^3$)(CH$_2$)$_n$; m and n are 0; R$^1$ and R$^2$ are independently selected from the group consisting of hydrogen and alkoxy; and R$^3$, R$^4$, R$^7$, and R$^5$ are hydrogen.

In another embodiment, the present invention provides a compound of formula (I) wherein X is S and A, R$^1$, R$^2$, R$^3$, R$^4$, and R$^5$ are as defined in formula (I).

In another embodiment, the present invention provides a compound of formula (I) wherein A is phenyl; X is S; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and (NR$^c$R$^d$)alkyl; L is (CH$_2$)$_m$N(R$^7$)C(O)N(R$^8$)(CH$_2$)$_n$; and m, n, R$^c$, R$^d$, R$^2$, R$^3$, R$^4$, R$^7$, and R$^8$ are as defined in formula (I).

In another embodiment, the present invention provides a compound of formula (I) wherein A is phenyl; X is S; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and (NR$^c$R$^d$)alkyl; L is (CH$_2$)$_m$N(R$^7$)C(O)N(R$^8$)(CH$_2$)$_n$; m and n are 0; R$^1$ and R$^2$ are independently selected from the group consisting of hydrogen and alkoxy; R$^3$, R$^4$, R$^7$, and R$^8$ are hydrogen; and R$^c$ and R$^d$ are selected from the group consisting of hydrogen and alkyl.

In another embodiment, the present invention provides a compound of formula (I) wherein A is phenyl; X is S; R$^5$ is LR$^6$; R$^6$ is 1,3-benzodioxolyl; L is (CH$_2$)$_m$N(R$^7$)C(O)N(R$^3$)(CH$_2$)$_n$; m and n are 0; R$^1$ and R$^2$ are independently selected from the group consisting of hydrogen and alkoxy; and R$^3$, R$^4$, R$^7$, and R$^8$ are hydrogen.

In another embodiment, the present invention provides a compound of formula (I) wherein X is NR$^9$; and A, R$^1$, R$^2$, R$^3$, R$^4$, R$^5$, and R$^9$ are as defined in formula (I).

In another embodiment, the present invention provides a compound of formula (I) wherein A is phenyl; X is NR$^9$; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and R$^c$R$^d$)alkyl; L is (CH$_2$)$_m$N(R$^7$)C(O)N(R$^8$)(CH$_2$)$_n$; and m, n, R$^c$, R$^d$, R$^1$, R$^2$, R$^3$, R$^7$, R$^8$, and R$^9$ are as defined in formula (I).

In another embodiment, the present invention provides a compound of formula (I) wherein A is phenyl; X is NR$^9$; R$^5$ is LR$^6$; R$^6$ is 1,3-benzodioxolyl optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and R$^c$R$^d$)alkyl; L is (CH$_2$)$_m$N(R$^7$)C(O)N(R$^8$)(CH$_2$)$_n$; m and n are 0; R$^1$ and R$^2$ are independently selected from the group consisting of hydrogen and alkoxy; R$^3$, R$^4$, R$^7$, and R$^8$ are hydrogen; R$^9$ is selected from the group consisting of hydrogen and alkyl; and R$^c$ and R$^d$ are selected from the group consisting of hydrogen and alkyl.

In another embodiment, the present invention provides a compound of formula (I) wherein A is phenyl; X is NR$^9$; R$^5$ is LR$^6$; R$^6$ is 1,3-benzodioxolyl; L is (CH$_2$)$_m$N(R$^7$)C(O)N(R$^8$)(CH$_2$)$_n$; m and n are 0; R$^1$ and R$^2$ are independently selected from the group consisting of hydrogen and alkoxy; R$^3$, R$^4$, R$^7$, and R$^8$ are hydrogen; and R$^9$ is selected from the group consisting of hydrogen and alkyl.

In another embodiment, the present invention provides a compound of formula (I) wherein A is phenyl; X is O; R$^5$ is LR$^6$; R$^6$ is cycloalkyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —NR$^c$R$^d$, (NR$^c$R$^d$)alkyl, and oxo; L is $(CH_2)_mN(R^7)C(O)N(R^8)(CH_2)_n$; and m, n, $R^c$, $R^d$, $R^1$, $R^2$, $R^3$, $R^4$ $R^7$, and $R^8$ are as defined in formula (I).

In another embodiment, the present invention provides a compound of formula (I) wherein A is phenyl; X is O; $R^5$ is $LR^6$; $R^6$ is cycloalkyl wherein the cycloalkyl is selected from the group consisting of cyclobutyl, cyclopentyl, and cyclohexyl, wherein the cycloalkyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(NR^cR^d)$alkyl, and oxo; L is $(CH_2)_mN(R^7)C(O)N(R^3)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(NR^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is O; $R^5$ is $LR^6$; $R^6$ is cycloalkyl wherein the cycloalkyl is cyclopentyl; L is $(CH_2)_mN(R^7)C(O)N(R^8)(CH_2)_n$; m and n are 0; $R^1$ and $R^2$ are independently selected from the group consisting of hydrogen and alkoxy; and $R^3$, $R^4$, $R^7$, and $R^8$ are hydrogen.

In another embodiment, the present invention provides a compound of formula (I) wherein A is phenyl; X is S; $R^5$ is $LR^6$; $R^6$ is cycloalkyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(NR^cR^d)$alkyl, and oxo; L is $(CH_2)_mN(R^7)C(O)N(R^8)(CH_2)_n$; and m, n, $R^c$, $R^d$, $R^1$, $R^2$, $R^3$, $R^4$, $R^7$, and $R^8$ are as defined in formula (I).

In another embodiment, the present invention provides a compound of formula (I) wherein A is phenyl; X is S; $R^5$ is $LR^6$; $R^6$ is cycloalkyl wherein the cycloalkyl is selected from the group consisting of cyclobutyl, cyclopentyl, and cyclohexyl, wherein the cycloalkyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(NR^cR^d)$alkyl, and oxo; L is $(CH_2)_mN(R^7)C(O)N(R^8)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(NR^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is S; $R^5$ is $LR^6$; $R^6$ is cycloalkyl wherein the cycloalkyl is cyclopentyl; L is $(CH_2)_mN(R^7)C(O)N(R^8)(CH_2)_n$; m and n are 0; $R^1$ and $R^2$ are independently selected from the group consisting of hydrogen and alkoxy; and $R^3$, $R^4$, $R^7$, and $R^8$ are hydrogen.

In another embodiment, the present invention provides a compound of formula (I) wherein A is phenyl; X is $NR^9$; $R^5$ is $LR^6$; $R^6$ is cycloalkyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$ $(NR^cR^d)$alkyl, and oxo; L is $(CH_2)_mN(R^7)C(O)N(R^8)(CH_2)_n$; and m, n, $R^c$, $R^d$, $R^1$, $R^2$, $R^3$, $R^4$, $R^7$, $R^8$, and $R^9$ are as defined in formula (I).

In another embodiment, the present invention provides a compound of formula (I) wherein A is phenyl; X is $NR^9$; $R^5$ is $LR^6$; $R^6$ is cycloalkyl wherein the cycloalkyl is selected from the group consisting of cyclobutyl, cyclopentyl, and cyclohexyl, wherein the cycloalkyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(NR^cR^d)$alkyl, and oxo; L is $(CH_2)_mN(R^7)C(O)N(R^8)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(R^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^9$ is selected from the group consisting of hydrogen and alkyl; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is $NR^9$; $R^5$ is $LR^6$; $R^6$ is cycloalkyl wherein the cycloalkyl is cyclopentyl; L is $(CH_2)_mN(R^7)C(O)N(R^8)(CH_2)_n$; m and n are 0; $R^1$ and $R^2$ are independently selected from the group consisting of hydrogen and alkoxy; $R^3$, $R^4$, $R^7$, and $R^8$ are hydrogen; and $R^9$ is selected from the group consisting of hydrogen and alkyl.

In another embodiment, the present invention provides a compound of formula (I) wherein A is phenyl; X is O; $R^5$ is $LR^6$; $R^6$ is heterocyclyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(R^cR^d)$alkyl, and oxo; L is $(CH_2)_mN(R^7)C(O)N(R^8)(CH_2)_n$; and m, n, $R^c$, $R^d$, $R^1$, $R^2$, $R^3$, $R^4$, $R^7$, and $R^8$ are as defined in formula (I).

In another embodiment, the present invention provides a compound of formula (I) wherein A is phenyl; X is O; $R^5$ is $LR^6$; $R^6$ is heterocyclyl wherein the heterocyclyl is selected from the group consisting of furyl, isoxazolyl, isothiazolyl, oxazolyl, pyridinyl, thiazolyl, and thienyl, wherein the heterocyclyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, $-NR^cR^d$, $(R^cR^d)$alkyl, and oxo; L is $(CH_2)_mN(R^7)C(O)N(R^8)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(NR^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is O; $R^5$ is $LR^6$; $R^6$ is heterocyclyl wherein the heterocyclyl is thienyl; L is $(CH_2)_mN(R^7)C(O)N(R^8)(CH_2)_n$; m and n are 0; $R^1$ and $R^2$ are independently selected from the group consisting of hydrogen and alkoxy; and $R^3$, $R^4$, $R^7$, and $R^8$ are hydrogen.

In another embodiment, the present invention provides a compound of formula (I) wherein A is phenyl; X is S; $R^5$ is $LR^6$; $R^6$ is heterocyclyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —$NR^cR^d$, $(NR^cR^d)$alkyl, and oxo; L is $(CH_2)_mN(R^7)C(O)N(R^8)(CH_2)_n$; and m, n, $R^c$, $R^d$, $R^1$, $R^2$, $R^3$, $R^4 R^7$, and $R^8$ are as defined in formula (I).

In another embodiment, the present invention provides a compound of formula (I) wherein A is phenyl; X is S; $R^5$ is $LR^6$; $R^6$ is heterocyclyl wherein the heterocyclyl is selected from the group consisting of furyl, isoxazolyl, isothiazolyl, oxazolyl, pyridinyl, thiazolyl, and thienyl, wherein the heterocyclyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —$NR^cR^d$, $(NR^cR^d)$alkyl, and oxo; L is $(CH_2)_mN(R^7)C(O)N(R^8)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(NR^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is S; $R^5$ is $LR^6$; $R^6$ is heterocyclyl wherein the heterocyclyl is thienyl; L is $(CH_2)_mN(R^7)C(O)N(R^8)(CH_2)_n$; m and n are 0; $R^1$ and $R^2$ are independently selected from the group consisting of hydrogen and alkoxy; and $R^3$, $R^4$, $R^7$, and $R^8$ are hydrogen.

In another embodiment, the present invention provides a compound of formula (I) wherein A is phenyl; X is $NR^9$; $R^5$ is $LR^6$; $R^6$ is heterocyclyl optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —$NR^cR^d$, $(NR^cR^d)$alkyl, and oxo; L is $(CH_2)_mN(R^7)C(O)N(R^8)(CH_2)_n$; and m, n, $R^c$, $R^d$, $R^1$, $R^2$, $R^3$, $R^4$, $R^7$, $R^8$, and $R^9$ are as defined in formula (I).

In another embodiment, the present invention provides a compound of formula (I) wherein A is phenyl; X is $NR^9$; $R^5$ is $LR^6$; $R^6$ is heterocyclyl wherein the heterocyclyl is selected from the group consisting of furyl, isoxazolyl, isothiazolyl, oxazolyl, pyridinyl, thiazolyl, and thienyl, wherein the heterocyclyl is optionally substituted with one, two, or three substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —$NR^cR^d$, $(NR^cR^d)$alkyl, and oxo; L is $(CH_2)_mN(R^7)C(O)N(R^8)(CH_2)_n$; m and n are 0; $R^1$ and $R^2$ are independently selected from the group consisting of hydrogen, alkoxy, alkoxyalkoxy, alkyl, halo, hydroxy, $(NR^aR^b)$alkoxy, $(NR^aR^b)$alkyl, and $(NR^aR^b)$carbonylalkenyl; $R^3$ and $R^4$ are independently selected from the group consisting of hydrogen, alkyl, alkoxy, alkoxyalkoxy, halo, haloalkoxy, and hydroxy; $R^7$ and $R^8$ are hydrogen; $R^9$ is selected from the group consisting of hydrogen and alkyl; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (I) wherein A is phenyl; X is $NR^9$; $R^5$ is $LR^6$; $R^6$ is heterocyclyl wherein the heterocyclyl is thienyl; L is $(CH_2)_mN(R^7)C(O)N(R^8)(CH_2)_n$; m and n are 0; $R^1$ and $R^2$ are independently selected from the group consisting of hydrogen and alkoxy; $R^3$, $R^4$, $R^7$, and $R^8$ are hydrogen; and $R^9$ is selected from the group consisting of hydrogen and alkyl.

In another embodiment, the present invention provides a pharmaceutical composition comprising a compound of formula (I), or a therapeutically acceptable salt thereof, in combination with a therapeutically acceptable carrier.

In another embodiment, the present invention provides a method for inhibiting protein kinase in a patient in recognized need of such treatment comprising administering to the patient a therapeutically acceptable amount of a compound of formula (I), or a therapeutically acceptable salt thereof.

In another embodiment, the present invention provides a method for treating cancer in a patient in recognized need of such treatment comprising administering to the patient a therapeutically acceptable amount of a compound of formula (I), or a therapeutically acceptable salt thereof.

In another embodiment, the present invention provides a compound of formula (II) wherein L is $CH_2C(O)NR^7$; and X, $R^1$, $R^2$, $R^3$, $R^4$, $R^7$, $R^{10}$, and $R^{11}$ are as defined in formula (II).

In another embodiment, the present invention provides a compound of formula (II) wherein X is $NR^9$; L is $CH_2C(O)NR^7$; and $R^1$, $R^2$, $R^3$, $R^4$, $R^7$, $R^9$, $R^{10}$, and $R^{11}$ are as defined in formula (II).

In another embodiment, the present invention provides a compound of formula (II) wherein X is $NR^9$; L is $CH_2C(O)NR^7$; and $R^1$, $R^2$, $R^3$, $R^4$, $R^7$, $R^9$, $R^{10}$, and $R^{11}$ are as defined in formula (II).

In another embodiment, the present invention provides a compound of formula (II) wherein X is $NR^9$; L is $CH_2C(O)NR^7$; $R^1$, $R^2$, $R^3$, $R^4$, and $R^7$ are hydrogen; $R^9$ is selected from the group consisting of hydrogen and alkyl; $R^{10}$ and $R^{11}$ are as defined in formula (II).

In another embodiment, the present invention provides a compound of formula (II) wherein X is $NR^9$; L is $CH_2C(O)NR^7$; $R^1$, $R^2$, $R^3$, $R^4$, and $R^7$ are hydrogen; $R^9$ is selected from the group consisting of hydrogen and alkyl; $R^{10}$ and $R^{11}$ independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $CH_2C(O)NR^7$; $R^1$, $R^2$, $R^3$, $R^4$, and $R^7$ are hydrogen; $R^9$ is selected from the group consisting of hydrogen and alkyl; $R^{10}$ and $R^{11}$ independently selected from the group consisting of hydrogen, alkyl, halo, and haloalkyl.

In another embodiment, the present invention provides a compound of formula (II) wherein L is $(CH_2)_mN(R^7)C(O)N(R^3)(CH_2)_n$; and m, n, X, $R^1$, $R^2$, $R^3$, $R^4$, $R^7$, $R^8$, $R^{10}$, and $R^{11}$ are as defined in formula (II).

In another embodiment, the present invention provides a compound of formula (II) wherein X is $NR^9$; and L, $R^1$, $R^2$, $R^3$, $R^4$, $R^9$, $R^{10}$, and $R^{11}$ are as defined in formula (II).

In another embodiment, the present invention provides a compound of formula (II) wherein X is $NR^9$; L is $(CH_2)_mN(R^7)C(O)N(R^5)(CH_2)_n$; and m, n, $R^1$, $R^2$, $R^3$, $R^4$, $R^7$, $R^8$, $R^9$, $R^{10}$, and $R^{11}$ are as defined in formula (II).

In another embodiment, the present invention provides a compound of formula (II) wherein X is $NR^9$; L is $(CH_2)_mN$ $(R^7)C(O)N(R^8)(CH_2)_n$; m and n are 0; $R^7$ and $R^8$ are hydrogen; $R^9$ is selected from the group consisting of alkoxyalkyl, alkyl, alkylcarbonyl, aryl, heterocyclylalkyl, hydroxyalkyl, and $(NR^aR^b)$alkyl; and $R^a$, $R^b$, $R^1$, $R^2$, $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; and $R^1$, $R^2$, $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is selected from the group consisting of hydrogen and halo and the other is selected from the group consisting of hydroxy, hydroxyalkyl, and $(NR^aR^b)$alkyl; and $R^a$, $R^b$, $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is selected from the group consisting of hydrogen and halo and the other is selected from the group consisting of hydroxy, hydroxyalkyl, and $(NR^aR^b)$alkyl; one of $R^3$ and $R^4$ is hydrogen and the other is selected from the group consisting of alkoxyalkoxy, alkyl, halo, haloalkoxy, and hydroxy; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and $-NR^cR^d$; $R^a$ and $R^b$ are independently selected from the group consisting of hydrogen and alkyl; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, $R^8$, and $R^9$ are hydrogen; $R^4$ is selected from the group consisting of hydrogen and halo; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and $-NR^cR^d$; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, $R^8$, and $R^9$ are hydrogen; $R^4$ is selected from the group consisting of hydrogen and halo; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, $-NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, $R^8$, and $R^9$ are hydrogen; $R^4$ is selected from the group consisting of hydrogen and halo; and $R^{10}$ and $R^{11}$ are independently selected from the group consisting of hydrogen, alkyl, halo, and haloalkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, and $R^8$ are hydrogen; $R^9$ is alkyl; $R^4$ is selected from the group consisting of hydrogen and halo; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and $-NR^cR^d$; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, and $R^8$ are hydrogen; $R^9$ is alkyl; $R^4$ is selected from the group consisting of hydrogen and halo; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, $-NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^1$, $R^2$, $R^3$, $R^7$, and $R^8$ are hydrogen; $R^9$ is alkyl; $R^4$ is selected from the group consisting of hydrogen and halo; and $R^{10}$ and $R^{11}$ are independently selected from the group consisting of hydrogen, alkyl, halo, and haloalkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is halo; and $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is halo; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, $-NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$, L is $(CH_2)_mN(R^7)C(O)N(R^8)(CH_2)_n$, m and n are 0, $R^7$ and $R^8$ are hydrogen, $R^9$ is hydrogen, one of $R^1$ and $R^2$ is hydrogen and the other is heterocyclylalkoxy; and $R^3$, $R^4$, $R^{10}$, and $R^{11}$ are as defined in formula (II).

In another embodiment, the present invention provides a compound of formula (II) wherein X is $NR^9$, L is $(CH_2)_mN(R^7)C(O)N(R^8)(CH_2)_n$, m and n are 0, $R^7$ and $R^8$ are hydrogen, $R^9$ is hydrogen, one of $R^1$ and $R^2$ is hydrogen and the other is heterocyclylalkoxy; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, $-NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$, L is $(CH_2)_mN(R^7)C(O)N(R^8)(CH_2)_n$, m and n are 0, $R^7$ and $R^8$ are hydrogen, $R^9$ is hydrogen, one of $R^1$ and $R^2$ is hydrogen and the other is heterocyclylalkoxy wherein the heterocyclyl is selected from the group consisting of morpholinyl, piperidinyl, pyridinyl, pyrrolyl, pyrrolidinyl optionally substituted with oxo, and 3,4,4-trimethyl-2,5-dioxo-1-imidazolidinyl;

$R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of $(NR^aR^b)$carbonylalkenyl and $(NR^aR^b)$alkoxy; and $R^a$, $R^b$, $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of $(NR^aR^b)$carbonylalkenyl and $(NR^aR^b)$alkoxy; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; $R^a$ and $R^b$ are independently selected from the group consisting of hydrogen, alkyl, alkylsulfonyl, arylsulfonyl, haloalkylsulfonyl, and heterocyclylsulfonyl; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of $(NR^aR^b)$carbonylalkenyl and $(NR^aR^b)$alkoxy; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; $R^a$ and $R^b$ are independently selected from the group consisting of hydrogen, alkyl, alkylsulfonyl, arylsulfonyl wherein the aryl is phenyl, haloalkylsulfonyl, and heterocyclylsulfonyl wherein the heterocyclyl is thienyl; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of aryloxyalkyl, heterocyclyl, heterocyclylalkyl and heterocyclyloxyalkyl; and $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of aryloxyalkyl, heterocyclyl, heterocyclylalkyl and heterocyclyloxyalkyl; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is aryloxyalkyl wherein the aryl is phenyl optionally substituted with halo; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is heterocyclyl wherein the heterocyclyl is selected from the group consisting of pyridinyl and thienyl; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is heterocyclylalkyl wherein the heterocyclyl is selected from the group consisting of morpholinyl and piperazinyl wherein the piperazinyl is optionally substituted with alkyl; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is heterocyclyloxyalkyl wherein the heterocyclyl is pyridinyl; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of alkoxy, alkoxyalkoxy, and alkyl; and $R^3$, $R^4$, $R^{10}$, and $R^{11}$ are as defined in formula (II).

In another embodiment, the present invention provides a compound of formula (II) wherein X is $NR^9$; L is $(CH_2)_mN$ $(R^7)C(O)N(R^8)(CH_2)_n$; m and n are 0; $R^7$ and $R^8$ are hydrogen; $R^9$ is hydrogen; one of $R^1$ and $R^2$ is hydrogen and the other is selected from the group consisting of alkoxy, alkoxyalkoxy, and alkyl; $R^3$ and $R^4$ are independently selected from the group consisting of hydrogen, alkoxyalkoxy, alkyl, halo, haloalkoxy, and hydroxy; $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; and $R^3$, $R^4$, $R^{10}$, and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; one of $R^3$ and $R^4$ is hydrogen and the other is selected from the group consisting of alkoxyalkoxy, alkyl, halo, haloalkoxy, and hydroxy; and $R^{10}$ and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; one of $R^3$ and $R^4$ is hydrogen and the other is selected from the group consisting of alkoxyalkoxy, alkyl, halo, haloalkoxy, and hydroxy; and $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; $R^3$ and $R^4$ are hydrogen; and $R^{10}$ and $R^{11}$ are as defined in formula (II).

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; $R^3$ and $R^4$ are hydrogen; and $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein X is $NR^9$; L is $(CH_2)_mN(R^7)C(O)N(R^8)(CH_2)_n$; m and n are 0; $R^7$ and $R^8$ are hydrogen; $R^9$ is hydrogen; $R^1$ and $R^2$ are hydrogen; $R^3$ and $R^4$ are alkyl; and $R^{10}$ and $R^{11}$ are selected from the group consisting of hydrogen, alkoxy, alkoxycarbonyl, alkyl, carboxy, cyano, halo, haloalkoxy, haloalkyl, hydroxy, hydroxyalkyl, nitro, —$NR^cR^d$, and aryloxy wherein the aryloxy is phenoxy; and $R^c$ and $R^d$ are independently selected from the group consisting of hydrogen and alkyl.

In another embodiment, the present invention provides a compound of formula (II) wherein $R^1$ and $R^2$ are independently selected from the group consisting of hydrogen, alkoxy, alkoxyalkoxy, alkoxyalkyl, aryloxy, aryloxyalkyl, halo, haloalkoxy, haloalkyl, hydroxy, hydroxyalkoxy, hydroxyalkyl, $(NR^aR^b)$alkoxy, $(NR^aR^b)$alkenyl, $(NR^aR^b)$alkyl, $(NR^aR^b)$carbonylalkenyl, and $(NR^aR^b)$carbonylalkyl; and X, L, $R^a$, $R^b$, $R^3$, $R^4$, $R^{10}$, and $R^{11}$ are as defined in formula (II).

In another embodiment, the present invention provides a compound of formula (II) wherein X is O and L, $R^1$, $R^2$, $R^3$, $R^4$, $R^{10}$, and $R^{11}$ are as defined in formula (II).

In another embodiment, the present invention provides a compound of formula (II) wherein X is O; L is $(CH_2)_mN(R^7)C(O)N(R^8)(CH_2)_n$; and m, n, $R^1$, $R^2$, $R^3$, $R^4$, $R^7$, $R^8$, $R^{10}$, and $R^{11}$ are as defined in formula (II).

In another embodiment, the present invention provides a compound of formula (II) wherein X is O; L is $(CH_2)_mN(R^7)C(O)N(R^8)(CH_2)_n$; m and n are 0; $R^1$, $R^2$, $R^3$, $R^4$, $R^7$, and $R^8$ are hydrogen; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^aR^b$; and $R^a$ and $R^b$ are independently selected from the group consisting of hydrogen and alkyl.

In another embodiment, the present invention provides a compound of formula (II) wherein X is O; L is $(CH_2)_mN(R^7)C(O)N(R^3)(CH_2)_n$; m and n are 0; $R^1$, $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^aR^b$, and aryloxy wherein the aryloxy is phenoxy; and $R^a$ and $R^b$ are independently selected from the group consisting of hydrogen and alkyl.

In another embodiment, the present invention provides a compound of formula (II) wherein X is O; L is $(CH_2)_mN(R^7)C(O)N(R^3)(CH_2)_n$; m and n are 0; $R^1$ is heterocyclylalkoxy; $R^2$, $R^3$, $R^4$, $R^7$, and $R^8$ are hydrogen; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^aR^b$; and $R^a$ and $R^b$ are independently selected from the group consisting of hydrogen and alkyl.

In another embodiment, the present invention provides a compound of formula (II) wherein X is O; L is $(CH_2)_mN(R^7)C(O)N(R^3)(CH_2)_n$; m and n are 0; $R^1$ is heterocyclylalkoxy wherein the heterocyclyl is morpholinyl; $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^aR^b$, and aryloxy wherein the aryloxy is phenoxy; and $R^a$ and $R^b$ are independently selected from the group consisting of hydrogen and alkyl.

In another embodiment, the present invention provides a compound of formula (II) wherein X is O; L is $(CH_2)_mN(R^7)C(O)N(R^8)(CH_2)_n$; m and n are 0; $R^1$ is selected from the group consisting of alkoxy, alkyl, halo, and haloalkoxy; $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^aR^b$, and aryloxy wherein the aryloxy is phenoxy; and $R^a$ and $R^b$ are independently selected from the group consisting of hydrogen and alkyl.

In another embodiment, the present invention provides a compound of formula (II) wherein X is S and L, $R^1$, $R^2$, $R^3$, $R^4$, $R^{10}$, and $R^{11}$ are as defined in formula (II).

In another embodiment, the present invention provides a compound of formula (II) wherein X is S; L is $(CH_2)_mN(R^7)C(O)N(R^8)(CH_2)_n$; and m, n, $R^1$, $R^2$, $R^3$, $R^4$, $R^7$, $R^8$, $R^{10}$, and $R^{11}$ are as defined in formula (II).

In another embodiment, the present invention provides a compound of formula (II) wherein X is S; L is $(CH_2)_m N(R^7)C(O)N(R^8)(CH_2)_n$; m and n are 0; $R^1$, $R^2$, $R^3$, $R^4$, $R^7$, and $R^8$ are hydrogen; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^a R^b$; and $R^a$ and $R^b$ are independently selected from the group consisting of hydrogen and alkyl.

In another embodiment, the present invention provides a compound of formula (II) wherein X is S; L is $(CH_2)_m N(R^7)C(O)N(R^8)(CH_2)_n$; m and n are 0; $R^1$, $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^a R^b$, and aryloxy wherein the aryloxy is phenoxy; and $R^a$ and $R^b$ are independently selected from the group consisting of hydrogen and alkyl.

In another embodiment, the present invention provides a compound of formula (II) wherein X is S; L is $(CH_2)_m N(R^7)C(O)N(R^8)(CH_2)_n$; m and n are 0; $R^1$, $R^2$, $R^3$, $R^4$, $R^7$, and $R^8$ are hydrogen; and $R^{10}$ and $R^{11}$ are independently selected from the group consisting of hydrogen, alkyl, halo, and haloalkyl.

In another embodiment, the present invention provides a compound of formula (II) wherein X is S; L is $(CH_2)_m N(R^7)C(O)N(R^8)(CH_2)_n$; m and n are 0; $R^1$ is heterocyclylalkoxy; $R^2$, $R^3$, $R^4$, $R^7$, and $R^8$ are hydrogen; $R^{10}$ and $R^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^a R^b$; and $R^a$ and $R^b$ are independently selected from the group consisting of hydrogen and alkyl.

In another embodiment, the present invention provides a compound of formula (II) wherein X is S; L is $(CH_2)_m N(R^7)C(O)N(R^8)(CH_2)_n$; m and n are 0; $R^1$ is heterocyclylalkoxy wherein the heterocyclyl is morpholinyl; $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^a R^b$, and aryloxy wherein the aryloxy is phenoxy; and $R^a$ and $R^b$ are independently selected from the group consisting of hydrogen and alkyl.

In another embodiment, the present invention provides a compound of formula (II) wherein X is S; L is $(CH_2)_m N(R^7)C(O)N(R^8)(CH_2)_n$; m and n are 0; $R^1$ is selected from the group consisting of alkoxy, alkyl, halo, and haloalkoxy; $R^2$, $R^3$, $R^4$, $R^7$, and $R^8$ are hydrogen; $R^{10}$ and $R^{11}$ are independently selected from the group consisting of hydrogen, alkoxy, alkoxycarbonyl, alkyl, carboxy, cyano, halo, haloalkoxy, haloalkyl, hydroxy, hydroxyalkyl, nitro, —$NR^a R^b$, and aryloxy wherein the aryloxy is phenoxy; and $R^a$ and $R^b$ are independently selected from the group consisting of hydrogen and alkyl.

In another embodiment, the present invention provides a pharmaceutical composition comprising a compound of formula (II), or a therapeutically acceptable salt thereof, in combination with a therapeutically acceptable carrier.

In another embodiment, the present invention provides a method for inhibiting protein kinase in a patient in recognized need of such treatment comprising administering to the patient a therapeutically acceptable amount of a compound of formula (II), or a therapeutically acceptable salt thereof.

In another embodiment, the present invention provides a method for treating cancer in a patient in recognized need of such treatment comprising administering to the patient a therapeutically acceptable amount of a compound of formula (II), or a therapeutically acceptable salt thereof.

DETAILED DESCRIPTION OF THE INVENTION

All publications, issued patents, and patent applications cited herein are hereby incorporated by reference.

As used herein, the singular forms "a", "an", and "the" include plural reference unless the context clearly dictates otherwise.

As used in the present specification the following terms have the meanings indicated:

The term "alkenyl," as used herein, refers to a straight or branched chain group of one to six carbon atoms containing at least one carbon-carbon double bond.

The term "alkoxy," as used herein, refers to an alkyl group attached to the parent molecular moiety through an oxygen atom.

The term "alkoxyalkoxy," as used herein, refers to an alkoxy group attached to the parent molecular moiety through another alkoxy group.

The term "alkoxyalkyl," as used herein, refers to an alkyl group substituted with at least one alkoxy group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon of one to six carbon atoms. Preferred alkyl groups of the present invention are of one to three carbon atoms. Most preferred alkyl groups are methyl and ethyl.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, a second aryl group, arylalkoxy, arylalkyl, aryloxy, carboxy, cyano, cycloalkyl, halo, haloalkoxy, haloalkyl, heterocyclyl, heterocyclylalkyl, hydroxy, hydroxyalkyl, nitro, —$NR^c R^d$, $(R^c R^d)$alkyl, and oxo; wherein the second aryl group, the aryl part of the arylalkoxy, the arylalkyl, and the aryloxy, the heterocyclyl, and the heterocyclyl part of the heterocyclylalkyl can be further optionally substituted with one, two, three, four, or five groups independently selected from the group consisting of alkenyl, alkoxy, alkoxyalkyl, alkyl, cyano, halo, haloalkoxy, haloalkyl, hydroxy, hydroxyalkyl, nitro, and oxo.

The term "arylalkyl," as used herein, refers to an alkyl group substituted with at least one aryl group.

The term "arylcarbonyl," as used herein, refers to an aryl group attached to the parent molecular moiety through a carbonyl group.

The term "arylalkoxy," as used herein, refers to an aryl group attached to the parent molecular moiety through an alkoxy group.

The term "aryloxy," as used herein, refers to an aryl group attached to the parent molecular moiety through an oxygen atom.

The term "aryloxyalkyl," as used herein, refers to an aryloxy group attached to the parent molecular moiety through an alkyl group.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —CO$_2$H.

The term "cyano," as used herein, refers to —CN.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Examples of cycloalkyl groups include, but are not limited to, cyclopropyl, cyclopentyl, cyclohexyl, bicyclo[3.1.1]heptyl, and adamantyl.

The cycloalkyl groups of the present invention can be optionally substituted with one, two, three, four, or five substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, —NR$^c$R$^d$, (NR$^c$R$^d$)alkyl, and oxo.

The terms "halo," and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylsulfonyl," as used herein, refers to a haloalkyl group attached to the parent molecular moiety through a sulfonyl group.

The term "heterocyclyl," as used herein, represents a monocyclic, bicyclic, or tricyclic ring system wherein one or more rings is a four-, five-, six-, or seven-membered ring containing one, two, or three heteroatoms independently selected from the group consisting of nitrogen, oxygen, and sulfur. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 3- and 4-membered rings have no double bonds, the 5-membered ring has from 0-2 double bonds and the 6- and 7-membered rings have from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, and trithiane. Bicyclic ring systems are exemplified by any of the above monocyclic ring systems fused to phenyl ring, a monocyclic cycloalkyl group as defined herein, a monocyclic cycloalkenyl group, as defined herein, or another monocyclic heterocyclyl ring system. Representative examples of bicyclic ring systems include but are not limited to, benzimidazole, benzothiazole, benzothiophene, benzoxazole, benzofuran, benzopyran, benzothiopyran, benzodioxine, 1,3-benzodioxole, cinnoline, dihydrobenzimidazole, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, and thiopyranopyridine. Tricyclic rings systems are exemplified by any of the above bicyclic ring systems fused to a phenyl ring, a monocyclic cycloalkyl group as defined herein, a monocyclic cycloalkenyl group as defined herein, or another monocyclic heterocyclyl ring system. Representative examples of tricyclic ring systems include, but are not limited to, acridine, carbazole, carboline, dibenzofuran, dibenzothiophene, naphthofuran, naphthothiophene, oxanthrene, phenazine, phenoxathiin, phenoxazine, phenothiazine, thianthrene, thioxanthene, and xanthene. Heterocyclyl groups can be attached to the parent molecular moiety through a carbon atom or a nitrogen atom in the group.

The heterocyclyl groups of the present invention can be optionally substituted with one, two, three, four, or five substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, (NR$^c$R$^d$)alkyl, and oxo; wherein the aryl, the aryl part of the arylalkoxy, the arylalkyl, and the aryloxy, the second heterocyclyl group, and the heterocyclyl part of the heterocyclylalkyl can be further optionally substituted with one, two, three, four, or five groups independently selected from the group consisting of alkenyl, alkoxy, alkoxyalkyl, alkyl, cyano, halo, haloalkoxy, haloalkyl, hydroxy, hydroxyalkyl, nitro, and oxo.

The term "heterocyclylalkenyl," as used herein, refers to an alkenyl group substituted with at least one heterocyclyl group.

The term "heterocyclylalkoxy," as used herein, refers to a heterocyclyl group attached to the parent molecular moiety through an alkoxy group.

The term "heterocyclylalkyl," as used herein, refers to an alkyl group substituted with at least one heterocyclyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with at least one heterocyclyloxy group.

The term "heterocyclylsulfonyl," as used herein, refers to a heterocyclyl group attached to the parent molecular moiety through a sulfonyl group.

The term "hydroxy," as used herein, refers to —OH.

The term "hydroxyalkoxy," as used herein, refers to a hydroxy group attached to the parent molecular moiety through an alkoxy group.

The term "hydroxyalkyl," as used herein, refers to an alkyl group substituted with at least one hydroxy group.

The term "nitro," as used herein, refers to —NO$_2$.

The term "—NR$^a$R$^b$," as used herein, represents two groups, R$^a$ and R$^b$, which are attached to the parent molecular moiety through a nitrogen atom. R$^a$ and R$^b$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, cycloalkyl, heterocyclyl, heterocyclylalkyl, and heterocyclylsulfonyl, wherein the aryl, the aryl part of the arylalkyl and the arylcarbonyl, the heterocyclyl, the heterocyclyl part of the heterocyclylalkyl and the heterocyclylsulfonyl can be further optionally substituted with one, two, three, four, or five substituents independently selected from the group consisting of alkenyl, alkoxy, alkyl, cyano, halo, haloalkyl, haloalkoxy, nitro, and oxo.

The term "(NR$^a$R$^b$)alkenyl," as used herein, represents an alkenyl group substituted with at least one —NR$^a$R$^b$ group.

The term "(NR$^a$R$^b$)alkoxy," as used herein, represents an —NR$^a$R$^b$ group attached to the parent molecular moiety through an alkoxy group.

The term "(NR$^a$R$^b$)alkyl," as used herein, represents an alkyl group substituted with at least one —NR$^a$R$^b$ group.

The term "(NR$^a$R$^b$)alkynyl," as used herein, represents an alkynyl group substituted with at least one —NR$^a$R$^b$ group.

The term "(NR$^a$R$^b$)carbonyl," as used herein, represents an (NR$^a$R$^b$) group attached to the parent molecular moiety through a carbonyl group.

The term "(NR$^a$R$^b$)carbonylalkenyl," as used herein, represents an alkenyl group substituted with at least one (R$^a$R$^b$) carbonyl group.

The term "(NR$^a$R$^b$)carbonylalkyl," as used herein, represents an alkyl group substituted with at least one (R$^a$R$^b$) carbonyl group.

The term "—NR$^c$R$^d$," as used herein, represents two groups, R$^c$ and R$^d$, which are attached to the parent molecular moiety through a nitrogen atom. R$^c$ and R$^d$ are independently selected from the group consisting of hydrogen, alkyl, alkylcarbonyl, aryl, arylalkyl, cycloalkyl, cycloalkylalkyl, heterocyclyl, and heterocyclylalkyl, wherein the aryl, the aryl part of the arylalkyl, the heterocyclyl, and the heterocyclyl part of the heterocyclylalkyl can be further optionally substituted with one, two, three, four, or five substituents independently selected from the group consisting of alkenyl, alkoxy, alkyl, cyano, halo, haloalkyl, haloalkoxy, nitro, and oxo.

The term "(NR$^c$R$^d$)alkyl," as used herein, represents an alkyl group substituted with at least one —NR$^c$R$^d$ group.

The term "oxo," as used herein, refers to =O.

The term "sulfonyl," as used herein, refers to —SO$_2$.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an —NR$^a$R$^b$ group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, —NR$^a$R$^b$ groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) or (II) for example, by hydrolysis in blood.

When it is possible that, for use in therapy, therapeutically effective amounts of a compound of formula (I) or (II), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or (II), or therapeutically acceptable salts thereof, and one or more pharmaceutically acceptable carriers, diluents, or excipients. The compounds of formula (I) and (II) and therapeutically acceptable salts thereof are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I) or (II), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of formula (I) or (II), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s). In addition, compounds of the present invention can be administered using conventional drug delivery technology, for example, intra-arterial stents.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by cumminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I) and (II), and therapeutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and (II), and therapeutically acceptable salts thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) or (II) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the above-mentioned conditions. In particular, in anti-cancer therapy, combination with other chemotherapeutic, hormonal, or antibody agents is envisaged as well as combination with surgical therapy and radiotherapy. Combination therapies according to the present invention thus comprise the administration of at least one compound of formula (I) or (II), or a therapeutically acceptable salt thereof, and the use of at least one other cancer treatment method. Preferably, combination therapies according to the present invention comprise the administration of at least one other pharmaceutically active agent, preferably an anti-neoplastic agent. The compound(s) of formula (I) or (II) and the other pharmaceutically active agent(s) may be administered together or separately and when administered separately this may occur simultaneously or sequentially in any order. The amounts of the compound(s) of formula (I) or (II) and the other pharmaceutically active agent(s) and the relative timings of administration will be selected in order to achieve the desired combined therapeutic effect.

The compounds of formula (I) or (II), or therapeutically acceptable salts thereof, and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or (II), or therapeutically acceptable salts thereof, with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts of formula (I) or (II) include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine, and thioguanine; and camptothecins such as 9-amino camptothecin, irinotecan, topotecan, CPT-11, and the various optical forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR and TIE-2 (other than those VEGFR and TIE-2 inhibitors described in the present invention)); and other tyrosine kinase inhibitors such as inhibitors of CDK2 and CDK4 inhibitors.

Determination of Biological Activity

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature. 373:536-539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$ KDR (aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Compounds of the present invention inhibited KDR at $IC_{50}$'s between about 0.003 µM and about 40 µM. Preferred compounds inhibited KDR at $IC_{50}$'s between about 0.003 µM and about 0.1 µM.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein in a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 µL) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids $M(H)_6$ $LVPR_9S$ was placed 5' to the region encoding the entirety of ZAP70 (amino acids 1-619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g., from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: Manual of Clinical Immunology, 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu4 Tyr), 20,000-50,000 MW) was employed together with ATP (typically 5 µM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM $MgCl_2$, 4 mM $MnCl_2$, 5 mM DTT, 0.02% BSA, 200 µM $NaVO_4$, pH 7.10

ATP: Store aliquots of 100 mM at −20° C. Dilute to 20 μM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 μg/ml. Add 125 μl per well of Corning modified flat bottom high affinity ELISA plates (Corning #25805-96). Add 125 μl PBS to blank wells. Cover with sealing tape and incubate overnight 37° C. Wash 1× with 250 μl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 μl, e.g. for KDR make to 1 ng/μl for a total of 50 ng per well in the reactions. Store on ice.

Make 4×ATP solution to 20 μM from 100 mM stock in water. Store on ice

Add 50 μl of the enzyme solution per well (typically 5-50 ng enzyme/well depending on the specific activity of the kinase)

Add 25 μl 4× inhibitor

Add 25 μl 4×ATP for inhibitor assay

Incubate for 10 minutes at room temperature

Stop reaction by adding 50 μl 0.05N HCl per well

Wash plate

**Final Concentrations for Reaction: 5 μM ATP, 5% DMSO

3. Antibody Binding

Dilute 1 mg/ml aliquot of PY20-HRP (Pierce) antibody (a phosphotyrosine antibody) to 50 ng/ml in 0.1% BSA in PBS by a 2 step dilution (100×, then 200×)

Add 100 μl Ab per well. Incubate 1 hr at room temp. Incubate 1 hr at 4° C.

Wash 4× plate

4. Color Reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM MnCl$_2$, 20 mM MgCl$_2$, 5 mM DTT, 0.2% BSA, 200 mM NaVO$_4$ under the analogous assay conditions.

Compounds of formulas 1-109 may have therapeutic utility in the treatment of diseases involving both identified, including those not mentioned herein, and as yet unidentified protein tyrosine kinases which are inhibited by compounds of formulas 1-109.

Cdc2 Source

The human recombinant enzyme and assay buffer may be obtained commercially (New England Biolabs, Beverly, Mass. USA) or purified from known natural or recombinant sources using conventional methods.

Cdc2 Assay

A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 μM ATP (31 μCi/ml) and 30 μg/ml histone type IIIss final concentrations. A reaction volume of 80 μL, containing units of enzyme, is run for 20 minutes at 25 degrees C. in the presence or absence of inhibitor. The reaction is terminated by the addition of 120 μL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source

The catalytic subunit of PKC may be obtained commercially (Calbiochem).

PKC Kinase Assay

A radioactive kinase assay is employed following a published procedure (Yasuda, I., Kirshimoto, A., Tanaka, S., Tominaga, M., Sakurai, A., Nishizuka, Y. Biochemical and Biophysical Research Communication 3:166, 1220-1227 (1990)). Briefly, all reactions are performed in a kinase buffer consisting of 50 mM Tris-HCl pH7.5, 11 mM MgCl$_2$, 2 mM DTT, 1 mM EGTA, 100 μM ATP, 8 μM peptide, 5% DMSO and $^{33}$P ATP (8Ci/mM). Compound and enzyme are mixed in the reaction vessel and the reaction is initiated by addition of the ATP and substrate mixture. Following termination of the reaction by the addition of 10 μL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction is carried out in a buffer consisting of 50 mM Tris pH 7.5, 1 mM EGTA, 2 mM DTT, 0.01% Brij, 5% DMSO and 10 mM MgCl$_2$ (commercial buffer) supplemented with fresh 100 μM ATP (31 μCi/ml) and 30 μM myelin basic protein under conditions recommended by the supplier. Reaction volumes and method of assaying incorporated radioactivity are as described for the PKC assay (vide supra).

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3-8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at 0.5-1.0×10$^5$ cells/well in each well of 6-well cluster plates (Costar; Cambridge, Mass.).

3. 3-4 days after seeding, plates are typically 90-100% confluent. Medium is removed from all the wells, cells are rinsed with 5-10 ml of PBS and incubated 18-24 h with 5 ml of EBM base media with no supplements added (i.e., serum starvation).

4. Serial dilutions of inhibitors are added in 1 ml of EBM media (25 μM, 5 μM, or 1 μM final concentration to cells and incubated for one hour at 37° C. Human recombinant $VEGF_{165}$ (R & D Systems) is then added to all the wells in 2 ml of EBM medium at a final concentration of 50 ng/ml and incubated at 37° C. for 10 minutes. Control cells untreated or treated with VEGF only are used to assess background phosphorylation and phosphorylation induction by VEGF.

All wells are then rinsed with 5-10 ml of cold PBS containing 1 mM Sodium Orthovanadate (Sigma) and cells are lysed and scraped in 200 μl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St Louis, Mo.). The lysate is spun at 14,000 rpm for 30 min, to eliminate nuclei.

Equal amounts of proteins are then precipitated by addition of cold (−20° C.) Ethanol (2 volumes) for a minimum of 1 hour or a maximum of overnight. Pellets are reconstituted in Laemli sample buffer containing 5%-mercaptoethanol (Bio-Rad; Hercules, Calif.) and boiled for 5 min. The proteins are resolved by polyacrylamide gel electrophoresis (6%, 1.5 mm Novex, San Diego, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated $F(ab)_2$ of goat anti-rabbit or goat-anti-mouse IgG the bands are visualized using the emission chemiluminescence (ECL) system (Amersham Life Sciences, Arlington Heights, Ill.).

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8-12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p. Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g., kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (J. Thorac. Cardiovasc. Surg. 2001, 122 (1), 65-73).

Synthetic Methods

Abbreviations which have been used in the descriptions of the scheme and the examples that follow are: AIBN for 2,2'-azobis(2-methylpropionitrile); THF for tetrahydrofuran; MTBE for methyl tert-butyl ether, PPh₃ for triphenylphosphine; o-tol₃P for tri-o-tolylphosphine; dppf for diphenylphosphinoferrocene; DMF for N,N-dimethylformamide; DME for 1,2-dimethoxyethane; NBS for N-bromosuccinimide; NMP for N-methylpyrrolidinone; DMSO for dimethylsulfoxide; LDA for lithium diisopropylamide; TFA for trifluoroacetic acid; min for minutes; TBTU for O-benzotriazol-1-yl-N,N,N',N'-tetramethyluronium tetrafluoroborate; and DEAD for diethyl azodicarboxylate.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, X, $R^1$, $R^2$, $R^3$, $R^4$, $R^5$, and $R^6$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

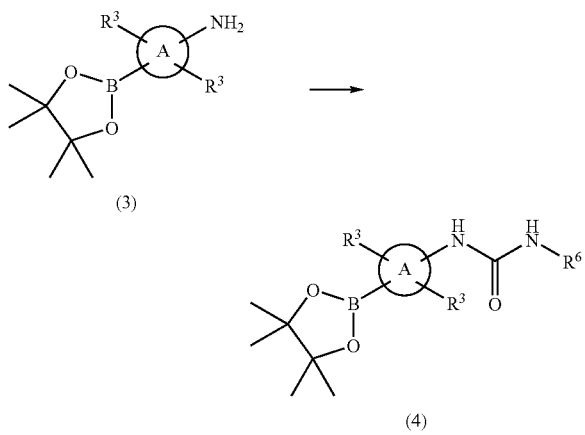

Scheme 1

Scheme 1 shows the synthesis of compounds of formula (4). Compounds of formula (3) can be reacted with an appropriately substituted isocyanate ($R^6$NCO) to provide compounds of formula (4). Examples of solvents used in these reactions include THF, dichloromethane, and MTBE. The reaction is typically conducted at a temperature of about 0° C. to about 25° C. for about 1 hour to about 14 hours.

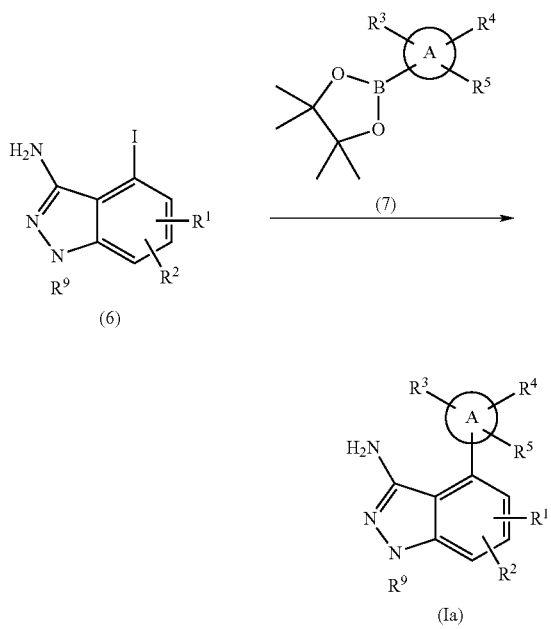

Compounds of formula (Ia) can be prepared following the procedures described in Scheme 2. Compounds of formula (5) can be converted to compounds of formula (6) by treatment with hydrazine. Examples of solvents include n-butanol, ethanol, n-pentanol, and n-hexanol. The reaction is typically conducted at about 80° C. to about 120° C. for about 2 to about 12 hours. Compounds of formula (6) where $R^9$ is hydrogen can be converted to compounds of formula (6) where $R^9$ is alkenyl, alkoxyalkyl, alkyl, heterocyclylalkyl, hydroxyalkyl, or (NR$^a$R$^b$)alkyl by treatment with the appropriately substituted alkylating agent in the presence of a base under conditions known to those of ordinary skill in the art.

Conversion of compounds of formula (6) to compounds of formula (Ia) can be accomplished by treatment with compounds of formula (7) in the presence of a palladium catalyst and a base. Representative palladium catalysts include Pd(PPh₃)₄, Pd(o-tol₃P)₂Cl₂, PdCl₂(dppf), and PdCl₂(dppf).CH₂Cl₂. Examples of bases include sodium carbonate, cesium carbonate, and potassium carbonate. Solvents typically used in these reactions include DMF, DME, toluene, ethanol, water, and mixtures thereof. The reaction is typically conducted at temperatures between about 60° C. and about 130° C. (optionally in a microwave for about 5 to about 25 minutes) for about 4 to about 24 hours.

Scheme 2

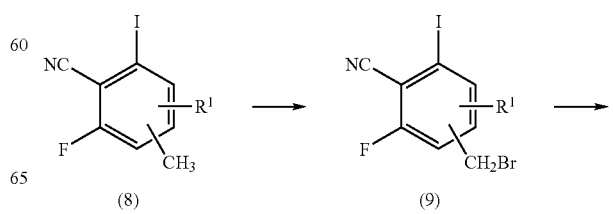

Scheme 3

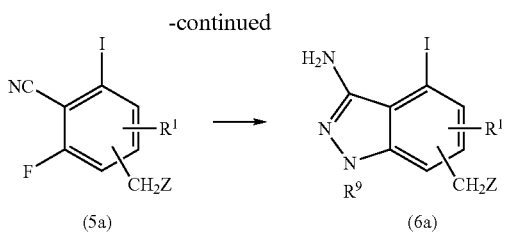

As shown in Scheme 3, compounds of formula (8) can be converted to compounds of formula (9) by treatment with NBS in the presence of a radical initiator such as benzoyl peroxide AIBN. Examples of solvents used in this reaction include $CCl_4$, benzene, and $CHCl_3$. The reaction is typically conducted at about 60 to about 80° C. for about 4 to about 48 hours.

Compounds of formula (9) can be converted to compounds of formula (5a) by treatment with a nucleophile (Z) (for example, an amine or an alcohol). Examples of solvents used in these reactions include THF, DMF, NMP, and DME. The reaction is typically conducted at about 20° C. to about 60° C. for about 12 to about 24 hours.

Conversion of compounds of formula (5a) to compounds of formula (6a) can be accomplished by the methods described in Scheme 2.

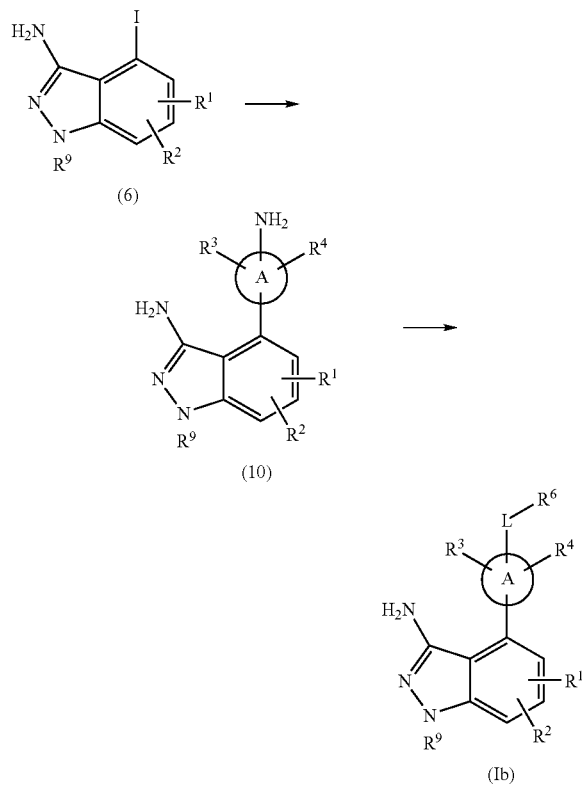

Scheme 4 shows the synthesis of compounds of formula (Ib). Compounds of formula (6) (prepared by the methods described in Scheme 2) can be converted to compounds of formula (10) by treatment with an appropriately substituted borane or other organometallic reagent such as a stannane or organozinc reagent in the presence of a palladium catalyst and optionally a base. Representative palladium catalysts include $Pd(PPh_3)_4$, $Pd(o\text{-}tol_3P)_2Cl_2$, $PdCl_2(dppf)$, and $PdCl_2(dppf).CH_2Cl_2$. Examples of bases include sodium carbonate, cesium carbonate, and potassium carbonate. Solvents typically used in these reactions include DMF, DME, toluene, ethanol, water, and mixtures thereof. The reaction is typically conducted at temperatures between about 60° C. and about 130° C. for about 4 to about 24 hours.

Compounds of formula (10) can be converted to compounds of formula (Ib) by treatment with the appropriately substituted electrophile to generate L (i.e., an isocyanate of formula $R^6NCO$). Examples of solvents include dichloromethane, chloroform, THF, DMF, and MTBE. The reaction is typically conducted at about −5° C. to about 25° C. for about 12 to about 24 hours.

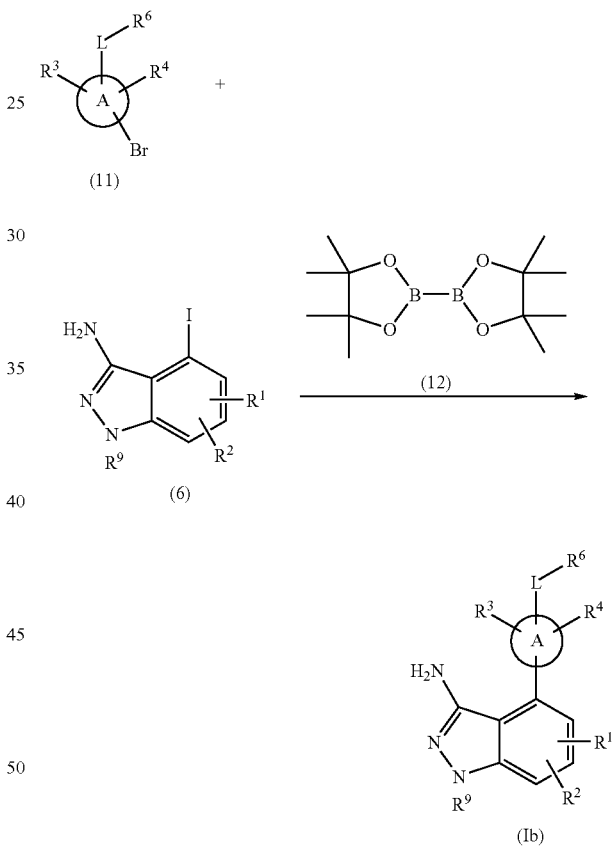

As shown in Scheme 5, compounds of formula (11) can be reacted with the compound of formula (12), a palladium catalyst, and potassium acetate, then treated with compounds of formula (6) in the presence of a palladium catalyst and a base to provide compounds of formula (Ib). Representative palladium catalysts include $Pd(PPh_3)_4$, $Pd(o\text{-}tol_3P)_2Cl_2$, $PdCl_2(dppf)$, and $PdCl_2(dppf)$ $CH_2Cl_2$. Examples of bases include sodium carbonate, cesium carbonate, and potassium carbonate. Solvents typically used in these reactions include DMF, DME, toluene, ethanol, water, and mixtures thereof. The reaction is typically conducted at temperatures between about 60° C. and about 130° C. for about 4 to about 24 hours.

Scheme 6

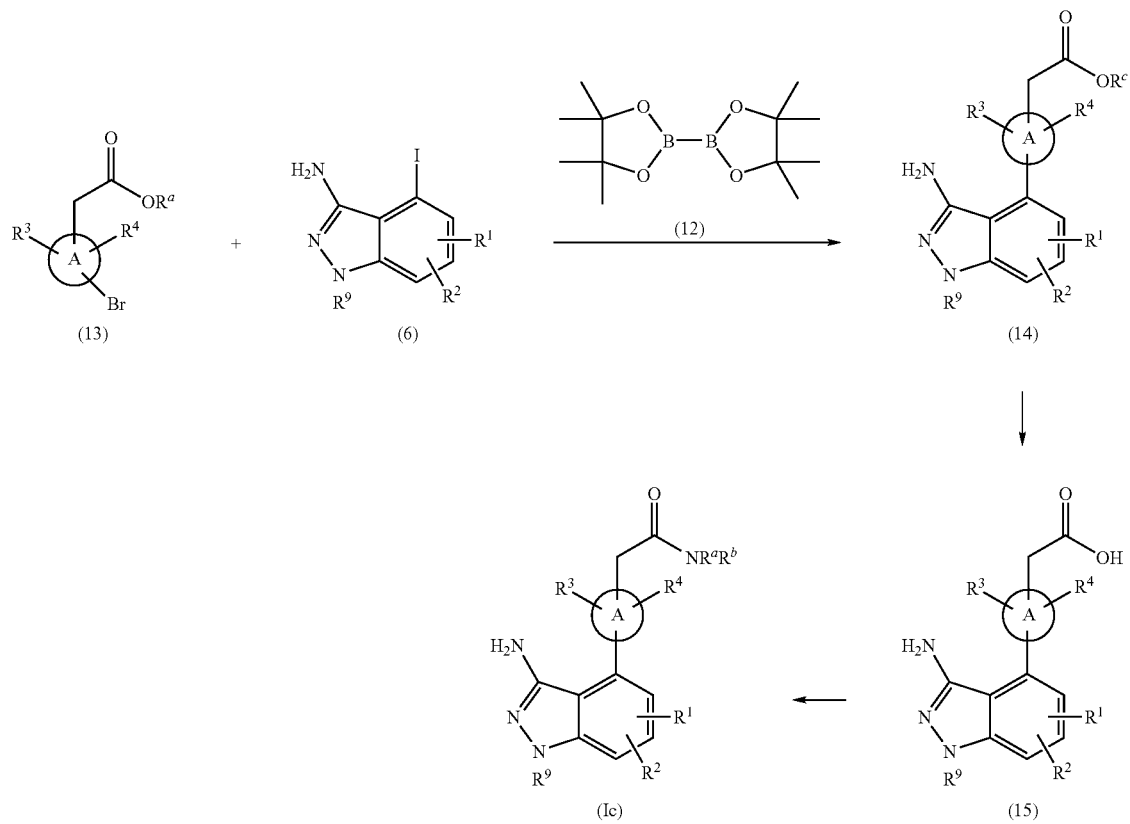

The synthesis of compounds of formula (Ic) is shown in Scheme 6. Compounds of formula (13) can be reacted with the compound of formula (12) then with compounds of formula (6) using the conditions described in Scheme 5 to provide compounds of formula (14). Compounds of formula (14) can be hydrolyzed to compounds of formula (15) using conditions known to those of ordinary skill in the art (i.e., KOH). Compounds of formula (15) can be converted to compounds of formula (Ic) by treatment with an appropriately substituted amine in the presence of a coupling agent under conditions known to those of ordinary skill in the art.

-continued

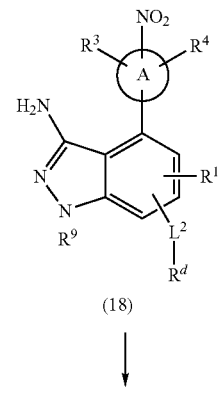

(18)

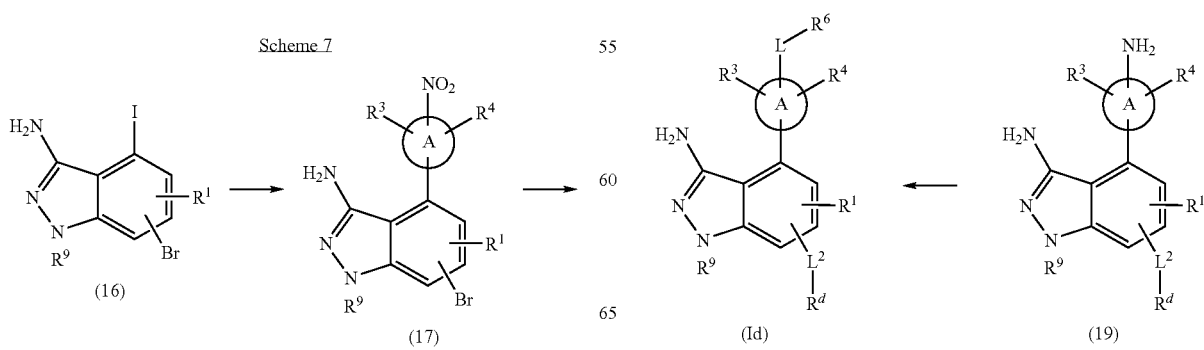

Compounds of formula (Id) can be prepared as described in Scheme 7. Compounds of formula (16) can be converted to compounds of formula (17) using the conditions described in Schemes 2 and 4. Compounds of formula (17) can be converted to compounds of formula (18) (where $L^2$ is an alkenyl group and $R^d$ is $(NR^aR^b)$carbonyl or alkoxycarbonyl) by treatment with a palladium catalyst and a base such as triethylamine or diisopropylethylamine. Examples of solvents include THF and 1,4-dioxane. The reaction is typically conducted at about 80 to about 150° C. for about 30 minutes to about 6 hours.

Conversion of compounds of formula (18) to compounds of formula (19) can be accomplished by methods known to those of ordinary skill in the art. Compounds of formula (19) can be converted to compounds of formula (Id) by the methods described in Scheme 4.

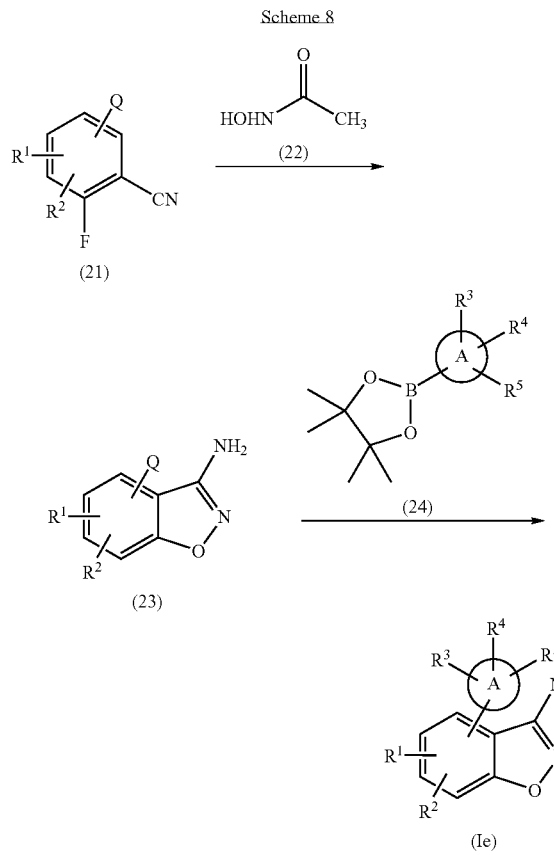

Scheme 8 shows the synthesis of compounds of formula (Ie). Compounds of formula (21) (where Q is Br or J) can be reacted with the compound of formula (22) in the presence of potassium tert-butoxide to provide compounds of formula (23). Examples of solvents used in this reaction include DMF, DME, and NMP. The reaction is typically conducted at about 20° C. to about 35° C. for about 15 minutes to about 12 hours.

Compounds of formula (23) can be coupled with compounds of formula (24) using the conditions described in Schemes 2, 4, and 7 to provide compounds of formula (Ie).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada).

Example 1

N-[4-(3-amino-1H-indazol-4-yl)phenyl]-N'-(3-methylphenyl)urea

Example 1A 4-iodo-1H-indazol-3-amine

A mixture of 2-fluoro-6-iodobenzonitrile (2 g, 8.1 mmol) and hydrazine hydrate (4 mL) in n-butanol (40 mL) was heated to 105-110° C. for 5 hours, cooled to room temperature, poured into water, and extracted twice with ethyl acetate. The combined extracts were washed with water and brine, dried (MgSO$_4$), filtered, and concentrated to provide 1.88 g of the desired product. $R_f$=0.25 (5% methanol/dichloromethane).

Example 1B

N-(3-methylphenyl)-N'-[4-(4,4,5,5-tetramethyl-1,3, 2-dioxaborolan-2-yl)phenyl]urea A 0° C. mixture of 4-(4,4,5,5-tetramethyl-1,3,2-dioxaborolan-2-yl)aniline (5.03 g, 23 mmol) and 1-isocyanato-3-methylbenzene (2.95 mL, 23 mmol) in THF (90 mL) was stirred at room temperature for 1 hour, concentrated, suspended in acetonitrile, and filtered. The filter cake was dried to provide 8.09 g of the desired product.

Example 1C

N-[4-(3-amino-1H-indazol-4-yl)phenyl]-N'-(3-methylphenyl)urea

A mixture of Example 1A (60 mg, 0.24 mmol), Example 1B (103 mg, 0.29 mmol) and Na$_2$CO$_3$ (64 mg, 0.6 mmol) under a nitrogen atmosphere was treated with DME (8 mL), water (2 mL), and Pd(PPh$_3$)$_4$ (14 mg, 0.012 mmol). The mixture was purged with bubbling nitrogen for 2 minutes, heated to 80-90° C. for about 18 hours, cooled to room temperature, poured into water, and extracted twice with ethyl acetate. The combined extracts were washed with water and brine, dried (MgSO$_4$), filtered, and concentrated. The concentrate was purified by flash column chromatography on silica gel with 5-8% methanol dichloromethane to provide 56 mg (66% yield) of the desired product. MS (ESI(+)) m/e 358 (M+H)$^+$; $^1$H NMR (300 MHz, DMSO-d$_6$) δ 2.29 (s, 3H), 4.33 (s, 2H), 6.76-6.83 (m, 2H), 7.17 (t, J=7.80 Hz, 1H), 7.23-7.28 (m, 3H), 7.32 (s, 1H), 7.39 (d, J=8.48 Hz, 2H), 7.59 (d, J=8.48 Hz, 2H), 8.64 (s, 1H), 8.79 (s, 1H), 11.70 (s, 1H).

Example 2

N-[4-(3-amino-1H-indazol-4-yl)phenyl]-N'-(3,5-dimethoxyphenyl)urea

The desired product was prepared by substituting 1-isocyanato-3,5-dimethoxy-benzene for 1-isocyanato-3-methylbenzene in Examples 1B-C. $^1$H NMR (300 MHz, DMSO-$d_6$) δ 3.73 (s, 6H), 4.33 (s, 2H), 6.15 (t, J=2.20 Hz, 1H), 6.70 (d, J=2.03 Hz, 2H), 6.78 (dd, J=5.76, 2.37 Hz, 1H), 7.22-7.31 (m, 2H), 7.39 (d, J=8.48 Hz, 2H), 7.58 (d, J=8.81 Hz, 2H), 8.73 (s, 1H), 8.78 (s, 1H), 11.71 (s, 1H); MS (ESI(+)) m/e 404 (M+H)$^+$.

Example 3

N-[4-(3-amino-1H-indazol-4-yl)phenyl]-N'-(3-chlorophenyl)urea

The desired product was prepared as the trifluoroacetate salt by substituting 1-chloro-3-isocyanatobenzene for 1-isocyanato-3-methylbenzene in Examples 1B-C and purifying the crude product by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. $^1$H NMR (300 MHz, DMSO-$d_6$) δ 6.89 (dd, J=6.44, 1.70 Hz, 1H), 7.03 (m, 1H), 7.28-7.38 (m, 4H), 7.42 (d, J=8.81 Hz, 2H), 7.61 (d, J=8.82 Hz, 2H), 7.74 (m, 1H), 9.00 (s, 1H), 9.03 (s, 1H); MS (ESI(+)) m/e 378 (M+H)$^+$; Anal. calcd. for $C_{20}H_{16}ClN_5O \cdot CF_3CO_2H$: C, 52.76; H, 3.62; N, 13.98. Found: C, 52.40; H, 3.50; N, 13.86.

Example 4

N-[4-(3-amino-1H-indazol-4-yl)phenyl]-N'-[3-(trifluoromethyl)phenyl]urea

The desired product was prepared as the trifluoroacetate salt by substituting 1-isocyanato-3-(trifluoromethyl)benzene for 1-isocyanato-3-methylbenzene in Examples 1B-C and purifying the product by preparative HPLC using the conditions described in Example 3. $^1$H NMR (300 MHz, DMSO-$d_6$) δ 6.86 (dd, J=6.10, 2.03 Hz, 1H), 7.29-7.35 (m, 3H), 7.42 (d, J=8.81 Hz, 2H), 7.53 (t, J=7.97 Hz, 1H), 7.58-7.65 (m, 3H), 8.05 (s, 1H), 9.01 (s, 1H), 9.16 (s, 1H); MS (ESI(+)) m/e 412 (M+H)$^+$; Anal. calcd. for $C_{21}H_{16}F_3N_5O \cdot 0.7CF_3CO_2H$: C, 54.77; H, 3.43; N, 14.26. Found: C, 54.64; H, 3.32; N, 14.12.

Example 5

N-[4-(3-amino-1H-indazol-4-yl)phenyl]-N'-(2-fluoro-5-methylphenyl)urea

Example 5A

N-(2-fluoro-5-methylphenyl)-N'-[4-(4,4,5,5-tetramethyl-1,3,2-dioxaborolan-2-yl)phenyl]urea A 0° C. mixture of 4-(4,4,5,5-tetramethyl-1,3,2-dioxaborolan-2-yl)aniline (0.5 g, 2.28 mmol) and 1-fluoro-2-isocyanato-4-methylbenzene (0.297 mL, 2.28 mmol) in dichloromethane (15 mL) was allowed to gradually warm to room temperature and stirred overnight. The resulting suspension was diluted with hexanes resulting in the formation of more precipitate, which was collected by filtration to provide 0.68 g of the desired product. MS (ESI(+)) m/e 370.7 (M+H)$^+$.

Example 5B

N-[4-(3-amino-1H-indazol-4-yl)phenyl]-N'-(2-fluoro-5-methylphenyl)urea

A mixture of Example 1A (80 mg, 0.32 mmol), Example 5A (144 mg, 0.39 mmol) and $Na_2CO_3$ (58 mg) in DME (3 mL) and water (1 mL) was degassed with nitrogen for 2 minutes, treated with $Pd(PPh_3)_4$ (19 mg, 0.0161 mmol), and degassed with nitrogen for another 2 minutes. The vial was capped and heated to 160° C. for 10 minutes with stirring in a Smith Synthesizer microwave oven (at 300 W). The reaction was concentrated and the residue was purified by HPLC using the conditions in Example 3 to provide 63 mg of the desired product as the trifluoroacetate salt. $^1$H NMR (300 MHz, DMSO-$d_6$) δ 2.28 (s, 3H), 6.78-6.85 (m, 1H), 6.87 (dd, J=6.10, 1.70 Hz, 1H), 7.12 (dd, J=11.53, 8.48 Hz, 1H), 7.30-7.39 (m, 2H), 7.42 (d, J=8.81 Hz, 2H), 7.60 (d, J=8.48 Hz, 2H), 8.01 (dd, J=7.80, 2.37 Hz, 1H), 8.54 (d, J=2.71 Hz, 1H), 9.23 (s, 1H); MS (ESI(+)) m/e 376 (M+H)$^+$; Anal calcd. for $C_{21}H_{18}FN_5O \cdot 0.8CF_3CO_2H$: C, 58.17; H, 4.06; N, 15.01. Found: C, 58.17; H, 4.29; N, 15.12.

Example 6

N-[4-(3-amino-1H-indazol-4-yl)phenyl]-N'-[2-fluoro-5-(trifluoromethyl)phenyl]urea The desired product was prepared by substituting 1-fluoro-2-isocyanato-4-(trifluoromethyl)benzene for 1-isocyanato-3-methylbenzene in Examples 5A-B and purifying the crude product as described in Example 1C. $^1$H NMR (300 MHz, DMSO-$d_6$) δ 4.33 (s, 2H), 6.79 (dd, J=5.26, 2.54 Hz, 1H), 7.24-7.31 (m, 2H), 7.42 (m, 3H), 7.52 (m, 1H), 7.61 (d, J=8.48 Hz, 2H), 8.65 (dd, J=7.29, 2.20 Hz, 1H), 8.96 (d, J=3.05 Hz, 1H), 9.32 (s, 1H), 11.72 (s, 1H); MS (ESI(+)) m/e 430 (M+H)$^+$.

Example 7

N-[4-(3-amino-1H-indazol-4-yl)phenyl]-N'-(3-bromophenyl)urea

The desired product was prepared as the trifluoroacetate salt by substituting 1-bromo-3-isocyanatobenzene for 1-isocyanato-3-methylbenzene in Examples 5A-B. $^1$H NMR (300 MHz, DMSO-$d_6$) δ 6.87 (dd, J=6.10, 1.70 Hz, 1H), 7.13-7.18 (m, 1H), 7.25 (t, J=7.97 Hz, 1H), 7.31-7.26 (m, 3H), 7.42 (d, J=8.82 Hz, 2H), 7.61 (d, J=8.48 Hz, 2H), 7.88 (t, J=1.86 Hz, 1H), 8.99 (s, 1H); MS (ESI(−)) m/e 420, 422 (M−H)$^-$.

Example 8

N-[4-(3-amino-1H-indazol-4-yl)phenyl]-N'-(3-bromo-4-methylphenyl)urea

The desired product was prepared as the trifluoroacetate salt by substituting 2-bromo-4-isocyanato-1-methylbenzene for 1-isocyanato-3-methylbenzene in Examples 5A-B. $^1$H NMR (300 MHz, DMSO-$d_6$) δ 2.33 (s, 3H), 6.88 (dd, J=6.10, 1.70 Hz, 1H), 7.25-7.50 (m, 7H), 7.61 (d, J=8.48 Hz, 2H), 8.85 (s, 1H), 8.93 (s, 1H); MS (ESI(−)) m/e 434, 435 (M−H)$^-$.

Example 9

N-[4-(3-amino-1H-indazol-4-yl)phenyl]-N'-(3-ethylphenyl)urea

The desired product was prepared as the trifluoroacetate salt by substituting 1-ethyl-3-isocyanatobenzene for 1-isocyanato-3-methylbenzene in Examples 5A-B. $^1$H NMR (300 MHz, DMSO-$d_6$) δ 1.19 (t, J=7.63 Hz, 3H), 2.58 (q, J=7.68 Hz, 2H), 6.81-6.88 (m, 2H), 7.19 (t, J=7.80 Hz, 1H), 7.25-

7.36 (m, 4H), 7.40 (d, J=8.48 Hz, 2H), 7.60 (d, J=8.81 Hz, 2H), 8.70 (s, 1H), 8.85 (s, 1H); MS (ESI(+)) m/e 372 (M+H)$^+$.

Example 10

N-[4-(3-amino-1H-indazol-4-yl)phenyl]-N'-phenylurea

The desired product was prepared by substituting isocyanatobenzene for 1-isocyanato-3-methylbenzene in Examples 5A-B and purifying the crude product as described in Example 1C. $^1$H NMR (300 MHz, DMSO-d$_6$) δ 4.33 (s, 2H), 6.78 (dd, J=5.42, 2.37 Hz, 1H), 6.98 (t, J=7.29 Hz, 1H), 7.28 (m, 4H), 7.39 (d, J=8.81 Hz, 2H), 7.48 (d, J=7.46 Hz, 2H), 7.59 (d, J=8.82 Hz, 2H), 8.72 (s, 1H), 8.81 (s, 1H), 11.70 (s, 1H); MS (ESI(+)) m/e 344 (M+H)$^+$.

Example 11

N-[4-(3-amino-1H-indazol-4-yl)phenyl]-N'-(3-fluoro-4-methylphenyl)urea

The desired product was prepared by substituting 2-fluoro-4-isocyanato-1-methylbenzene for 1-isocyanato-3-methylbenzene in Examples 5A-B and purifying the crude product as described in Example 1C. $^1$H NMR (300 MHz, DMSO-d$_6$) δ 2.17 (s, 3H), 4.33 (s, 2H), 6.78 (dd, J=5.42, 2.71 Hz, 1H), 7.05 (dd, J=8.14, 2.03 Hz, 1H), 7.17 (t, J=8.65 Hz, 1H), 7.23-7.30 (m, 2H), 7.39 (d, J=8.48 Hz, 2H), 7.45 (dd, J=12.54, 2.03 Hz, 1H), 7.58 (d, J=8.81 Hz, 2H), 8.84 (s, 2H), 11.70 (s, 1H); MS ESI(+)) m/e 376 (M+H)$^+$.

Example 12

N-[4-(3-amino-1H-indazol-4-yl)phenyl]-N'-(2-fluorophenyl)urea

The desired product was prepared by substituting 1-fluoro-2-isocyanatobenzene for 1-isocyanato-3-methylbenzene in Examples 5A-B and purifying the crude product as described in Example 1C. $^1$H NMR (300 MHz, DMSO-d$_6$) δ 4.33 (s, 2H), 6.79 (dd, J=5.42, 2.71 Hz, 1H), 6.97-7.06 (m, 1H), 7.16 (t, J=7.63 Hz, 1H), 7.22-7.30 (m, 3H), 7.41 (d, J=8.48 Hz, 2H), 7.60 (d, J=8.48 Hz, 2H), 8.18 (m, 1H), 8.61 (d, J=2.37 Hz, 1H), 9.22 (s, 1H), 11.71 (s, 1H); MS (ESI(+)) m/e 362 (M+H)$^+$.

Example 13

N-[4-(3-amino-1H-indazol-4-yl)phenyl]-N'-(4-fluorophenyl)urea

The desired product was prepared by substituting 1-fluoro-4-isocyanatobenzene for 1-isocyanato-3-methylbenzene in Examples 5A-B and purifying the crude product as described in Example 1C. $^1$H NMR (300 MHz, DMSO-d$_6$) δ 4.33 (s, 2H), 6.78 (dd, J=5.43, 2.37 Hz, 1H), 7.13 (t, J=8.99 Hz, 2H), 7.22-7.29 (m, 2H), 7.39 (d, J=8.48 Hz, 2H), 7.49 (m, 2H), 7.59 (d, J=8.82 Hz, 2H), 8.80 (d, J=15.60 Hz, 2H), 11.70 (s, 1H); MS (ESI(+)) 362 (M+H)$^+$.

Example 14

N-[4-(3-amino-1H-indazol-4-yl)phenyl]-N'-(3-fluorophenyl)urea

The desired product was prepared by substituting 1-fluoro-3-isocyanatobenzene for 1-isocyanato-3-methylbenzene in Examples 5A-B and purifying the crude product as described in Example 1C. $^1$H NMR (300 MHz, DMSO-d$_6$) δ 4.33 (s, 2H), 6.75-6.83 (m, 2H), 7.15 (m, 1H), 7.23-7.36 (m, 3H), 7.40 (d, J=8.48 Hz, 2H), 7.52 (m, 1H), 7.59 (d, J=8.48 Hz, 2H), 8.89 (s, 1H), 8.97 (s, 1H), 11.71 (s, 1H); MS (ESI(+)) m/e 362 (M+H)$^+$.

Example 15

N-{4-[3-amino-7-(4-morpholinylmethyl)-1H-indazol-4-yl]phenyl}-N'-(3-fluorophenyl)urea

Example 15A 2-fluoro-6-iodo-3-methylbenzoic acid

A −78° C. solution of 2-fluoro-4-iodo-1-methylbenzene (25 g, 105.9 mmol) in THF (200 mL) was treated dropwise with LDA (2M solution in THF, 58.5 mL, 116 mmol), stirred at −78° C. for 1 hour, treated with excess powdered dry ice, stirred at −78° C. for 30 minutes, and warmed to room temperature gradually over about 18 hours. The mixture was concentrated and the residue was partitioned between 4N NaOH and diethyl ether. The aqueous phase was adjusted to pH 2 with 2N HCl and extracted three times with ethyl acetate. The combined extracts were washed with water and brine, dried (MgSO$_4$), filtered, and concentrated to provide 19.4 g (66% yield) of the desired product. MS (ESI(+)) m/e 279 (M+H)$^+$.

Example 15B 2-fluoro-6-iodo-3-methylbenzamide

A solution of Example 15A (19.3 g, 69.1 mmol) in thionyl chloride (60 mL) was heated to 80° C. for 3 hours, cooled to room temperature, and concentrated. The residue was dissolved in THF (100 mL), cooled to 0° C., treated with concentrated NH$_4$OH (80 mL), stirred at room temperature for about 18 hours, and concentrated. The concentrate was suspended in water and filtered. The filter cake was washed with water and dried to provide 18.67 g of the desired product. MS (CI/NH$_3$) m/e 280 (M+H)$^+$.

Example 15C 2-fluoro-6-iodo-3-methylbenzonitrile

A solution of Example 15B (18.6 g, 66.7 mmol) in DMF (190 mL) was treated dropwise with thionyl chloride (24 mL, 333 mmol), heated to 115° C. for 16 hours, cooled to room temperature, poured into ice, and extracted three times with ethyl acetate. The combined extracts were washed with water and brine, dried (MgSO$_4$), filtered, and concentrated. The concentrate was purified by flash column chromatography on silica gel with 25% ethyl acetate/hexanes to provide 12.35 g (71% yield) of the desired product. MS (CI/NH$_3$) m/e 279 (M+NH$_4$)$^+$.

Example 15D 3-(bromomethyl)-2-fluoro-6-iodobenzonitrile

A mixture of Example 15C (8.0 g, 30.6 mmol), NBS (6.54 g, 36.78 mmol), and benzoyl peroxide (0.5 g) in CCl$_4$ (100 mL) was heated to reflux for 36 hours during which time additional NBS (9 g) and benzoyl peroxide (1.5 g) was added in 3 portions. The suspension was filtered and the filtrate was concentrated. The residue was purified by flash column chromatography on silica gel with 20% ethyl acetate/hexanes to provide 4.83 g (46% yield) of the desired product. $R_f$=0.27 (20% ethyl acetate/hexanes).

Example 15E 2-fluoro-6-iodo-3-(4-morpholinylmethyl)benzonitrile

A solution of Example 15D (710 mg, 2.09 mmol) and morpholine (0.546 mL, 6.25 mmol) in DMF (8 mL) was stirred at room temperature overnight, poured into water, and extracted twice with ethyl acetate. The combined extracts were washed with water and brine, dried (MgSO$_4$), filtered, and concentrated to provide 0.71 g of the desired product. $R_f$=0.4 (ethyl acetate).

Example 15F 4-iodo-7-(4-morpholinylmethyl)-1H-indazol-3-amine

The desired product was prepared by substituting Example 15E for 2-fluoro-6-iodobenzonitrile in Example 1A. $R_f$=0.18 (ethyl acetate).

Example 15G 4-(4-aminophenyl)-7-(4-morpholinylmethyl)-1H-indazol-3-amine

The desired product was prepared by substituting Example 15F and 4-(4,4,5,5-tetramethyl-1,3,2-dioxaborolan-2-yl)aniline for Example 1A and 1B, respectively, in Example 1C. $^1$H NMR (300 MHz, DMSO-d$_6$) δ 2.42 (d, J=4.07 Hz, 4H), 3.58 (m, 4H), 3.65 (s, 2H), 4.36 (s, 2H), 5.24 (s, 2H), 6.66 (dd, J=7.80, 4.41 Hz, 3H), 7.12 (m, 3H), 11.45 (s, 1H); MS (ESI (+)) m/e 324 (M+H)$^+$.

Example 15H

N-{4-[3-amino-7-(4-morpholinylmethyl)-1H-indazol-4-yl]phenyl}-N'-(3-fluorophenyl)urea A solution of Example 15G (50 mg, 0.155 mmol) in dichloromethane was cooled to 0° C., treated with 1-fluoro-3-isocyanatobenzene (0.021 mL), stirred at room temperature overnight, and concentrated. The concentrate was purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min to provide 24 mg of the desired product as the trifluoroacetate salt. $^1$H NMR (300 MHz, DMSO-d$_6$) δ 3.20-4.20 (m, 8H), 4.56 (s, 2H), 6.79 (m, 1H), 6.92 (d, J=7.12 Hz, 1H), 7.16 (m, 1H), 7.32 (m, 1H), 7.42 (m, 3H), 7.52 (m, 1H), 7.63 (d, J=8.81 Hz, 2H), 9.12 (s, 1H), 9.16 (s, 1H); MS (ESI(+)) m/e 461 (M+H)$^+$.

Example 16

N-{4-[3-amino-7-(4-morpholinylmethyl)-1H-indazol-4-yl]phenyl}-N'-(3-methylphenyl)urea The desired product was prepared as the trifluoroacetate salt by substituting 1-isocyanato-3-methylbenzene for 1-fluoro-3-isocyanatobenzene in Example 15H. $^1$H NMR (300 MHz, DMSO-d$_6$) δ 2.29 (s, 3H), 3.20-4.20 (m, 8H), 4.56 (s, 2H), 6.80 (d, J=7.12 Hz, 1H), 6.92 (d, J=7.12 Hz, 1H), 7.17 (t, J=7.80 Hz, 2H), 7.27 (d, J=7.23 Hz, 1H), 7.32 (s, 1H), 7.42 (m, 3H), 7.63 (d, J=8.48 Hz, 2H), 8.79 (s, 1H), 8.98 (s, 1H).

Example 17

N-{4-[3-amino-7-(4-morpholinylmethyl)-1H-indazol-4-yl]phenyl}-N'-[2-fluoro-5-(trifluoromethyl)phenyl]urea The desired product was prepared as the trifluoroacetate salt by substituting 1-fluoro-2-isocyanato-4-(trifluoromethyl)benzene for 1-fluoro-3-isocyanatobenzene in Example 15H. $^1$H NMR (300 MHz, DMSO-d$_6$) δ 3.20-4.10 (m, 8H), 4.56 (s, 2H), 6.92 (d, J=7.12 Hz, 1H), 7.38-7.47 (m, 4H), 7.52 (m, 1H), 7.64 (d, J=8.81 Hz, 2H), 8.64 (dd, J=7.46, 2.03 Hz, 1H), 9.00 (d, J=2.71 Hz, 1H), 9.40 (s, 1H); MS (ESI(+)) m/e 529 (M+H)$^+$.

Example 18

N-{4-[3-amino-7-(4-morpholinylmethyl)-1H-indazol-4-yl]phenyl}-N'-[4-fluoro-3-(trifluoromethyl)phenyl]urea The desired product was prepared as the trifluoroacetate salt by substituting 1-fluoro-4-isocyanato-2-(trifluoromethyl)benzene for 1-fluoro-3-isocyanatobenzene in Example 15H. $^1$H NMR (300 MHz, DMSO-d$_6$) δ 3.15-4.05 (m, 8H), 4.56 (s, 2H), 6.92 (d, J=7.12 Hz, 1H), 7.44 (m, 4H), 7.64 (d, J=8.81 Hz, 2H), 7.66 (m, 1H), 8.05 (dd, J=6.44, 2.71 Hz, 1H), 9.18 (s, 1H), 9.30 (s, 1H); MS (ESI(+)) m/e 529 (M+H)$^+$.

Example 19

N-{4-[3-amino-7-(4-morpholinylmethyl)-1H-indazol-4-yl]phenyl}-N'-[3-(trifluoromethyl)phenyl]urea A solution of Example 15F (80 mg, 0.22 mmol) and N-[4-(4,4,5,5-tetramethyl-1,3,2-dioxaborolan-2-yl)phenyl]-N'-[3-(trifluoromethyl)phenyl]urea (108 mg, 0.268 mmol) in toluene (2 mL) and ethanol (1.5 mL) was treated with a solution of Na$_2$CO$_3$ (58 mg) in water (1 mL), degassed with nitrogen for 2 minutes, treated with Pd(PPh$_3$)$_4$ (13 mg, 0.011 mmol), and degassed with nitrogen for another 2 minutes. The vial was capped and heated to 140-150° C. for 8-10 minutes with stirring in a Smith Synthesizer microwave oven (at 300 W). The reaction was poured into water and extracted three times with ethyl acetate. The combined extracts were washed with water and brine, dried (MgSO$_4$), filtered, and concentrated. The concentrate was purified by HPLC using the conditions in Example 15H to provide 55 mg of the desired product as the trifluoroacetate salt. $^1$H NMR (300 MHz, DMSO-d$_6$) δ 3.10-4.08 (m, 8H), 4.55 (s, 2H), 6.92 (d, J=7.12 Hz, 1H), 7.32 (d, J=7.46 Hz, 1H), 7.38-7.47 (m, 3H), 7.53 (t, J=7.80 Hz, 1H), 7.58-7.69 (m, 3H), 8.06 (s, 1H), 9.17 (s, 1H), 9.30 (s, 1H); MS (ESI(+)) m/e 511 (M+H)$^+$.

Example 20

N-(4-{3-amino-7-[(4-methyl-1-piperazinyl)methyl]-1H-indazol-4-yl}phenyl)-N'-(3-chlorophenyl)urea

Example 20A 4-iodo-7-[(4-methyl-1-piperazinyl)methyl]-1H-indazol-3-amine

The desired product was prepared by substituting 1-methylpiperazine for morpholine in Examples 15E-F. MS (ESI(+)) m/e 372 (M+H)$^+$.

Example 20B

N-(4-{3-amino-7-[(4-methyl-1-piperazinyl)methyl]-1H-indazol-4-yl}phenyl)-N'-(3-chlorophenyl)urea The desired product was prepared as the trifluoroacetate salt by substituting Example 20A and N-(3-chlorophenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-$d_6$) δ 2.80 (s, 3H), 3.00-3.50 (m, 8H), 3.97 (s, 2H), 6.85 (d, J=7.12 Hz, 1H), 7.03 (m, 1H), 7.25-7.33 (m, 3H), 7.40 (d, J=8.48 Hz, 2H), 7.62 (d, J=8.48 Hz, 2H), 7.74 (m, 1H), 9.14 (s, 1H), 9.17 (s, 1H); MS (ESI(+)) m/e 490 (M+H)$^+$.

Example 21

N-(4-{3-amino-7-[(4-methyl-1-piperazinyl)methyl]-1H-indazol-4-yl}phenyl)-N'-(3-methylphenyl)urea The desired product was prepared as the trifluoroacetate salt by substituting Example 20A and N-(3-methylphenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-$d_6$) δ 2.29 (s, 3H), 2.79 (s, 3H), 3.00-3.50 (m, 8H), 3.95 (s, 2H), 6.80 (d, J=7.46 Hz, 1H), 6.84 (d, J=7.46 Hz, 1H), 7.17 (t, J=7.63 Hz, 1H), 7.23-7.29 (m, 2H), 7.32 (s, 1H), 7.39 (d, J=8.48 Hz, 2H), 7.61 (d, J=8.81 Hz, 2H), 8.76 (s, 1H), 8.94 (s, 1H); MS (ESI(+)) m/e 470 (M+H)$^+$.

Example 22

N-(4-{3-amino-7-[(4-methyl-1-piperazinyl)methyl]-1H-indazol-4-yl}phenyl)-N'-(3-fluorophenyl)urea The desired product was prepared as the trifluoroacetate salt by substituting Example 20A and N-(3-fluorophenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-$d_6$) δ 2.79 (s, 3H), 3.00-3.50 (m, 8H), 3.95 (s, 2H), 6.75-6.86 (m, 2H), 7.15 (m, 1H), 7.25-7.35 (m, 2H), 7.40 (d, J=8.81 Hz, 2H), 7.52 (m, 1H), 7.62 (d, J=8.48 Hz, 2H), 9.09 (s, 1H), 9.15 (s, 1H); MS (ESI(+)) m/e 474 (M+H)$^+$.

Example 23

N-(4-{3-amino-7-[(4-methyl-1-piperazinyl)methyl]-1H-indazol-4-yl}phenyl)-N'-[3-(trifluoromethyl)phenyl]urea The desired product was prepared as the trifluoroacetate salt by substituting Example 20A for Example 15F in Example 19. $^1$H NMR (300 MHz, DMSO-$d_6$) δ 2.80 (s, 3H), 3.00-3.50 (m, 8H), 3.97 (s, 2H), 6.85 (d, J=7.46 Hz, 1H), 7.28 (d, J=7.12 Hz, 1H), 7.32 (d, J=7.80 Hz, 1H), 7.41 (d, J=8.81 Hz, 2H), 7.58-7.66 (m, 3H), 8.06 (s, 1H), 8.06 (s, 1H), 9.18 (s, 1H), 9.32 (s, 1H); MS (ESI(+)) m/e 524 (M+H)$^+$.

Example 24

N-(4-{3-amino-7-[(4-methyl-1-piperazinyl)methyl]-1H-indazol-4-yl}phenyl)-N'-[2-fluoro-5-(trifluoromethyl)phenyl]urea The desired product was prepared as the trifluoroacetate salt by substituting Example 20A and N-[2-fluoro-5-(trifluoromethyl)phenyl]-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-$d_6$) δ 2.80 (s, 3H), 3.00-3.50 (m, 8H), 3.95 (d, J=2.37 Hz, 2H), 6.84 (d, J=7.12 Hz, 1H), 7.28 (d, J=7.12 Hz, 1H), 7.38-7.45 (m, 3H), 7.52 (m, 1H), 7.62 (d, J=8.48 Hz, 2H), 8.64 (dd, J=7.29, 2.20 Hz, 1H), 8.99 (d, J=2.71 Hz, 1H), 9.38 (s, 1H); MS (ESI(+)) m/e 542 (M+H)$^+$.

Example 25

N-(4-{3-amino-7-[(4-methyl-1-piperazinyl)methyl]-1H-indazol-4-yl}phenyl)-N'-(2-fluoro-5-methylphenyl)urea The desired product was prepared as the trifluoroacetate salt by substituting Example 20A and N-(2-fluoro-5-methylphenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-$d_6$) δ 2.28 (s, 3H), 2.79 (s, 3H), 3.00-3.50 (m, 8H), 3.96 (s, 2H), 6.78-6.86 (m, 2H), 7.12 (dd, J=11.36, 8.31 Hz, 1H), 7.27 (d, J=7.46 Hz, 1H), 7.40 (d, J=8.81 Hz, 2H), 7.60 (d, J=8.48 Hz, 2H), 7.99 (dd, J=7.97, 1.86 Hz, 1H), 8.56 (d, J=2.71 Hz, 1H), 9.25 (s, 1H); MS (ESI(+)) m/e 488 (M+H)$^+$.

Example 26

N-[4-(3-amino-7-fluoro-1H-indazol-4-yl)phenyl]-N'-(3-bromophenyl)urea

Example 26A 2,3-difluoro-6-iodobenzonitrile

The desired product was prepared by substituting 1,2-difluoro-4-iodobenzene for 2-fluoro-4-iodo-1-methylbenzene in Examples 15A-C.

Example 26B 4-(4-aminophenyl)-7-fluoro-1H-indazol-3-amine

The desired product was prepared by substituting Example 26A for Example 15E in Examples 15F-G. MS (ESI(+)) m/e 243 (M+H)$^+$.

Example 26C

N-[4-(3-amino-7-fluoro-1H-indazol-4-yl)phenyl]-N'-(3-bromophenyl)urea

The desired product was prepared as the trifluoroacetate salt by substituting Example 26B and 1-bromo-3-isocyanatobenzene for Example 15G and 1-fluoro-3-isocyanatobenzene, respectively, in Example 15H. $^1$H NMR (300 MHz, DMSO-d$_6$) δ 6.73 (dd, J=7.80, 4.07 Hz, 1H), 7.13 (dd, J=11.19, 7.80 Hz, 1H), 7.16 (m, 1H), 7.25 (t, J=7.97 Hz, 1H), 7.34 (m, 1H), 7.38 (d, J=8.48 Hz, 2H), 7.59 (d, J=8.48 Hz, 2H), 7.88 (t, J=2.03 Hz, 1H), 8.91 (s, 1H), 8.94 (s, 1H); MS (ESI(+)) m/e 440, 442 (M+H)$^+$.

Example 27

N-[4-(3-amino-7-fluoro-1H-indazol-4-yl)phenyl]-N'-(3-chlorophenyl)urea

The desired product was prepared as the trifluoroacetate salt by substituting Example 26B and 1-chloro-3-isocyanatobenzene for Example 15G and 1-fluoro-3-isocyanatobenzene, respectively, in Example 15H. $^1$H NMR (300 MHz, DMSO-d$_6$) δ 6.74 (dd, J=7.80, 4.07 Hz, 1H), 7.03 (td, J=4.41, 2.37 Hz, 1H), 7.13 (dd, J=11.19, 7.80 Hz, 1H), 7.27-7.35 (m, 2H), 7.38 (d, J=8.48 Hz, 2H), 7.59 (d, J=8.48 Hz, 2H), 7.74 (m, 1H), 8.92 (s, 1H), 8.96 (s, 1H); MS (ESI(+)) m/e 396 (M+H)$^+$.

Example 28

N-[4-(3-amino-7-fluoro-1H-indazol-4-yl)phenyl]-N'-[3-(trifluoromethyl)phenyl]urea The desired product was prepared as the trifluoroacetate salt by substituting Example 26B and 1-isocyanato-3-(trifluoromethyl)benzene for Example 15G and 1-fluoro-3-isocyanatobenzene, respectively, in Example 15H. $^1$H NMR (300 MHz, DMSO-d$_6$) δ 6.75 (dd, J=7.80, 4.07 Hz, 1H), 7.14 (dd, J=11.19, 7.80 Hz, 1H), 7.32 (d, J=7.46 Hz, 1H), 7.39 (d, J=8.48 Hz, 2H), 7.53 (t, J=7.80 Hz, 1H), 7.61 (m, 3H), 8.04 (s, 1H), 8.98 (s, 1H), 9.14 (s, 1H); MS (ESI(−)) m/e 615 (M−H)$^−$.

Example 29

N-[4-(3-amino-7-fluoro-1H-indazol-4-yl)phenyl]-N'-(3-methylphenyl)urea

The desired product was prepared as the trifluoroacetate salt by substituting Example 26B and 1-isocyanato-3-methylbenzene for Example 15G and 1-fluoro-3-isocyanatobenzene, respectively, in Example 15H. $^1$H NMR (300 MHz, DMSO-d$_6$) δ 2.29 (s, 3H), 6.75 (dd, J=7.80, 4.41 Hz, 1H), 6.80 (d, J=7.46 Hz, 1H), 7.15 (m, 2H), 7.25 (m, 1H), 7.32 (s, 1H), 7.37 (d, J=8.48 Hz, 2H), 7.59 (d, J=8.48 Hz, 2H), 8.66 (s, 1H), 8.82 (s, 1H); MS (ESI(+)) m/e 376 (M+H)$^+$.

Example 30

N-[4-(3-amino-7-fluoro-1H-indazol-4-yl)phenyl]-N'-(3-cyanophenyl)urea

The desired product was prepared as the trifluoroacetate salt by substituting Example 26B and 3-isocyanatobenzonitrile for Example 15G and 1-fluoro-3-isocyanatobenzene, respectively, in Example 15H. $^1$H NMR (300 MHz, DMSO-d$_6$) δ 6.73 (dd, J=7.80, 4.41 Hz, 1H), 7.12 (dd, J=11.19, 7.80 Hz, 1H), 7.39 (d, J=8.81 Hz, 2H), 7.43 (dt, J=7.71, 1.40 Hz, 1H), 7.51 (t, J=7.97 Hz, 1H), 7.60 (d, J=8.48 Hz, 2H), 7.70 (ddd, J=8.22, 2.29, 1.36 Hz, 1H), 8.00 (t, J=1.70 Hz, 1H), 9.00 (s, 1H), 9.09 (s, 1H); MS (ESI(+)) m/e 387 (M+H)$^+$.

Example 31

N-(4-{3-amino-7-[(dimethylamino)methyl]-1H-indazol-4-yl}phenyl)-N'-(2-fluoro-5-methylphenyl)urea

Example 31A

7-[(dimethylamino)methyl]-4-iodo-1H-indazol-3-amine

The desired product was prepared by substituting N,N-dimethylamine for morpholine in Examples 15E-F. MS (ESI(+)) m/e 317 (M+H)$^+$.

Example 31B

N-(4-{3-amino-7-[(dimethylamino)methyl]-1H-indazol-4-yl}phenyl)-N'-(2-fluoro-5-methylphenyl)urea The desired product was prepared as the bis(trifluoroacetate) salt by substituting Example 31A and N-(2-fluoro-5-methylphenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-d$_6$) δ 2.28 (s, 3H), 2.82 (s, 6H), 4.51 (s, 2H), 6.82 (m, 1H), 6.91 (d, J=7.12 Hz, 1H), 7.12 (dd, J=11.53, 8.48 Hz, 1H), 7.43 (d, J=8.81 Hz, 2H), 7.43 (d, J=6.78 Hz, 1H), 7.62 (d, J=6.44 Hz, 2H), 7.99 (dd, J=7.80, 2.03 Hz, 1H), 8.56 (d, J=2.71 Hz, 1H), 9.26 (s, 1H); MS (ESI(+)) m/e 433 (M+H)$^+$; Anal. calcd. for C$_{24}$H$_{25}$FN$_6$O.2.3CF$_3$CO$_2$H: C, 49.44; H, 3.96; H, 12.10. Found: C, 49.51; H, 3.78; N, 12.31.

Example 32

N-(4-{3-amino-7-[(dimethylamino)methyl]-1H-indazol-4-yl}phenyl)-N'-(3-chlorophenyl)urea The desired product was prepared as the bis(trifluoroacetate) salt by substituting Example 31A and N-(3-chlorophenyl)-N'-[4-(4,4,5,5-tetramethyl-1,3,2-dioxaborolan-2-yl)phenyl]urea for Example 15F and N-[4-(4,4,5,5-tetramethyl-1,3,2-dioxaborolan-2-yl)phenyl]-N'-[3-(trifluoromethyl)phenyl]urea, respectively, in Example 19. $^1$H NMR (300 MHz, DMSO-d$_6$) δ 2.82 (s, 6H), 4.50 (s, 2H), 6.91 (d, J=7.12 Hz, 1H), 7.03 (m, 1H), 7.28-7.36 (m, 2H), 7.40-7.45 (m, 3H), 7.63 (d, J=8.82 Hz, 2H), 7.74 (m, 1H), 9.07 (s, 1H), 9.09 (s, 1H); MS (ESI(+)) m/e 435 (M+H)$^+$; Anal calcd. for C$_{23}$H$_{23}$ClN$_6$O.2.2CF$_3$CO$_2$H: C, 47.99; H, 3.70; N, 12.25. Found: C, 48.01; H, 3.41; H, 12.52.

Example 33

N-(4-{3-amino-7-[(dimethylamino)methyl]-1H-indazol-4-yl}phenyl)-N'-[3-(trifluoromethyl)phenyl]urea The desired product was prepared as the bis(trifluoroacetate) salt by substituting Example 31A for Example 15F in Example 19. $^1$H NMR (300 MHz, DMSO-$d_6$) δ 2.82 (s, 6H), 4.50 (s, 2H), 6.91 (d, J=7.46 Hz, 1H), 7.33 (d, J=7.46 Hz, 1H), 7.43 (d, J=8.48 Hz, 2H), 7.43 (d, J=7.46 Hz, 1H), 7.53 (t, J=7.80 Hz, 1H), 7.61 (d, J=8.82 Hz, 1H), 7.65 (d, J=8.48 Hz, 2H), 8.06 (s, 1H), 9.13 (s, 1H), 9.26 (s, 1H); MS (ESI(+)) m/e 469 (M+H)$^+$.

Example 34

N-[4-(3-amino-1-methyl-1H-indazol-4-yl)phenyl]-N'-(3-methylphenyl)urea

Example 34A 4-iodo-1-methyl-1H-indazol-3-amine

The desired product was prepared by substituting N-methylhydrazine for hydrazine hydrate in Example 1A. MS (ESI(+)) m/e 274 (M+H)$^+$.

Example 34B 4-(4-aminophenyl)-1-methyl-1H-indazol-3-amine

The desired product was prepared by substituting Example 34A and 4-(4,4,5,5-tetramethyl-1,3,2-dioxaborolan-2-yl)aniline for Example 1A and 1B, respectively, in Example 1C. MS (ESI(+)) m/e 239 (M+H)$^+$.

Example 34C

N-[4-(3-amino-1-methyl-1H-indazol-4-yl)phenyl]-N'-(3-methylphenyl)urea

The desired product was prepared by substituting 1-isocyanato-3-methylbenzene and Example 34B for 1-fluoro-3-isocyanatobenzene and Example 15G, respectively, in Example 15H. The resulting product was purified by flash column chromatography on silica gel with 5-8% methanol/dichloromethane to provide the desired product. MS (ESI(+)) m/e 372 (M+H)$^+$; $^1$H NMR (300 MHz, DMSO-$d_6$) δ 2.29 (s, 3H), 3.79 (s, 3H), 4.39 (s, 2H), 6.79 (dd, J=6.10, 1.70 Hz, 2H), 7.17 (t, J=7.80 Hz, 1H), 7.24-7.40 (m, 6H), 7.59 (d, J=8.48 Hz, 2H), 8.64 (s, 1H), 8.80 (s, 1H).

Example 35

N-[4-(3-amino-1-methyl-1H-indazol-4-yl)phenyl]-N'-phenylurea

The desired product was prepared as the trifluoroacetate salt by substituting isocyanatobenzene and Example 34B for 1-fluoro-3-isocyanatobenzene and Example 15G, respectively, in Example 15H. MS (ESI(+)) m/e 372 (M+H)$^+$; $^1$H NMR (500 MHz, DMSO-$d_6$) δ 3.79 (s, 3H), 6.80 (dd, J=6.55, 0.94 Hz, 1H), 6.98 (t, J=7.49 Hz, 1H), 7.39 (d, J=8.42 Hz, 2H), 7.28-7.36 (m, 4H), 7.47 (d, J=7.49 Hz, 2H), 7.59 (d, J=8.42 Hz, 2H), 8.70 (s, 1H), 8.80 (s, 1H).

Example 36

N-[4-(3-amino-1-methyl-1H-indazol-4-yl)phenyl]-N'-(2-methylphenyl)urea

The desired product was prepared as the trifluoroacetate salt by substituting 1-isocyanato-2-methylbenzene and Example 34B for 1-fluoro-3-isocyanatobenzene and Example 15G, respectively, in Example 15H. MS (ESI(+)) m/e 372 (M+H)$^+$; $^1$H NMR (500 MHz, DMSO-$d_6$) δ 2.27 (s, 3H), 3.79 (s, 3H), 4.38 (s, 2H), 6.80 (d, J=6.55 Hz, 1H), 6.96 (t, J=7.96 Hz, 1H), 7.16 (t, J=7.18 Hz, 1H), 7.19 (d, J=7.49 Hz, 1H), 7.30-7.36 (m, 2H), 7.39 (d, J=8.42 Hz, 2H), 7.60 (d, J=6.55 Hz, 2H), 7.84 (d, J=7.18 Hz, 1H), 7.97 (s, 1H), 9.15 (s, 1H).

Example 37

N-[4-(3-amino-1-methyl-1H-indazol-4-yl)phenyl]-N'-(4-methylphenyl)urea

The desired product was prepared as the trifluoroacetate salt by substituting 1-isocyanato-4-methylbenzene and Example 34B for 1-fluoro-3-isocyanatobenzene and Example 15G, respectively, in Example 15H. MS (ESI(+)) m/e 372 (M+H)$^+$; $^1$H NMR (500 MHz, DMSO-$d_6$) δ 2.25 (s, 3H), 3.79 (s, 3H), 6.80 (dd, J=6.55, 1.25 Hz, 1H), 7.10 (d, J=8.11 Hz, 2H), 7.30-7.39 (m, 6H), 7.58 (d, J=8.42 Hz, 2H), 8.59 (s, 1H), 8.76 (s, 1H).

Example 38

N-[4-(3-amino-1-methyl-1H-indazol-4-yl)phenyl]-N'-(3-methoxyphenyl)urea

The desired product was prepared as the trifluoroacetate salt by substituting 1-isocyanato-3-methoxybenzene and Example 34B for 1-fluoro-3-isocyanatobenzene and Example 15G, respectively, in Example 15H. MS (ESI(+)) m/e 388 (M+H)$^+$; $^1$H NMR (500 MHz, DMSO-$d_6$) δ 3.74 (s, 3H), 3.80 (s, 3H), 6.57 (dd, J=8.11, 2.50 Hz, 1H), 6.82 (dd, J=6.71, 1.09 Hz, 1H), 6.96 (dd, J=7.96, 1.09 Hz, 1H), 7.19 (t, J=8.11 Hz, 1H), 7.21 (t, J=2.18 Hz, 1H), 7.32-7.40 (m, 4H), 7.59 (d, J=8.42 Hz, 2H), 8.73 (s, 1H), 8.81 (s, 1H).

Example 39

N-[4-(3-amino-1-methyl-1H-indazol-4-yl)phenyl]-N'-(3-fluorophenyl)urea

The desired product was prepared as the trifluoroacetate salt by substituting Example 34B for Example 15G in Example 15H. MS (ESI(+)) m/e 376 (M+H)$^+$; $^1$H NMR (500 MHz, DMSO-$d_6$) δ 3.79 (s, 3H), 4.37 (s, 2H), 6.77-6.81 (m, 1H), 6.80 (dd, J=6.55, 1.25 Hz, 1H), 7.14 (dd, J=8.11, 1.25 Hz, 1H), 7.29-7.36 (m, 3H), 7.40 (d, J=8.42 Hz, 2H), 7.51 (dt, J=11.85, 2.18 Hz, 1H), 7.59 (d, J=8.42 Hz, 2H), 8.87 (s, 1H), 8.94 (s, 1H).

Example 40

N-[4-(3-amino-1-methyl-1H-indazol-4-yl)phenyl]-N'-(3-chlorophenyl)urea

The desired product was prepared as the trifluoroacetate salt by substituting 1-chloro-3-isocyanatobenzene and Example 34B for 1-fluoro-3-isocyanatobenzene and Example 15G, respectively, in Example 15H. MS (ESI(+)) m/e 376 (M+H)+; $^1$H NMR (500 MHz, DMSO-d$_6$) δ 3.79 (s, 3H), 4.22-4.56 (br s, 2H), 6.80 (dd, J=6.55, 1.25 Hz, 1H), 7.03 (dt, J=6.63, 2.14 Hz, 1H), 7.28-7.36 (m, 4H), 7.40 (d, J=8.42 Hz, 2H), 7.60 (d, J=8.42 Hz, 2H), 7.73 (s, 1H), 8.89 (s, 1H), 8.93 (s, 1H).

Example 41

N-[4-(3-amino-1-methyl-1H-indazol-4-yl)phenyl]-N'-(3-bromophenyl)urea

The desired product was prepared as the trifluoroacetate salt by substituting 1-bromo-3-isocyanatobenzene and Example 34B for 1-fluoro-3-isocyanatobenzene and Example 15G, respectively, in Example 15H. MS (ESI(+)) m/e 384, 386 (M+H)+; $^1$H NMR (500 MHz, DMSO-d$_6$) δ 3.79 (s, 3H), 4.40 (s, 2H), 6.80 (dd, J=6.71, 1.09 Hz, 1H), 7.16 (d, J=8.11 Hz, 1H), 7.25 (t, J=7.96 Hz, 1H), 7.30-7.36 (m, 3H), 7.39 (d, J=8.42 Hz, 2H), 7.59 (d, J=8.42 Hz, 2H), 7.88 (t, J=1.87 Hz, 1H), 8.89 (s, 1H), 8.91 (s, 1H).

Example 42

N-[4-(3-amino-1-methyl-1H-indazol-4-yl)phenyl]-N'-[3-(trifluoromethyl)phenyl]urea The desired product was prepared as the trifluoroacetate salt by substituting 1-isocyanato-3-(trifluoromethyl)benzene and Example 34B for 1-fluoro-3-isocyanatobenzene and Example 15G, respectively, in Example 15H. MS (ESI(+)) m/e 426 (M+H)+; $^1$H NMR (500 MHz, DMSO-d$_6$) δ 3.80 (s, 3H), 6.81 (dd, J=6.71, 1.09 Hz, 1H), 7.31-7.37 (m, 3H), 7.40 (d, J=8.42 Hz, 2H), 7.53 (t, J=7.80 Hz, 1H), 7.60 (d, J=9.05 Hz, 1H), 7.61 (d, J=8.73 Hz, 2H), 8.03 (s, 1H), 8.94 (s, 1H), 9.10 (s, 1H).

Example 43

N-[4-(3-amino-1-methyl-1H-indazol-4-yl)phenyl]-N'-(2-fluoro-5-methylphenyl)urea

The desired product was prepared as the trifluoroacetate salt by substituting 1-fluoro-2-isocyanato-4-methylbenzene and Example 34B for 1-fluoro-3-isocyanatobenzene and Example 15G, respectively, in Example 15H. MS (ESI(+)) m/e 390 (M+H)+; $^1$H NMR (500 MHz, DMSO-d$_6$) δ 2.28 (s, 3H), 3.80 (s, 3H), 6.81 (d, J=5.93 Hz, 2H), 7.11 (dd, J=11.39, 8.27 Hz, 1H), 7.31-7.37 (m, 2H), 7.40 (d, J=8.73 Hz, 2H), 7.59 (d, J=8.42 Hz, 2H), 8.00 (dd, J=7.64, 1.72 Hz, 1H), 8.52 (d, J=2.50 Hz, 1H), 9.20 (s, 1H).

Example 44

N-[4-(3-amino-1H-indazol-4-yl)-2-fluorophenyl]-N'-(3-methylphenyl)urea

Example 44A

N-(4-bromo-2-fluorophenyl)-N'-(3-methylphenyl)urea

A 0° C. solution of 4-bromo-2-fluoroaniline (1 g, 5.26 mmol) in dichloromethane (10 mL) was treated dropwise with 1-isocyanato-3-methylbenzene (0.71 mL, 5.26 mmol), warmed to room temperature, stirred for 18 hours, and fil- tered. The filter cake was washed with dichloromethane and dried to provide 0.62 g of the desired product. MS (ESI(−)) m/e 321 (M−H)−.

Example 44B

N-[4-(3-amino-1H-indazol-4-yl)-2-fluorophenyl]-N'-(3-methylphenyl)urea

A mixture of Example 44A (100 mg, 0.31 mmol), bis (pinacolato)diboron (86 mg, 0.33 mmol), Pd(dppf)Cl$_2$ (10 mg) and potassium acetate (270 mg) in DMF (3 mL) was heated to 80° C. for 2 hours, treated with Example 1A (64 mg, 0.24 mmol), Pd(dppf)Cl$_2$ (6 mg), Na$_2$CO$_3$ (78 mg), and water (1 mL), heated to 80° C. for 18 hours, cooled to room temperature, and concentrated. The concentrate was purified by preparative HPLC using the conditions described in Example 15H to provide 27 mg of the desired product as the trifluoroacetate salt. MS (ESI(+)) m/e 376 (M+H)+; $^1$H NMR (300 MHz, DMSO-d$_6$) δ 2.28 (d, J=7.12 Hz, 3H), 6.82 (d, J=6.78 Hz, 1H), 6.86 (t, J=3.90 Hz, 1H), 7.18 (t, J=7.63 Hz, 1H), 7.26 (d, J=8.48 Hz, 2H), 7.31-7.34 (m, 3H), 7.37 (dd, J=12.21, 1.70 Hz, 1H), 8.30 (t, J=8.65 Hz, 1H), 8.66 (d, J=2.37 Hz, 1H), 9.05 (s, 1H).

Example 45

N-[4-(3-amino-1H-indazol-4-yl)-2-fluorophenyl]-N'-(3-fluorophenyl)urea

The desired product was prepared as the trifluoroacetate salt by substituting 1-fluoro-3-isocyanatobenzene for 1-isocyanato-3-methylbenzene in Examples 44A-B. MS (ESI(+)) m/e 380 (M+H)+; $^1$H NMR (500 MHz, DMSO-d$_6$) δ 6.82 (td, J=8.42, 1.87 Hz, 1H), 6.86 (t, J=3.90 Hz, 1H), 7.12 (dd, J=8.11, 1.25 Hz, 1H), 7.28 (dd, J=8.27, 1.72 Hz, 1H), 7.32 (m, 3H), 7.38 (dd, J=12.01, 2.03 Hz, 1H), 7.53 (dt, J=11.85, 2.18 Hz, 1H), 8.26 (t, J=8.42 Hz, 1H), 8.72 (d, J=2.18 Hz, 1H), 9.33 (s, 1H).

Example 46

N-[4-(3-amino-1H-indazol-4-yl)-2-fluorophenyl]-N'-(3,5-dimethylphenyl)urea

The desired product was prepared as the trifluoroacetate salt by substituting 1-isocyanato-3,5-dimethylbenzene for 1-isocyanato-3-methylbenzene in Examples 44A-B. MS (ESI(+)) m/e 390 (M+H)+; $^1$H NMR (500 MHz, DMSO-d$_6$) δ 2.25 (s, 6H), 6.65 (s, 1H), 6.85 (t, J=3.90 Hz, 1H), 7.10 (br s, 2H), 7.26 (d, J=8.42 Hz, 1H), 7.30 (d, J=4.06 Hz, 2H), 7.36 (dd, J=12.32, 1.72 Hz, 1H), 8.29 (t, J=8.42 Hz, 1H), 8.63 (d, J=2.50 Hz, 1H), 8.96 (s, 1H).

Example 47

N-[4-(3-amino-1H-indazol-4-yl)-2-fluorophenyl]-N'-(3-ethylphenyl)urea

The desired product was prepared as the trifluoroacetate salt by substituting 1-isocyanato-3-ethylbenzene for 1-isocyanato-3-methylbenzene in Examples 44A-B. MS (ESI(+)) m/e 390 (M+H)+; $^1$H NMR (500 MHz, DMSO-d$_6$) δ 1.19 (t, J=7.49 Hz, 3H), 2.59 (q, J=7.80 Hz, 2H), 6.85-6.87 (m, 2H), 7.21 (t, J=7.80 Hz, 1H), 7.28 (m, J=4.06 Hz, 2H), 7.31 (br s, 1H), 7.32 (br s, 1H), 7.34 (br s, 1H), 7.37 (dd, J=12.17, 1.87 Hz, 1H), 8.30 (t, J=8.42 Hz, 1H), 8.64 (d, J=2.18 Hz, 1H), 9.06 (s, 1H).

Example 48

N-[4-(3-amino-1H-indazol-4-yl)-2-fluorophenyl]-N'-(3-chloro-4-fluorophenyl)urea

The desired product was prepared as the trifluoroacetate salt by substituting 2-chloro-1-fluoro-4-isocyanatobenzene for 1-isocyanato-3-methylbenzene in Examples 44A-B. MS (ESI(+)) m/e 414 (M+H)$^+$; $^1$H NMR (500 MHz, DMSO-d$_6$) δ 6.83 (dd, J=4.68, 3.12 Hz, 1H), 7.24-7.40 (m, 6H), 7.84 (dd, J=6.55, 2.50 Hz, 1H), 8.23 (t, J=8.58 Hz, 1H), 8.71 (s, 1H), 9.28 (s, 1H).

Example 49

N-[4-(3-amino-1H-indazol-4-yl)-2-fluorophenyl]-N'-(3-fluoro-4-methylphenyl)urea

The desired product was prepared as the trifluoroacetate salt by substituting 2-fluoro-4-isocyanato-1-methylbenzene for 1-isocyanato-3-methylbenzene in Examples 44A-B. MS (ESI(+)) m/e 394 (M+H)$^+$; $^1$H NMR (500 MHz, DMSO-d$_6$) δ 2.18 (s, 3H), 6.85 (m, 1H), 7.03 (dd, J=8.11, 1.87 Hz, 1H), 7.19 (t, J=8.58 Hz, 1H), 7.27 (dd, J=8.27, 1.72 Hz, 1H), 7.30 (br s, 1H), 7.31 (s, 1H), 7.37 (dd, J=12.17, 2.18 Hz, 1H), 7.46 (dd, J=12.48, 2.18 Hz, 1H), 8.26 (t, J=8.58 Hz, 1H), 8.67 (d, J=2.18 Hz, 1H), 9.20 (s, 1H).

Example 50

N-[4-(3-amino-1H-indazol-4-yl)-2-fluorophenyl]-N'-(3-chlorophenyl)urea

The desired product was prepared as the trifluoroacetate salt by substituting 1-chloro-3-isocyanatobenzene for 1-isocyanato-3-methylbenzene in Examples 44A-B. MS (ESI(−)) m/e 394 (M−H)$^−$; $^1$H NMR (500 MHz, DMSO-d$_6$) δ 6.85 (t, J=3.84 Hz, 1H), 7.05 (d, J=7.80, 1H), 7.26-7.35 (m, 5H), 7.38 (dd, J=12.17, 1.87 Hz, 1H), 7.75 (t, J=2.03 Hz, 1H), 8.25 (t, J=8.42 Hz, 1H), 8.72 (d, J=2.18 Hz, 1H), 9.30 (s, 1H).

Example 51

N-[4-(3-amino-7-bromo-1H-indazol-4-yl)phenyl]-N'-(3-methylphenyl)urea

The desired product was prepared by substituting 3-bromo-2-fluoro-6-iodobenzonitrile for 2-fluoro-6-iodobenzonitrile in Examples 1A-C. MS (ESI(−)) m/e 434, 436 (M−H)$^−$; $^1$H NMR (300 MHz, DMSO-d$_6$) δ 2.29 (s, 3H), 4.46 (s, 2H), 6.73 (d, J=7.46 Hz, 1H), 6.80 (d, J=6.78 Hz, 1H), 7.17 (t, J=7.63 Hz, 1H), 7.24-7.32 (m, 2H), 7.39 (d, J=8.48 Hz, 2H), 7.50 (d, J=7.80 Hz, 1H), 7.60 (d, J=8.14 Hz, 2H), 8.64 (s, 1H), 8.82 (s, 1H), 12.08 (s, 1H).

Example 52

N-{4-[3-amino-1-(2-hydroxyethyl)-1H-indazol-4-yl]phenyl}-N'-(3-methylphenyl)urea The desired product was prepared by substituting 2-hydrazinoethanol for hydrazine hydrate in Examples 1A-C. MS (ESI(+)) m/e 402 (M+H)$^+$; $^1$H NMR (300 MHz, DMSO-d$_6$) δ 2.29 (s, 3H), 3.74 (t, J=5.76 Hz, 2H), 4.20 (t, J=5.59 Hz, 2H), 6.79 (d, J=6.78 Hz, 1H), 6.80 (d, J=7.12 Hz, 1H), 7.17 (t, J=7.63 Hz, 1H), 7.23-7.40 (m, 6H), 7.59 (d, J=8.81 Hz, 2H), 8.65 (s, 1H), 8.80 (s, 1H).

Example 53

2-[4-(3-amino-1H-indazol-4-yl)phenyl]-N-phenylacetamide

Example 53A methyl [4-(3-amino-1H-indazol-4-yl)phenyl]acetate

The desired product was prepared by substituting methyl (4-bromophenyl)acetate and K$_3$PO$_4$ for Example 44A and Na$_2$CO$_3$, respectively, in Example 44B. Additionally the reaction was carried our under anhydrous conditions. MS (ESI(+)) m/e 304 (M+H)$^+$.

Example 53B

[4-(3-amino-1H-indazol-4-yl)phenyl]acetic acid

A solution of Example 53A (140 mg) in 1:1 methanol/10% NaOH (1 mL) was stirred at room temperature for 2 hours and adjusted to pH 3 with 10% HCl. The resulting precipitate was collected by filtration to provide 108 mg of the desired product. MS (ESI(+)) m/e 268 (M+H)$^+$.

Example 53C

2-[4-(3-amino-1H-indazol-4-yl)phenyl]-N-phenylacetamide

A mixture of Example 53B (40 mg, 015 mmol), diisopropylethylamine (0.078 mL, 0.45 mmol), TBTU (57 mg, 0.18 mmol), and aniline in THF (1 mL) was stirred for 18 hours at room temperature and concentrated. The residue was purified by preparative HPLC using the conditions described in Example 15H to provide 15 mg of the desired product as the trifluoroacetate salt. MS (ESI(+)) m/e 343 (M+H)$^+$; $^1$H NMR (300 MHz, DMSO-d$_6$) δ 3.74 (s, 2H), 6.84 (dd, J=5.09, 3.05 Hz, 1H), 7.02-7.07 (m, 1H), 7.28-7.33 (m, 4H), 7.43-7.50 (m, 4H), 7.62 (d, J=7.80 Hz, 2H).

Example 54

2-[4-(3-amino-1H-indazol-4-yl)phenyl]-N-(3-chlorophenyl)acetamide

The desired product was prepared as the trifluoroacetate salt by substituting 3-chloroaniline for aniline in Example 53C. MS (ESI(+)) m/e 377 (M+H)$^+$; $^1$H NMR (500 MHz, DMSO-d$_6$) δ 3.75 (s, 1H), 6.84 (dd, J=5.30, 2.50 Hz, 1H), 7.11 (dd, J=7.96, 2.03 Hz, 1H), 7.31-7.36 (m, 3H), 7.44-7.49 (m, 6H), 7.85 (d, J=1.87 Hz, 1H), 10.39 (s, 1H).

Example 55

2-[4-(3-amino-1H-indazol-4-yl)phenyl]-N-(4-fluoro-3-methylphenyl)acetamide

The desired product was prepared as the trifluoroacetate salt by substituting 4-fluoro-3-methylaniline for aniline in Example 53C. MS (ESI(+)) m/e 375 (M+H)$^+$; $^1$H NMR (500 MHz, DMSO-d$_6$) δ 2.20 (d, J=1.56 Hz, 3H), 3.71 (s, 2H), 6.84

(dd, J=5.46, 2.34 Hz, 1H), 7.07 (t, J=9.20 Hz, 1H), 7.31 (s, 1H), 7.32 (d, J=3.43 Hz, 1H), 7.40-7.60 (m, 3H), 7.45 (d, J=4.99 Hz, 2H), 7.54 (dd, J=7.02, 2.34 Hz, 1H), 10.16 (s, 1H).

Example 56

2-[4-(3-amino-1H-indazol-4-yl)phenyl]-N-[3-(trifluoromethyl)phenyl]acetamide

The desired product was prepared by substituting 3-(trifluoromethyl)aniline for aniline in Example 53C, then purifying the resulting product by flash column chromatography on silica gel with 5-8% methanol/dichloromethane. MS (ESI(+)) m/e 411 (M+H)$^+$; $^1$H NMR (300 MHz, DMSO-d$_6$) δ 3.77 (s, 2H), 4.29 (s, 2H), 6.79 (dd, J=4.41, 3.39 Hz, 1H), 7.27 (s, 1H), 7.28 (d, J=1.36 Hz, 1H), 7.40-7.49 (m, 3H), 7.46 (d, J=3.39 Hz, 2H), 7.56 (t, J=7.63 Hz, 1H), 7.81 (d, J=9.83 Hz, 1H), 8.14 (s, 1H), 10.57 (s, 1H), 11.74 (s, 1H).

Example 57

2-[4-(3-amino-1H-indazol-4-yl)phenyl]-N-(3-methylphenyl)acetamide

The desired product was prepared as the trifluoroacetate salt by substituting 3-methylaniline for aniline in Example 53C. MS (ESI(+)) m/e 357 (M+H)$^+$; $^1$H NMR (300 MHz, DMSO-d$_6$) δ 2.27 (s, 3H), 3.72 (s, 2H), 6.83 (dd, J=4.75, 3.05 Hz, 1H), 6.86 (d, J=7.46 Hz, 1H), 7.18 (t, J=7.80 Hz, 1H), 7.30 (s, 1H), 7.32 (d, J=2.03 Hz, 1H), 7.39-7.49 (m, 6H), 10.13 (s, 1H).

Example 58

N-[4-(3-amino-7-methoxy-1H-indazol-4-yl)phenyl]-N'-(3-methylphenyl)urea

Example 58A 2-fluoro-6-iodo-3-methoxybenzonitrile

The desired product was prepared by substituting 2-fluoro-4-iodo-1-methoxybenzene for 2-fluoro-4-iodo-1-methylbenzene in Examples 15A-C.

Example 58B 4-(4-aminophenyl)-7-methoxy-1H-indazol-3-amine

The desired product was prepared by substituting Example 58A for Example 15E in Examples 15F-G. MS (ESI(+)) m/e 290 (M+H)$^+$.

Example 58C

N-[4-(3-amino-7-methoxy-1H-indazol-4-yl)phenyl]-N'-(3-methylphenyl)urea

The desired product was prepared by substituting Example 58B and 1-isocyanato-3-methylbenzene for Example 15G and 1-fluoro-3-isocyanatobenzene, respectively, in Example 15H then purifying the resulting product by flash column chromatography on silica gel with 5-8% methanol/dichloromethane. MS (ESI(+)) m/e 388 (M+H)$^+$; $^1$H NMR (300 MHz, DMSO-d$_6$) δ 2.29 (s, 3H), 3.92 (s, 3H), 4.30 (s, 2H), 6.69 (d, J=7.80 Hz, 1H), 6.78 (d, J=7.79 Hz, 1H), 6.80 (d, J=7.46 Hz, 1H), 7.16 (t, J=7.80 Hz, 1H), 7.25 (m, 1H), 7.31 (s, 1H), 7.34 (d, J=8.48 Hz, 2H), 7.55 (d, J=8.82 Hz, 2H), 8.62 (s, 1H), 8.75 (s, 1H), 11.86 (s, 1H).

Example 59

N-[4-(3-amino-7-methoxy-1H-indazol-4-yl)phenyl]-N'-[2-fluoro-5-(trifluoromethyl)phenyl]urea The desired product was prepared by substituting Example 58B and 1-fluoro-2-isocyanato-4-(trifluoromethyl)benzene for Example 15G and 1-fluoro-3-isocyanatobenzene, respectively, in Example 15H then purifying the resulting product by flash column chromatography on silica gel with 5-8% methanol/dichloromethane. MS (ESI(−)) m/e 458 (M−H)$^-$; $^1$H NMR (300 MHz, DMSO-d$_6$) δ 3.93 (s, 3H), 4.30 (s, 2H), 6.71 (d, J=7.80 Hz, 1H), 6.79 (d, J=7.80 Hz, 1H), 7.38 (d, J=8.48 Hz, 2H), 7.41 (m, 1H), 7.50 (d, J=10.85 Hz, 1H), 7.58 (d, J=8.82 Hz, 2H), 8.65 (dd, J=7.46, 2.03 Hz, 1H), 8.95 (d, J=2.71 Hz, 1H), 9.29 (s, 1H), 11.88 (s, 1H).

Example 60

N-[4-(3-amino-7-methoxy-1H-indazol-4-yl)phenyl]-N'-phenylurea

The desired product was prepared as the trifluoroacetate salt by substituting Example 58B and isocyanatobenzene for Example 15G and 1-fluoro-3-isocyanatobenzene, respectively, in Example 15H. MS (ESI(+)) m/e 374 (M+H)$^+$; $^1$H NMR (500 MHz, DMSO-d$_6$) δ 3.94 (s, 3H), 6.75 (d, J=7.49 Hz, 1H), 6.84 (d, J=7.80 Hz, 1H), 6.98 (t, J=7.33 Hz, 1H), 7.29 (t, J=7.95 Hz, 2H), 7.36 (d, J=8.74 Hz, 2H), 7.47 (d, J=7.49 Hz, 2H), 7.57 (d, J=8.42 Hz, 2H), 8.71 (s, 1H), 8.79 (s, 1H).

Example 61

N-[4-(3-amino-7-methoxy-1H-indazol-4-yl)phenyl]-N'-(3-bromophenyl)urea

The desired product was prepared as the trifluoroacetate salt by substituting Example 58B and 1-bromo-3-isocyanatobenzene for Example 15G and 1-fluoro-3-isocyanatobenzene, respectively, in Example 15H. MS (ESI(+)) m/e 452 and 454 (M+H)$^+$; $^1$H NMR (500 MHz, DMSO-d$_6$) δ 3.94 (s, 3H), 6.73 (d, J=7.80 Hz, 1H), 6.82 (d, J=7.80 Hz, 1H), 7.16 (d, J=8.73 Hz, 1H), 7.25 (t, J=8.11 Hz, 1H), 7.33 (d, J=9.36 Hz, 1H), 7.36 (d, J=8.73 Hz, 2H), 7.56 (d, J=8.74 Hz, 2H), 7.88 (t, J=1.87 Hz, 1H), 8.87 (s, 1H), 8.92 (s, 1H).

Example 62

N-[4-(3-amino-7-methoxy-1H-indazol-4-yl)phenyl]-N'-(3-ethylphenyl)urea

The desired product was prepared as the trifluoroacetate salt by substituting Example 58B and 1-isocyanato-3-ethylbenzene for Example 15G and 1-fluoro-3-isocyanatobenzene, respectively, in Example 15H. MS (ESI(+)) m/e 402 (M+H)$^+$; $^1$H NMR (500 MHz, DMSO-d$_6$) δ 1.19 (t, J=7.64 Hz, 3H), 2.58 (q, J=7.70 Hz, 2H), 3.94 (s, 3H), 6.73 (d, J=7.49 Hz, 1H), 6.82 (t, J=7.80 Hz, 2H), 7.19 (t, J=7.80 Hz, 1H), 7.27

(d, J=7.80 Hz, 1H), 7.34 (s, 1H), 7.35 (d, J=8.42 Hz, 2H), 7.56 (d, J=8.42 Hz, 2H), 8.64 (s, 1H), 8.75 (s, 1H).

Example 63

N-[4-(3-amino-7-methoxy-1H-indazol-4-yl)phenyl]-N'-(3-fluoro-4-methylphenyl)urea The desired product was prepared as the trifluoroacetate salt by substituting Example 58B and 2-fluoro-4-isocyanato-1-methylbenzene for Example 15G and 1-fluoro-3-isocyanatobenzene, respectively, in Example 15H. MS (ESI(+)) m/e 406 (M+H)$^+$; $^1$H NMR (500 MHz, DMSO-d$_6$) δ 2.17 (s, 3H), 3.94 (s, 3H), 6.75 (d, J=7.49 Hz, 1H), 6.83 (d, J=7.80 Hz, 1H), 7.05 (dd, J=8.27, 2.03 Hz, 1H), 7.17 (t, J=8.58 Hz, 1H), 7.36 (d, J=8.73 Hz, 2H), 7.45 (dd, J=12.48, 1.87 Hz, 1H), 7.56 (d, J=8.73 Hz, 2H), 8.82 (s, 1H), 8.83 (s, 1H).

Example 64

N-[4-(3-amino-7-methoxy-1H-indazol-4-yl)phenyl]-N'-[4-fluoro-3-(trifluoromethyl)phenyl]urea The desired product was prepared as the trifluoroacetate salt by substituting Example 58B and 1-fluoro-4-isocyanato-2-(trifluoromethyl)benzene for Example 15G and 1-fluoro-3-isocyanatobenzene, respectively, in Example 15H. MS (ESI(+)) m/e 460 (M+H)$^+$; $^1$H NMR (500 MHz, DMSO-d$_6$) δ 3.95 (s, 3H), 6.79 (d, J=7.80 Hz, 1H), 6.86 (d, J=7.80 Hz, 1H), 7.38 (d, J=8.42 Hz, 2H), 7.44 (t, J=9.67 Hz, 1H), 7.59 (d, J=8.73 Hz, 2H), 7.67 (dt, J=8.66, 3.78 Hz, 1H), 8.03 (dd, J=6.40, 2.65 Hz, 1H), 9.01 (s, 1H), 9.17 (s, 1H).

Example 65

N-[4-(3-amino-7-methoxy-1H-indazol-4-yl)phenyl]-N'-(3-chlorophenyl)urea

The desired product was prepared as the trifluoroacetate salt by substituting Example 58B and 1-chloro-3-isocyanatobenzene for Example 15G and 1-fluoro-3-isocyanatobenzene, respectively, in Example 15H. MS (ESI(+)) m/e 408 (M+H)$^+$; $^1$H NMR (500 MHz, DMSO-d$_6$) δ 3.94 (s, 3H), 6.76 (d, J=7.49 Hz, 1H), 6.84 (d, J=7.80 Hz, 1H), 7.02 (dt, J=6.63, 2.14 Hz, 1H), 7.31 (m, 2H), 7.37 (d, J=8.74 Hz, 2H), 7.57 (d, J=8.42 Hz, 2H), 7.74 (m, 1H), 8.90 (s, 1H), 8.96 (s, 1H).

Example 66

N-[4-(3-amino-7-methoxy-1H-indazol-4-yl)phenyl]-N'-[3-(trifluoromethyl)phenyl]urea The desired product was prepared as the trifluoroacetate salt by substituting Example 58B and 1-isocyanato-3-(trifluoromethyl)benzene for Example 15G and 1-fluoro-3-isocyanatobenzene, respectively, in Example 15H. MS (ESI(+)) m/e 442 (M+H)$^+$; $^1$H NMR (500 MHz, DMSO-d$_6$) δ 3.94 (s, 3H), 6.76 (d, J=7.80 Hz, 1H), 6.84 (d, J=7.80 Hz, 1H), 7.32 (d, J=7.80 Hz, 1H), 7.38 (d, J=8.42 Hz, 2H), 7.52 (t, J=7.95 Hz, 1H), 7.59 (d, J=8.42 Hz, 2H), 7.57-7.61 (m, 1H), 8.04 (s, 1H), 8.96 (s, 1H), 9.14 (s, 1H).

Example 67

N-[4-(3-amino-7-methoxy-1H-indazol-4-yl)phenyl]-N'-(3-fluorophenyl)urea

The desired product was prepared as the trifluoroacetate salt by substituting Example 58B for Example 15G in Example 15H. MS (ESI(+)) m/e 392 (M+H)$^+$; $^1$H NMR (500 MHz, DMSO-d$_6$) δ 3.94 (s, 3H), 6.77 (d, J=7.80 Hz, 1H), 6.77-6.81 (m, 1H), 6.85 (d, J=7.80 Hz, 1H), 7.14 (dd, J=8.11, 0.94 Hz, 1H), 7.29-7.34 (m, 1H), 7.37 (d, J=8.73 Hz, 2H), 7.51 (dt, J=11.93, 2.30 Hz, 1H), 7.57 (d, J=8.73 Hz, 2H), 8.89 (s, 1H), 8.98 (s, 1H).

Example 68

N-{4-[3-amino-7-(2-methoxyethoxy)-1H-indazol-4-yl]phenyl}-N'-(3-methylphenyl)urea Example 68A 2-fluoro-3-hydroxy-6-iodobenzonitrile A —78° C. solution of 2-fluoro-6-iodo-3-methoxybenzonitrile (148 mg, 0.53 mmol) in dichloromethane (5 mL) was treated dropwise with BBr$_3$ (2.5 mL, 1M in dichloromethane, 2.5 mmol), warmed to room temperature, stirred for 18 hours, poured into water, and extracted with diethyl ether. The extract was dried (MgSO$_4$), filtered, and concentrated. The residue was purified by flash column chromatography on silica gel with 20% ethyl acetate/hexanes to provide 110 mg of the desired product. MS (ESI(−)) m/e 262 (M−H)$^−$.

Example 68B 2-fluoro-6-iodo-3-(2-methoxyethoxy)benzonitrile

A mixture of Example 68A (104 mg, 0.39 mmol), 1-bromo-2-methoxyethane (0.088 mL) and K$_2$CO$_3$ (163 mg) in acetone (3 mL) was heated to 60° C. for 18 hours, cooled to room temperature, and partitioned between diethyl ether and water. The extract was dried (MgSO$_4$), filtered, and concentrated to provide 122 mg of the desired product. MS (ESI(+)) m/e 334 (M+H)$^+$.

Example 68C 4-(4-aminophenyl)-7-(2-methoxyethoxy)-1H-indazol-3-amine

The desired product was prepared by substituting Example 68B for Example 15E in Examples 15F-G. MS (ESI(+)) m/e 299 (M+H)$^+$.

Example 68D

N-{4-[3-amino-7-(2-methoxyethoxy)-1H-indazol-4-yl]phenyl}-N'-(3-methylphenyl)urea The desired product was prepared by substituting Example 68C and 1-isocyanato-3-methylbenzene for Example 15G and 1-fluoro-3-isocyanatobenzene, respectively, in Example 15, then purifying the resulting producty by flash column chromatography on silica gel with 5-8% methanol/dichloromethane. MS (ESI(+)) m/e 432 (M+H)$^+$; $^1$H NMR (300 MHz, DMSO-d$_6$) δ 2.29 (s, 3H), 3.35 (s, 3H), 3.76 (dd, J=5.09, 3.73 Hz, 2H), 4.27 (t, J=3.05 Hz, 2H), 4.29 (s, 2H), 6.67 (d, J=7.46 Hz, 1H), 6.79 (d, J=7.80 Hz, 2H), 7.16 (t, J=7.63 Hz, 1H), 7.25 (m, 1H), 7.31 (s, 1H), 7.34 (d, J=8.48 Hz, 2H), 7.55 (d, J=8.48 Hz, 2H), 8.63 (s, 1H), 8.76 (s, 1H), 11.83 (s, 1H).

Example 69

N-{4-[3-amino-7-(2-methoxyethoxy)-1H-indazol-4-yl]phenyl}-N'-phenylurea

The desired product was prepared as the trifluoroacetate salt by substituting Example 68C and isocyanatobenzene for Example 15G and 1-fluoro-3-isocyanatobenzene, respectively, in Example 15H. MS (ESI(+)) m/e 418 (M+H)+; $^1$H NMR (300 MHz, DMSO-$d_6$) δ 3.36 (s, 3H), 3.76 (t, J=4.41 Hz, 2H), 4.30 (t, J=4.75 Hz, 2H), 6.74 (d, J=7.80 Hz, 1H), 6.86 (d, J=7.80 Hz, 1H), 6.98 (t, J=7.29 Hz, 1H), 7.29 (t, J=7.46 Hz, 2H), 7.36 (d, J=8.82 Hz, 2H), 7.47 (d, J=7.46 Hz, 2H), 7.57 (d, J=8.48 Hz, 2H), 8.72 (s, 1H), 8.80 (s, 1H).

Example 70

N-{4-[3-amino-7-(2-methoxyethoxy)-1H-indazol-4-yl]phenyl}-N'-(3-fluorophenyl)urea The desired product was prepared as the trifluoroacetate salt by substituting Example 68C for Example 15G in Example 15H. MS (ESI(+)) m/e 436 (M+H)+; $^1$H NMR (500 MHz, DMSO-$d_6$) δ 3.36 (s, 3H), 3.75-3.77 (m, 2H), 4.28-4.30 (m, 2H), 6.73 (d, J=7.80 Hz, 1H), 6.79 (td, J=8.58, 2.18 Hz, 1H), 6.85 (d, J=7.80 Hz, 1H), 7.14 (dd, J=8.27, 1.09 Hz, 1H), 7.31 (m, 1H), 7.37 (d, J=8.74 Hz, 2H), 7.51 (dt, J=11.93, 2.30 Hz, 1H), 7.57 (d, J=8.42 Hz, 2H), 8.89 (s, 1H), 8.98 (s, 1H).

Example 71

N-{4-[3-amino-7-(2-methoxyethoxy)-1H-indazol-4-yl]phenyl}-N'-(3-bromophenyl)urea The desired product was prepared as the trifluoroacetate salt by substituting Example 68C and 1-bromo-3-isocyanatobenzene for Example 15G and 1-fluoro-3-isocyanatobenzene, respectively, in Example 15H. MS (ESI(+)) m/e 496 and 498 (M+H)+; $^1$H NMR (500 MHz, DMSO-$d_6$) δ 3.36 (s, 3H), 3.75-3.77 (m, 2H), 4.28-4.30 (m, 2H), 6.73 (d, J=7.49 Hz, 1H), 6.84 (d, J=7.80 Hz, 1H), 7.16 (d, J=7.80 Hz, 1H), 7.25 (t, J=7.95 Hz, 1H), 7.33 (dd, J=8.27, 1.09 Hz, 1H), 7.37 (d, J=8.42 Hz, 2H), 7.57 (d, J=8.42 Hz, 2H), 7.88 (t, J=1.87 Hz, 1H), 8.87 (s, 1H), 8.92 (s, 1H).

Example 72

N-{4-[3-amino-7-(2-methoxyethoxy)-1H-indazol-4-yl]phenyl}-N'-(3-chlorophenyl)urea The desired product was prepared by as the trifluoroacetate salt substituting Example 68C and 1-chloro-3-isocyanatobenzene for Example 15G and 1-fluoro-3-isocyanatobenzene, respectively, in Example 15H. MS (ESI(+)) m/e 452 (M+H)+; $^1$H NMR (500 MHz, DMSO-$d_6$) δ 3.36 (s, 3H), 3.76 (t, J=4.68 Hz, 2H), 4.29 (t, J=4.68 Hz, 2H), 6.74 (d, J=7.80 Hz, 1H), 6.85 (d, J=7.80 Hz, 1H), 7.02 (dt, J=6.86, 2.03 Hz, 1H), 7.30 (m, 2H), 7.37 (d, J=8.42 Hz, 2H), 7.57 (d, J=8.42 Hz, 2H), 7.73 (s, 1H), 8.89 (s, 1H), 8.95 (s, 1H).

Example 73

N-{4-[3-amino-7-(2-methoxyethoxy)-1H-indazol-4-yl]phenyl}-N'-[3-(trifluoromethyl)phenyl]urea The desired product was prepared as the trifluoroacetate salt by substituting Example 68C and 1-isocyanato-3-(trifluoromethyl)benzene for Example 15G and 1-fluoro-3-isocyanatobenzene, respectively, in Example 15H. MS (ESI(+)) m/e 486 (M+H)+; $^1$H NMR (500 MHz, DMSO-$d_6$) δ 3.36 (s, 3H), 3.75-3.77 (m, 2H), 4.29-4.31 (m, 2H), 6.75 (d, J=7.80 Hz, 1H), 6.86 (d, J=7.80 Hz, 1H), 7.32 (d, J=8.11 Hz, 1H), 7.38 (d, J=8.42 Hz, 2H), 7.52 (t, J=7.95 Hz, 1H), 7.59 (d, J=8.42 Hz, 2H), 7.58-7.61 (m, 1H), 8.04 (s, 1H), 8.95 (s, 1H), 9.12 (s, 1H).

Example 74

N-{4-[3-amino-7-(2-methoxyethoxy)-1H-indazol-4-yl]phenyl}-N'-[2-fluoro-5-(trifluoromethyl)phenyl]urea The desired product was prepared as the trifluoroacetate salt by substituting Example 68C and 1-fluoro-2-isocyanato-4-(trifluoromethyl)benzene for Example 15G and 1-fluoro-3-isocyanatobenzene, respectively, in Example 15H. MS (ESI(+)) m/e 504 (M+H)+; $^1$H NMR (500 MHz, DMSO-$d_6$) δ 3.36 (s, 3H), 3.76 (t, J=4.68 Hz, 2H), 4.29 (t, J=4.68 Hz, 2H), 6.73 (d, J=7.80 Hz, 1H), 6.85 (d, J=7.80 Hz, 1H), 7.39 (d, J=8.74 Hz, 2H), 7.39-7.41 (m, 1H), 7.51 (m, 1H), 7.58 (d, J=8.42 Hz, 2H), 8.64 (dd, J=7.18, 2.18 Hz, 1H), 8.93 (d, J=2.81 Hz, 1H), 9.28 (s, 1H).

Example 75

N-(4-{3-amino-7-[2-(4-morpholinyl)ethoxy]-1H-indazol-4-yl}phenyl)-N'-(3-methylphenyl)urea

Example 75A 2-fluoro-6-iodo-3-[2-(4-morpholinyl)ethoxy]benzonitrile

A mixture of Example 68A (250 mg, 0.95 mmol), 2-(4-morpholinyl)ethanol (0.19 mL) and triphenylphosphine on resin (630 mg, 3 mmol/g, 1.9 mmol) in THF (5 mL) was treated with DEAD (0.179 mL) and stirred at room temperature for about 18 hours. The mixture was filtered and the filtrate was concentrated. The residue was purified twice by flash column chromatography on silica gel, first eluting with 5% methanol/dichloromethane then with 50% ethyl acetate/hexanes to provide 180 mg of the desired product. MS (ESI (+)) m/e 377 (M+H)+.

Example 75B 4-(4-aminophenyl)-7-[2-(4-morpholinyl)ethoxy]-1H-indazol-3-amine The desired product was prepared by substituting Example 75A for Example 15E in Examples 15F-G. MS (ESI(+)) m/e 354 (M+H)+.

Example 75C

N-(4-{3-amino-7-[2-(4-morpholinyl)ethoxy]-1H-indazol-4-yl}phenyl)-N'-(3-methylphenyl)urea The desired product was prepared by substituting Example 75B and 1-isocyanato-3-methylbenzene for Example 15G and 1-fluoro-3-isocyanatobenzene, respectively, in Example 15H then purifying the resulting producty by flash column chromatography on silica gel with 5-8% methanol/dichloromethane. MS (ESI(+)) m/e 487 (M+H)$^+$; $^1$H NMR (300 MHz, DMSO-d$_6$) δ 2.29 (s, 3H), 2.52-2.55 (m, 4H), 2.79 (t, J=5.76 Hz, 2H), 3.57-3.60 (m, 4H), 4.26 (t, J=5.76 Hz, 2H), 4.30 (s, 2H), 6.68 (d, J=7.46 Hz, 1H), 6.80 (d, J=7.80 Hz, 2H), 7.16 (t, J=7.80 Hz, 1H), 7.25 (m, 1H), 7.31 (s, 1H), 7.34 (d, J=8.48 Hz, 2H), 7.55 (d, J=8.82 Hz, 2H), 8.64 (s, 1H), 8.77 (s, 1H), 11.81 (s, 1H).

Example 76

N-(4-{3-amino-7-[2-(4-morpholinyl)ethoxy]-1H-indazol-4-yl}phenyl)-N'-phenylurea

The desired product was prepared as the bis(trifluoroacetate) salt by substituting Example 75B and isocyanatobenzene for Example 15G and 1-fluoro-3-isocyanatobenzene, respectively, in Example 15H. MS (ESI(+)) m/e 473 (M+H)$^+$; $^1$H NMR (500 MHz, DMSO-d$_6$) δ 3.66 (m, 2H), 3.33-4.45 (br m, 8H), 4.54 (m, 2H), 6.75 (d, J=7.80 Hz, 1H), 6.90 (d, J=7.80 Hz, 1H), 6.98 (t, J=7.33 Hz, 1H), 7.29 (t, J=7.80 Hz, 2H), 7.36 (d, J=8.73 Hz, 2H), 7.48 (d, J=7.49 Hz, 2H), 7.59 (d, J=8.42 Hz, 2H), 8.86 (s, 1H), 8.95 (s, 1H).

Example 77

N-(4-{3-amino-7-[2-(4-morpholinyl)ethoxy]-1H-indazol-4-yl}phenyl)-N'-(3-fluorophenyl)urea The desired product was prepared as the bis(trifluoroacetate) salt by substituting Example 75B for Example 15G in Example 15H. MS (ESI(+)) m/e 491 (M+H)$^+$; $^1$H NMR (500 MHz, DMSO-d$_6$) δ 3.66 (t, J=4.37 Hz, 2H), 3.71 (br m, 8H), 4.53 (t, J=4.99 Hz, 2H), 6.75 (d, J=7.80 Hz, 1H), 6.79 (td, J=8.42, 1.87 Hz, 1H), 6.89 (d, J=7.80 Hz, 1H), 7.15 (dd, J=8.27, 1.09 Hz, 1H), 7.31 (m, 1H), 7.36 (d, J=8.74 Hz, 2H), 7.52 (dt, J=12.09, 2.22 Hz, 1H), 7.58 (d, J=8.74 Hz, 2H), 8.97 (s, 1H), 9.06 (s, 1H).

Example 78

N-(4-{3-amino-7-[2-(4-morpholinyl)ethoxy]-1H-indazol-4-yl}phenyl)-N'-(3-bromophenyl)urea The desired product was prepared as the bis(trifluoroacetate) salt by substituting Example 75B and 1-bromo-3-isocyanatobenzene for Example 15G and 1-fluoro-3-isocyanatobenzene, respectively, in Example 15H. MS (ESI(+)) m/e 551 (M+H)$^+$; $^1$H NMR (500 MHz, DMSO-d$_6$) δ 3.66 (t, J=4.36 Hz, 2H), 3.30-4.32 (br m, 8H), 4.54 (t, J=4.68 Hz, 2H), 6.75 (d, J=7.49 Hz, 1H), 6.89 (d, J=7.80 Hz, 1H), 7.16 (d, J=8.73 Hz, 1H), 7.25 (t, J=7.95 Hz, 1H), 7.34-7.35 (m, 1H), 7.36 (d, J=8.42 Hz, 2H), 7.59 (d, J=8.42 Hz, 2H), 7.89 (t, J=1.87 Hz, 1H), 9.07 (s, 1H), 9.11 (s, 1H).

Example 79

N-(4-{3-amino-7-[2-(4-morpholinyl)ethoxy]-1H-indazol-4-yl}phenyl)-N'-(3-ethylphenyl)urea The desired product was prepared as the bis(trifluoroacetate) salt by substituting Example 75B and 1-ethyl-3-isocyanatobenzene for Example 15G and 1-fluoro-3-isocyanatobenzene, respectively, in Example 15H. MS (ESI(+)) m/e 501 (M+H)$^+$; $^1$H NMR (500 MHz, DMSO-d$_6$) δ 1.19 (t, J=7.49 Hz, 3H), 2.58 (q, J=7.49 Hz, 2H), 3.66 (m, 2H), 3.31-4.01 (br m, 8H), 4.53 (m, 2H), 6.74 (d, J=7.80 Hz, 1H), 6.83 (d, J=7.49 Hz, 1H), 6.89 (d, J=7.80 Hz, 1H), 7.19 (t, J=7.80 Hz, 1H), 7.27 (d, J=8.42 Hz, 1H), 7.35 (m, J=8.42 Hz, 3H), 7.58 (d, J=8.73 Hz, 2H), 8.70 (s, 1H), 8.82 (s, 1H).

Example 80

N-(4-{3-amino-7-[2-(4-morpholinyl)ethoxy]-1H-indazol-4-yl}phenyl)-N'-[2-fluoro-5-(trifluoromethyl)phenyl]urea The desired product was prepared as the bis(trifluoroacetate) salt by substituting Example 75B and 1-fluoro-2-isocyanato-4-(trifluoromethyl)benzene for Example 15G and 1-fluoro-3-isocyanatobenzene, respectively, in Example 15H. MS (ESI(−)) m/e 557 (M−H)$^−$; $^1$H NMR (500 MHz, DMSO-d$_6$) δ 3.66 (t, J=4.68 Hz, 2H), 3.32-4.20 (br m, 8H), 4.54 (t, J=4.68 Hz, 2H), 6.76 (d, J=7.49 Hz, 1H), 6.89 (d, J=7.80 Hz, 1H), 7.39 (d, J=8.73 Hz, 2H), 7.41 (m, J=4.06 Hz, 1H), 7.51 (t, J=8.73 Hz, 1H), 7.59 (d, J=8.73 Hz, 2H), 8.64 (dd, J=7.33, 2.03 Hz, 1H), 8.97 (d, J=2.81 Hz, 1H), 9.34 (s, 1H).

Example 81

N-(4-{3-amino-7-[2-(4-morpholinyl)ethoxy]-1H-indazol-4-yl}phenyl)-N'-[4-fluoro-3-(trifluoromethyl)phenyl]urea The desired product was prepared as the bis(trifluoroacetate) salt by substituting Example 75B and 1-fluoro-4-isocyanato-2-(trifluoromethyl)benzene for Example 15G and 1-fluoro-3-isocyanatobenzene, respectively, in Example 15H. MS (ESI(−)) m/e 557 (M−H)$^−$; $^1$H NMR (500 MHz, DMSO-d$_6$) δ 3.66 (m, 2H), 3.83 (m, 8H), 4.53 (m, 2H), 6.74 (d, J=7.80 Hz, 1H), 6.89 (d, J=7.80 Hz, 1H), 7.36 (d, J=8.42 Hz, 2H), 7.45 (t, J=9.67 Hz, 1H), 7.59 (d, J=8.73 Hz, 2H), 7.66 (dt, J=8.74, 3.74 Hz, 1H), 8.04 (dd, J=6.40, 2.65 Hz, 1H), 9.08 (s, 1H), 9.25 (s, 1H).

Example 82

N-(4-{3-amino-7-[2-(4-morpholinyl)ethoxy]-1H-indazol-4-yl}phenyl)-N'-(3-chlorophenyl)urea The desired product was prepared as the bis(trifluoroacetate) salt by substituting Example 75B and 1-chloro-3-isocyanatobenzene for Example 15G and 1-fluoro-3-isocyanatobenzene, respectively, in Example 15H. MS (ESI(+)) m/e 507 (M+H)$^+$; $^1$H NMR (500 MHz, DMSO-d$_6$) δ 3.31-4.00 (br m, 8H), 3.65 (m, 2H), 4.53 (m, 2H), 6.75 (d, J=7.80 Hz, 1H), 6.89 (d, J=7.80 Hz, 1H), 7.01 (td, J=4.45, 2.03 Hz, 1H), 7.30 (d, J=4.99 Hz, 2H), 7.35 (d, J=8.42 Hz, 2H), 7.58 (d, J=8.42 Hz, 2H), 7.73 (s, 1H), 9.10 (s, 1H), 9.15 (s, 1H).

Example 83

N-(4-{3-amino-7-[2-(4-morpholinyl)ethoxy]-1H-indazol-4-yl}phenyl)-N'-[3-(trifluoromethyl)phenyl]urea The desired product was prepared as the bis(trifluoroacetate) salt by substituting Example 75B and 1-isocyanato-3-(trifluoromethyl)benzene for Example 15G and 1-fluoro-3-isocyanatobenzene, respectively, in Example 15H. MS (ESI(−)) m/e 539 (M−H)$^−$; $^1$H NMR (500 MHz, DMSO-d$_6$) δ 3.66

(m, 2H), 3.32-4.11 (m, 8H), 4.54 (m, 2H), 6.75 (d, J=7.80 Hz, 1H), 6.89 (d, J=7.80 Hz, 1H), 7.31 (d, J=7.80 Hz, 1H), 7.37 (d, J=8.42 Hz, 2H), 7.52 (s, 1H), 7.61 (d, J=8.42 Hz, 2H), 7.62 (m, 1H), 8.06 (s, 1H), 9.18 (s, 1H), 9.36 (s, 1H).

Example 84

(2E)-3-{3-amino-4-[4-({[(3-methylphenyl)amino] carbonyl}amino)phenyl]-1H-indazol-7-yl}-N,N-dimethylacrylamide

Example 84A 7-bromo-4-iodo-1H-indazol-3-amine

The desired product was prepared by substituting 4-bromo-2-fluoro-6-iodobenzonitrile for 2-fluoro-6-iodobenzonitrile in Example 1A.

Example 84B 7-bromo-4-(4-nitrophenyl)-1H-indazol-3-amine

The desired product was prepared by substituting Example 84A and 4-nitrophenylboronic acid for Example 1A and Example 1B, respectively, in Example 1C. MS (ESI(+)) m/e 333, 335 (M+H)⁺.

Example 84C (2E)-3-[3-amino-4-(4-nitrophenyl)-1H-indazol-7-yl]-N,N-dimethylacrylamide A mixture of Example 84B (165 mg), N,N-dimethylacrylamide (0.102 mL), triethylamine (0.207 mL), and Pd(o-tol₃P)₂Cl₂ (30 mg) in THF (2 mL) in a sealed tube was heated in a Smith Synthesizer microwave oven (at 300 W) to 150° C. and concentrated. The residue was purified by flash column chromatography on silica gel with 3% methanol/dichloromethane to provide 163 mg of the desired product. MS (ESI(+)) m/e 352 (M+H)⁺.

Example 84D (2E)-3-[3-amino-4-(4-aminophenyl)-1H-indazol-7-yl]-N,N-dimethylacrylamide A solution of Example 84C (113 mg, 0.32 mmol) in a mixture of ethanol (1 mL), methanol (1 mL), and THF (1 mL) was treated with iron powder (144 mg) and NH₄Cl (17 mg), heated to 85° C. for 4 hours, cooled to room temperature, and filtered. The filtrate was partitioned between water and ethyl acetate and the organic phase was dried (MgSO₄), filtered, and concentrated. The residue was purified by flash column chromatography on silica gel with 5% methanol/dichloromethane to provide 75 mg of the desired product. MS (ESI(+)) m/e 322 (M+H)⁺.

Example 84E (2E)-3-{3-amino-4-[4-({[(3-methylphenyl)amino] carbonyl}amino)phenyl]-1H-indazol-7-yl}N,N-dimethylacrylamide The desired product was prepared as the trifluoroacetate salt by substituting Example 84D and 1-isocyanato-3-methylbenzene for Example 15G and 1-fluoro-3-isocyanatobenzene, respectively, in Example 15H. MS (ESI(+)) m/e 455 (M+H)⁺; ¹H NMR (300 MHz, DMSO-d₆) δ 2.28 (s, 3H), 2.97 (s, 3H), 3.21 (s, 3H), 6.80 (d, J=8.14 Hz, 1H), 6.86 (d, J=7.46 Hz, 1H), 7.17 (m, 1H), 7.24 (m, 2H), 7.32 (s, 1H), 7.41 (d, J=8.82 Hz, 2H), 7.61 (d, J=8.81 Hz, 2H), 7.70 (d, J=7.80 Hz, 1H), 7.85 (d, J=15.60 Hz, 1H), 8.65 (s, 1H), 8.83 (s, 1H).

Example 85

(2E)-3-{3-amino-4-[4-({[(3-chlorophenyl)amino] carbonyl}amino)phenyl]-1H-indazol-7-yl}-N,N-dimethylacrylamide The desired product was prepared by substituting Example 84D and 1-chloro-3-isocyanatobenzene for Example 15G and 1-fluoro-3-isocyanatobenzene, respectively, in Example 15H then purifying the resulting producty by flash column chromatography on silica gel with 5-8% methanol/dichloromethane. MS (ESI(+)) m/e 475 (M+H)⁺; ¹H NMR (300 MHz, DMSO-d₆) δ 2.97 (s, 3H), 3.21 (s, 3H), 4.44 (s, 2H), 6.86 (d, J=7.46 Hz, 1H), 7.01-7.06 (m, 1H), 7.23 (d, J=15.60 Hz, 1H), 7.30-7.32 (m, 2H), 7.43 (d, J=8.48 Hz, 2H), 7.61 (d, J=8.82 Hz, 2H), 7.70 (d, J=7.46 Hz, 1H), 7.74 (m, 1H), 7.85 (d, J=15.60 Hz, 1H), 8.96 (s, 1H), 8.98 (s, 1H), 12.17 (s, 1H).

Example 86

(2E)-3-(3-amino-4-{4-[({[3-(trifluoromethyl)phenyl] amino}carbonyl)amino]phenyl}-1H-indazol-7-yl)-N,N-dimethylacrylamide The desired product was prepared by substituting Example 84D and 1-isocyanato-3-(trifluoromethyl)benzene for Example 15G and 1-fluoro-3-isocyanatobenzene, respectively, in Example 15H then purifying the resulting producty by flash column chromatography on silica gel with 5-8% methanol/dichloromethane. MS (ESI(-)) m/e 507 (M-H)⁻; ¹H NMR (300 MHz, DMSO-d₆) δ 2.97 (s, 3H), 3.21 (s, 3H), 4.44 (s, 2H), 6.86 (d, J=7.12 Hz, 1H), 7.23 (d, J=15.60 Hz, 1H), 7.32 (d, J=7.80 Hz, 1H), 7.43 (d, J=8.48 Hz, 2H), 7.53 (t, J=7.97 Hz, 1H), 7.59 (s, 1H), 7.63 (d, J=8.81 Hz, 2H), 7.70 (d, J=7.80 Hz, 1H), 7.85 (d, J=15.26 Hz, 1H), 8.04 (s, 1H), 8.99 (s, 1H), 9.13 (s, 1H), 12.17 (s, 1H).

Example 87

N-(4-{3-amino-7-[2-(dimethylamino)ethoxy]-1H-indazol-4-yl}phenyl)-N'-phenylurea

Example 87A 4-(4-aminophenyl)-7-[2-(dimethylamino)ethoxy]-1H-indazol-3-amine The desired product was prepared by substituting 2-(dimethylamino)ethanol for 2-(4-morpholinyl)ethanol in Example 75A-B. MS (ESI(+)) m/e 312 (M+H)⁺.

Example 87B

N-(4-{3-amino-7-[2-(dimethylamino)ethoxy]-1H-indazol-4-yl}phenyl)-N'-phenylurea

The desired product was prepared as the bis(trifluoroacetate) salt by substituting Example 87A and isocyanatobenzene for Example 15G and 1-fluoro-3-isocyanatobenzene, respectively, in Example 15H. MS (ESI(+)) m/e 431 (M+H)⁺;

$^1$H NMR (500 MHz, DMSO-d$_6$) δ 2.95 (s, 6H), 3.61 (br s, 2H), 4.49 (m, 2H), 6.77 (d, J=7.63 Hz, 1H), 6.90 (d, J=7.63 Hz, 1H), 6.98 (t, J=7.32 Hz, 1H), 7.29 (t, J=7.93 Hz, 2H), 7.36 (d, J=8.54 Hz, 2H), 7.48 (d, J=7.93 Hz, 2H), 7.59 (d, J=8.54 Hz, 2H), 8.88 (s, 1H), 8.97 (s, 1H).

Example 88

N-(4-{3-amino-7-[2-(dimethylamino)ethoxy]-1H-indazol-4-yl}phenyl)-N'-(3-bromophenyl)urea The desired product was prepared as the bis(trifluoroacetate) salt by substituting Example 87A and 1-bromo-3-isocyanatobenzene for Example 15G and 1-fluoro-3-isocyanatobenzene, respectively, in Example 15H. MS (ESI(+)) m/e 509 and 511 (M+H)$^+$; $^1$H NMR (500 MHz, DMSO-d$_6$) δ 2.95 (s, 6H), 3.61 (s, 2H), 4.50 (m, 2H), 6.77 (d, J=7.63 Hz, 1H), 6.90 (d, J=7.63 Hz, 1H), 7.16 (d, J=8.85 Hz, 1H), 7.25 (t, J=8.09 Hz, 1H), 7.35 (m, J=10.68 Hz, 1H), 7.37 (d, J=8.54 Hz, 2H), 7.60 (d, J=8.54 Hz, 2H), 7.90 (t, J=1.83 Hz, 1H), 9.17 (s, 1H), 9.21 (s, 1H).

Example 89

N-(4-{3-amino-7-[2-(dimethylamino)ethoxy]-1H-indazol-4-yl}phenyl)-N'-(3-methylphenyl)urea The desired product was prepared as the bis(trifluoroacetate) salt by substituting Example 87A and 1-isocyanato-3-methylbenzene for Example 15G and 1-fluoro-3-isocyanatobenzene, respectively, in Example 15H. MS (ESI(+)) m/e 445 (M+H)$^+$; $^1$H NMR (500 MHz, DMSO-d$_6$) δ 2.29 (s, 3H), 2.95 (s, 6H), 3.61 (br s, 2H), 4.50 (m, 2H), 6.77 (d, J=7.63 Hz, 1H), 6.80 (d, J=7.32 Hz, 1H), 6.90 (d, J=7.63 Hz, 1H), 7.16 (t, J=7.78 Hz, 1H), 7.26 (d, J=8.54 Hz, 1H), 7.33 (s, 1H), 7.36 (d, J=8.54 Hz, 2H), 7.59 (d, J=8.54 Hz, 2H), 8.81 (s, 1H), 8.97 (s, 1H).

Example 90

N-(4-{3-amino-7-[2-(dimethylamino)ethoxy]-1H-indazol-4-yl}phenyl)-N'-(3-chlorophenyl)urea The desired product was prepared as the bis(trifluoroacetate) salt by substituting Example 87A and 1-chloro-3-isocyanatobenzene for Example 15G and 1-fluoro-3-isocyanatobenzene, respectively, in Example 15H. MS (ESI(−)) m/e 463 (M−H)$^−$; $^1$H NMR (500 MHz, DMSO-d$_6$) δ 2.95 (s, 6H), 3.61 (br s, 2H), 4.50 (m, 2H), 6.77 (d, J=7.63 Hz, 1H), 6.90 (d, J=7.93 Hz, 1H), 7.02 (td, J=4.42, 2.14 Hz, 1H), 7.31 (m, 2H), 7.37 (d, J=8.85 Hz, 2H), 7.60 (d, J=8.54 Hz, 2H), 7.75 (s, 1H), 9.14 (s, 1H), 9.20 (s, 1H).

Example 91

N-(4-{3-amino-7-[2-(2-oxo-1-pyrrolidinyl)ethoxy]-1H-indazol-4-yl}phenyl)-N'-(3-methylphenyl)urea

Example 91A 1-(2-{[3-amino-4-(4-aminophenyl)-1H-indazol-7-yl]oxy}ethyl)-2-pyrrolidinone The desired product was prepared by substituting 1-(2-hydroxyethyl)-2-pyrrolidinone for 2-(4-morpholinyl)ethanol in Example 75A-B. MS (ESI(+)) m/e 352 (M+H)$^+$.

Example 91B

N-(4-{3-amino-7-[2-(2-oxo-1-pyrrolidinyl)ethoxy]-1H-indazol-4-yl}phenyl)-N'-(3-methylphenyl)urea The desired product was prepared as the trifluoroacetate salt by substituting Example 91A and 1-isocyanato-3-methylbenzene for Example 15G and 1-fluoro-3-isocyanatobenzene, respectively, in Example 15H. MS (ESI(+)) m/e 485 (M+H)$^+$; $^1$H NMR (300 MHz, DMSO-d$_6$) δ 1.93 (m, 2H), 2.24 (t, J=8.14 Hz, 2H), 2.29 (s, 3H), 3.55 (m, 2H), 3.62 (m, 2H), 4.27 (t, J=5.43 Hz, 2H), 6.73 (d, J=7.80 Hz, 1H), 6.80 (d, J=7.12 Hz, 1H), 6.86 (d, J=7.80 Hz, 1H), 7.16 (t, J=7.80 Hz, 1H), 7.25 (m, 1H), 7.32 (s, 1H), 7.35 (d, J=8.48 Hz, 2H), 7.56 (d, J=8.48 Hz, 2H), 8.64 (s, 1H), 8.78 (s, 1H).

Example 92

2-[4-(3-amino-1-methyl-1H-indazol-4-yl)phenyl]-N-(3-methylphenyl)acetamide

The desired product was prepared by substituting Example 34A and 2-[4-(4,4,5,5-tetramethyl-[1,3,2]dioxaborolan-2-yl)-phenyl]-N-m-tolyl-acetamide for Example 1A and Example 1B, respectively, in Example 53C. The crude product was purified by preparative HPLC using the conditions described in Example 3 to provide the desired product as the trifluoroacetate salt. MS (ESI(+)) m/e 371 (M+H)$^+$; $^1$H NMR (300 MHz, DMSO-d$_6$) δ 2.27 (s, 3H), 3.72 (s, 2H), 3.80 (s, 3H), 6.82 (dd, J=6.61, 1.19 Hz, 1H), 6.86 (d, J=7.46 Hz, 1H), 7.18 (t, J=7.80 Hz, 1H), 7.31-7.48 (m, 8H), 10.13 (s, 1H).

Example 93

N-[4-(3-amino-1H-indazol-4-yl)-2-methylphenyl]-N'-(3-methylphenyl)urea

The desired product was prepared as the trifluoroacetate salt by substituting 4-bromo-2-methylaniline for 4-bromo-2-fluoroaniline in Example 44A-B. MS (ESI(−)) m/e 370 (M−H)$^−$; $^1$H NMR (300 MHz, DMSO-d$_6$) δ 2.29 (s, 3H), 2.33 (s, 3H), 6.80 (d, J=7.46 Hz, 1H), 6.85 (dd, J=6.10, 1.70 Hz, 1H), 7.17 (t, J=7.80 Hz, 1H), 7.25-7.34 (m, 6H), 8.03 (m, 2H), 9.03 (s, 1H).

Example 94

N-(4-{3-amino-7-[2-(2-oxo-1-pyrrolidinyl)ethoxy]-1H-indazol-4-yl}phenyl)-N'-(3-chlorophenyl)urea The desired product was prepared as the trifluoroacetate salt by substituting Example 91A and 1-chloro-3-isocyanatobenzene for Example 15G and 1-fluoro-3-isocyanatobenzene, respectively, in Example 15H. MS (ESI(+)) m/e 505 (M+H)$^+$; $^1$H NMR (300 MHz, DMSO-d$_6$) δ 1.93 (m, 2H), 2.24 (t, J=8.14 Hz, 2H), 3.55 (m, 2H), 3.62 (t, J=5.43 Hz, 2H), 4.27 (t, J=5.59 Hz, 2H), 6.74 (d, J=7.80 Hz, 1H), 6.87 (d, J=8.14 Hz, 1H), 7.03 (dt, J=6.53, 2.33 Hz, 1H), 7.30 (s, 1H), 7.31 (d, J=3.73 Hz, 1H), 7.37 (d, J=8.48 Hz, 2H), 7.57 (d, J=8.48 Hz, 2H), 7.74 (d, J=1.70 Hz, 1H), 8.89 (s, 1H), 8.95 (s, 1H).

Example 95

N-[4-(3-amino-1,2-benzisoxazol-4-yl)phenyl]-N'-(3-methylphenyl)urea

Example 95A 4-bromo-1,2-benzisoxazol-3-amine

A suspension of acetylhydroxamic acid (2.46 g, 32.8 mmol) and potassium tert-butoxide (3.68 g, 32.8 mmol) in DMF (40 mL) was stirred at room temperature for 30 minutes, treated with 2-bromo-6-fluorobenzonitrile (4.36 g, 21.8 mmol), stirred for three hours, poured into water, and extracted three times with ethyl acetate. The combined extracts were washed with brine, dried (MgSO$_4$), filtered, and concentrated. The residue was purified by flash column chromatography on silica gel with 5 to 20% ethyl acetate/hexanes to provide 2.5 g of the desired product. MS (ESI(+)) m/e 212.9, 214.9 (M+H)$^+$.

Example 95B

N-[4-(3-amino-1,2-benzisoxazol-4-yl)phenyl]-N'-(3-methylphenyl)urea

The desired product was prepared by substituting Example 95A for Example 1A in Example 1C. $^1$H NMR (300 MHz, DMSO-d$_6$) δ 2.29 (s, 3H), 5.22 (s, 2H), 6.81 (d, J=7.12 Hz, 1H), 7.10-7.70 (m, 10H), 8.66 (s, 1H), 8.85 (s, 1H); MS (ESI(+)) m/e 359 (M+H)$^+$.

Example 96

N-[4-(3-amino-1,2-benzisoxazol-4-yl)phenyl]-N'-[2-(trifluoromethyl)phenyl]urea

Example 96A

N-[4-(4,4,5,5-tetramethyl-1,3,2-dioxaborolan-2-yl)phenyl]-N'-[2-(trifluoromethyl)phenyl]urea The desired product was prepared by substituting 1-isocyanato-2-(trifluoromethyl)benzene for 1-isocyanato-3-methylbenzene in Example 1B.

Example 96B

N-[4-(3-amino-1,2-benzisoxazol-4-yl)phenyl]-N'-[2-(trifluoromethyl)phenyl]urea

The desired product was prepared by substituting Example 95A and Example 96A for Example 1A and Example 1B, respectively, in Example 1C. $^1$H NMR (300 MHz, DMSO-d$_6$) δ 5.22 (s, 2H), 7.00-7.75 (m, 10H), 7.95 (d, J=7.80 Hz, 1H), 8.16 (s, 1H), 9.57 (s, 1H); MS (ESI(+)) m/e 413 (M+H)$^+$.

Example 97

N-[4-(3-amino-1,2-benzisoxazol-4-yl)phenyl]-N'-(2-fluoro-5-methylphenyl)urea

The desired product was prepared by substituting Example 95A and Example 5A for Example 1A and Example 1B, respectively, in Example 1C. $^1$H NMR (300 MHz, DMSO-d$_6$) δ 2.28 (s, 3H), 5.22 (s, 2H), 6.75-6.85 (m, 1H), 7.06-7.18 (m, 2H), 7.40-7.66 (m, 6H), 8.00 (dd, J=7.97, 1.86 Hz, 1H), 8.55 (d, J=2.37 Hz, 1H), 9.25 (s, 1H); MS (ESI(+)) m/e 377 (M+H)$^+$.

Example 98

N-[4-(3-amino-1,2-benzisoxazol-4-yl)phenyl]-N'-[3-(trifluoromethyl)phenyl]urea

Example 98A

N-[4-(4,4,5,5-tetramethyl-1,3,2-dioxaborolan-2-yl)phenyl]-N'-[3-(trifluoromethyl)phenyl]urea The desired product was prepared by substituting 1-isocyanato-3-(trifluoromethyl)benzene for 1-isocyanato-3-methylbenzene in Example 1B.

Example 98B

N-[4-(3-amino-1,2-benzisoxazol-4-yl)phenyl]-N'-[3-(trifluoromethyl)phenyl]urea

The desired product was prepared by substituting Example 95A and Example 98A for Example 1A and Example 1B, respectively, in Example 1C. $^1$H NMR (300 MHz, DMSO-d$_6$) δ 5.22 (s, 2H), 7.14 (d, J=6.78 Hz, 1H), 7.33 (d, J=7.12 Hz, 1H), 7.40-7.75 (m, 8H), 8.04 (s, 1H), 9.00 (s, 1H), 9.12 (s, 1H); MS (ESI(+)) m/e 413 (M+H)$^+$.

Example 99

N-[4-(3-amino-1,2-benzisoxazol-4-yl)phenyl]-N'-[2-fluoro-5-(trifluoromethyl)phenyl]urea

Example 99A

N-[2-fluoro-5-(trifluoromethyl)phenyl]-N'-[4-(4,4,5,5-tetramethyl-1,3,2-dioxaborolan-2-yl)phenyl]urea The desired product was prepared by substituting 1-fluoro-2-isocyanato-4-(trifluoromethyl)benzene for 1-isocyanato-3-methylbenzene in Example 1B.

Example 99B

N-[4-(3-amino-1,2-benzisoxazol-4-yl)phenyl]-N'-[2-fluoro-5-(trifluoromethyl)phenyl]urea The desired product was prepared by substituting Example 95A and Example 99A for Example 1A and Example 1B, respectively, in Example 1C. $^1$H NMR (300 MHz, DMSO-d$_6$) δ 5.22 (s, 2H), 7.15 (d, J=7.12 Hz, 1H), 7.40-7.70 (m, 8H), 8.64 (d, J=7.46 Hz, 1H), 8.98 (s, 1H), 9.38 (s, 1H); MS (ESI(+)) m/e 431 (M+H)$^+$.

Example 100

N-[4-(3-amino-7-methoxy-1,2-benzisoxazol-4-yl)phenyl]-N'-[2-fluoro-5-(trifluoromethyl)phenyl]urea

Example 100A 2-fluoro-6-iodo-3-methoxybenzonitrile

The desired product was prepared by substituting 2-fluoro-4-iodo-1-methoxybenzene for 2-fluoro-4-iodo-1-methylbenzene in Examples 15A-C.

Example 100B 4-iodo-7-methoxy-1,2-benzisoxazol-3-amine

The desired product was prepared by substituting Example 100A for 2-bromo-6-fluorobenzonitrile in Example 95A.

Example 100C 4-(4-aminophenyl)-7-methoxy-1,2-benzisoxazol-3-amine

The desired product was prepared by substituting Example 100B for Example 15F in Example 15G. $^1$H NMR (300 MHz, DMSO-$d_6$) δ 3.93 (s, 3H), 5.19 (s, 2H), 5.31 (s, 2H), 6.67 (d, J=8.48 Hz, 2H), 6.94 (d, J=8.14 Hz, 1H), 7.10 (m, 3H); MS (ESI(+)) m/e 256.0 (M+H)$^+$.

Example 100D

N-[4-(3-amino-7-methoxy-1,2-benzisoxazol-4-yl)phenyl]-N'-[2-fluoro-5-(trifluoromethyl)phenyl]urea The desired product was prepared by substituting Example 100C and 1-fluoro-2-isocyanato-4-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 3.97 (s, 3H), 5.21 (s, 2H), 7.05 (d, J=8.14 Hz, 1H), 7.17 (d, J=8.14 Hz, 1H), 7.41 (d, J=8.82 Hz, 3H), 7.45-7.56 (m, 1H), 7.61 (d, J=8.48 Hz, 2H), 8.64 (dd, J=7.12, 2.37 Hz, 1H), 8.96 (d, J=2.71 Hz, 1H), 9.34 (s, 1H); MS (ESI(+)) m/e 461 (M+H)$^+$.

Example 101

N-[4-(3-amino-7-methoxy-1,2-benzisoxazol-4-yl)phenyl]-N'-(3-methylphenyl)urea

The desired product was prepared by substituting Example 100C and 1-isocyanato-3-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.29 (s, 3H), 3.96 (s, 3H), 5.21 (s, 2H), 6.80 (d, J=7.46 Hz, 1H), 7.04 (d, J=8.14 Hz, 1H), 7.10-7.35 (m, 4H), 7.37 (d, J=8.48 Hz, 2H), 7.59 (d, J=8.82 Hz, 2H), 8.64 (s, 1H), 8.81 (s, 1H); MS (ESI(+)) m/e 389 (M+H)$^+$.

Example 102

N-[4-(3-amino-7-methoxy-1,2-benzisoxazol-4-yl)phenyl]-N'-[3-(trifluoromethyl)phenyl]urea The desired product was prepared by substituting Example 100C and 1-isocyanato-3-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 3.96 (s, 3H), 5.21 (s, 2H), 7.05 (d, J=7.80 Hz, 1H), 7.17 (d, J=8.14 Hz, 1H), 7.32 (d, J=7.46 Hz, 1H), 7.39 (d, J=8.48 Hz, 2H), 7.53 (t, J=7.80 Hz, 1H), 7.61 (m, 3H), 8.04 (s, 1H), 8.96 (s, 1H), 9.10 (s, 1H); MS (ESI(+)) m/e 443.0 (M+H)$^+$.

Example 103

N-[4-(3-amino-7-methoxy-1,2-benzisoxazol-4-yl)phenyl]-N'-(3-chlorophenyl)urea

The desired product was prepared by substituting Example 100C and 1-chloro-3-isocyanatobenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 3.96 (s, 3H), 5.20 (s, 2H), 7.00-7.06 (m, 2H), 7.16 (d, J=8.14 Hz, 1H), 7.25-7.35 (m, 2H), 7.39 (d, J=8.81 Hz, 2H), 7.60 (d, J=8.48 Hz, 2H), 7.73 (t, J=2.03 Hz, 1H), 8.92 (s, 1H), 8.94 (s, 1H); MS (ESI(+)) m/e 409 (M+H)$^+$.

Example 104

N-[4-(3-amino-7-methoxy-1,2-benzisoxazol-4-yl)phenyl]-N'-(2-fluoro-5-methylphenyl)urea The desired product was prepared by substituting Example 100C and 1-fluoro-2-isocyanato-4-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.28 (s, 3H), 3.96 (s, 3H), 5.21 (s, 2H), 6.75-6.90 (m, 1H), 7.00-7.20 (m, 3H), 7.39 (d, J=8.81 Hz, 2H), 7.59 (d, J=8.48 Hz, 2H), 8.00 (dd, J=7.63, 1.86 Hz, 1H), 8.53 (d, J=2.37 Hz, 1H), 9.22 (s, 1H); MS (ESI(+)) m/e 407.0 (M+H)$^+$.

Example 105

N-{4-[3-amino-7-(4-morpholinylmethyl)-1,2-benzisoxazol-4-yl]phenyl}-N'-[2-fluoro-5-(trifluoromethyl)phenyl]urea

Example 105A 4-iodo-7-(4-mompholinylmethyl)-1,2-benzisoxazol-3-amine

The desired product was prepared by substituting Example 15E for 2-bromo-6-fluorobenzonitrile in Example 95A.

Example 105B 4-(4-aminophenyl)-7-(4-morpholinylmethyl)-1,2-benzisoxazol-3-amine The desired product was prepared by substituting Example 105A for Example 15F in Example 15G. $^1$H NMR (300 MHz, DMSO-$d_6$) δ 2.38-2.45 (m, 4H), 3.55-3.63 (m, 4H), 3.70 (s, 2H), 5.21 (s, 2H), 5.38 (s, 2H), 6.69 (d, J=8.48 Hz, 2H), 7.02 (d, J=7.46 Hz, 1H), 7.15 (d, J=8.48 Hz, 2H), 7.45 (d, J=7.46 Hz, 1H).

Example 105C

N-{4-[3-amino-7-(4-morpholinylmethyl)-1,2-benzisoxazol-4-yl]phenyl}-N'-[2-fluoro-5-(trifluoromethyl)phenyl]urea The desired product was prepared by substituting Example 105B and 1-fluoro-2-isocyanato-4-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.44 (s, 4H), 3.59 (s, 4H), 3.74 (s, 2H), 5.23 (s, 2H), 7.13 (d, J=7.46 Hz, 1H), 7.35-7.55 (m, 5H), 7.64 (d, J=8.81 Hz, 2H), 8.64 (dd, J=7.29, 2.20 Hz, 1H), 8.99 (d, J=2.71 Hz, 1H), 9.40 (s, 1H); MS (ESI(+)) m/e 530 (M+H)$^+$.

Example 106

N-{4-[3-amino-7-(4-morpholinylmethyl)-1,2-benzisoxazol-4-yl]phenyl}-N'-[3-(trifluoromethyl)phenyl]urea The desired product was prepared by substituting Example 105B and 1-isocyanato-3-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, CF$_3$CO$_2$D) δ 2.44 (s, 4H), 3.59 (s, 4H), 3.74 (s, 2H), 5.23 (s, 2H), 7.12 (d, J=7.46 Hz, 1H), 7.33 (d, J=7.46 Hz, 1H), 7.44 (d, J=8.48 Hz, 2H), 7.50-7.68 (m, 5H), 8.04 (s, 1H), 9.04 (s, 1H), 9.16 (s, 1H); MS (ESI(+)) m/e 512 (M+H)$^+$.

Example 107

N-{4-[3-amino-7-(4-morpholinylmethyl)-1,2-benzisoxazol-4-yl]phenyl}-N'-(3-chlorophenyl)urea The desired product was prepared by substituting Example 105B and 1-chloro-3-isocyanatobenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.44 (s, 4H), 3.59 (s, 4H), 3.73 (s, 2H), 5.22 (s, 2H), 6.95-7.06 (m, 1H), 7.12 (d, J=7.46 Hz, 1H), 7.25-7.38 (m, 2H), 7.44 (d, J=8.48 Hz, 2H), 7.52 (d, J=7.80 Hz, 1H), 7.62 (d, J=8.48 Hz, 2H), 7.70-7.78 (m, 1H), 8.99 (s, 2H); MS (ESI(+)) m/e 478 (M+H)$^+$.

Example 108

N-{4-[3-amino-7-(4-morpholinylmethyl)-1,2-benzisoxazol-4-yl]phenyl}-N'-(3-methylphenyl)urea The desired product was prepared by substituting Example 105B and 1-isocyanato-3-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.29 (s, 3H), 2.44 (s, 4H), 3.59 (s, 4H), 3.73 (s, 2H), 5.23 (s, 2H), 6.80 (d, J=7.80 Hz, 1H), 7.05-7.35 (m, 5H), 7.42 (d, J=8.48 Hz, 1H), 7.52 (d, J=7.12 Hz, 1H), 7.62 (d, J=8.48 Hz, 2H), 8.67 (s, 1H), 8.86 (s, 1H); MS (ESI(+)) m/e 458 (M+H)$^+$.

Example 109

N-{4-[3-amino-7-(4-morpholinylmethyl)-1,2-benzisoxazol-4-yl]phenyl}-N'-(2-fluoro-5-methylphenyl)urea The desired product was prepared by substituting Example 105B and 1-fluoro-2-isocyanato-4-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.28 (s, 3H), 2.35-2.48 (m, 4H), 3.50-3.65 (m, 4H), 3.74 (s, 2H), 5.23 (s, 2H), 6.75-6.85 (m, J=2.37 Hz, 1H), 7.05-7.18 (m, 2H), 7.44 (d, J=8.48 Hz, 2H), 7.52 (d, J=7.80 Hz, 1H), 7.62 (d, J=8.48 Hz, 2H), 8.00 (dd, J=7.80, 1.70 Hz, 1H), 8.55 (d, J=2.37 Hz, 1H), 9.25 (s, 1H); MS (ESI(+)) m/e 476 (M+H)$^+$.

Example 110

N-{4-[3-amino-7-(4-morpholinylmethyl)-1,2-benzisoxazol-4-yl]phenyl}-N'-(3,5-dimethylphenyl)urea The desired product was prepared by substituting Example 105B and 1-isocyanato-3,5-dimethylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.24 (s, 6H), 2.44 (s, 4H), 3.59 (s, 4H), 3.73 (s, 2H), 5.23 (s, 2H), 6.63 (s, 1H), 7.05-7.15 (m, 3H), 7.42 (d, J=8.48 Hz, 2H), 7.52 (d, J=7.46 Hz, 1H), 7.61 (d, J=8.81 Hz, 2H), 8.59 (s, 1H), 8.84 (s, 1H); MS (ESI(+)) m/e 472 (M+H)$^+$.

Example 111

N-{4-[3-amino-7-(4-morpholinylmethyl)-1,2-benzisoxazol-4-yl]phenyl}-N'-(3-phenoxyphenyl)urea The desired product was prepared by substituting Example 105B and 1-isocyanato-3-phenoxybenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.40-2.48 (m, 4H), 3.55-3.64 (m, 4H), 3.73 (s, 2H), 5.21 (s, 2H), 6.60-6.68 (m, 1H), 7.00-7.20 (m, 5H), 7.25-7.32 (m, 2H), 7.35-7.45 (m, 4H), 7.51 (d, J=7.46 Hz, 1H), 7.59 (d, J=8.82 Hz, 2H), 8.84 (s, 1H), 8.87 (s, 1H); MS (ESI(+)) m/e 536.1 (M+H)$^+$.

Example 112

N-{4-[3-amino-7-(4-morpholinylmethyl)-1,2-benzisoxazol-4-yl]phenyl}-N'-(3-bromophenyl)urea The desired product was prepared by substituting Example 105B and 1-bromo-3-isocyanatobenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-$d_6$) δ 2.40-2.48 (m, 4H), 3.50-3.65 (m, 4H), 3.73 (s, 2H), 5.22 (s, 2H), 7.10-7.35 (m, 4H), 7.43 (d, J=8.48 Hz, 2H), 7.52 (d, J=7.46 Hz, 1H), 7.62 (d, J=8.48 Hz, 2H), 7.88 (t, J=1.86 Hz, 1H), 8.96 (s, 2H); MS (ESI(+)) m/e 524 (M+H)$^+$.

Example 113

N-(4-{3-amino-7-[2-(4-morpholinyl)ethoxy]-1,2-benzisoxazol-4-yl}phenyl)-N'-[3-(trifluoromethyl)phenyl]urea

Example 113A 4-iodo-7-[2-(4-morpholinyl)ethoxy]-1,2-benzisoxazol-3-amine

The desired product was prepared by substituting Example 75A for 2-bromo-6-fluorobenzonitrile in Example 95A.

Example 113B 4-(4-aminophenyl)-7-[2-(4-morpholinyl)ethoxy]-1,2-benzisoxazol-3-amine The desired product was prepared by substituting Example 113A for Example 15F in Example 15G. $^1$H NMR (300 MHz, DMSO-d$_6$) δ 2.45-2.60 (m, 4H), 2.76 (t, J=5.59 Hz, 2H), 3.50-3.70 (m, 4H), 4.28 (t, J=5.59 Hz, 2H), 5.19 (s, 2H), 5.31 (s, 2H), 6.67 (d, J=8.48 Hz, 2H), 6.92 (d, J=7.80 Hz, 1H), 7.05-7.18 (m, 3H); MS (ESI(+)) m/e 355.0 (M+H)$^+$.

Example 113C

N-(4-{3-amino-7-[2-(4-morpholinyl)ethoxy]-1,2-benzisoxazol-4-yl}phenyl)-N'-[3-(trifluoromethyl)phenyl]urea The desired product was prepared by substituting Example 113B and 1-isocyanato-3-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-d$_6$) δ 2.45-2.60 (m, 4H), 2.78 (t, J=5.59 Hz, 2H), 3.50-3.65 (m, 4H), 4.31 (t, J=5.59 Hz, 2H), 5.21 (s, 2H), 7.03 (d, J=8.14 Hz, 1H), 7.19 (d, J=8.14 Hz, 1H), 7.32 (d, J=7.46 Hz, 1H), 7.39 (d, J=8.81 Hz, 2H), 7.53 (t, J=7.80 Hz, 1H), 7.57-7.66 (m, 3H), 8.04 (s, 1H), 8.96 (s, 1H), 9.10 (s, 1H); MS (ESI(+)) m/e 542.1, 540.1.

Example 114

N-(4-{3-amino-7-[2-(4-morpholinyl)ethoxy]-1,2-benzisoxazol-4-yl}phenyl)-N'-(2-fluoro-5-methylphenyl)urea The desired product was prepared by substituting Example 113B and 1-fluoro-2-isocyanato-4-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-d$_6$) δ 2.28 (s, 3H), 2.45-2.55 (m, 4H), 2.78 (t, J=5.59 Hz, 2H), 3.50-3.65 (m, 4H), 4.31 (t, J=5.76 Hz, 2H), 5.21 (s, 2H), 6.75-6.84 (m, 1H), 7.03 (d, J=8.14 Hz, 1H), 7.11 (dd, J=11.36, 8.31 Hz, 1H), 7.19 (d, J=8.14 Hz, 1H), 7.39 (d, J=8.48 Hz, 2H), 7.59 (d, J=8.48 Hz, 2H), 8.00 (dd, J=7.80, 2.03 Hz, 1H), 8.53 (d, J=2.37 Hz, 1H), 9.22 (s, 1H); MS (ESI(+)) m/e 506.1 (M+H)$^+$.

Example 115

N-(4-{3-amino-7-[2-(4-morpholinyl)ethoxy]-1,2-benzisoxazol-4-yl}phenyl)-N'-[2-fluoro-5-(trifluoromethyl)phenyl]urea The desired product was prepared by substituting Example 113B and 1-fluoro-2-isocyanato-4-(trifluoromethyl)benzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-d$_6$) δ 2.45-2.55 (m, 4H), 2.78 (t, J=5.26 Hz, 2H), 3.50-3.67 (m, 4H), 4.31 (t, J=5.09 Hz, 2H), 5.21 (s, 2H), 7.03 (d, J=7.80 Hz, 1H), 7.19 (d, J=7.80 Hz, 1H), 7.35-7.70 (m, 6H), 8.64 (dd, J=6.78, 1.36 Hz, 1H), 8.96 (d, J=2.37 Hz, 1H), 9.34 (s, 1H); MS (ESI(+)) m/e 560.1 (M+H)$^+$.

Example 116

N-(4-{3-amino-7-[2-(4-morpholinyl)ethoxy]-1,2-benzisoxazol-4-yl}phenyl)-N'-(3-methylphenyl)urea The desired product was prepared by substituting Example 113B and 1-isocyanato-3-methylbenzene for Example 15G and 1-fluoro-3-isocyanatobenzene, respectively, in Example 15H. The crude suspension was filtered and the solid collected was washed with dichloromethane to provide the desired product. $^1$H NMR (300 MHz, DMSO-d$_6$) δ 2.29 (s, 3H), 2.45-2.55 (m, 4H), 2.78 (t, J=5.26 Hz, 2H), 3.50-3.70 (m, 4H), 4.31 (t, J=4.92 Hz, 2H), 5.21 (s, 2H), 6.80 (d, J=7.46 Hz, 1H), 7.02 (d, J=7.80 Hz, 1H), 7.10-7.30 (m, 4H), 7.37 (d, J=8.48 Hz, 2H), 7.59 (d, J=8.48 Hz, 2H), 8.66 (s, 1H), 8.83 (s, 1H); MS (ESI(+)) m/e 488 (M+H)$^+$.

Example 117

N-{4-[3-amino-7-(2-methoxyethoxy)-1H-indazol-4-yl]phenyl}-N'-(2-fluoro-5-methylphenyl)urea The desired product was prepared by substituting Example 68C and 1-fluoro-2-isocyanato-4-methylbenzene for Example 15G and 1-fluoro-3-isocyanatobenzene, respectively, in Example 15H. The crude suspension was filtered and the solid collected was washed with dichloromethane to provide the desired product. MS (ESI(+)) m/e 450 (M+H)$^+$; $^1$H NMR (300 MHz, DMSO-d$_6$) δ 2.28 (s, 3H), 3.36 (s, 3H), 3.76 (t, J=4.75 Hz, 2H), 4.26-4.29, (m, 2H), 4.29 (s, 2H), 6.68 (d, J=7.80 Hz, 1H), 6.80 (d, J=7.80 Hz, 1H), 6.82 (m, 1H), 7.11 (dd, J=11.53, 8.14 Hz, 1H), 7.36 (d, J=8.82 Hz, 2H), 7.56 (d, J=8.48 Hz, 2H), 8.01 (dd, J=7.80, 2.03 Hz, 1H), 8.52 (d, J=2.37 Hz, 1H), 9.16 (s, 1H).

Example 118

N-(4-{3-amino-7-[2-(4-morpholinyl)ethoxy]-1H-indazol-4-yl}phenyl)-N'-(2-fluoro-5-methylphenyl)urea The desired product was prepared as the bis(trifluoroacetate) salt by substituting Example 75B and 1-fluoro-2-isocyanato-4-methylbenzene for Example 15G and 1-fluoro-3-isocyanatobenzene, respectively, in Example 15H. MS (ESI (+)) m/e 505 (M+H)+; 1H NMR (300 MHz, DMSO-d6) δ 2.28 (s, 3H), 2.73 (m, 2H), 3.71 (m, 6H), 4.04 (m, 2H), 4.53 (m, 2H), 6.74 (d, J=7.80 Hz, 1H), 6.81 (m, 1H), 6.88 (d, J=7.80 Hz, 1H), 7.12 (dd, J=11.36, 8.31 Hz, 1H), 7.36 (d, J=8.82 Hz, 2H), 7.57 (d, J=8.48 Hz, 2H), 8.01 (s, 1H), 8.52 (d, J=2.71 Hz, 1H), 9.18 (s, 1H).

Example 119

N-{4-[3-amino-7-(methoxymethoxy)-1H-indazol-4-yl]phenyl}-N'-(2-fluoro-5-methylphenyl)urea

Example 119A 2-fluoro-6-iodo-3-(methoxymethoxy)benzonitrile

A 0° C. solution of Example 68A (250 mg, 0.95 mmol) in THF (5 mL) at room temperature was treated with NaH (25 mg, 95%, 1.05 mmol), stirred for 5 minutes, treated with chloromethyl methyl ether (0.108 mL, 1.4 mmol), stirred overnight, and partitioned between water and ethyl acetate. The organic extract was washed with brine, dried (MgSO4), filtered, and concentrated. The residue was purified by flash column chromatography on silica gel with 2% ethyl acetate/hexanes to provide 0.21 g of the desired product. $R_f$=0.4 (10% ethyl acetate/hexanes).

Example 119B

N-{4-[3-amino-7-(methoxymethoxy)-1H-indazol-4-yl]phenyl}-N'-(2-fluoro-5-methylphenyl)urea The desired product was prepared by substituting Example 119A and 1-fluoro-2-isocyanato-4-methylbenzene for 2-fluoro-6-iodobenzonitrile and 1-isocyanato-3-methylbenzene, respectively, in Examples 1A-1C. MS (ESI(+)) m/e 436 (M+H)+; 1H NMR (300 MHz, DMSO-d6) δ 2.28 (s, 3H), 3.46 (s, 3H), 4.33 (s, 2H), 5.34 (s, 2H), 6.69 (d, J=7.80 Hz, 1H), 6.78-6.83 (m, 1H), 6.92 (d, J=7.80 Hz, 1H), 7.11 (dd, J=11.36, 8.31 Hz, 1H), 7.36 (d, J=8.48 Hz, 2H), 7.56 (d, J=8.48 Hz, 2H), 8.01 (dd, J=7.80, 1.70 Hz, 1H), 8.52 (d, J=2.71 Hz, 1H), 9.17 (s, 1H), 11.90 (s, 1H).

Example 120

N-[4-(3-amino-7-hydroxy-1H-indazol-4-yl)phenyl]-N'-(2-fluoro-5-methylphenyl)urea A mixture of Example 119B (90 mg) and a 1:1:1 mixture of 3N HCl/methanol/THF (3 mL) was heated to 50° C. for 3 hours, concentrated to half its original volume, and partitioned between saturated NaHCO3 and ethyl acetate. The organic extract was dried (MgSO4), filtered, and concentrated. The residue was purified by flash column chromatography on silica gel with 5% methanol/dichloromethane to provide 30 mg of the desired product. MS (ESI(+)) m/e 392 (M+H)+; 1H NMR (300 MHz, DMSO-d6) δ 2.28 (s, 3H), 4.25 (s, 2H), 6.60 (d, J=5.76 Hz, 2H), 6.82 (m, J=5.09, 3.05 Hz, 1H), 7.11 (m, 2H), 7.33 (d, J=8.48 Hz, 1H), 7.54 (d, J=8.81 Hz, 2H), 8.01 (dd, J=7.97, 2.20 Hz, 1H), 8.51 (d, J=2.71 Hz, 1H), 9.14 (s, 1H), 9.84 (s, 1H), 11.58 (s, 1H).

Example 121

N-[4-(3-amino-7-hydroxy-1H-indazol-4-yl)phenyl]-N'-(3-fluorophenyl)urea

Example 121A 4-(4-aminophenyl)-7-(methoxymethoxy)-1H-indazol-3-amine

The desired product was prepared by substituting Example 119A for Example 15E in Examples 15F-G. MS (ESI(+)) m/e 285 (M+H)+.

Example 121B

N-{4-[3-amino-7-(methoxymethoxy)-1H-indazol-4-yl]phenyl}-N'-(3-fluorophenyl)urea The desired product was prepared by substituting Example 121A for Example 15G in Example 15H.

Example 121C

N-[4-(3-amino-7-hydroxy-1H-indazol-4-yl)phenyl]-N'-(3-fluorophenyl)urea

The desired product was prepared as the trifluoroacetate salt by substituting Example 121B for Example 119B in Example 120, then purifying the resulting product by HPLC using the conditions described in Example 15H. MS (ESI(+)) m/e 378 (M+H)+; 1H NMR (500 MHz, DMSO-d6) δ 6.68-6.72 (m, 2H), 6.79 (td, J=8.34, 2.34 Hz, 1H), 7.14 (d, J=8.11 Hz, 1H), 7.31 (m, 1H), 7.35 (d, J=8.42 Hz, 2H), 7.51 (dt, J=12.01, 2.26 Hz, 1H), 7.56 (d, J=8.42 Hz, 2H), 8.88 (s, 1H), 8.97 (s, 1H).

Example 122

N-[4-(3-amino-7-hydroxy-1H-indazol-4-yl)phenyl]-N'-(3-bromophenyl)urea

Example 122A

N-{4-[3-amino-7-(methoxymethoxy)-1H-indazol-4-yl]phenyl}-N'-(3-bromophenyl)urea

The desired product was prepared by substituting Example 121A and 1-bromo-3-isocyanatobenzene for Example 15G and 1-fluoro-3-isocyanatobenzene, respectively, in Example 15H.

Example 122B

N-[4-(3-amino-7-hydroxy-1H-indazol-4-yl)phenyl]-N'-(3-bromophenyl)urea

The desired product was prepared as the trifluoroacetate salt by substituting Example 122A for Example 119B in Example 120 then purifying the resulting product by HPLC using the conditions described in Example 15H. MS (ESI(+)) m/e 438 (M+H)+; 1H NMR (500 MHz, DMSO-d6) δ 6.69-6.73 (m, 2H), 7.16 (d, J=7.80 Hz, 1H), 7.25 (t, J=7.95 Hz, 1H), 7.32-7.34 (m, 1H), 7.35 (d, J=8.42 Hz, 2H), 7.56 (d, J=8.73 Hz, 2H), 7.88 (t, J=1.87 Hz, 1H), 8.90 (s, 1H), 8.95 (s, 1H).

Example 123

N-[4-(3-amino-7-hydroxy-1H-indazol-4-yl)phenyl]-N'-(3-ethylphenyl)urea

Example 123A

N-{4-[3-amino-7-(methoxymethoxy)-1H-indazol-4-yl]phenyl}-N'-(3-ethylphenyl)urea

The desired product was prepared by substituting Example 121A and 1-ethyl-3-isocyanatobenzene for Example 15G and 1-fluoro-3-isocyanatobenzene, respectively, in Example 15H.

Example 123B

N-[4-(3-amino-7-hydroxy-1H-indazol-4-yl)phenyl]-N'-(3-ethylphenyl)urea

The desired product was prepared as the trifluoroacetate salt by substituting Example 123A for Example 119B in Example 120 then purifying the resulting product by HPLC using the conditions described in Example 15H. MS (ESI(+)) m/e 388 (M+H)$^+$; $^1$H NMR (500 MHz, DMSO-d$_6$) δ 1.19 (t, J=7.49 Hz, 3H), 2.58 (q, J=7.49 Hz, 2H), 6.65-6.70 (m, 2H), 6.83 (d, J=7.49 Hz, 1H), 7.19 (t, J=7.80 Hz, 1H), 7.27 (d, J=8.11 Hz, 1H), 7.33-7.34 (m, 3H), 7.55 (d, J=8.42 Hz, 2H), 8.64 (s, 1H), 8.74 (s, 1H).

Example 124

N-[4-(3-amino-7-hydroxy-1H-indazol-4-yl)phenyl]-N'-[2-fluoro-5-(trifluoromethyl)phenyl]urea

Example 124A

N-{4-[3-amino-7-(methoxymethoxy)-1H-indazol-4-yl]phenyl}-N'-[2-fluoro-5-(trifluoromethyl)phenyl]urea The desired product was prepared by substituting Example 121A and 1-fluoro-2-isocyanato-4-(trifluoromethyl)benzene for Example 15G and 1-fluoro-3-isocyanatobenzene, respectively, in Example 15H.

Example 124B

N-[4-(3-amino-7-hydroxy-1H-indazol-4-yl)phenyl]-N'-[2-fluoro-5-(trifluoromethyl)phenyl]urea The desired product was prepared as the trifluoroacetate salt by substituting Example 124A for Example 119B in Example 120 then purifying the resulting product by HPLC using the conditions described in Example 15H. MS (ESI(+)) m/e 446 (M+H)$^+$; $^1$H NMR (500 MHz, DMSO-d$_6$) δ 6.68-6.72 (m, 2H), 7.37 (d, J=8.42 Hz, 2H), 7.38-7.40 (m, 1H), 7.51 (m, 1H), 7.57 (d, J=8.73 Hz, 2H), 8.64 (dd, J=7.17, 2.18 Hz, 1H), 8.93 (d, J=2.81 Hz, 1H), 9.28 (s, 1H).

Example 125

N-[4-(3-amino-7-hydroxy-1H-indazol-4-yl)phenyl]-N'-[4-fluoro-3-(trifluoromethyl)phenyl]urea

Example 125A

N-{4-[3-amino-7-(methoxymethoxy)-1H-indazol-4-yl]phenyl}-N'-[4-fluoro-3-(trifluoromethyl)phenyl]urea The desired product was prepared by substituting Example 121A and 1-fluoro-4-isocyanato-2-(trifluoromethyl)benzene for Example 15G and 1-fluoro-3-isocyanatobenzene, respectively, in Example 15H.

Example 125B

N-[4-(3-amino-7-hydroxy-1H-indazol-4-yl)phenyl]-N'-[4-fluoro-3-(trifluoromethyl)phenyl]urea The desired product was prepared as the trifluoroacetate salt by substituting Example 125A for Example 119B in Example 120 then purifying the resulting product by HPLC using the conditions described in Example 15H. MS (ESI(−)) m/e 444 (M−H)$^-$; $^1$H NMR (500 MHz, DMSO-d$_6$) δ 6.72-6.76 (m, 2H), 7.36 (d, J=8.42 Hz, 2H), 7.44 (t, J=9.67 Hz, 1H), 7.58 (d, J=8.73 Hz, 2H), 7.65-7.68 (m, 1H), 8.03 (dd, J=6.39, 2.65 Hz, 1H), 9.02 (s, 1H), 9.19 (s, 1H).

Example 126

N-[4-(3-amino-7-hydroxy-1H-indazol-4-yl)phenyl]-N'-(3-chlorophenyl)urea

Example 126A

N-{4-[3-amino-7-(methoxymethoxy)-1H-indazol-4-yl]phenyl}-N'-(3-chlorophenyl)urea The desired product was prepared as the trifluoroacetate salt by substituting Example 121A and 1-chloro-3-isocyanatobenzene for Example 15G and 1-fluoro-3-isocyanatobenzene, respectively, in Example 15H.

Example 126B

N-[4-(3-amino-7-hydroxy-1H-indazol-4-yl)phenyl]-N'-(3-chlorophenyl)urea

The desired product was prepared as the trifluoroacetate salt by substituting Example 126A for Example 119B in Example 120 then purifying the resulting product by HPLC using the conditions described in Example 15H. MS (ESI(−)) m/e 392 (M−H)$^-$; $^1$H NMR (500 MHz, DMSO-d$_6$) δ 6.69-6.73 (m, 1H), 7.01-7.03 (m, 1H), 7.30-7.31 (m, 2H), 7.35 (d, J=8.73 Hz, 2H), 7.56 (d, J=8.73 Hz, 2H), 7.74 (d, J=1.87 Hz, 1H), 8.91 (s, 1H), 8.98 (s, 1H).

Example 127

N-[4-(3-amino-7-hydroxy-1H-indazol-4-yl)phenyl]-N'-[3-(trifluoromethyl)phenyl]urea

Example 127A

N-{4-[3-amino-7-(methoxymethoxy)-1H-indazol-4-yl]phenyl}-N'-[3-(trifluoromethyl)phenyl]urea The desired product was prepared by substituting Example 121A and 1-isocyanato-3-(trifluoromethyl)benzene for Example 15G and 1-fluoro-3-isocyanatobenzene, respectively, in Example 15H.

Example 127B

N-[4-(3-amino-7-hydroxy-1H-indazol-4-yl)phenyl]-N'-[3-(trifluoromethyl)phenyl]urea The desired product was prepared as the trifluoroacetate salt by substituting Example 127A for Example 119B in Example 120 then purifying the resulting product by HPLC using the conditions described in Example 15H. MS (ESI(+)) m/e 428 (M+H)$^+$; $^1$H NMR (500 MHz, DMSO-d$_6$) δ 6.70-6.74 (m, 2H), 7.32 (d, J=7.49 Hz, 1H), 7.36 (d, J=8.42 Hz, 2H), 7.52 (t, J=7.95 Hz, 1H), 7.58 (d, J=8.42 Hz, 2H), 7.60 (d, J=9.04 Hz, 1H), 8.04 (s, 1H), 8.96 (s, 1H), 9.14 (s, 1H).

Example 128

N-[4-(3-amino-7-hydroxy-1H-indazol-4-yl)phenyl]-N'-phenylurea

Example 128A

N-{4-[3-amino-7-(methoxymethoxy)-1H-indazol-4-yl]phenyl}-N'-phenylurea

The desired product was prepared by substituting Example 121A and isocyanatobenzene for Example 15G and 1-fluoro-3-isocyanatobenzene, respectively, in Example 15H.

Example 128B

N-[4-(3-amino-7-hydroxy-1H-indazol-4-yl)phenyl]-N'-phenylurea

The desired product can be prepared by substituting Example 128A for Example 119B in Example 120. MS (ESI(−)) m/e 358 (M−H)$^−$; $^1$H NMR (300 MHz, DMSO-d$_6$) δ 6.57-6.64 (m, 2H), 6.97 (t, J=7.29 Hz, 1H), 7.29 (t, J=8.13 Hz, 2H), 7.32 (d, J=8.82 Hz, 2H), 7.47 (d, J=7.46 Hz, 2H), 7.54 (d, J=8.82 Hz, 2H), 8.71 (s, 1H), 8.77 (s, 1H).

Example 129

N-(4-{3-amino-7-[2-(1-pyrrolidinyl)ethoxy]-1H-indazol-4-yl}phenyl)-N'-phenylurea

Example 129A 4-(4-aminophenyl)-7-[2-(1-pyrrolidinyl)ethoxy]-1H-indazol-3-amine The desired product was prepared by substituting 2-(1-pyrrolidinyl)ethanol for 2-(4-morpholinyl)ethanol in Examples 75A and 75B. MS (ESI(+)) m/e 338 (M+H)$^+$.

Example 129B

N-(4-{3-amino-7-[2-(1-pyrrolidinyl)ethoxy]-1H-indazol-4-yl}phenyl)-N'-phenylurea The desired product was prepared as the bis(trifluoroacetate) salt by substituting Example 129A and isocyanatobenzene for Example 15G and 1-fluoro-3-isocyanatobenzene, respectively, in Example 15H. MS (ESI(+)) m/e 457 (M+H)$^+$; $^1$H NMR (500 MHz, DMSO-d$_6$) δ 1.93 (br s, 2H), 2.08 (br s, 2H), 3.25 (br s, 4H), 3.68 (br s, 2H), 4.46 (t, J=4.80 Hz, 2H), 6.74 (d, J=7.80 Hz, 1H), 6.88 (d, J=7.80 Hz, 1H), 6.98 (t, J=7.33 Hz, 1H), 7.29 (t, J=7.80 Hz, 2H), 7.36 (d, J=8.73 Hz, 2H), 7.47 (d, J=7.49 Hz, 2H), 7.58 (d, J=8.42 Hz, 2H), 8.74 (s, 1H), 8.82 (s, 1H).

Example 130

N-(4-{3-amino-7-[2-(1-pyrrolidinyl)ethoxy]-1H-indazol-4-yl}phenyl)-N'-(3-fluorophenyl)urea The desired product was prepared as the bis(trifluoroacetate) salt by substituting Example 129A for Example 15G in Example 15H. MS (ESI(+)) m/e 475 (M+H)$^+$; $^1$H NMR (500 MHz, DMSO-d$_6$) δ 1.92 (br s, 2H), 2.07 (br s, 2H), 3.24 (br s, 2H), 3.68 (br s, 4H), 4.47 (t, J=4.80 Hz, 2H), 6.75 (d, J=7.49 Hz, 1H), 6.79 (td, J=8.50, 2.34 Hz, 1H), 6.89 (d, J=7.80 Hz, 1H), 7.15 (dd, J=8.11, 1.25 Hz, 1H), 7.29-7.34 (m, 1H), 7.37 (d, J=8.73 Hz, 2H), 7.52 (dt, J=12.01, 2.26 Hz, 1H), 7.58 (d, J=8.73 Hz, 2H), 9.00 (s, 1H), 9.08 (s, 1H).

Example 131

N-(4-{3-amino-7-[2-(1-pyrrolidinyl)ethoxy]-1H-indazol-4-yl}phenyl)-N'-(2-fluoro-5-methylphenyl)urea The desired product was prepared as the bis(trifluoroacetate) salt by substituting Example 129A and 1-fluoro-2-isocyanato-4-methylbenzene for Example 15G and 1-fluoro-3-isocyanatobenzene, respectively, in Example 15H. MS (ESI(+)) m/e 489 (M+H)$^+$; $^1$H NMR (500 MHz, DMSO-d$_6$) δ 1.93 (br s, 2H), 2.07 (br s, 2H), 2.28 (s, 3H), 3.25 (br s, 2H), 3.69 (br s, 4H), 4.47 (t, J=4.80 Hz, 2H), 6.74 (d, J=7.80 Hz, 1H), 6.80-6.82 (m, 1H), 6.88 (d, J=7.80 Hz, 1H), 7.11 (dd, J=11.38, 8.26 Hz, 1H), 7.37 (d, J=8.42 Hz, 2H), 7.58 (d, J=8.73 Hz, 2H), 7.99 (dd, J=7.80, 1.56 Hz, 1H), 8.53 (d, J=2.49 Hz, 1H), 9.20 (s, 1H).

Example 132

N-(4-{3-amino-7-[2-(1-pyrrolidinyl)ethoxy]-1H-indazol-4-yl}phenyl)-N'-(3-methylphenyl)urea The desired product was prepared as the trifluoroacetate salt by substituting Example 129A and 1-isocyanato-3-methylbenzene for Example 15G and 1-fluoro-3-isocyanatobenzene, respectively, in Example 15H. MS (ESI(+)) m/e 471 (M+H)+; ¹H NMR (500 MHz, DMSO-d₆) δ 1.93 (br s, 2H), 2.07 (br s, 2H), 2.29 (s, 3H), 3.25 (br s, 2H), 3.69 (br s, 4H), 4.48 (t, J=4.80 Hz, 2H), 6.77 (d, J=7.80 Hz, 1H), 6.80 (d, J=7.49 Hz, 1H), 6.90 (d, J=7.80 Hz, 1H), 7.16 (t, J=7.80 Hz, 1H), 7.26 (d, J=8.11 Hz, 1H), 7.33 (s, 1H), 7.36 (d, J=8.73 Hz, 2H), 7.59 (d, J=8.73 Hz, 2H), 8.79 (s, 1H), 8.95 (s, 1H).

Example 133

N-(4-{3-amino-7-[2-(1-pyrrolidinyl)ethoxy]-1H-indazol-4-yl}phenyl)-N'-(3-bromophenyl)urea The desired product was prepared as the bis(trifluoroacetate) salt by substituting Example 129A and 1-bromo-3-isocyanatobenzene for Example 15G and 1-fluoro-3-isocyanatobenzene, respectively, in Example 15H. MS (ESI(+)) m/e 535 and 537 (M+H)+; ¹H NMR (500 MHz, DMSO-d₆) δ 1.93 (br s, 2H), 2.07 (br s, 2H), 3.25 (br s, 2H), 3.68 (br s, 4H), 4.47 (t, J=4.80 Hz, 2H), 6.75 (d, J=7.80 Hz, 1H), 6.89 (d, J=7.80 Hz, 1H), 7.15 (d, J=8.11 Hz, 1H), 7.25 (t, J=8.11 Hz, 1H), 7.34 (d, J=9.36 Hz, 1H), 7.37 (d, J=8.42 Hz, 2H), 7.59 (d, J=8.42 Hz, 2H), 7.89 (t, J=1.87 Hz, 1H), 9.06 (s, 1H), 9.10 (s, 1H).

Example 134

N-(4-{3-amino-7-[2-(1-pyrrolidinyl)ethoxy]-1H-indazol-4-yl}phenyl)-N'-[2-fluoro-5-(trifluoromethyl)phenyl]urea The desired product was prepared as the bis(trifluoroacetate) salt by substituting Example 129A and 1-fluoro-2-isocyanato-4-(trifluoromethyl)benzene for Example 15G and 1-fluoro-3-isocyanatobenzene, respectively, in Example 15H. MS (ESI(+)) m/e 543 (M+H)+; ¹H NMR (500 MHz, DMSO-d₆) δ 1.93 (br s, 2H), 2.08 (br s, 2H), 3.25 (br s, 2H), 3.69 (br s, 4H), 4.47 (t, J=4.80 Hz, 2H), 6.74 (d, J=7.80 Hz, 1H), 6.88 (d, J=7.80 Hz, 1H), 7.39 (d, J=8.42 Hz, 2H), 7.41 (m, 1H), 7.51 (t, J=9.67 Hz, 1H), 7.59 (d, J=8.42 Hz, 2H), 8.64 (dd, J=7.33, 2.34 Hz, 1H), 8.94 (d, J=2.49 Hz, 1H), 9.30 (s, 1H).

Example 135

N-(4-{3-amino-7-[2-(1-pyrrolidinyl)ethoxy]-1H-indazol-4-yl}phenyl)-N'-(3-chlorophenyl)urea The desired product was prepared as the bis(trifluoroacetate) salt by substituting Example 129A and 1-chloro-3-isocyanatobenzene for Example 15G and 1-fluoro-3-isocyanatobenzene, respectively, in Example 15H. MS (ESI(+)) m/e 491 (M+H)+; ¹H NMR (500 MHz, DMSO-d₆) δ 1.93 (br s, 2H), 2.07 (br s, 2H), 3.25 (br s, 2H), 3.68 (br s, 4H), 4.47 (t, J=4.80 Hz, 2H), 6.76 (d, J=7.49 Hz, 1H), 6.90 (d, J=7.80 Hz, 1H), 7.02 (m, 1H), 7.31 (d, J=5.30 Hz, 2H), 7.37 (d, J=8.42 Hz, 2H), 7.59 (d, J=8.73 Hz, 2H), 7.74 (s, 1H), 9.10 (s, 1H), 9.15 (s, 1H).

Example 136

N-(4-{3-amino-7-[2-(1-pyrrolidinyl)ethoxy]-1H-indazol-4-yl}phenyl)-N'-[3-(trifluoromethyl)phenyl]urea The desired product was prepared as the bis(trifluoroacetate) salt by substituting Example 129A and 1-isocyanato-3-(trifluoromethyl)benzene for Example 15G and 1-fluoro-3-isocyanatobenzene, respectively, in Example 15H. MS (ESI (+)) m/e 525 (M+H)+; ¹H NMR (500 MHz, DMSO-d₆) δ 1.93 (br s, 2H), 2.07 (br s, 2H), 3.25 (br s, 2H), 3.68 (br s, 4H), 4.47 (t, J=4.80 Hz, 2H), 6.74 (d, J=7.80 Hz, 1H), 6.88 (d, J=7.80 Hz, 1H), 7.32 (d, J=7.80 Hz, 1H), 7.37 (d, J=8.42 Hz, 2H), 7.52 (t, J=7.80 Hz, 1H), 7.60 (d, J=8.42 Hz, 2H), 7.60 (d, J=6.55 Hz, 1H), 8.05 (s, 1H), 9.10 (s, 1H), 9.28 (s, 1H).

Example 137

N-(4-{3-amino-7-[2-(diethylamino)ethoxy]-1H-indazol-4-yl}phenyl)-N'-phenylurea

Example 137A 4-(4-aminophenyl)-7-[2-(diethylamino)ethoxy]-1H-indazol-3-amine

The desired product was prepared by substituting 2-(diethylamino)ethanol for 2-(4-morpholinyl)ethanol in Examples 75A and 75B. MS (ESI(+)) m/e 340 (M+H)+.

Example 137B

N-(4-{3-amino-7-[2-(diethylamino)ethoxy]-1H-indazol-4-yl}phenyl)-N'-phenylurea

The desired product was prepared as the bis(trifluoroacetate) salt by substituting Example 137A and isocyanatobenzene for Example 15G and 1-fluoro-3-isocyanatobenzene, respectively, in Example 15H. MS (ESI(+)) m/e 459 (M+H)+; ¹H NMR (500 MHz, DMSO-d₆) δ 1.27 (t, J=7.17 Hz, 6H), 3.33 (br s, 4H), 3.62 (br s, 2H), 4.49 (t, J=4.80 Hz, 2H), 6.74 (d, J=7.80 Hz, 1H), 6.88 (d, J=7.80 Hz, 1H), 6.98 (t, J=7.49 Hz, 1H), 7.29 (t, J=7.95 Hz, 2H), 7.36 (d, J=8.42 Hz, 2H), 7.48 (d, J=7.80 Hz, 2H), 7.58 (d, J=8.73 Hz, 2H), 8.83 (s, 1H), 8.91 (s, 1H).

Example 138

N-(4-{3-amino-7-[2-(diethylamino)ethoxy]-1H-indazol-4-yl}phenyl)-N'-(3-fluorophenyl)urea The desired product was prepared as the bis(trifluoroacetate salt) by substituting Example 137A for Example 15G in Example 15H. MS (ESI(+)) m/e 477 (M+H)+; ¹H NMR (500 MHz, DMSO-d₆) δ 1.27 (t, J=7.33 Hz, 6H), 3.34 (br s, 4H), 3.60 (br s, 2H), 4.49 (t, J=4.80 Hz, 2H), 6.76 (d, J=7.80 Hz, 1H), 6.79 (t, J=8.58 Hz, 1H), 6.89 (d, J=7.80 Hz, 1H), 7.15 (d, J=8.11 Hz, 1H), 7.31 (q, J=7.61 Hz, 1H), 7.37 (d, J=8.42 Hz, 2H), 7.52 (dt, J=11.93, 2.14 Hz, 1H), 7.59 (d, J=8.42 Hz, 2H), 9.02 (s, 1H), 9.11 (s, 1H).

Example 139

N-(4-{3-amino-7-[2-(diethylamino)ethoxy]-1H-indazol-4-yl}phenyl)-N'-(2-fluoro-5-methylphenyl)urea The desired product was prepared as the bis(trifluoroacetate salt) by substituting Example 137A and 1-fluoro-2-isocyanato-4-methylbenzene for Example 15G and 1-fluoro-3-isocyanatobenzene, respectively, in Example 15H. MS (ESI(+)) m/e 491 (M+H)+; ¹H NMR (500 MHz, DMSO-d₆) δ 1.27 (t, J=7.33 Hz, 6H), 2.28 (s, 3H), 3.33 (br d, J=8.42 Hz, 4H), 3.62 (br s, 2H), 4.49 (t, J=4.80 Hz, 2H), 6.75 (d, J=7.80 Hz, 1H), 6.80-6.82 (m, 1H), 6.89 (d, J=7.80 Hz, 1H), 7.11 (dd, J=11.38, 8.26 Hz, 1H), 7.37 (d, J=8.42 Hz, 2H), 7.58 (d, J=8.42 Hz, 2H), 7.99 (dd, J=7.95, 1.72 Hz, 1H), 8.54 (d, J=2.50 Hz, 1H), 9.22 (s, 1H).

Example 140

N-(4-{3-amino-7-[2-(diethylamino)ethoxy]-1H-indazol-4-yl}phenyl)-N'-(3-methylphenyl)urea The desired product was prepared as the bis(trifluoroacetate salt) by substituting Example 137A and 1-isocyanato-3-methylbenzene for Example 15G and 1-fluoro-3-isocyanatobenzene, respectively, in Example 15H. MS (ESI(+)) m/e 473 (M+H)$^+$; $^1$H NMR (500 MHz, DMSO-d$_6$) δ 1.27 (t, J=7.33 Hz, 6H), 2.29 (s, 3H), 3.34 (br s, 4H), 3.61 (br s, 2H), 4.49 (t, J=4.80 Hz, 2H), 6.74 (d, J=7.49 Hz, 1H), 6.80 (d, J=7.17 Hz, 1H), 6.88 (d, J=7.80 Hz, 1H), 7.16 (t, J=7.80 Hz, 1H), 7.26 (d, J=8.11 Hz, 1H), 7.32 (s, 1H), 7.35 (d, J=8.42 Hz, 2H), 7.58 (d, J=8.42 Hz, 2H), 8.72 (s, 1H), 8.87 (s, 1H).

Example 141

N-(4-{3-amino-7-[2-(diethylamino)ethoxy]-1H-indazol-4-yl}phenyl)-N'-(3-bromophenyl)urea The desired product was prepared as the bis(trifluoroacetate salt) by substituting Example 137A and 1-bromo-3-isocyanatobenzene for Example 15G and 1-fluoro-3-isocyanatobenzene, respectively, in Example 15H. MS (ESI(+)) m/e 537 and 539 (M+H)$^+$; $^1$H NMR (500 MHz, DMSO-d$_6$) δ 1.27 (t, J=7.33 Hz, 6H), 3.30-3.35 (m, 4H), 3.61 (br s, 2H), 4.49 (t, J=4.80 Hz, 2H), 6.75 (d, J=7.80 Hz, 1H), 6.88 (d, J=7.80 Hz, 1H), 7.16 (d, J=7.80 Hz, 1H), 7.25 (t, J=7.95 Hz, 1H), 7.33-7.35 (m, 1H), 7.36 (d, J=8.42 Hz, 2H), 7.59 (d, J=8.42 Hz, 2H), 7.89 (m, 1H), 9.05 (s, 1H), 9.09 (s, 1H).

Example 142

N-(4-{3-amino-7-[2-(diethylamino)ethoxy]-1H-indazol-4-yl}phenyl)-N'-[2-fluoro-5-(trifluoromethyl)phenyl]urea The desired product was prepared as the bis(trifluoroacetate) salt by substituting Example 137A and 1-fluoro-2-isocyanato-4-(trifluoromethyl)benzene for Example 15G and 1-fluoro-3-isocyanatobenzene, respectively, in Example 15H. MS (ESI(+)) m/e 545 (M+H)$^+$; $^1$H NMR (500 MHz, DMSO-d$_6$) δ 1.27 (t, J=7.17 Hz, 6H), 3.33 (br s, 4H), 3.62 (br s, 2H), 4.50 (t, J=4.80 Hz, 2H), 6.77 (d, J=7.80 Hz, 1H), 6.89 (d, J=7.80 Hz, 1H), 7.39 (m, J=8.42 Hz, 3H), 7.51 (t, J=9.85 Hz 1H), 7.60 (d, J=8.73 Hz, 2H), 8.64 (dd, J=7.17, 2.18 Hz, 1H), 8.97 (d, J=2.81 Hz, 1H), 9.35 (s, 1H).

Example 143

N-(4-{3-amino-7-[2-(diethylamino)ethoxy]-1H-indazol-4-yl}phenyl)-N'-(3-chlorophenyl)urea The desired product was prepared as the bis(trifluoroacetate) salt by substituting Example 137A and 1-chloro-3-isocyanatobenzene for Example 15G and 1-fluoro-3-isocyanatobenzene, respectively, in Example 15H. MS (ESI(+)) m/e 493 (M+H)$^+$; $^1$H NMR (500 MHz, DMSO-d$_6$) δ 1.27 (t, J=7.17 Hz, 6H), 3.34 (br s, 4H), 3.62 (br s, 2H), 4.49 (t, J=4.80 Hz, 2H), 6.75 (d, J=7.80 Hz, 1H), 6.88 (d, J=7.80 Hz, 1H), 7.02 (td, J=4.37, 2.18 Hz, 1H), 7.30-7.31 (m, 2H), 7.37 (d, J=8.42 Hz, 2H), 7.58 (d, J=8.42 Hz, 2H), 7.74 (s, 1H), 9.01 (s, 1H), 9.06 (s, 1H).

Example 144

N-(4-{3-amino-7-[2-(diethylamino)ethoxy]-1H-indazol-4-yl}phenyl)-N'-[3-(trifluoromethyl)phenyl]urea The desired product was prepared as the bis(trifluoroacetate) salt by substituting Example 137A and 1-isocyanato-3-(trifluoromethyl)benzene for Example 15G and 1-fluoro-3-isocyanatobenzene, respectively, in Example 15H. MS (ESI(+)) m/e 527 (M+H)$^+$; $^1$H NMR (500 MHz, DMSO-d$_6$) δ 1.27 (t, J=7.33 Hz, 6H), 3.32-3.34 (br s, 4H), 3.61 (br s, 2H), 4.49 (t, J=4.80 Hz, 2H), 6.75 (d, J=7.80 Hz, 1H), 6.88 (d, J=7.49 Hz, 1H), 7.31 (d, J=7.80 Hz, 1H), 7.37 (d, J=8.42 Hz, 2H), 7.52 (t, J=7.95 Hz, 1H), 7.60-7.61 (m, 3H), 8.05 (s, 1H), 9.12 (s, 1H), 9.30 (s, 1H).

Example 145

N-(4-{3-amino-7-[2-(3,4,4-trimethyl-2,5-dioxo-1-imidazolidinyl)ethoxy]-1H-indazol-4-yl}phenyl)-N'-(3-methylphenyl)urea

Example 145A 3-(2-{[3-amino-4-(4-aminophenyl)-1H-indazol-7-yl]oxy}ethyl)-1,5,5-trimethyl-2,4-imidazolidinedione The desired product was prepared by substituting 3-(2-hydroxyethyl)-1,5,5-trimethyl-2,4-imidazolidinedione for 2-(4-morpholinyl)ethanol in Examples 75A and 75B. $^1$H NMR (300 MHz, DMSO-d$_6$) δ 1.27 (s, 6H), 2.80 (s, 3H), 3.81 (t, J=6.27 Hz, 2H), 4.32 (t, J=6.27 Hz, 2H), 5.19 (s, 2H), 6.57 (d, J=7.80 Hz, 1H), 6.65 (d, J=8.14 Hz, 2H), 6.76 (d, J=7.80 Hz, 1H), 7.07 (d, J=8.14 Hz, 2H), 11.59 (s, 1H); MS (ESI(+)) m/e 409 (M+H)$^+$.

Example 145B

N-(4-{3-amino-7-[2-(3,4,4-trimethyl-2,5-dioxo-1-imidazolidinyl)ethoxy]-1H-indazol-4-yl}phenyl)-N'-(3-methylphenyl)urea The desired product was prepared by substituting Example 145A and 1-isocyanato-3-methylbenzene for Example 15G and 1-fluoro-3-isocyanatobenzene, respectively, in Example 15H then purifying the resulting producty by flash column chromatography on silica gel with 5-8% methanol/dichloromethane. $^1$H NMR (300 MHz, DMSO-d$_6$) δ 1.27 (s, 6H), 2.29 (s, 3H), 2.81 (s, 3H), 3.83 (t, J=5.93 Hz, 2H), 4.35 (t, J=5.93 Hz, 2H), 6.68 (d, J=7.80 Hz, 1H), 6.81 (t, J=7.46 Hz, 2H), 7.05-7.45 (m, 5H), 7.56 (d, J=8.48 Hz, 2H), 8.62 (s, 1H), 8.75 (s, 1H), 11.75 (s, 1H); MS (ESI(+)) m/e 542 (M+H)$^+$.

Example 146

N-(4-{3-amino-7-[2-(3,4,4-trimethyl-2,5-dioxo-1-imidazolidinyl)ethoxy]-1H-indazol-4-yl}phenyl)-N'-(3-chlorophenyl)urea The desired product was prepared by substituting Example 145A and 1-chloro-3-isocyanatobenzene for Example 15G and 1-fluoro-3-isocyanatobenzene, respectively, in Example 15H. $^1$H NMR (300 MHz, DMSO-d$_6$) δ 1.27 (s, 6H), 2.81 (s, 3H), 3.83 (t, J=6.27 Hz, 2H), 4.35 (t, J=6.44 Hz, 2H), 6.68 (d, J=7.80 Hz, 1H), 6.82 (d, J=7.80 Hz, 1H), 6.95-7.06 (m, 1H), 7.25-7.40 (m, 4H), 7.56 (d, J=8.81 Hz, 2H), 7.73 (s, 1H), 8.86 (s, 1H), 8.93 (s, 1H), 11.74 (s, 1H); MS (ESI(+)) m/e 562 (M+H)+.

Example 147

N-(4-{3-amino-7-[2-(3,4,4-trimethyl-2,5-dioxo-1-imidazolidinyl)ethoxy]-1H-indazol-4-yl}phenyl)-N'-(2-fluoro-5-methylphenyl)urea The desired product was prepared by substituting Example 145A and 1-fluoro-2-isocyanato-4-methylbenzene for Example 15G and 1-fluoro-3-isocyanatobenzene, respectively, in Example 15H then purifying the resulting producty by flash column chromatography on silica gel with 5-8% methanol/dichloromethane. $^1$H NMR (300 MHz, DMSO-$d_6$) δ 1.27 (s, 6H), 2.28 (s, 3H), 2.81 (s, 3H), 3.83 (t, J=6.27 Hz, 2H), 4.35 (t, J=6.27 Hz, 2H), 6.67 (d, J=7.80 Hz, 1H), 6.70-6.90 (m, 2H), 7.11 (dd, J=11.36, 8.31 Hz, 1H), 7.36 (d, J=8.48 Hz, 2H), 7.56 (d, J=8.48 Hz, 2H), 7.90-8.10 (dd, J=7.97, 1.86 Hz, 1H), 8.52 (d, J=2.71 Hz, 1H), 9.17 (s, 1H), 11.72 (s, 1H); MS (ESI(+)) m/e 560 (M+H)+.

Example 148

N-(4-{3-amino-7-[2-(3,4,4-trimethyl-2,5-dioxo-1-imidazolidinyl)ethoxy]-1H-indazol-4-yl}phenyl)-N'-[3-(trifluoromethyl)phenyl]urea The desired product was prepared by substituting Example 145A and 1-isocyanato-3-(trifluoromethyl)benzene for Example 15G and 1-fluoro-3-isocyanatobenzene, respectively, in Example 15H. $^1$H NMR (300 MHz, DMSO-$d_6$) δ 1.27 (s, 6H), 2.81 (s, 3H), 3.83 (t, J=6.27 Hz, 2H), 4.35 (t, J=6.44 Hz, 2H), 6.68 (d, J=7.80 Hz, 1H), 6.82 (d, J=8.14 Hz, 1H), 7.25-7.45 (m, 3H), 7.45-7.65 (m, 4H), 8.04 (s, 1H), 8.90 (s, 1H), 9.09 (s, 1H), 11.73 (s, 1H); MS (ESI(+)) m/e 596 (M+H)+.

Example 149

N-[4-(3-amino-1H-indazol-4-yl)-2-ethylphenyl]-N'-(2-fluoro-5-methylphenyl)urea

Example 149A

N-(4-bromo-2-ethylphenyl)-N'-(2-fluoro-5-methylphenyl)urea

A solution of 4-bromo-2-ethylaniline (200 mg) in dichloromethane (10 mL) was treated with 1-fluoro-2-isocyanato-4-methylbenzene (151 mg), stirred at room temperature overnight, diluted with hexanes, and filtered. The filter cake provided 227 mg of the desired product. MS (ESI(+)) m/e 351,353 (M+H)+.

Example 149B

N-[2-ethyl-4-(4,4,5,5-tetramethyl-1,3,2-dioxaborolan-2-yl)phenyl]-N'-(2-fluoro-5-methylphenyl)urea A mixture of Example 149A (219 mg, 0.62 mmol), 4,4,4',4',5,5,5',5'-octamethyl-2,2'-bi-1,3,2-dioxaborolane (190 mg, 0.75 mmol), potassium acetate (183 mg), and PdCl$_2$(dppf) .CH$_2$Cl$_2$ (15 mg) in DMF (6 mL) was degassed then heated to 80° C. for 2 hours. The mixture was used directly in the next reaction.

Example 149C

N-[4-(3-amino-1H-indazol-4-yl)-2-ethylphenyl]-N'-(2-fluoro-5-methylphenyl)urea

The desired product was prepared by substituting Example 149B and PdCl$_2$(dppf)-CH$_2$Cl$_2$ for Example 1B and Pd(PPh$_3$)$_4$, respectively, in Example 1C. Additionally, DMF was used in place of DME. $^1$H NMR (300 MHz, DMSO-$d_6$) δ 1.24 (t, J=7.46 Hz, 3H), 2.28 (s, 3H), 2.71 (q, J=7.46 Hz, 2H), 4.35 (s, 2H), 6.75-6.85 (m, 2H), 7.12 (dd, J=11.53, 8.14 Hz, 1H), 7.25-7.35 (m, 4H), 7.99 (d, J=8.14 Hz, 1H), 8.06 (dd, J=7.80, 2.03 Hz, 1H), 8.44 (s, 1H), 8.99 (d, J=2.03 Hz, 1H), 11.71 (s, 1H); MS (ESI(+)) m/e 404 (M+H)+.

Example 150

N-[4-(3-amino-1H-indazol-4-yl)-2-ethylphenyl]-N'-[3-(trifluoromethyl)phenyl]urea The desired product was prepared by substituting 1-isocyanato-3-(trifluoromethyl)benzene for 1-fluoro-2-isocyanato-4-methylbenzene in Examples 149A-C. $^1$H NMR (300 MHz, DMSO-$d_6$) δ 1.24 (t, J=7.46 Hz, 3H), 2.71 (q, J=7.69 Hz, 2H), 4.35 (s, 2H), 6.75-6.90 (m, 1H), 7.20-7.40 (m, 4H), 7.45-7.60 (m, 3H), 7.94 (d, J=8.14 Hz, 1H), 8.07 (s, 1H), 8.13 (s, 1H), 9.43 (s, 1H), 11.72 (s, 1H); MS (ESI(+)) m/e 440 (M+H)+.

Example 151

N-[4-(3-amino-7-fluoro-1H-indazol-4-yl)phenyl]-N'-(2-fluoro-5-methylphenyl)urea

The desired product was prepared as the trifluoroacetate salt by substituting Example 26B and 1-fluoro-2-isocyanato-4-methylbenzene for Example 15G and 1-fluoro-3-isocyanatobenzene, respectively, in Example 15H. $^1$H NMR (400 MHz, DMSO-$d_6$) δ 2.27 (s, 3H), 6.74-6.83 (m, 2H), 7.13 (m, 2H), 7.38 (d, J=8.29 Hz, 2H), 7.58 (d, J=8.59 Hz, 2H), 7.99 (d, J=6.44 Hz, 1H), 8.52 (d, J=2.45 Hz, 1H), 9.21 (s, 1H); MS (ESI(+)) m/e 394 (M+H)+.

Example 152

N-{4-[3-amino-7-fluoro-6-(hydroxymethyl)-1H-indazol-4-yl]phenyl}-N'-(2-fluoro-5-methylphenyl)urea Example 152A 2,3-difluoro-4-(hydroxymethyl)-6-iodobenzonitrile A −78° C. solution of Example 26A (5.0 g, 18.9 mmol) in THF was treated with LDA (2M in hexanes, 11.5 mL, 22.6 mmol), stirred for 1 hour at −78° C., treated with methyl formate (2.34 mL, 37.8 mmol), stirred at −78° C. for 30 minutes, warmed to 0° C. for 1 hour, quenched with saturated NH$_4$Cl and extracted three times with ethyl acetate. The combined extracts were washed with brine, dried (MgSO$_4$), filtered, and concentrated. The residue was immediately dissolved in ethanol (100 mL), cooled to 0° C., and treated portionwise with NaBH$_4$ (1.08 g). The reaction was stirred at 0° C. for 2 hours, quenched with acetone, stirred for 5 minutes, poured into water, and extracted three times with ethyl acetate. The combined extracts were washed with brine, dried (MgSO$_4$), filtered, and concentrated. The residue was purified by flash column chromatography on silica gel with 2:1 hexanes/ethyl acetate to give 1.02 g of the desired product. R$_f$=0.84 (ethyl acetate).

Example 152B (3-amino-7-fluoro-4-iodo-1H-indazol-6-yl)methanol

The desired product was prepared by substituting Example 152A for 2-fluoro-6-iodobenzonitrile in Example 1A. R$_f$=0.53 (ethyl acetate).

Example 152C

N-{4-[3-amino-7-fluoro-6-(hydroxymethyl)-1H-indazol-4-yl]phenyl}-N'-(2-fluoro-5-methylphenyl)urea A mixture of Example 152B (50 mg, 0.16 mmol), Example 5A (66 mg, 0.18 mmol), Pd(PPh$_3$)$_4$ (9 mg, 0.008 mmol), and Na$_2$CO$_3$ (43 mg, 0.4 mmol) in toluene (2 mL), ethanol (1 mL), and water (1 mL) was degassed and heated at 140° C. for 8 minutes with stirring using a Smith Synthesizer in a septa capped 5 mL process vial at 300 W. The samples were cooled using 40 psi pressurized air. The mixture was concentrated and the residue was purified by preparative HPLC on a Waters Symmetry C8 column (25 mm×100 mm, 7 µm particle size) using a gradient of 10% to 100% acetonitrile/0.1% aqueous TFA over 8 minutes (10 minute run time) at a flow rate of 40 mL/min to provide 26 mg of the desired product as the trifluoroacetate salt. $^1$H NMR (300 MHz, DMSO-d$_6$) δ 2.28 (s, 3H), 4.65 (d, J=1.36 Hz, 2H), 6.81 (m, 1H), 6.86 (d, J=5.76 Hz, 1H), 7.11 (dd, J=11.36, 8.31 Hz, 1H), 7.39 (d, J=8.48 Hz, 2H), 7.59 (d, J=8.48 Hz, 2H), 8.01 (dd, J=7.80, 2.03 Hz, 1H), 8.53 (d, J=2.37 Hz, 1H), 9.21 (s, 1H); MS (ESI(+)) m/e 424 (M+H)$^+$.

Example 153

N-{4-[3-amino-7-fluoro-6-(hydroxymethyl)-1H-indazol-4-yl]phenyl}-N'-[3-(trifluoromethyl)phenyl]urea The desired product was prepared as the trifluoroacetate salt by substituting Example 98A for Example 5A in Example 152C. $^1$H NMR (300 MHz, DMSO-d$_6$) δ 4.65 (d, J=1.70 Hz, 2H), 6.87 (d, J=5.76 Hz, 1H), 7.32 (d, J=7.46 Hz, 1H), 7.39 (d, J=8.48 Hz, 2H), 7.53 (t, J=7.97 Hz, 1H), 7.58-7.64 (m, 3H), 8.04 (s, 1H), 8.99 (s, 1H), 9.14 (s, 1H); MS (ESI(+)) m/e 460 (M+H)$^+$; Anal. calcd. for C$_{22}$H$_{17}$F$_4$N$_5$O$_2$.1.0CF$_3$CO$_2$H: C, 50.27; H, 3.15; N, 12.21;
Found: C, 50.15; H, 3.15; N, 12.41.

Example 154

N-{4-[3-amino-7-fluoro-6-(hydroxymethyl)-1H-indazol-4-yl]phenyl}-N'-(3-chlorophenyl)urea The desired product was prepared as the trifluoroacetate salt by substituting N-(3-chlorophenyl)-N'-[4-(4,4,5,5-tetramethyl-1,3,2-dioxaborolan-2-yl)phenyl]urea for Example 5A in Example 152C. $^1$H NMR (300 MHz, DMSO-d$_6$) δ 4.65 (d, J=1.36 Hz, 2H), 6.86 (d, J=5.76 Hz, 1H), 7.03 (td, J=4.41, 2.03 Hz, 1H), 7.27-7.36 (m, 2H), 7.39 (d, J=8.48 Hz, 2H), 7.60 (d, J=8.48 Hz, 2H), 7.74 (m, 1H), 8.93 (s, 1H), 8.96 (s, 1H); MS (ESI(+)) m/e 426 (M+H)$^+$.

Example 155

N-{4-[3-amino-7-fluoro-6-(hydroxymethyl)-1H-indazol-4-yl]phenyl}-N'-(3-methylphenyl)urea The desired product was prepared as the trifluoroacetate salt by substituting Example 1B for Example 5A in Example 152C. $^1$H NMR (300 MHz, DMSO-d$_6$) δ 2.29 (s, 3H), 4.65 (d, J=1.36 Hz, 2H), 6.80 (d, J=7.46 Hz, 1H), 6.84 (d, J=5.76 Hz, 1H), 7.17 (t, J=7.80 Hz, 1H), 7.25 (d, J=7.80 Hz, 1H), 7.32 (s, 1H), 7.37 (d, J=8.48 Hz, 2H), 7.59 (d, J=8.48 Hz, 2H), 8.64 (s, 1H), 8.80 (s, 1H); MS (ESI(+)) m/e 406 (M+H)$^+$.

Example 156

N-{4-[3-amino-7-fluoro-6-(hydroxymethyl)-1H-indazol-4-yl]phenyl}-N'-(3-fluorophenyl)urea The desired product was prepared as the trifluoroacetate salt by substituting N-(3-fluorophenyl)-N'-[4-(4,4,5,5-tetramethyl-1,3,2-dioxaborolan-2-yl)phenyl]urea for Example 5A in Example 152C. $^1$H NMR (300 MHz, DMSO-d$_6$) δ 4.65 (d, J=1.02 Hz, 2H), 6.80 (td, J=8.65, 2.71 Hz, 1H), 6.84 (d, J=5.76 Hz, 1H), 7.14 (d, J=9.16 Hz, 1H), 7.32 (m, 1H), 7.38 (d, J=8.48 Hz, 2H), 7.51 (dt, J=11.87, 2.20 Hz, 1H), 7.59 (d, J=8.48 Hz, 2H), 12.13 (s, 1H); MS (ESI(+)) m/e 410 (M+H)$^+$.

Example 157

N-(4-{3-amino-6-[(diethylamino)methyl]-7-fluoro-1H-indazol-4-yl}phenyl)-N'-(2-fluoro-5-methylphenyl)urea Example 157A 4-[(diethylamino)methyl]-2,3-difluoro-6-iodobenzonitrile A 0° C. solution of Example 152A (350 mg, 1.18 mmol) in dichloromethane (10 mL) was treated with triethylamine (0.25 mL, 1.78 mmol) and methanesulfonyl chloride (0.1 mL, 1.3 mmol), stirred at 0° C. for 1 hour, treated with diethylamine (0.245 mL, 2.37 mmol), and overnight at room temperature. The mixture was partitioned between 1N NaOH and dichloromethane and the organic extract was dried (MgSO$_4$), filtered, and concentrated. The residue was purified by flash column chromatography on silica gel with 3:1 hexanes/ethyl acetate to provide 0.263 g of the desired product. MS (ESI(+)) 351 (M+H)$^+$.

Example 157B

6-[(diethylamino)methyl]-7-fluoro-4-iodo-1H-indazol-3-amine

The desired product was prepared by substituting Example 157A for 2-fluoro-6-iodobenzonitrile in Example 1A. MS (ESI(+)) 363 (M+H)$^+$.

Example 157C

N-(4-{3-amino-6-[(diethylamino)methyl]-7-fluoro-1H-indazol-4-yl}phenyl)-N'-(2-fluoro-5-methylphenyl)urea The desired product was prepared as the trifluoroacetate salt by substituting Example 157B for Example 152B in Example 152C. ¹H NMR (300 MHz, DMSO-d₆) δ 1.27 (t, J=7.29 Hz, 6H), 2.28 (s, 3H), 3.18 (m, 4H), 4.48 (d, J=4.75 Hz, 2H), 6.82 (ddd, J=7.71, 5.17, 2.03 Hz, 1H), 6.94 (d, J=5.76 Hz, 1H), 7.12 (dd, J=11.36, 8.31 Hz, 1H), 7.44 (d, J=8.48 Hz, 2H), 7.63 (d, J=8.82 Hz, 2H), 7.99 (dd, J=7.97, 1.87 Hz, 1H), 8.56 (d, J=2.71 Hz, 1H), 9.27 (s, 1H), 9.36 (br s, 1H); MS (ESI(+) 477 (M+H)⁺.

Example 158

N-(4-{3-amino-6-[(diethylamino)methyl]-7-fluoro-1H-indazol-4-yl}phenyl)-N'-[3-(trifluoromethyl)phenyl]urea The desired product was prepared as the trifluoroacetate salt by substituting Example 157B and Example 98A for Example 152B and Example 5A, respectively, in Example 152C. ¹H NMR (300 MHz, DMSO-d₆) δ 1.27 (t, J=7.29 Hz, 6H), 3.18 (m, 4H), 4.48 (d, J=4.75 Hz, 2H), 6.94 (d, J=5.76 Hz, 1H), 7.33 (d, J=7.80 Hz, 1H), 7.44 (d, J=8.48 Hz, 2H), 7.53 (t, J=7.80 Hz, 1H), 7.60 (m, 1H), 7.65 (d, J=8.48 Hz, 2H), 8.06 (s, 1H), 9.14 (s, 1H), 9.27 (s, 1H), 9.34 (br s, 1H); MS (ESI(+)) m/e 515 (M+H)⁺.

Example 159

N-(4-{3-amino-6-[(diethylamino)methyl]-7-fluoro-1H-indazol-4-yl}phenyl)-N'-(3-chlorophenyl)urea The desired product was prepared as the trifluoroacetate salt by substituting Example 157B and N-(3-chlorophenyl)-N'-[4-(4,4,5,5-tetramethyl-1,3,2-dioxaborolan-2-yl)phenyl]urea for Example 152B and Example 5A, respectively, in Example 152C. ¹H NMR (300 MHz, DMSO-d₆) δ 1.27 (t, J=7.29 Hz, 6H), 3.19 (m, 4H), 4.48 (d, J=4.75 Hz, 2H), 6.94 (d, J=5.76 Hz, 1H), 7.03 (dt, J=6.44, 2.20 Hz, 1H), 7.27-7.37 (m, 2H), 7.44 (d, J=8.82 Hz, 2H), 7.63 (d, J=8.48 Hz, 2H), 7.75 (m, 1H), 9.06 (s, 1H), 9.32 (br s, 1H); MS (ESI(+)) m/e 481 (M+H)⁺.

Example 160

N-(4-{3-amino-6-[(diethylamino)methyl]-7-fluoro-1H-indazol-4-yl}phenyl)-N'-(3-methylphenyl)urea The desired product was prepared as the trifluoroacetate salt by substituting Example 157B and Example 1B for Example 152B and Example 5A, respectively, in Example 152C. ¹H NMR (300 MHz, DMSO-d₆) δ 1.27 (t, J=7.12 Hz, 6H), 2.29 (s, 3H), 3.18 (m, 4H), 4.48 (d, J=4.75 Hz, 2H), 6.81 (d, J=7.12 Hz, 1H), 6.94 (d, J=5.76 Hz, 1H), 7.17 (t, J=7.80 Hz, 1H), 7.26 (m, 1H), 7.32 (s, 1H), 7.42 (d, J=8.48 Hz, 2H), 7.63 (d, J=8.48 Hz, 2H), 8.74 (s, 1H), 8.93 (s, 1H), 9.34 (br s, 1H); MS (ESI(+)) m/e 461 (M+H)⁺.

Example 161

N-(4-{3-amino-7-[(3-pyridinyloxy)methyl]-1H-indazol-4-yl}phenyl)-N'-[3-(trifluoromethyl)phenyl]urea

Example 161A 4-iodo-7-[(3-pyridinyloxy)methyl]-1H-indazol-3-amine

The desired product was prepared by substituting 3-pyridinol for morpholine in Examples 15E-F.

Example 161B

N-(4-{3-amino-7-[(3-pyridinyloxy)methyl]-1H-indazol-4-yl}phenyl)-N'-[3-(trifluoromethyl)phenyl]urea The desired product was prepared by substituting Example 161A and Example 98A for Example 152B and Example 5A, respectively, in Example 152C then purifying the resulting producty by flash column chromatography on silica gel with 5-8% methanol/dichloromethane. ¹H NMR (500 MHz, DMSO-d₆) δ 4.38 (s, 2H), 5.40 (s, 2H), 7.32 (d, J=7.17 Hz, 1H), 7.34-7.38 (m, 2H), 7.42 (d, J=8.42 Hz, 2H), 7.52 (dd, J=15.59, 7.80 Hz, 2H), 7.58-7.64 (m, 4H), 8.04 (s, 1H), 8.19 (d, J=4.68 Hz, 1H), 8.39 (d, J=2.50 Hz, 1H), 8.96 (s, 1H), 9.12 (s, 1H), 11.92 (s, 1H); MS (ESI(+)) m/e 519 (M+H)⁺.

Example 162

N-(4-{3-amino-1-[2-(4-morpholinyl)ethyl]-1H-indazol-4-yl}phenyl)-N'-(2-fluoro-5-methylphenyl)urea

Example 162A 2-(4-iodo-1H-indazol-3-yl)-1H-isoindole-1,3(2H)-dione

A mixture of Example 1A (1.09 g) and phthalic anhydride (0.75 g) in dioxane (15 mL) was stirred overnight at 120° C. and concentrated. The residue was triturated from diethyl ether (15 mL) to provide 0.51 g of the desired product. MS (ESI(+)) m/e 388 (M+H)⁺.

Example 162B

2-{4-iodo-1-[2-(4-morpholinyl)ethyl]-1H-indazol-3-yl}-1H-isoindole-1,3(2H)-dione A mixture of Example 162A (100 mg), 4-(2-chloroethyl)morpholine (48 mg), and Na₂CO₃ (82 mg) in DMF (5 mL) was heated overnight at 80° C., cooled to room temperature, and partitioned between 1N HCl and ethyl acetate. The aqueous layer was basified with 1N KOH and extracted with ethyl acetate. The extract was dried (MgSO₄), filtered, and concentrated to provide 45 mg of the desired product. MS (ESI(+)) m/e 503 (M+H)⁺.

Example 162C 4-iodo-1-[2-(4-morpholinyl)ethyl]-1H-indazol-3-amine

A mixture of hydrazine hydrate (0.058 mL) and Example 162B (120 mg, 0.24 mmol) in ethanol (5 mL) was stirred at 0° C. for 3 hours and concentrated. The residue was purified by flash column chromatography on silica gel with 5-8% methanol/dichloromethane to provide 95 mg of the desired product.

Example 162D

N-(4-{3-amino-1-[2-(4-morpholinyl)ethyl]-1H-indazol-4-yl}phenyl)-N'-(2-fluoro-5-methylphenyl)urea The desired product was prepared as the bis(trifluoroacetate) salt by substituting Example 162C for Example 152B in Example 152C. MS (ESI(+)) m/e 489 (M+H)⁺; ¹H NMR (300 MHz, DMSO-d₆) δ 2.28 (s, 3H), 2.45 (d, J=4.07 Hz, 4H), 2.68 (t, J=6.61 Hz, 2H), 3.54 (t, J=4.05 Hz, 4H), 4.26 (t, J=6.44 Hz, 2H), 4.41 (s, 2H), 6.78-6.83 (d, J=6.78 Hz, 2H), 7.11 (dd, J=11.36, 8.31 Hz, 1H), 7.31 (t, J=8.48 Hz, 1H), 7.36-7.41 (m, 3H), 7.59 (d, J=8.48 Hz, 2H), 8.01 (d, J=7.46 Hz, 1H), 8.54 (s, 1H), 9.21 (s, 1H).

Example 163

N-(4-{3-amino-1-[2-(4-morpholinyl)ethyl]-1H-indazol-4-yl}phenyl)-N'-(3-fluorophenyl)urea The desired product was prepared as the bis(trifluoroacetate) salt by substituting 162C for Example 15F in Examples 15G-H. MS (ESI(+)) m/e 475 (M+H)$^+$; $^1$H NMR (500 MHz, DMSO-d$_6$) δ 3.58 (t, J=5.77 Hz, 2H), 3.32-3.83 (br m, 8H), 4.55 (t, J=6.24 Hz, 2H), 6.79 (td, J=8.42, 1.87 Hz, 1H), 6.88 (d, J=6.55 Hz, 1H), 7.15 (dd, J=8.26, 1.09 Hz, 1H), 7.29-7.34 (m, 1H), 7.38-7.42 (m, J=8.11, 8.11 Hz, 3H), 7.48 (d, J=8.11 Hz, 1H), 7.52 (dt, J=11.85, 2.18 Hz, 1H), 7.62 (d, J=8.73 Hz, 2H), 9.06 (s, 1H), 9.12 (s, 1H).

Example 164

N-(4-{3-amino-1-[2-(4-morpholinyl)ethyl]-1H-indazol-4-yl}phenyl)-N'-(3-chlorophenyl)urea The desired product was prepared as the bis(trifluoroacetate) salt by substituting Example 162C and 1-chloro-3-isocyanatobenzene for Example 15F and 1-fluoro-3-isocyanatobenzene, respectively, in Examples 15G-H. MS (ESI (+)) m/e 491 (M+H)$^+$; $^1$H NMR (500 MHz, DMSO-d$_6$) δ 3.58 (t, J=5.92 Hz, 2H), 3.38-3.92 (br m, 8H), 4.55 (t, J=6.39 Hz, 2H), 6.88 (d, J=6.86 Hz, 1H), 7.02-7.04 (m, 1H), 7.31-7.32 (m, 2H), 7.38-7.41 (m, J=7.95, 7.95 Hz, 3H), 7.48 (d, J=8.11 Hz, 1H), 7.62 (d, J=8.73 Hz, 2H), 7.74 (s, 1H), 9.09 (s, 1H), 9.11 (s, 1H).

Example 165

N-(4-{3-amino-1-[2-(4-morpholinyl)ethyl]-1H-indazol-4-yl}phenyl)-N'-[3-(trifluoromethyl)phenyl]urea The desired product was prepared as the bis(trifluoroacetate) salt by substituting Example 162C and 1-isocyanato-3-(trifluoromethyl)benzene for Example 15F and 1-fluoro-3-isocyanatobenzene, respectively, in Examples 15G-H. MS (ESI(+)) m/e 525 (M+H)$^+$; $^1$H NMR (500 MHz, DMSO-d$_6$) δ 3.32-3.83 (br m, 8H), 3.58 (t, J=5.77 Hz, 2H), 4.55 (t, J=6.39 Hz, 2H), 6.88 (d, J=7.17 Hz, 1H), 7.32 (d, J=7.80 Hz, 1H), 7.39-7.42 (m, 3H), 7.48 (d, J=8.42 Hz, 1H), 7.53 (t, J=7.95 Hz, 1H), 7.61 (d, J=8.73 Hz, 1H), 7.64 (d, J=8.73 Hz, 2H), 8.05 (s, 1H), 9.15 (s, 1H), 9.29 (s, 1H).

Example 166

N-(4-{3-amino-1-[2-(4-morpholinyl)ethyl]-1H-indazol-4-yl}phenyl)-N'-(3-methylphenyl)urea The desired product was prepared as the bis(trifluoroacetate) salt by substituting Example 162C and 1-isocyanato-3-methylbenzene for Example 15F and 1-fluoro-3-isocyanatobenzene, respectively, in Examples 15G-H. MS (ESI(+)) m/e 471 (M+H)$^+$; $^1$H NMR (500 MHz, DMSO-d$_6$) δ 2.29 (s, 3H), 3.58 (t, J=5.77 Hz, 2H), 3.39-3.88 (br m, 8H), 4.55 (t, J=6.39 Hz, 2H), 6.80 (d, J=7.49 Hz, 1H), 6.87 (d, J=6.86 Hz, 1H), 7.17 (t, J=7.80 Hz, 1H), 7.26 (d, J=8.42 Hz, 1H), 7.32 (s, 1H), 7.37-7.41 (m, 3H), 7.48 (d, J=8.11 Hz, 1H), 7.61 (d, J=8.42 Hz, 2H), 8.75 (s, 1H), 8.93 (s, 1H).

Example 167-I and 167-II

N-[4-(3-amino-6-bromo-1H-indazol-4-yl)phenyl]-N'-(3-methylphenyl)urea and N-[4-(3-amino-4-bromo-1H-indazol-6-yl)phenyl]-N'-(3-methylphenyl)urea

Example 167A 2,4-dibromo-6-fluorobenzonitrile

The desired product was prepared by substituting 2,4-dibromo-6-fluorobenzoic acid (prepared as described in Tetrahedron Lett. 1996, 37, 6551-6554) for Example 15A in Examples 15B and 15C.

Example 167B 4,6-dibromo-1H-indazol-3-amine

The desired product was prepared by substituting Example 167A for 2-fluoro-6-iodobenzonitrile in Example 1A. $^1$H NMR (DMSO-d$_6$) δ 11.99 (1H, br s), 7.48 (1H, d, J=1.6 Hz), 7.24 (1H, s), 5.22 (1H, d, J=8.0 Hz).

Example 167-I and 167-II

N-[4-(3-amino-6-bromo-1H-indazol-4-yl)phenyl]-N'-(3-methylphenyl)urea and N-[4-(3-amino-4-bromo-1H-indazol-6-yl)phenyl]-N'-(3-methylphenyl)urea A mixture of Example 167B (0.060 g, 0.021 mmol), Example 1B (0.073 g, 0.21 mmol), Na$_2$CO$_3$ (0.052 g, 0.49 mmol), and Pd(PPh$_3$)$_4$ (0.014 g, 0.012 mmol) in 2:1 DME/water (1.2 mL) was heated to 85° C. in a sealed tube overnight. The reaction was treated with additional Pd(PPh$_3$)$_4$ (0.028 g, 0.024 mmol), heated for two days, treated with additional catalyst (0.028 g, 0.024 mmol), heated to 160° C. for 2 hours, and cooled to room temperature. The mixture was diluted with ethyl acetate and dichloromethane, filtered, and concentrated. The concentrate was purified by flash column chromatography on silica gel with methanol/dichloromethane (2:100 to 5:100), then purified by preparative HPLC with 30-100% CH$_3$CN/5 mM ammonium acetate buffer over 9 minutes to provide the desired products.

Example 167-I

LC/MS 434.2 (M−H)$^-$, LC retention time 3.00 min. $^1$H NMR (DMSO-d$_6$) δ 7.508 (2H, d, J=8.4 Hz), 7.454 (1H, d, J=1.2 Hz), 7.407 (2H, d, J=8.4 Hz), 7.325 (1H, s), 7.257 (1H, d, J=6.0 Hz), 7.166 (1H, m), 6.888 (1H, s), 6.799 (1H, d, J=7.6 Hz), 4.397 (2H, s), 2.328 (3H, s).

Example 167-II

LC/MS 434.0 (M−H)$^-$, LC retention time 2.87 min. $^1$H NMR (DMSO-d$_6$) δ 11.88 (1H, br s), 8.961 (1H, br s), 8.782 (1H, br s), 7.637 (2H, d, J=8.8 Hz), 7.560 (1H, d, J=8.8 Hz), 7.414 (2H, d, J=1.2 Hz), 7.352 (1H, d, J=1.2 Hz), 7.319 (1H, s), 7.252 (1H, d, J=7.6 Hz), 7.181-7.142 (1H, m), 6.796 (1H, d, J=7.6 Hz), 5.147 (2H, d, J=9.2 Hz), 2.285 (3H, s).

Example 168

N-(4-{3-amino-1-[2-(dimethylamino)ethyl]-1H-indazol-4-yl}phenyl)-N'-(2-fluoro-5-methylphenyl)urea The desired product was prepared as the bis(trifluoroacetate) salt by substituting N-(2-chloroethyl)-N,N-dimethylamine for 4-(2-chloroethyl)morpholine in Example 162. MS (ESI(+)) m/e 447 (M+H)$^+$; $^1$H NMR (300 MHz, DMSO-d$_6$) δ 2.28 (s, 3H), 2.87 (s, 3H), 2.88 (s, 3H), 3.54 (q, J=5.65 Hz, 2H), 4.52 (t, J=6.10 Hz, 2H), 6.79-6.84 (m, 1H), 6.88 (d, J=6.10 Hz, 1H), 7.12 (dd, J=11.36, 8.31 Hz, 1H), 7.37-7.42 (m, 3H), 7.50 (d, J=7.79 Hz, 2H), 7.61 (d, J=8.48 Hz, 2H), 7.99 (dd, J=8.14, 2.03 Hz, 1H), 8.55 (d, J=2.37 Hz, 1H), 9.24 (s, 1H).

Example 169

N-(4-{3-amino-1-[2-(dimethylamino)ethyl]-1H-indazol-4-yl}phenyl)-N'-(3-chlorophenyl)urea

Example 169A

1-[2-(dimethylamino)ethyl]-4-iodo-1H-indazol-3-amine

The desired product was prepared by substituting N-(2-chloroethyl)-N,N-dimethylamine for 4-(2-chloroethyl)morpholine in Example 162A-C.

Example 169B

N-(4-{3-amino-1-[2-(dimethylamino)ethyl]-1H-indazol-4-yl}phenyl)-N'-(3-chlorophenyl)urea The desired product was prepared as the bis(trifluoroacetate) salt by substituting Example 169A and N-(3-chlorophenyl)-N'-[4-(4,4,5,5-tetramethyl-1,3,2-dioxaborolan-2-yl)phenyl]urea for Example 152B (50 mg, 0.16 mmol) and Example 5A, respectively, in Example 152C. MS (ESI(+)) m/e 449 (M+H)$^+$; $^1$H NMR (300 MHz, DMSO-d$_6$) δ 2.87 (s, 3H) 2.88 (s, 3H) 3.55 (q, J=5.65 Hz, 2H) 4.52 (t, J=6.27 Hz, 2H) 6.87 (dd, J=6.95, 0.85 Hz, 1H) 7.01-7.05 (m, 1H) 7.30-7.32 (m, 2H) 7.38-7.42 (m, 3H) 7.50 (d, J=8.48 Hz, 1H) 7.61 (d, J=8.48 Hz, 2H) 7.73-7.75 (m, 1H) 9.01 (s, 1H) 9.04 (s, 1H).

Example 170

N-[2-({3-amino-4-[4-({[(2-fluoro-5-methylphenyl)amino]carbonyl}amino)phenyl]-1H-indazol-7-yl}oxy)ethyl]methanesulfonamide

Example 170A tert-butyl 2-(3-cyano-2-fluoro-4-iodophenoxy)ethylcarbamate

The desired product was prepared by substituting tert-butyl 2-hydroxyethylcarbamate for 2-(4-morpholinyl)ethanol in Example 75A. R$_f$=0.8 (1:1 ethyl acetate/hexanes).

Example 170B

N-[2-(3-cyano-2-fluoro-4-iodophenoxy)ethyl]methanesulfonamide

A mixture of Example 170A (317 mg, 0.78 mmol) in TFA (1 mL) and CH$_2$Cl$_2$ (1 mL) was stirred at room temperature for 10 minutes and concentrated. The residue was partitioned between saturated NaHCO$_3$ and dichloromethane. The aqueous phase was extracted twice with dichloromethane and the combined organic extracts were dried (Na$_2$SO$_4$), filtered, and concentrated. The concentrate was dissolved in pyridine (5 mL), treated with methanesulfonyl chloride (0.07 mL), stirred at room temperature for 6 hours, concentrated, and partitioned between ethyl acetate and 1N HCl. The organic extract was dried (Na$_2$SO$_4$), filtered, and concentrated to provide the desired product. MS (ESI) m/e 383 (M–H)$^-$.

Example 170C

N-{2-[(3-amino-4-iodo-1H-indazol-7-yl)oxy]ethyl}methanesulfonamide

The desired product was prepared by substituting Example 170B for 2-fluoro-6-iodobenzonitrile in Example 1A.

Example 170D

N-[2-({3-amino-4-[4-({[(2-fluoro-5-methylphenyl)amino]carbonyl}amino)phenyl]-1H-indazol-7-yl}oxy)ethyl]methanesulfonamide The desired product was prepared as the trifluoroacetate salt by substituting Example 170C for Example 152B in Example 152C. MS (APCI(+)) m/e 513 (M+H)$^+$; $^1$H NMR (300 MHz, DMSO-d$_6$) δ 2.28 (s, 3H) 2.99 (s, 3H) 3.43 (q, J=5.76 Hz, 2H) 4.22 (t, J=5.42 Hz, 2H) 4.35 (s, 2H) 6.70 (d, J=7.46 Hz, 1H) 6.80 (d, J=7.80 Hz, 1H) 6.80-6.83 (m, 1H) 7.08-7.19 (m, 2H) 7.37 (d, J=8.81 Hz, 2H) 7.56 (d, J=8.81 Hz, 2H) 8.01 (dd, J=7.97, 1.86 Hz, 1H) 8.52 (d, J=2.37 Hz, 1H) 9.17 (s, 1H) 11.77 (s, 1H).

Example 171

4-(1H-indol-5-yl)-1H-indazol-3-amine

The desired product was prepared by substituting 5-indolylboronic acid and Example 1A for 4-(4,4,5,5-tetramethyl-1,3,2-dioxaborolan-2-yl)aniline and Example 15F, respectively, in Example 15G. $^1$H NMR (300 MHz, DMSO-d$_6$) δ 4.28 (s, 2H), 6.50 (ddd, J=3.05, 2.03, 0.68 Hz, 1H), 6.80 (dd, J=6.27, 1.53 Hz, 1H), 7.18 (dd, J=8.14, 1.70 Hz, 1H), 7.25 (m, 2H), 7.43 (m, 1H), 7.51 (d, J=8.14 Hz, 1H), 7.60 (m, 1H), 11.23 (s, 1H), 11.63 (s, 1H); MS (ESI(+)) m/e 249 (M+H)$^+$.

Example 172

N-{4-[3-amino-1-(2-methoxyethyl)-1H-indazol-4-yl]phenyl}-N'-(2-fluoro-5-methylphenyl)urea

Examples 172A and 172B

2-[4-iodo-2-(2-methoxyethyl)-2H-indazol-3-yl]-1H-isoindole-1,3(2H)-dione and 2-[4-iodo-1-(2-methoxyethyl)-1H-indazol-3-yl]-1H-isoindole-1,3(2H)-dione A mixture of Example 162A (1.2 g, 3.1 mmol), 1-bromo-2-methoxyethane (0.35 mL, 3.7 mmol) and K$_2$CO$_3$ (857 mg, 6.2 mmol) in DMF (15 mL) was stirred overnight at rt, then concentrated to dryness. The residue was partitioned between EtOAc and H$_2$O. The extract was dried (Na$_2$SO$_4$) and concentrated, and the residue was purified by flash chromatography on silica gel, eluting with 2% MeOH/CH$_2$Cl$_2$. The product was obtained as a mixture of Examples 172A and 172B (~3:1).

Example 172C and 172D 4-iodo-1-(2-methoxyethyl)-1H-indazol-3-amine and 4-iodo-2-(2-methoxyethyl)-1H-indazol-3-amine A mixture of the isomers 172A and 172B (970 mg, 2.2 mmol) was dissolved in EtOH (10 mL) and the solution was chilled to 0° C. and treated dropwise with hydrazine monohydrate (0.58 mL), then stirred for 3 h at rt. The mixture was concentrated to dryness and the residue was purified by flash chromatography on silica gel, eluting with 0-4% MeOH/CH$_2$Cl$_2$. A mixture of isomers 172C and 172D was obtained. MS (ESI(+)) m/e 317.8 (M+H)$^+$.

Example 172E and 172F 4-(4-aminophenyl)-1-(2-methoxyethyl)-1H-indazol-3-amine and 4-(4-aminophenyl)-2-(2-methoxyethyl)-1H-indazol-3-amine A mixture of Examples 172E and 172F was prepared by substituting a mixture of Examples 172C and 172D for Example 15F in Example 15G. MS (ESI(+)) m/e 283.0 (M+H)$^+$.

Example 172G

N-{4-[3-amino-1-(2-methoxyethyl)-1H-indazol-4-yl]phenyl}-N'-(2-fluoro-5-methylphenyl)urea The desired product was obtained by substituting a mixture of Examples 172E and 172F for Example 15G and 1-fluoro-2-isocyanato-4-methylbenzene for 1-fluoro-3-isocyanatobenzene in Example 15H. Additionally, DMF was used in place of CH$_2$Cl$_2$. The mixture was concentrated and the residue was purified by preparative HPLC as in example 3 to provide the desired product as the trifluoroacetate salt. $^1$H NMR (300 MHz, DMSO-D$_6$) δ ppm 2.28 (s, 3H) 3.21 (s, 3H) 3.69 (t, J=5.4 Hz, 2H) 4.32 (t, J=5.4 Hz, 2H) 6.79-6.84 (m, 2H) 7.12 (dd, J=11.4, 8.3 Hz, 1H) 7.31 (dd, J=8.5, 6.8 Hz, 1H) 7.38-7.43 (m, 3H) 7.59 (d, J=8.5 Hz, 2H) 8.01 (dd, J=7.8, 2.0 Hz, 1H) 8.54 (d, J=2.4 Hz, 1H) 9.21 (s, 1H) MS (ESI(+)) m/e 434.0 (M+H)$^+$.

Example 174

N-(4-{3-amino-7-[2-(3,4,4-trimethyl-2,5-dioxoimidazolidin-1-yl)ethoxy]-1H-indazol-4-yl}phenyl)-N'-(3,5-dimethylphenyl)urea The desired product was prepared by substituting Example 145A and 1-isocyanato-3,5-dimethylbenzene for Example 15G and 1-fluoro-3-isocyanatobenzene, respectively, in Example 15H. The product was purified by preparative HPLC as in example 3. $^1$H NMR (300 MHz, DMSO-D$_6$) δ ppm 1.27 (s, 6H) 2.24 (s, 6H) 2.81 (s, 3H) 3.83 (t, J=6.4 Hz, 2H) 4.35 (t, J=6.4 Hz, 2H) 6.62 (s, 1H) 6.68 (d, J=7.8 Hz, 1H) 6.83 (d, J=7.8 Hz, 1H) 7.09 (s, 2H) 7.34 (d, J=8.8 Hz, 2H) 7.55 (d, J=8.8 Hz, 2H) 8.54 (s, 1H) 8.74 (s, 1H) 11.75-11.85 (br. s., 1H) MS (ESI(+)) m/e 556.3 (M+H)$^+$.

Example 175

N-[4-(3-amino-1H-indazol-4-yl)-2,6-dimethylphenyl]-N'-(2-fluoro-5-methylphenyl)urea The desired product was prepared by substituting 4-bromo-2,6-dimethylaniline for 4-bromo-2-ethylaniline in Examples 149A-C. $^1$H NMR (300 MHz, DMSO-D$_6$) δ ppm 2.25 (s, 3H) 2.30 (s, 6H) 6.77-6.80 (m, 1H) 6.87 (dd, J=5.8, 2.4 Hz, 1H) 7.10 (dd, J=11.5, 8.5 Hz, 1H) 7.20 (s, 2H) 7.33 (s, 1H) 7.35 (d. J=3.4 Hz, 1H) 7.98 (d, J=6.8 Hz, 1H) 8.23 (s, 1H) 8.54-8.65 (br. s., 1H) 11.99-12.20 (br. s., 1H) MS (ESI(+)) m/e 404.2 (M+H)$^+$.

Example 176

N-[4-(3-amino-1H-indazol-4-yl)-2,6-dimethylphenyl]-N'-[3-(trifluoromethyl)phenyl]urea The desired product was prepared by substituting 1-isocyanato-3-(trifluoromethyl)benzene and 4-bromo-2,6-dimethylaniline for 1-fluoro-2-isocyanato-4-methylbenzene and 4-bromo-2-ethylaniline, respectively, in Examples 149A-C. $^1$H NMR (300 MHz, DMSO-D$_6$) δ ppm 2.30 (s, 6H) 6.84 (dd, J=5.3, 2.5 Hz, 1H) 7.21 (s, 2H) 7.27-7.32 (m, 3H) 7.50 (t, J=8.0 Hz, 1H) 7.62 (d, J=8.5 Hz, 1H) 7.96 (s, 1H) 8.03 (s, 1H) 9.17 (s, 1H) 11.88-11.99 (m, 1H) MS (ESI(+)) m/e 440.2 (M+H)$^+$.

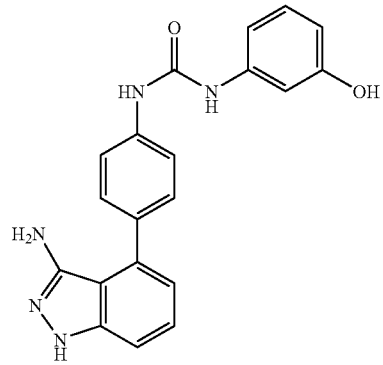

Example 177

N-[4-(3-amino-1H-indazol-4-yl)phenyl]-N'-(3-hydroxyphenyl)urea

The desired product was prepared by substituting 4-iodo-1-isocyanatobenzene and 3-hydroxyaniline for 1-fluoro-2-isocyanato-4-methylbenzene and 4-bromo-2-ethylaniline, respectively, in Examples 149A-C. $^1$H NMR (300 MHz, DMSO-D$_6$) δ ppm 6.38 (ddd, J=8.1, 2.3, 0.9 Hz, 1H) 6.82 (ddd, J=8.0, 2.0, 0.9 Hz, 1H) 6.86 (dd, J=6.4, 1.7 Hz, 1H) 7.03-7.08 (m, 2H) 7.29-7.35 (m, 2H) 7.40 (d, J=8.5 Hz, 2H) 7.59 (d, J=8.8 Hz, 2H) 8.65 (s, 1H) 8.80 (s, 1H) 9.12-9.53 (br. s., 1H) 11.80-12.39 (br. s., 1H) MS (ESI(+)) m/e 360.2 (M+H)$^+$.

Example 178

N-[2-({3-amino-4-[4-({[(3-methylphenyl)amino]carbonyl}amino)phenyl]-1H-indazol-7-yl}oxy)ethyl]methanesulfonamide

Example 178A

N-(2-{[3-amino-4-(4-aminophenyl)-1H-indazol-7-yl]oxy}ethyl)methanesulfonamide

The desired product was prepared by substituting Example 170C and 4-(4,4,5,5-tetramethyl-1,3,2-dioxaborolan-2-yl)aniline for Examples 1A and 1B, respectively, in Example 1C.

Example 178B

N-[2-({3-amino-4-[4-({[(3-methylphenyl)amino]carbonyl}amino)phenyl]-1H-indazol-7-yl}oxy)ethyl]methanesulfonamide The desired product was prepared by substituting Example 178A and 1-isocyanato-3-methylbenzene for Example 15G and 1-fluoro-3-isocyanatobenzene, respectively, in Example 15H. $^1$H NMR (300 MHz, DMSO-D$_6$) δ ppm 2.29 (s, 3H) 2.99 (s, 3H) 3.44 (q, J=5.8 Hz, 2H) 4.23 (t, J=5.4 Hz, 2H) 6.73 (d, J=7.8 Hz, 1H) 6.80 (d, J=7.8 Hz, 1H) 6.84 (d, J=7.8 Hz, 1H) 7.12-7.19 (m, 2H) 7.25 (d, J=8.1 Hz, 1H) 7.31 (s, 1H) 7.36 (d, J=8.5 Hz, 2H) 7.56 (d, J=8.5 Hz, 2H) 8.63 (s, 1H) 8.77 (s, 1H), 11.91-12.07 (br. s., 1H) MS (ESI(+)) m/e 495.1 (M+H)$^+$.

Example 179

N-{2-[(3-amino-4-{4-[({[2-fluoro-5-(trifluoromethyl)phenyl]amino}carbonyl)amino]phenyl}-1H-indazol-7-yl)oxy]ethyl}methanesulfonamide The desired product was prepared by substituting Example 178A and 1-fluoro-2-isocyanato-4-(trifluoromethyl)benzene for Example 15G and 1-fluoro-3-isocyanatobenzene, respectively, in Example 15H. $^1$H NMR (300 MHz, DMSO-D$_6$) δ ppm 2.99 (s, 3H) 3.44 (q, J=6.1 Hz, 2H) 4.22 (t, J=5.4 Hz, 2H) 6.72 (d, J=7.8 Hz, 1H) 6.82 (d, J=7.8 Hz, 1H) 7.17 (t, J=6.1 Hz, 1H) 7.38-7.42 (m, 3H) 7.48-7.54 (m, 1H) 7.58 (d, J=8.8 Hz, 2H) 8.65 (dd, J=7.5, 2.0 Hz, 1H) 8.94 (d, J=3.1 Hz, 1H) 9.29 (s, 1H) 11.87 (s, 1H) MS (ESI(+)) m/e 567.2 (M+H)$^+$.

Example 180

N-[2-({3-amino-4-[4-({[(3-chlorophenyl)amino]carbonyl}amino)phenyl]-1H-indazol-7-yl}oxy)ethyl]methanesulfonamide The desired product was prepared by substituting Example 178A and 1-chloro-3-isocyanatobenzene for Example 15G and 1-fluoro-3-isocyanatobenzene, respectively, in Example 15H. $^1$H NMR (300 MHz, DMSO-D$_6$) δ ppm 2.99 (s, 3H) 3.43 (q, J=5.8 Hz, 2H) 4.22 (t, J=5.4 Hz, 2H) 6.71 (d, J=7.8 Hz, 1H) 6.81 (d, J=7.8 Hz, 1H) 7.03 (dt, J=6.7, 2.3 Hz, 1H) 7.15-7.19 (m, 1H) 7.27-7.32 (m, 2H) 7.37 (d, J=8.5 Hz, 2H) 7.57 (d, J=8.5 Hz, 2H) 7.73 (t, J=1.9 Hz, 1H) 8.86 (s, 1H) 8.93 (s, 1H) 11.84 (s, 1H) MS (ESI(+))_1515.1 (M+H)$^+$.

Example 181

N-{2-[(3-amino-4-{4-[({[3-(trifluoromethyl)phenyl]amino}carbonyl)amino]phenyl}-1H-indazol-7-yl)oxy]ethyl}methanesulfonamide The desired product was prepared by substituting Example 178A and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 2.99 (s, 3H) 3.43 (q, J=5.8 Hz, 2H) 4.22 (t, J=5.4 Hz, 2H) 6.71 (d, J=7.5 Hz, 1H) 6.81 (d, J=7.8 Hz, 1H) 7.17 (t, J=5.8 Hz, 1H) 7.30-7.34 (m, 1H) 7.37 (d, J=8.5 Hz, 2H) 7.50-7.61 (m, 4H) 8.04 (t, J=2.2 Hz, 1H) 8.91 (s, 1H) 9.09 (s, 1H) 11.82 (s, 1H) MS (ESI(−)) m/e 547.1 (M−H)$^−$.

Example 182

N-[4-(3-amino-1H-indazol-6-yl)phenyl]-N'-(3-methylphenyl)urea

Example 182A 6-bromo-1H-indazol-3-amine

The desired product was prepared by substituting 4-bromo-2-fluorobenzonitrile for 2-fluoro-6-iodobenzonitrile in Example 1A. $^1$H NMR (300 MHz, DMSO-D$_6$) δ ppm 5.44 (s, 2H) 7.02 (dd, J=8.48, 1.70 Hz, 1H) 7.41 (d, J=1.70 Hz, 1H) 7.63 (d, J=8.48 Hz, 1H) 11.49 (s, 1H).

Example 182C

N-[4-(3-amino-1H-indazol-6-yl)phenyl]-N'-(3-methylphenyl)urea

The desired product was prepared by substituting Example 182A and 1B for 1A and 5A respectively, in Example 5B. MS (ESI(+)Q1MS m/z 358 (M+H)$^+$; $^1$H NMR (500 MHz, DMSO-D$_6$) δ ppm 2.29 (s, 3H) 5.34 (s, 2H) 6.79 (d, J=7.32 Hz, 1H) 7.15-7.20 (m, 2H) 7.25 (d, J=8.24 Hz, 1H) 7.31 (s, 1H) 7.38 (s, 1H) 7.55 (d, J=8.85 Hz, 2H) 7.62 (m, 2H) 7.72 (d, J=8.54 Hz, 1H) 8.75 (s, 1H) 8.89 (s, 1H) 11.38 (s, 1H)

Example 183

3-amino-N-(3-methylphenyl)-6-[4-({[(3-methylphenyl)amino]carbonyl}amino)phenyl]-1H-indazole-1-carboxamide

Example 183A 6-(4-aminophenyl)-1H-indazol-3-amine

The desired product was prepared by substituting Example 182A for Example 1A and 4-(4,4,5,5-tetramethyl-1,3,2-dioxaborolan-2-yl)aniline for Example 5A in Example 5B. $^1$H NMR (300 MHz, DMSO-D$_6$) δ ppm 5.19 (s, 2H) 5.27 (s, 2H)

6.64 (d, J=8.48 Hz, 2H) 7.10 (dd, J=8.48, 1.36 Hz, 1H) 7.25 (s, 1H) 7.37 (d, J=8.48 Hz, 2H) 7.64 (d, J=8.48 Hz, 1H) 11.25 (s, 1H).

Example 183B 3-amino-N-(3-methylphenyl)-6-[4-({[(3-methylphenyl)amino]carbonyl}amino)phenyl]-1H-indazole-1-carboxamide The desired product was prepared by substituting example 183A and 1-isocyanato-3-methylbenzene for 15G and 1-fluoro-3-isocyanatobenzene, respectively in example 15H. $^1$H NMR (300 MHz, DMSO-D$_6$) δ ppm 2.29 (s, 3H) 2.32 (s, 3H) 6.37 (s, 2H) 6.80 (d, J=7.1 Hz, 1H) 6.91 (d, J=7.5 Hz, 1H) 7.17 (t, J=7.8 Hz, 1H) 7.22 (t, J=7.8 Hz, 1H) 7.25 (d, J=8.5 Hz, 1H) 7.33 (s, 1H) 7.46-7.50 (m, 1H) 7.55-7.61 (m, 4H) 7.68 (d, J=8.8 Hz, 2H) 7.95 (d, J=8.1 Hz, 1H) 8.39 (d, J=0.7 Hz, 1H) 8.62 (s, 1H) 8.83 (s, 1H) 9.37 (s, 1H) MS (ESI(+)) m/e 490.0 (M+H)$^+$.

Example 184

N-[3-(3-amino-1H-indazol-4-yl)phenyl]-N'-(3-methylphenyl)urea

Example 184A

N-(3-methylphenyl)-N'-[3-(4,4,5,5-tetramethyl-1,3,2-dioxaborolan-2-yl)phenyl]urea The desired product was prepared by substituting 3-(4,4,5,5-tetramethyl-1,3,2-dioxaborolan-2-yl)aniline for 4-(4,4,5,5-tetramethyl-1,3,2-dioxaborolan-2-yl)aniline in Example 1B. MS (ESI(+)) m/e 352.9 (M+H)$^+$.

Example 184B

N-[3-(3-amino-1H-indazol-4-yl)phenyl]-N'-(3-methylphenyl)urea

The desired product was prepared by substituting Example 184A for Example 5A in Example 5B. $^1$H NMR (300 MHz, DMSO-D$_6$) δ ppm 2.27 (s, 3H) 6.78-6.83 (m, 2H) 7.05-7.09 (m, 1H) 7.15 (t, J=7.8 Hz, 1H) 7.22 (d, J=8.1 Hz, 1H) 7.28-7.31 (m, 3H) 7.38-7.43 (m, 2H) 7.63 (s, 1H) 8.63 (s, 1H) 8.81 (s, 1H) 11.74 (s, 1H) MS (ESI(+)) m/e 358.1 (M+H)$^+$.

Example 185

N-[4-(3-amino-7-methyl-1H-indazol-4-yl)phenyl]-N'-(3-methylphenyl)urea

Example 185A 4-iodo-7-methyl-1H-indazol-3-amine

The desired compound was prepared by substituting Example 15C for 2-fluoro-6-iodobenzonitrile in Example 1A. MS (ESI(+)) m/e 273.8 (M+H)$^+$.

Example 185B 4-(4-aminophenyl)-7-methyl-1H-indazol-3-amine

The desired product was prepared by substituting Example 185A and 4-(4,4,5,5-tetramethyl-1,3,2-dioxaborolan-2-yl) aniline for Examples 1A and 1B, respectively, in Example 1C. MS (ESI(+)) m/e 239.0 (M+H)$^+$.

Example 185C

N-[4-(3-amino-7-methyl-1H-indazol-4-yl)phenyl]-N'-(3-methylphenyl)urea

The desired product was prepared by substituting Example 185B and 1-isocyanato-3-methylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.29 (s, 3H) 2.42 (s, 3H) 6.70 (d, J=7.1 Hz, 1H) 6.80 (d, J=7.5 Hz, 1H) 7.05 (dd, J=7.1, 1.0 Hz, 1H) 7.16 (t, J=7.8 Hz, 1H) 7.25 (d, J=8.5 Hz, 1H) 7.32 (s, 1H) 7.36 (d, J=8.5 Hz, 2H) 7.57 (d, J=8.5 Hz, 2H) 8.63 (s, 1H) 8.77 (s, 1H) 11.75 (s, 1H) MS (ESI(+)) m/e 371.6 (M+H)$^+$.

Example 186

N-[4-(3-amino-7-methyl-1H-indazol-4-yl)phenyl]-N'-(3-chlorophenyl)urea

The desired product was prepared by substituting Example 185B and 1-chloro-3-isocyanatobenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.45 (s, 3H) 6.80 (d, J=7.1 Hz, 1H) 7.00-7.06 (m, 1H) 7.15 (dd, J=7.1, 1.0 Hz, 1H) 7.28-7.32 (m, 2H) 7.39 (d, J=8.8 Hz, 2H) 7.60 (d, J=8.8 Hz, 2H) 7.73-7.75 (m, 1H) 8.98 (s, 1H) 9.01 (s, 1H) 12.01-12.46 (br. s., 1H) MS (ESI(+)) m/e 382.0 (M+H)$^+$.

Example 187

N-[4-(3-amino-7-methyl-1H-indazol-4-yl)phenyl]-N'-[3-(trifluoromethyl)phenyl]urea The desired product was prepared by substituting Example 185B and 1-isocyanato-3-(trifluoromethyl)benzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.43 (s, 3H) 6.73 (d, J=7.1 Hz, 1H) 7.08 (d, J=7.1 Hz, 1H) 7.32 (d, J=8.1 Hz, 1H) 7.39 (d, J=8.5 Hz, 2H) 7.53 (t, J=7.8 Hz, 1H) 7.58-7.61 (m, 3H) 8.04 (s, 1H) 8.94 (s, 1H) 9.11 (s, 1H) 11.87 (s, 1H) MS (ESI(+)) m/e 426.0 (M+H)$^+$.

Example 188

N-[4-(3-amino-7-methyl-1H-indazol-4-yl)phenyl]-N'-[2-fluoro-5-(trifluoromethyl)phenyl]urea The desired product was prepared by substituting Example 185B and 1-fluoro-2-isocyanato-4-(trifluoromethyl)benzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.43 (s, 3H) 6.71 (d, J=7.1 Hz, 1H) 7.06 (d, J=7.8 Hz, 1H) 7.38-7.43 (m, 3H) 7.48-7.55 (m, 1H) 7.59 (d, J=8.5 Hz, 2H) 8.65 (dd, J=7.3, 2.2 Hz, 1H) 8.95 (d, J=2.7 Hz, 1H) 9.30 (s, 1H) 11.78 (s, 1H) MS (ESI(+)) m/e 444.1 (M+H)$^+$.

Example 189

N-[4-(3-amino-7-methyl-1H-indazol-4-yl)phenyl]-N'-(3-bromophenyl)urea

The desired product was prepared by substituting Example 185B and 1-bromo-3-isocyanatobenzene for Example 15G and 1-fluoro-3-isocyanatobenzene, respectively, in Example 15H. Additionally, DMF was used in place of $CH_2Cl_2$. $^1H$ NMR (300 MHz, DMSO-$D_6$) δ ppm 2.44 (s, 3H) 6.76 (d, J=7.1 Hz, 1H) 7.11 (dd, J=7.3, 0.9 Hz, 1H) 7.16 (ddd, J=7.8, 2.0, 1.0 Hz, 1H) 7.25 (t, J=8.0 Hz, 1H) 7.33 (ddd, J=8.1, 2.0, 1.0 Hz, 1H) 7.39 (d, J=8.5 Hz, 2H) 7.59 (d, J=8.8 Hz, 2H) 7.88 (t, J=1.9 Hz, 1H) 8.94 (s, 1H) 8.97 (s, 1H) 12.06 (s, 1H) MS (ESI(+)) m/e 463.0, 438.0 (M+H)$^+$.

Example 190

N-[4-(3-amino-7-methyl-1H-indazol-4-yl)phenyl]-N'-(3-fluorophenyl)urea

The desired product was prepared by substituting Example 185B for Example 15G in Example 15H. Additionally, DMF was used in place of $CH_2Cl_2$. $^1H$ NMR (300 MHz, DMSO-$D_6$) δ ppm 2.45 (s, 3H) 6.76-6.82 (m, 2H) 7.13-7.17 (m, 2H) 7.32 (td, J=8.5, 6.8 Hz, 1H) 7.39 (d, J=8.8 Hz, 2H) 7.52 (dt, J=12.1, 2.3 Hz, 1H) 7.60 (d, J=8.5 Hz, 2H) 8.96 (s, 1H) 9.03 (s, 1H) 12.08-12.44 (br. s., 1H) MS (ESI(+)) m/e 376.1 (M+H)$^+$.

Example 191

N-[4-(3-amino-7-methyl-1H-indazol-4-yl)phenyl]-N'-(2-fluoro-5-methylphenyl)urea

The desired product was prepared by substituting Example 185B and 1-fluoro-2-isocyanato-4-methylbenzene for Example 15G and 1-fluoro-3-isocyanatobenzene, respectively, in Example 15H. Additionally, DMF was used in place of $CH_2Cl_2$. $^1H$ NMR (300 MHz, DMSO-$D_6$) δ ppm 2.28 (s, 3H) 2.45 (s, 3H) 6.78 (d, J=6.8 Hz, 1H) 6.79-6.84 (m, 1H) 7.08-7.15 (m, 2H) 7.39 (d, J=8.5 Hz, 2H) 7.59 (d, J=8.8 Hz, 2H) 8.01 (dd, J=7.8, 1.7 Hz, 1H) 8.53 (d, J=2.4 Hz, 1H) 9.21 (s, 1H) 12.00-12.33 (br. s., 1H) MS (ESI(+)) m/e 390.0 (M+H)$^+$.

Example 192

N-[4-(3-amino-7-methyl-1H-indazol-4-yl)phenyl]-N'-(3-cyanophenyl)urea

The desired product was prepared by substituting Example 185B and 3-isocyanatobenzonitrile for Example 15G and 1-fluoro-3-isocyanatobenzene, respectively, in Example 15H. Additionally, DMF was used in place of $CH_2Cl_2$. $^1H$ NMR (300 MHz, DMSO-$D_6$) δ ppm 2.44 (s, 3H) 6.77 (d, J=7.1 Hz, 1H) 7.12 (dd, J=7.1, 1.0 Hz, 1H) 7.40 (d, J=8.5 Hz, 2H) 7.43 (dt, J=7.8, 1.4 Hz, 1H) 7.51 (t, J=8.0 Hz, 1H) 7.60 (d, J=8.5 Hz, 2H) 7.70 (ddd, J=8.3, 2.2, 1.0 Hz, 1H) 8.01 (t, J=1.7 Hz, 1H) 9.05 (s, 1H) 9.14 (s, 1H) 11.98-12.22 (br. s., 1H) MS nm/>(ESI(+)) 383.1 (M+H)$^+$.

Example 193

N-[4-(3-amino-1H-indazol-4-yl)-2-(trifluoromethoxy)phenyl]-N'-(2-fluoro-5-methylphenyl)urea The desired product was prepared by substituting 4-bromo-2-(trifluoromethoxy)aniline for 4-bromo-2-ethyla-niline in Examples 149A-C. $^1H$ NMR (300 MHz, DMSO-$D_6$) δ ppm 2.29 (s, 3H) 6.82-6.91 (m, 2H) 7.14 (dd, J=1.5, 8.1 Hz, 1H) 7.32 (d, J=1.0 Hz, 1H) 7.34 (s, 1H) 7.47-7.52 (m, 2H) 8.03 (dd, J=8.0, 1.9 Hz, 1H) 8.42 (d, J=8.8 Hz, 1H) 9.03 (s, 1H) 9.24 (d, J=2.4 Hz, 1H) 11.83-12.13 (br. s., 1H) MS (ESI(+)) m/e 460.1 (M+H)$^+$.

Example 194

N-[5-(3-amino-1H-indazol-4-yl)pyridin-2-yl]-N'-(2-fluoro-5-methylphenyl)urea

Example 194A

N-(5-bromopyridin-2-yl)-N'-(2-fluoro-5-methylphenyl)urea

The desired product was prepared by substituting 2-amino-5-bromopyridine and 1-fluoro-2-isocyanato-4-methylbenzene for Example 15G and 1-fluoro-3-isocyanatobenzene, respectively, in Example 15H. MS (ESI(+)) m/e 324.0 (M+H)$^+$.

Example 194B

N-[5-(3-amino-1H-indazol-4-yl)pyridin-2-yl]-N'-(2-fluoro-5-methylphenyl)urea

The desired product was prepared by substituting Example 194A for Example 44A in Example 44B. $^1H$ NMR (300 MHz, DMSO-$D_6$) δ ppm 2.30 (s, 3H) 6.83-6.92 (m, 2H) 7.15 (dd, J=11.2, 8.5 Hz, 1H) 7.34 (s, 1H) 7.35 (s, 1H) 7.54 (d, J=8.5 Hz, 1H) 7.90 (dd, J=8.7, 2.5 Hz, 1H) 8.07 (dd, J=7.5, 2.0 Hz, 1H) 8.38 (d, J=2.4 Hz, 1H) 9.95 (s, 1H) 10.88 (s, 1H) 12.02 (s, 1H) MS (ESI(+)) me/377.1 (M+H)$^+$.

Example 195

N-[4-(3-amino-7-fluoro-1H-indazol-4-yl)phenyl]-N'-[2-fluoro-5-(trifluoromethyl)phenyl]urea

Example 195A 7-fluoro-4-iodo-1H-indazol-3-amine

The desired product was prepared by substituting Example 26A for 2-fluoro-6-iodobenzonitrile in Example 1A.

Example 195B

N-[4-(3-amino-7-fluoro-1H-indazol-4-yl)phenyl]-N'-[2-fluoro-5-(trifluoromethyl)phenyl]urea The desired product was prepared by substituting Example 195A for Example 1A and N-(2-fluoro-5-(trifluoromethyl)phenyl)-N'-[4-(4,4,5,5-tetramethyl-1,3,2-dioxaborolan-2-yl)phenyl]urea for Example 5A in Example 5B. $^1H$ NMR (300 MHz, DMSO-$D_6$) δ ppm 6.74 (dd, J=7.8, 4.1 Hz, 1H) 7.13 (dd, J=11.5, 7.8 Hz, 1H) 7.37-7.43 (m, 3H) 7.51 (dd, J=10.9, 8.5 Hz, 1H) 7.61 (d, J=8.5 Hz, 2H) 8.64 (dd, J=7.3, 2.2 Hz, 1H) 8.96 (d, J=3.1 Hz, 1H) 9.32 (s, 1H) 12.25 (s, 1H) MS (ESI(+)) m/e 448.0 (M+H)$^+$.

Example 196

N-[4-(3-amino-7-fluoro-1H-indazol-4-yl)phenyl]-N'-(4-fluorophenyl)urea

The desired product was prepared by substituting Example 195A for Example 1A and N-(4-fluorophenyl)-N'-[4-(4,4,5, 5-tetramethyl-1,3,2-dioxaborolan-2-yl)phenyl]urea for Example 5A in Example 5B. $^1$H NMR (300 MHz, DMSO-D$_6$) δ ppm 6.74 (dd, J=7.8, 4.1 Hz, 1H) 7.11 (dd, J=7.8, 1.4 Hz, 1H) 7.15 (d, J=8.5 Hz, 2H) 7.37 (d, J=8.5 Hz, 2H) 7.49 (dd, J=9.3, 4.9 Hz, 2H) 7.58 (d, J=8.5 Hz, 2H) 8.77 (s, 1H) 8.83 (s, 1H) 12.29 (s, 1H) MS (ESI(+)) m/e 380.0 (M+H)$^+$.

Example 197

N-[4-(3-amino-7-fluoro-1H-indazol-4-yl)phenyl]-N'-(2-fluorophenyl)urea

The desired product was prepared by substituting Example 195A for Example 1A and N-(2-fluorophenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 6.98-7.06 (m, 1H) 7.14 (dd, J=11.2, 7.8 Hz, 1H) 7.16 (dt, J=7.5, 1.4 Hz, 1H) 7.25 (ddd, J=11.5, 8.1, 1.4 Hz, 1H) 7.33-7.38 (m, 1H) 7.39 (d, J=8.5 Hz, 2H) 7.59 (d, J=8.5 Hz, 2H) 8.17 (td, J=8.3, 1.7 Hz, 1H) 8.61 (d, J=2.7 Hz, 1H) 9.23 (s, 1H) 11.99-12.62 (br. s., 1H) MS (ESI(+)) m/e 380.0 (M+H)$^+$.

Example 198

N-[4-(3-amino-7-fluoro-1H-indazol-4-yl)phenyl]-N'-(3-fluoro-4-methylphenyl)urea

The desired product was prepared by substituting Example 195A for Example 1A and N-(3-fluoro-4-methylphenyl)-N'-[4-(4,4,5,5-tetramethyl-1,3,2-dioxaborolan-2-yl)phenyl] urea for Example 5A in Example 5B. $^1$H NMR (300 MHz, DMSO-D$_6$) δ ppm 2.17 (d, J=1.4 Hz, 3H) 6.73 (dd, J=7.8, 4.1 Hz, 1H) 7.05 (dd, J=8.3, 2.2 Hz, 1H) 7.13 (dd, J=11.2, 7.8 Hz, 1H) 7.17 (t, J=8.7 Hz, 1H) 7.37 (d, J=8.5 Hz, 2H) 7.45 (dd, J=12.5, 2.0 Hz, 1H) 7.58 (d, J=8.5 Hz, 2H) 8.84 (s, 1H) 8.86 (s, 1H) 12.11-12.41 (br. s., 1H) MS (ESI(+)) m/e 394.1 (M+H)$^+$.

Example 199

N-[4-(3-amino-7-fluoro-1H-indazol-4-yl)phenyl]-N'-phenylurea

The desired product was prepared by substituting Example 195A for Example 1A and N-phenyl-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 6.74 (dd, J=7.8, 4.4 Hz, 1H) 6.98 (t, J=7.3 Hz, 1H) 7.13 (dd, J=11.2, 7.8 Hz, 1H) 7.26-7.32 (m, 2H) 7.37 (d, J=8.5 Hz, 2H) 7.46-7.49 (m, 2H) 7.59 (d, J=8.5 Hz, 2H) 8.74 (s, 1H) 8.84 (s, 1H) 11.99-12.59 (br. s., 1H) MS (ESI(+)) m/e 362.0 (M+H)$^+$.

Example 200

N-[2-({3-amino-4-[4-({[(3-methylphenyl)amino]carbonyl}amino)phenyl]-1H-indazol-7-yl}oxy)ethyl]-1,1,1-trifluoromethanesulfonamide Example 200A N-{2-[(3-amino-4-iodo-1H-indazol-7-yl)oxy]ethyl}-1,1,1-trifluoromethanesulfonamide The desired product was prepared by substituting trifluoromethanesulfonic anhydride for methanesulfonyl chloride in Example 170B.

Example 200B

N-[2-({3-amino-4-[4-({[(3-methylphenyl)amino]carbonyl}amino)phenyl]-1H-indazol-7-yl}oxy)ethyl]-1,1,1-trifluoromethanesulfonamide The desired product was prepared by substituting Example 200A and Example 1B for Example 1A and Example 5A, respectively, in Example 5B. $^1$H NMR (300 MHz, DMSO-D$_6$) δ ppm 2.29 (s, 3H) 3.65 (q, J=6.1 Hz, 2H) 4.24 (t, J=5.3 Hz, 2H) 6.73 (d, J=7.8 Hz, 1H) 6.80 (d, J=6.8 Hz, 1H) 6.85 (d, J=7.8 Hz, 1H) 7.16 (t, J=7.6 Hz, 1H) 7.25 (d, J=8.5 Hz, 1H) 7.31 (s, 1H) 7.36 (d, J=8.5 Hz, 2H) 7.57 (d, J=8.5 Hz, 2H) 8.63 (s, 1H) 8.78 (s, 1H) 9.52 (t, J=5.6 Hz, 1H) 11.83 (s, 1H) MS (ESI(+)) m/e 549.1 (M+H)$^+$.

Example 201

N-[4-(3-amino-1H-indazol-4-yl)-2-fluorophenyl]-N'-(2-fluoro-5-methylphenyl)urea

The desired product was prepared by substituting 1-fluoro-2-isocyanato-4-methylbenzene for 1-isocyanato-3-methylbenzene in Examples 44A-B. $^1$H NMR (300 MHz, DMSO-D$_6$) δ ppm 2.29 (s, 3H) 6.80-6.87 (m, 2H) 7.13 (dd, J=11.4, 8.3 Hz, 1H) 7.26-7.40 (m, 4H) 8.04 (dd, J=8.1, 1.7 Hz, 1H) 8.32 (t, J=8.5 Hz, 1H) 9.04 (d, J=2.4 Hz, 1H) 9.16 (d, J=2.7 Hz, 1H) 11.90 (s, 1H) MS (ESI(+)) m/e 394.2 (M+H)$^+$.

Example 202

N-[4-(3-amino-1H-indazol-4-yl)phenyl]-N'-[4-fluoro-3-(trifluoromethyl)phenyl]urea The desired product was prepared by substituting N-(4-fluoro-3-trifluoromethylphenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 6.83 (dd, J=5.8, 2.3 Hz, 1H) 7.27-7.34 (m, 2H) 7.40-7.48 (m, 3H) 7.61 (d, J=8.8 Hz, 2H) 7.63-7.69 (m, 1H) 8.03 (dd, J=6.4, 2.7 Hz, 1H) 8.99 (s, 1H) 9.13 (s, 1H) 11.94 (s, 1H) MS (ESI(+)) m/e 430.0 (M+H)$^+$.

Example 203

N-[4-(3-amino-1H-indazol-4-yl)phenyl]-N'-[2-fluoro-3-(trifluoromethyl)phenyl]urea The desired product was prepared by substituting N-(2-fluoro-3-trifluoromethylphenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 6.85 (dd, J=5.8, 2.0 Hz, 1H) 7.29-7.39 (m, 4H) 7.43 (d, J=8.5 Hz, 2H) 7.62 (d, J=8.5 Hz, 2H) 8.45-8.50 (m, 1H) 8.90 (d, J=2.7 Hz, 1H) 9.31 (s, 1H) 12.01 (m, 1H) MS (ESI(+)) m/e 430.1 (M+H)$^+$.

Example 204

N-[4-(3-amino-1H-indazol-4-yl)phenyl]-N'-(4-bromo-2-fluorophenyl)urea

The desired product was prepared by substituting N-(4-bromo-2-fluorophenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 6.83 (dd, J=5.8, 2.0 Hz, 1H) 7.30 (d, J=0.7 Hz, 1H) 7.31 (dd, J=13.2, 8.1 Hz, 1H) 7.37 (ddd, J=8.8, 2.0, 1.4 Hz, 1H) 7.42 (d, J=8.8 Hz, 2H) 7.56-7.61 (m, 3H) 8.16 (t, J=8.8 Hz, 1H) 8.71 (d, J=2.4 Hz, 1H) 9.25 (s, 1H) 11.97 (s, 1H) MS (ESI(+)) m/e 440.0, 440.9 (M+H)+.

Example 205

N-[4-(3-amino-1H-indazol-4-yl)phenyl]-N'-(5-fluoro-2-methylphenyl)urea

The desired product was prepared by substituting N-(5-fluoro-2-methylphenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 2.24 (s, 3H) 6.76 (td, J=8.5, 2.7 Hz, 1H) 6.87 (dd, J=6.1, 1.7 Hz, 1H) 7.16-7.24 (m, 1H) 7.30-7.38 (m, 2H) 7.43 (d, J=8.5 Hz, 2H) 7.62 (d, J=8.5 Hz, 2H) 7.87 (dd, J=12.2, 2.7 Hz, 1H) 8.12 (s, 1H) 9.34 (s, 1H) 11.94-12.25 (br. s., 1H) MS (ESI(+)) m/e 376.1 (M+H)+.

Example 206

N-[4-(3-amino-1H-indazol-4-yl)phenyl]-N'-(4-fluoro-3-methylphenyl)urea

The desired product was prepared by substituting N-(4-fluoro-3-methylphenyl)-N'-[4-(4,4,5,5-tetramethyl-1,3,2-dioxaborolan-2-yl)phenyl]urea for Example 5A in Example 5B. $^1$H NMR (300 MHz, DMSO-D$_6$) δ ppm 2.22 (d, J=1.7 Hz, 3H) 6.84 (dd, J=6.1, 1.7 Hz, 1H) 7.06 (t, J=9.2 Hz, 1H) 7.25-7.34 (m, 3H) 7.37-7.41 (m, 3H) 7.59 (d, J=8.5 Hz, 2H) 8.69 (s, 1H) 8.84 (s, 1H) 11.86-12.20 (br. s., 1H) MS (ESI(+)) m/e 376.1 (M+H)+.

Example 207

N-{4-[3-amino-7-(3-morpholin-4-ylpropoxy)-1H-indazol-4-yl]phenyl}-N'-phenylurea

Example 207A 2-fluoro-6-iodo-3-(3-morpholin-4-ylpropoxy)benzonitrile

The desired product was prepared by substituting 3-(4-morpholinyl)-propan-1-ol for 2-(4-morpholinyl)ethanol in Example 75A. MS (ESI(+)) m/e 391 (M+H)+.

Example 207B 4-(4-aminophenyl)-7-(3-morpholin-4-ylpropoxy)-1H-indazol-3-amine

The desired product was prepared by substituting Example 207A for Example 15E in Examples 15F-G.

Example 207C

N-{4-[3-amino-7-(3-morpholin-4-ylpropoxy)-1H-indazol-4-yl]phenyl}-N'-phenylurea

The desired product was prepared by substituting Example 207B and isocyanatobenzene for Example 15G and 1-fluoro-3-isocyanatobenzene, respectively, in Example 15H. $^1$H NMR (500 MHz, DMSO-D$_6$) δ ppm 2.18-2.23 (m, 2H) 3.08-3.20 (m, 4H) 3.51-3.53 (m, 2H) 3.65-3.70 (m, 2H) 4.02-4.05 (m, 2H) 4.24 (t, J=5.9 Hz, 2H) 6.72 (d, J=7.8 Hz, 1H) 6.82 (d, J=7.8 Hz, 1H) 6.98 (t, J=7.3 Hz, 1H) 7.27-7.31 (m, 2H) 7.35 (d, J=8.4 Hz, 2H) 7.48 (d, J=7.8 Hz, 2H) 7.57 (d, J=8.4 Hz, 2H) 8.76 (s, 1H) 8.84 (s, 1H) 9.68 (s, 1H) 11.86 (s, 1H) MS (ESI(+)) m/e 487.2 (M+H)+.

Example 208

N-{4-[3-amino-7-(3-morpholin-4-ylpropoxy)-1H-indazol-4-yl]phenyl}-N'-(3-fluorophenyl)urea The desired product was prepared by substituting Example 207 for Example 15G in Example 15H. $^1$H NMR (500 MHz, DMSO-D$_6$) δ ppm 2.18-2.23 (m, 2H) 3.08-3.18 (m, 4H) 3.51-3.53 (m, 2H) 3.65-3.70 (m, 2H) 4.02-4.05 (m, 2H) 4.23 (t, J=5.8 Hz, 2H) 6.72 (d, J=7.8 Hz, 1H) 6.78 (dt, J=8.1, 2.5 Hz, 1H) 6.82 (d, J=7.8 Hz, 1H) 7.15 (dd, J=8.1, 1.3 Hz, 1H) 7.31 (dd, J=15.3, 8.4 Hz, 1H) 7.36 (d, J=8.7 Hz, 2H) 7.52 (dt, J=11.9, 2.2 Hz, 1H) 7.57 (d, J=8.7 Hz, 2H) 8.96 (s, 1H) 9.06 (s, 1H) 9.71 (s, 1H) 11.86 (s, 1H) MS (ESI(+)) m/e 505.1 (M+H)+.

Example 209

N-{4-[3-amino-7-(3-morpholin-4-ylpropoxy)-1H-indazol-4-yl]phenyl}-N'-(2-fluoro-5-methylphenyl)urea The desired product was prepared by substituting Example 207B and 1-fluoro-2-isocyanato-4-methylbenzene for Example 15G and 1-fluoro-3-isocyanatobenzene, respectively, in Example 15H. $^1$H NMR (500 MHz, DMSO-D$_6$) δ ppm 2.19-2.24 (m, 2H) 2.28 (s, 3H) 3.08-3.18 (m, 2H) 3.42-3.45 (m, 2H) 3.50-3.55 (m, 2H) 3.68-3.72 (m, 2H) 4.03-4.08 (m, 2H) 4.24 (t, J=5.8 Hz, 2H) 6.75 (d, J=7.8 Hz, 1H) 6.80-6.84 (m, 1H) 6.84 (d, J=7.8 Hz, 1H) 7.11 (dd, J=11.2, 8.4 Hz, 1H) 7.37 (d, J=8.4 Hz, 2H) 7.58 (d, J=8.4 Hz, 2H) 7.99 (dd, J=7.8, 1.9 Hz, 1H) 8.56 (d, J=2.5 Hz, 1H) 9.24 (s, 1H) 9.76-10.28 (br. s., 1H) MS (ESI(+)) m/e 519.2 (M+H)+.

Example 210

N-{4-[3-amino-7-(3-morpholin-4-ylpropoxy)-1H-indazol-4-yl]phenyl}-N'-(3-methylphenyl)urea The desired product was prepared by substituting Example 207B and 1-isocyanato-3-methylbenzene for Example 15G and 1-fluoro-3-isocyanatobenzene, respectively, in Example 15H. $^1$H NMR (500 MHz, DMSO-D$_6$) δ ppm 2.19-2.23 (m, 2H) 2.29 (s, 3H) 3.08-3.17 (m, 2H) 3.43-3.51 (m, 4H) 3.66-3.70 (m, 2H) 4.02-4.05 (m, 2H) 4.24 (t, J=5.8 Hz, 2H) 6.72 (d, J=7.8 Hz, 1H) 6.80 (d, J=8.1 Hz, 1H) 6.82 (d, J=7.8 Hz, 1H) 7.16 (t, J=7.6 Hz, 1H) 7.26 (d, J=8.1 Hz, 1H) 7.32 (s, 1H) 7.35 (d, J=8.4 Hz, 2H) 7.57 (d, J=8.4 Hz, 2H) 8.70 (s, 1H) 8.84 (s, 1H) 9.72 (s, 1H) 11.88 (s, 1H) MS (ESI(+)) m/e 501.2 (M+H)+.

Example 211

N-{4-[3-amino-7-(3-morpholin-4-ylpropoxy)-1H-indazol-4-yl]phenyl}-N'-[2-fluoro-5-(trifluoromethyl)phenyl]urea The desired product was prepared by substituting Example 207B and 1-fluoro-2-isocyanato-4-(trifluoromethyl)benzene for Example 15G and 1-fluoro-3-isocyanatobenzene, respectively, in Example 15H. $^1$H NMR (500 MHz, DMSO-D$_6$) δ ppm 2.18-2.24 (m, 2H) 3.08-3.18 (m, 2H) 3.42-3.45 (m, 2H)

3.51-3.57 (m, 2H) 3.65-3.71 (m, 2H) 4.02-4.05 (m, 2H) 4.24 (t, J=5.8 Hz, 2H) 6.73 (d, J=7.5 Hz, 1H) 6.83 (d, J=7.8 Hz, 1H) 7.37-7.41 (m, 3H) 7.49-7.53 (m, 1H) 7.59 (d, J=8.7 Hz, 2H) 8.64 (dd, J=7.3, 2.0 Hz, 1H) 8.96 (d, J=2.8 Hz, 1H) 9.32 (s, 1H) 9.77 (s, 1H) 11.92 (s, 1H) MS (ESI(+)) m/e 573.1 (M+H)+.

Example 212

N-{4-[3-amino-7-(3-morpholin-4-ylpropoxy)-1H-indazol-4-yl]phenyl}-N'-(3-chlorophenyl)urea The desired product was prepared by substituting Example 207B and 1-chloro-3-isocyanatobenzene for Example 15G and 1-fluoro-3-isocyanatobenzene, respectively, in Example 15H. $^1$H NMR (500 MHz, DMSO-D$_6$) δ ppm 2.18-2.23 (m, 2H) 3.08-3.18 (m, 4H) 3.66-3.70 (m, 4H) 4.02-4.05 (m, 2H) 4.24 (t, J=5.8 Hz, 2H) 6.73 (d, J=7.8 Hz, 1H) 6.82 (d, J=7.8 Hz, 1H) 7.01-7.03 (m, 1H) 7.29-7.33 (m, 2H) 7.36 (d, J=8.4 Hz, 2H) 7.58 (d, J=8.7 Hz, 2H) 7.74 (s, 1H) 9.00 (s, 1H) 9.07 (s, 1H) 9.74 (s, 1H) 11.89 (s, 1H) MS (ESI(+)) m/e 521.1 (M+H)+.

Example 213

N-{4-[3-amino-7-(3-morpholin-4-ylpropoxy)-1H-indazol-4-yl]phenyl}-N'-[3-(trifluoromethyl)phenyl]urea The desired product was prepared by substituting Example 207B and 1-isocyanato-3-(trifluoromethyl)benzene for Example 15G and 1-fluoro-3-isocyanatobenzene, respectively, in Example 15H. $^1$H NMR (500 MHz, DMSO-D$_6$) δ ppm 2.18-2.24 (m, 2H) 3.08-3.19 (m, 4H) 3.42-3.44 (m, 2H) 3.66-3.70 (m, 2H) 4.02-4.04 (m, 2H) 4.24 (t, J=5.8 Hz, 2H) 6.74 (d, J=7.8 Hz, 1H) 6.83 (d, J=7.8 Hz, 1H) 7.32 (d, J=7.8 Hz, 1H) 7.37 (d, J=8.4 Hz, 2H) 7.52 (t, J=8.0 Hz, 1H) 7.59-7.61 (m, 3H) 8.05 (s, 1H) 9.10 (s, 1H) 9.28 (s, 1H) 9.78 (s, 1H) 11.94 (s, 1H) MS (ESI(+)) m/e 555.2 (M+H)+.

Example 214

N-[2-({3-amino-4-[4-({[(2-fluoro-5-methylphenyl)amino]carbonyl}amino)phenyl]-1H-indazol-7-yl}oxy)ethyl]-1,1,1-trifluoromethanesulfonamide The desired product was prepared by substituting Example 200A for Example 1A in Example 5B. $^1$H NMR (300 MHz, DMSO-D$_6$) δ ppm 2.28 (s, 3H) 3.65 (q, J=4.9 Hz, 2H) 4.24 (t, J=5.3 Hz, 2H) 6.73 (d, J=7.8 Hz, 1H) 6.78-6.82 (m, 1H) 6.84 (d, J=7.5 Hz, 1H) 7.11 (dd, J=11.4, 8.3 Hz, 1H) 7.37 (d, J=8.5 Hz, 2H) 7.57 (d, J=8.5 Hz, 2H) 8.01 (dd, J=8.0, 2.2 Hz, 1H) 8.52 (d, J=2.7 Hz, 1H) 9.17 (s, 1H) 9.52 (t, J=5.8 Hz, 1H) 11.79 (s, 1H) MS (ESI(+)) 567.0 m/e (M+H)+.

Example 215

N-[2-({3-amino-4-[4-({[(3-fluorophenyl)amino]carbonyl}amino)phenyl]-1H-indazol-7-yl}oxy)ethyl]-1,1,1-trifluoromethanesulfonamide The desired product was prepared by substituting Example 200A and N-(3-fluorophenyl)N'-[4-(4,4,5,5-tetramethyl-1,3,2-dioxaborolan-2-yl)phenyl]urea for Example 1A and Example 5A, respectively, in Example 5B. $^1$H NMR (300 MHz, DMSO-D$_6$) δ ppm 3.65 (q, J=5.3 Hz, 2H) 4.23 (t, J=5.3 Hz, 2H) 6.71 (d, J=7.8 Hz, 1H) 6.78 (td, J=8.5, 2.0 Hz, 1H) 6.83 (d, J=7.8 Hz, 1H) 7.13 (m, 1H) 7.30 (m, 1H) 7.37 (d, J=8.5 Hz, 2H) 7.44-7.54 (m, 1H) 7.57 (d, J=8.5 Hz, 2H) 8.86 (s, 1H) 8.95 (s, 1H) 9.52 (t, J=5.3 Hz, 1H) 11.72 (s, 1H) MS (ESI(−)) m/e 550.9 (M−H)−.

Example 216

N-[2-({3-amino-4-[4-({[(2-fluoro-5-methylphenyl)amino]carbonyl}amino)phenyl]-1H-indazol-7-yl}oxy)ethyl]benzenesulfonamide Example 216A N-{2-[(3-amino-4-iodo-1H-indazol-7-yl)oxy]ethyl}benzenesulfonamide The desired product was prepared by substituting phenylsulfonyl chloride for methanesulfonyl chloride in Example 170B. MS (ESI(+)) m/e 459 (M+H)+.

Example 216B

N-[2-({3-amino-4-[4-({[(2-fluoro-5-methylphenyl)amino]carbonyl}amino)phenyl]-1H-indazol-7-yl}oxy)ethyl]benzenesulfonamide The desired product was prepared by substituting Example 216A and N-(2-fluoro-5-methylphenyl)N'-[4-(4,4,5,5-tetramethyl-1,3,2-dioxaborolan-2-yl)phenyl]urea for Example 1A and Example 5A, respectively, in Example 5B. $^1$H NMR (500 MHz, DMSO-D$_6$) δ ppm 2.28 (s, 3H) 3.26 (q, J=5.6 Hz, 2H) 4.08 (t, J=5.6 Hz, 2H) 6.67 (d, J=7.8 Hz, 1H) 6.70 (d, J=7.8 Hz, 1H) 6.79-6.82 (m, 1H) 7.11 (dd, J=11.2, 8.4 Hz, 1H) 7.36 (d, J=8.5 Hz, 2H) 7.55 (t, J=7.6 Hz, 2H) 7.56 (d, J=8.5 Hz, 2H) 7.61 (t, J=7.2 Hz, 1H) 7.78 (t, J=6.1 Hz, 1H) 7.84 (d, J=7.2 Hz, 2H) 8.00 (dd, J=8.0, 1.7 Hz, 1H) 8.50 (d, J=2.5 Hz, 1H) 9.16 (s, 1H) 11.84 (s, 1H) MS (ESI(−)) m/e 573.2 (M−H)−.

Example 217

N-{2-[(3-amino-4-{4-[({[3-(trifluoromethyl)phenyl]amino}carbonyl)amino]phenyl}-1H-indazol-7-yl)oxy]ethyl}benzenesulfonamide The desired product was prepared by substituting Example 216A and N-(3-trifluoromethylphenyl)N'-[4-(4,4,5,5-tetramethyl-1,3,2-dioxaborolan-2-yl)phenyl]urea for Example 1A and Example 5A, respectively, in Example 5B. $^1$H NMR (500 MHz, DMSO-D$_6$) δ ppm 3.26 (q, J=5.8 Hz, 2H) 4.10 (t, J=5.6 Hz, 2H) 6.70 (d, J=7.8 Hz, 1H) 6.73 (d, J=7.8 Hz, 1H) 7.32 (d, J=7.5 Hz, 1H) 7.37 (d, J=8.4 Hz, 2H) 7.51-7.63 (m, 7H) 7.78 (t, J=6.1 Hz, 1H) 7.84 (d, J=8.7 Hz, 2H) 8.04 (s, 1H) 8.93 (s, 1H) 9.11 (s, 1H) 12.01 (s, 1H) MS (ESI(+)) m/e 611.1 (M+H)+.

Example 218

N-[2-({3-amino-4-[4-({[(3-fluorophenyl)amino]carbonyl}amino)phenyl]-1H-indazol-7-yl}oxy)ethyl]benzenesulfonamide The desired product was prepared by substituting Example 216A and N-(3-fluorophenyl)-N'-[4-(4,4,5,5-tetramethyl-1,3,2-dioxaborolan-2-yl)phenyl]urea for Example 1A and Example 5A, respectively, in Example 5B. $^1$H NMR (500 MHz, DMSO-D$_6$) δ ppm 3.26 (q, J=5.6 Hz, 2H) 4.09 (t, J=5.6

Hz, 2H) 6.70 (d, J=7.8 Hz, 1H) 6.73 (d, J=7.8 Hz, 1H) 6.79 (td, J=8.4, 1.9 Hz, 1H) 7.14 (dd, J=8.3, 1.1 Hz, 1H) 7.29-7.34 (m, 1H) 7.37 (d, J=8.7 Hz, 2H) 7.49-7.58 (m, 5H) 7.61 (t, J=7.3 Hz, 1H) 7.78 (t, J=6.1 Hz, 1H) 7.83-7.85 (m, J=8.4 Hz, 2H) 8.88 (s, 1H) 8.97 (s, 1H) 12.00 (s, 1H) MS (ESI(−)) m/e 559.0 (M−H)⁻.

Example 219

N-[2-({3-amino-4-[4-({[(3-chlorophenyl)amino]carbonyl}amino)phenyl]-1H-indazol-7-yl}oxy)ethyl]benzenesulfonamide The desired product was prepared by substituting Example 216A and N-(3-chlorophenyl)N'-[4-(4,4,5,5-tetramethyl-1,3,2-dioxaborolan-2-yl)phenyl]urea for Example 1A and Example 5A, respectively, in Example 5B. $^1$H NMR (300 MHz, DMSO-D$_6$) δ ppm 3.26 (q, J=5.6 Hz, 2H) 4.10 (t, J=5.6 Hz, 2H) 6.70-6.75 (m, 2H) 7.03 (td, J=4.3, 2.2 Hz, 1H) 7.27-7.32 (m, 2H) 7.37 (d, J=8.5 Hz, 2H) 7.52-7.64 (m, 5H) 7.74-7.75 (m, 1H) 7.78-7.85 (m, 3H) 8.92 (s, 1H) 8.98 (s, 1H) 12.09 (s, 1H) MS (ESI(+)) m/e 577.0 (M+H)⁺.

Example 220

N-(4-{3-amino-7-[(isopropylamino)methyl]-1H-indazol-4-yl}phenyl)-N'-(2-fluoro-5-methylphenyl)urea

Example 220A 2-fluoro-3-formyl-6-iodobenzonitrile

LDA (24.3 mL, 2.0 M solution in THF) was added dropwise to a stirred solution of 2-fluoro-6-iodobenzonitrile (10.0 g, 40.5 mmol) in THF (200 mL) at −78° C., and the mixture was stirred for 1 h. Methyl formate (5.0 mL, 81.0 mmol) was added via syringe and the resulting mixture was stirred at −78° C. for 30 min then at rt for 1 h. H$_2$O was added and the mixture was extracted with EtOAc. The extracts were washed with brine, dried (MgSO$_4$) and concentrated. The residue was purified by flash chromatography on silica gel eluting with 20-25% EtOAc/hexanes to give the desired product (8.01 g). MS (ESI(+)) m/e 274.9 (M+H)⁺.

Example 220B 2-fluoro-6-iodo-3-[(isopropylamino)methyl]benzonitrile

A solution of Example 220A (1.00 g, 3.6 mmol) in MeOH (15 mL) was treated with isopropylamine (0.31 mL, 3.6 mmol) and sodium cyanoborohydride (227 mg, 3.6 mmol), and the mixture was stirred overnight at rt. HOAc (1 mL) was added and the reaction was stirred for 5 h, then treated with 1N NaOH and extracted with EtOAc. The extracts were washed with brine, dried (MgSO$_4$) and concentrated. The residue was purified by flash chromatography on silica gel eluting with 8% MeOH/CH$_2$Cl$_2$ to give the desired product (372 mg). MS (ESI(+)) m/e 318.9 (M+H)⁺.

Example 220C 4-iodo-7-[(isopropylamino)methyl]-1H-indazol-3-amine

The desired product was prepared by substituting Example 220B for 2-fluoro-6-iodobenzonitrile in Example 1A. MS (ESI(+)) m/e 330.9 (M+H)⁺.

Example 220D

N-(4-{3-amino-7-[(isopropylamino)methyl]-1H-indazol-4-yl}phenyl)-N'-(2-fluoro-5-methylphenyl)urea The desired product was prepared by substituting Example 220C and N-(2-fluoro-5-methylphenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 1.33 (d, J=6.4 Hz, 6H) 2.28 (s, 3H) 3.39-3.51 (m, 1H) 4.39 (t, J=6.1 Hz, 2H) 6.79-6.84 (m, 1H) 6.90 (d, J=7.1 Hz, 1H) 7.12 (dd, J=11.4, 8.3 Hz, 1H) 7.39-7.45 (m, 3H) 7.61 (d, J=8.5 Hz, 2H) 7.99 (dd, J=7.8, 2.0 Hz, 1H) 8.55 (d, J=2.4 Hz, 1H) 8.65-8.73 (m, 1H) 9.25 (s, 1H) 12.03 (s, 1H) MS (ESI(+)) m/e 447.1 (M+H)⁺.

Example 221

N-(4-{3-amino-7-[(isopropylamino)methyl]-1H-indazol-4-yl}phenyl)-N'-(3-chlorophenyl)urea The desired product was prepared by substituting Example 220C and N-(3-chlorophenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 1.33 (d, J=6.8 Hz, 6H) 3.37-3.49 (m, 1H) 4.38 (t, J=5.9 Hz, 2H) 6.90 (d, J=7.5 Hz, 1H) 7.03 (dt, J=6.4, 2.4 Hz, 1H) 7.28-7.35 (m, 2H) 7.39-7.45 (m, 3H) 7.62 (d, J=8.5 Hz, 2H) 7.74-7.75 (m, 1H) 8.63-8.73 (m, 2H) 9.03 (s, 1H) 9.04 (s, 1H) 12.03 (s, 1H) MS (ESI(+)) m/e 449.1 (M+H)⁺.

Example 222

N-(4-{3-amino-7-[(isopropylamino)methyl]-1H-indazol-4-yl}phenyl)-N'-[3-(trifluoromethyl)phenyl]urea The desired product was prepared by substituting Example 220C and N-(3-trifluoromethylphenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 1.33 (d, J=6.4 Hz, 6H) 3.39-3.51 (m, 1H) 4.39 (t, J=5.8 Hz, 2H) 6.91 (d, J=7.1 Hz, 1H) 7.32 (d, J=7.5 Hz, 1H) 7.39-7.45 (m, 3H) 7.53 (t, J=8.0 Hz, 1H) 7.59-7.66 (m, 3H) 8.05 (s, 1H) 8.67-8.73 (m, 2H) 9.14 (s, 1H) 9.28 (s, 1H) 12.05 (s, 1H) MS (ESI(−)) m/e 481.0 (M−H)⁻.

Example 223

N-(4-{3-amino-7-[(isopropylamino)methyl]-1H-indazol-4-yl}phenyl)-N'-(3-methylphenyl)urea The desired product was prepared by substituting Example 220C and N-(3-methylphenyl)N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 1.33 (d, J=6.4 Hz, 6H) 2.29 (s, 3H) 3.39-3.51 (m, 1H) 4.36-4.40 (m, 2H) 6.80 (d, J=7.8 Hz, 1H) 6.90 (d, J=7.1 Hz, 1H) 7.17 (t, J=7.8 Hz, 1H) 7.26 (d, J=8.5 Hz, 1H) 7.32 (s, 1H) 7.39 (d, J=8.8 Hz, 2H) 7.44 (d, J=7.5 Hz, 1H) 7.62 (d, J=8.8 Hz, 2H) 8.69 (m, 2H) 8.75 (s, 1H) 8.94 (s, 1H) 12.03 (s, 1H) MS (ESI(+)) m/e 429.1 (M+H)$^+$.

Example 224

N-(4-{3-amino-7-[(isopropylamino)methyl]-1H-indazol-4-yl}phenyl)-N'-(4-fluoro-3-methylphenyl)urea The desired product was prepared by substituting Example 220C and N-(4-fluoro-3-methylphenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 1.33 (d, J=6.4 Hz, 6H) 2.22 (d, J=1.7 Hz, 3H) 3.39-3.51 (m, 1H) 4.36-4.40 (m, 2H) 6.90 (d, J=7.1 Hz, 1H) 7.06 (t, J=9.2 Hz, 1H) 7.28 (ddd, J=8.4, 4.8, 3.1 Hz, 1H) 7.37-7.45 (m, 4H) 7.61 (d, J=8.5 Hz, 2H) 8.64-8.74 (m, 2H) 8.79 (s, 1H) 8.95 (s, 1H) 12.04 (s, 1H) MS (ESI(+)) m/e 447.1 (M+H)$^+$.

Example 225

N-(4-{3-amino-7-[(4-chlorophenoxy)methyl]-1H-indazol-4-yl}phenyl)-N'-(2-fluoro-5-methylphenyl)urea

Example 225A 2-fluoro-3-(hydroxymethyl)-6-iodobenzonitrile

A solution of Example 220A (5.0 g, 18 mmol) in MeOH (100 mL) at 0° C. was treated with NaBH$_4$ (822 mg, 22 mmol) and the mixture was stirred for 1 h at 0° C. Acetone was added and the mixture was stirred for 5 min, then concentrated to dryness. The residue was partitioned between H$_2$O and EtOAc. The extracts were washed with brine, dried (MgSO$_4$) and concentrated. The residue was purified by flash chromatography on silica gel, eluting with 3:2 hexanes/EtOAc to give the desired product (3.14 g). R$_f$=0.38 (3:2 hexane:EtOAc).

Example 225B

3-[(4-chlorophenoxy)methyl]-2-fluoro-6-iodobenzonitrile

The desired product was prepared by substituting Example 225A and 4-chlorophenol for Example 68A and 2-(4-morpholinyl)ethanol, respectively, in Example 75A. Additionally, diisopropyl azodicarboxylate was substituted for DEAD. MS (ESI(−)) m/e 385.8 (M−H)$^-$.

Example 225C

7-[(4-chlorophenoxy)methyl]-4-iodo-1H-indazol-3-amine

The desired product was prepared by substituting Example 225B for 2-fluoro-6-iodobenzonitrile in Example 1A. MS (ESI(+)) m/e 399.9 (M+H)$^+$.

Example 225D

N-(4-{3-amino-7-[(4-chlorophenoxy)methyl]-1H-indazol-4-yl}phenyl)-N'-(2-fluoro-5-methylphenyl)urea The desired product was prepared by substituting Example 225C for Example 1A and in Example 5B. Additionally, toluene/EtOH/H$_2$O (2:1:1) was substituted for DME/water as solvent. $^1$H NMR (300 MHz, DMSO-D$_6$) δ ppm 2.28 (s, 3H) 5.33 (s, 2H) 6.79-6.83 (m, 2H) 7.09 (d, J=9.2 Hz, 2H) 7.06-7.15 (m, 1H) 7.33-7.38 (m, 3H) 7.41 (d, J=8.5 Hz, 2H) 7.60 (d, J=8.5 Hz, 2H) 8.01 (dd, J=7.8, 2.0 Hz, 1H) 8.54 (d, J=2.7 Hz, 1H) 9.22 (s, 1H) 12.00 (s, 1H) MS (ESI(+)) m/e 516.1 (M+H)$^+$.

Example 226

N-(4-{3-amino-7-[(4-chlorophenoxy)methyl]-1H-indazol-4-yl}phenyl)-N'-(3-chlorophenyl)urea The desired product was prepared by substituting Example 226C and N-(3-chlorophenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 5.33 (s, 2H) 6.82 (d, J=7.5 Hz, 1H) 7.01-7.05 (m, 1H) 7.08 (d, J=8.8 Hz, 2H) 7.28-7.32 (m, 2H) 7.33-7.38 (m, 3H) 7.41 (d, J=8.8 Hz, 2H) 7.60 (d, J=8.8 Hz, 2H) 7.73-7.74 (m, 1H) 8.93 (s, 1H) 8.96 (s, 1H) 12.01 (s, 1H) MS (ESI(+)) m/e 518.5 (M+H)$^+$.

Example 227

N-(4-{3-amino-7-[(4-chlorophenoxy)methyl]-1H-indazol-4-yl}phenyl)-N'-[3-(trifluoromethyl)phenyl]urea The desired product was prepared by substituting Example 225C and N-(3-trifluoromethylphenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 5.32 (s, 2H) 6.82 (d, J=7.1 Hz, 1H) 7.08 (d, J=8.8 Hz, 2H) 7.31-7.37 (m, 4H) 7.41 (d, J=8.5 Hz, 2H) 7.53 (t, J=8.0 Hz, 1H) 7.59-7.63 (m, 3H) 8.04 (s, 1H) 8.96 (s, 1H) 9.11 (s, 1H) 11.96 (s, 1H) MS (ESI(+)) m/e 522.0 (M+H)$^+$.

Example 228

N-(4-{3-amino-7-[(4-chlorophenoxy)methyl]-1H-indazol-4-yl}phenyl)-N'-(3-methylphenyl)urea The desired product was prepared by substituting Example 225C and N-(3-methylphenyl)N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 2.29 (s, 3H) 5.33 (s, 2H) 6.80 (d, J=7.5 Hz, 1H) 6.83 (d, J=7.1 Hz, 1H) 7.08 (d, J=8.8 Hz, 2H) 7.17 (t, J=7.8 Hz, 1H) 7.25 (d, J=8.5 Hz, 1H) 7.32 (s, 1H) 7.33-7.41 (m, 5H) 7.60 (d, J=8.8 Hz, 2H) 8.65 (s, 1H) 8.82 (s, 1H) 12.08 (s, 1H) MS (ESI(+)) m/e 498.1 (M+H)$^+$.

Example 229

N-(4-{3-amino-7-[(4-chlorophenoxy)methyl]-1H-indazol-4-yl}phenyl)-N'-(4-fluoro-3-methylphenyl)urea The desired product was prepared by substituting Example 225C and N-(4-fluoro-3-methylphenyl)-N'-[4-(4,4,5,5-tetramethyl-1,3,2-dioxaborolan-2-yl)phenyl]urea for Example 1A and Example 5A, respectively, in Example 5B. Additionally, toluene/EtOH/H$_2$O (2:1:1) was substituted for DME/water as solvent. $^1$H NMR (300 MHz, DMSO-D$_6$) δ ppm 2.22 (d, J=1.7 Hz, 3H) 5.33 (s, 2H) 6.83 (d, J=7.1 Hz, 1H) 7.01-7.11 (m, 3H) 7.25-7.31 (m, 1H) 7.33-7.41 (m, 6H) 7.59 (d, J=8.8 Hz, 2H) 8.68 (s, 1H) 8.82 (s, 1H) 12.05 (s, 1H) MS (ESI(+)) m/e 516.1 (M+H)$^+$.

Example 230

N-(4-{3-amino-7-[3-(1H-pyrrol-1-yl)propoxy]-1H-indazol-4-yl}phenyl)-N'-(2-fluoro-5-methylphenyl)urea

Example 230A 2-fluoro-6-iodo-3-[3-(1H-pyrrol-1-yl)propoxy]benzonitrile

The desired product was prepared by substituting 3-pyrrol-1-yl-propan-1-ol for 2-(4-morpholinyl)ethanol in Example 75A.

Example 230B 4-iodo-7-[3-(1H-pyrrol-1-yl)propoxy]-1H-indazol-3-amine

The desired product was prepared by substituting Example 230A for 2-fluoro-6-iodobenzonitrile in Example 1A. MS (ESI(+)) m/e 383 (M+H)$^+$.

Example 230C

N-(4-{3-amino-7-[3-(1H-pyrrol-1-yl)propoxyl]-1H-indazol-4-yl}phenyl)-N'-(2-fluoro-5-methylphenyl)urea The desired product was prepared by substituting Example 230B for Example 1A in Example 5B. $^1$H NMR (500 MHz, DMSO-D$_6$) δ ppm 2.14-2.23 (m, 2H) 2.27 (s, 3H) 4.01 (t, J=6.1 Hz, 2H) 4.19 (t, J=6.9 Hz, 2H) 4.31 (s, 2H) 5.97 (t, J=2.2 Hz, 2H) 6.66 (d, J=7.5 Hz, 1H) 6.71 (d, J=7.8 Hz, 1H) 6.76 (t, J=2.2 Hz, 2H) 6.78-6.81 (m, 1H) 7.10 (dd, J=11.2, 8.4 Hz, 1H) 7.35 (d, J=8.4 Hz, 2H) 7.55 (d, J=8.4 Hz, 2H) 7.99 (dd, J=8.0, 2.0 Hz, 1H) 8.49 (d, J=2.2 Hz, 1H) 9.14 (s, 1H) 11.90 (s, 1H) MS (ESI(+)) m/e 499.1 (M+H)$^+$.

Example 231

4-(1H-indol-5-yl)-7-[3-(1H-pyrrol-1-yl)propoxyl]-1H-indazol-3-amine

The desired product was prepared by substituting Example 230B and indole-5-boronic acid for Example 1A and Example 5A, respectively, in Example 5B. $^1$H NMR (300 MHz, DMSO-D$_6$) δ ppm 2.16-2.24 (m, 2H) 4.02 (t, J=6.1 Hz, 2H) 4.21 (t, J=6.6 Hz, 2H) 4.29 (s, 2H) 5.98 (t, J=2.0 Hz, 2H) 6.47-6.49 (m, 1H) 6.67 (d, J=7.5 Hz, 1H) 6.72 (d, J=7.8 Hz, 1H) 6.78 (t, J=2.0 Hz, 2H) 7.14 (dd, J=8.3, 1.5 Hz, 1H) 7.41 (t, J=2.7 Hz, 1H) 7.49 (d, J=8.1 Hz, 1H) 7.56 (s, 1H) 11.19 (s, 1H) 11.86 (s, 1H) MS (ESI(+)) m/e 372.1 (M+H)$^+$.

Example 232

N-(4-{3-amino-7-[3-(1H-pyrrol-1-yl)propoxy]-1H-indazol-4-yl}phenyl)-N'-(3-methylphenyl)urea The desired product was prepared by substituting Example 230B and N-(3-methylphenyl)N'-[4-(4,4,5,5-tetramethyl-1,3,2-dioxaborolan-2-yl)phenyl]urea for Example 1A and Example 5A, respectively, in Example 5B. $^1$H NMR (300 MHz, DMSO-D$_6$) δ ppm 2.16-2.24 (m, 2H) 2.29 (s, 3H) 4.02 (t, J=5.9 Hz, 2H) 4.20 (t, J=6.8 Hz, 2H) 5.98 (t, J=2.2 Hz, 2H) 6.68 (d, J=7.8 Hz, 1H) 6.74 (d, J=7.8 Hz, 1H) 6.77 (t, J=2.0 Hz, 2H) 6.80 (d, J=7.1 Hz, 1H) 7.16 (t, J=7.6 Hz, 1H) 7.25 (d, J=8.1 Hz, 1H) 7.32 (s, 1H) 7.35 (d, J=8.8 Hz, 2H) 7.56 (d, J=8.8 Hz, 2H) 8.63 (s, 1H) 8.76 (s, 1H) 12.05 (s, 1H) MS (ESI(+)) m/e 481.1 (M+H)$^+$.

Example 233

N-(4-{3-amino-7-[3-(1H-pyrrol-1-yl)propoxy]-1H-indazol-4-yl}phenyl)-N'-(3-chlorophenyl)urea The desired product was prepared by substituting Example 230B and N-(3-chlorophenyl)-N'-[4-(4,4,5,5-tetramethyl-1,3,2-dioxaborolan-2-yl)phenyl]urea for Example 1A and Example 5A, respectively, in Example 5B. $^1$H NMR (300 MHz, DMSO-D$_6$) δ ppm 2.15-2.23 (m, 2H) 4.01 (t, J=5.9 Hz, 2H) 4.20 (t, J=6.8 Hz, 2H) 4.33 (s, 2H) 5.98 (t, J=2.2 Hz, 2H) 6.66 (d, J=7.5 Hz, 1H) 6.72 (d, J=7.8 Hz, 1H) 6.77 (t, J=2.2 Hz, 2H) 7.02 (dt, J=6.4, 2.2 Hz, 1H) 7.28 (m, 2H) 7.36 (d, J=8.5 Hz, 2H) 7.56 (d, J=8.5 Hz, 2H) 7.72-7.74 (m, 1H) 8.85 (s, 1H) 8.92 (s, 1H) 11.93 (s, 1H) MS (ESI(−)) m/e 499.3 (M−H)$^−$.

Example 234

N-[2-({3-amino-4-[4-({[(2-fluoro-5-methylphenyl)amino]carbonyl}amino)phenyl]-1H-indazol-7-yl}oxy)ethyl]thiophene-2-sulfonamide

Example 234A

N-{2-[(3-amino-4-iodo-1H-indazol-7-yl)oxy]-ethyl}thiophene-2-sulfonamide

The desired product was prepared by substituting 2-thiophenesulfonyl chloride for methanesulfonyl chloride in Example 170B. MS (ESI(+)) m/e 465 (M+H)$^+$.

Example 234B

N-[2-({3-amino-4-[4-({[(2-fluoro-5-methylphenyl)amino]carbonyl}amino)phenyl]-1H-indazol-7-yl}oxy)ethyl]thiophene-2-sulfonamide The desired product was prepared by substituting Example 234A for Example 1A in Example 5B. $^1$H NMR (300 MHz, DMSO-D$_6$) δ ppm 2.28 (s, 3H) 3.30-3.34 (m, 2H) 4.14 (t, J=5.9 Hz, 2H) 6.68 (d, J=7.5 Hz, 1H) 6.74 (d, J=7.5 Hz, 1H) 6.79-6.83 (m, 1H) 7.11 (dd, J=11.4, 8.3 Hz, 1H) 7.17 (dd, J=5.1, 3.7 Hz, 1H) 7.36 (d, J=8.8 Hz, 2H) 7.56 (d, J=8.8 Hz, 2H) 7.65 (dd, J=3.7, 1.4 Hz, 1H) 7.92-8.02 (m, 3H) 7.98 (d, J=6.4 Hz, 1H) 8.01 (dd, J=7.8, 2.0 Hz, 1H) 8.51 (d, J=2.4 Hz, 1H) 9.17 (s, 1H) 11.84 (s, 1H) MS (ESI(+)) m/e 580.6 (M+H)$^+$.

Example 235

N-[2-({3-amino-4-[4-({[(3-methylphenyl)amino]carbonyl}amino)phenyl]-1H-indazol-7-yl}oxy)ethyl]thiophene-2-sulfonamide The desired product was prepared by substituting Example 234A and N-(3-methylphenyl)-N'-[4-(4,4,5,5-tetramethyl-1,3,2-dioxaborolan-2-yl)phenyl]urea for Example 1A and Example 5A, respectively, in Example 5B. $^1$H NMR (300 MHz, DMSO-D$_6$) δ ppm 2.29 (s, 3H) 3.33 (q, J=5.8 Hz, 2H) 4.14 (t, J=5.8 Hz, 2H) 6.66-6.84 (m, 3H) 7.16 (t, J=7.8 Hz, 1H) 7.17 (dd, J=5.1, 3.7 Hz, 1H) 7.25 (d, J=8.8 Hz, 1H) 7.31 (s, 1H) 7.35 (d, J=8.5 Hz, 2H) 7.56 (d, J=8.5 Hz, 2H) 7.65 (dd, J=3.7, 1.4 Hz, 1H) 7.93 (dd, J=5.1, 1.4 Hz, 1H) 7.97 (t, J=5.9 Hz, 1H) 8.63 (s, 1H) 8.77 (s, 1H) 11.91 (s, 1H) MS (ESI(+)) m/e 563.0 (M+H)$^+$.

Example 236

N-(2-{[3-amino-4-(1H-indol-5-yl)-1H-indazol-7-yl]oxy}ethyl)thiophene-2-sulfonamide The desired product was prepared by substituting Example 234A and indole-5-boronic acid for Example 1A and Example 5A, respectively, in Example 5B. $^1$H NMR (300 MHz, DMSO-D$_6$) δ ppm 3.33 (q, J=5.4 Hz, 2H) 4.16 (t, J=5.6 Hz, 2H) 6.49-6.49 (m, 1H) 6.74 (d, J=7.8 Hz, 1H) 6.78 (d, J=7.8 Hz, 1H) 7.15 (dd, J=8.5, 1.7 Hz, 1H) 7.18 (dd, J=4.8, 3.7 Hz, 1H) 7.41 (t, J=2.7 Hz, 1H) 7.49 (d, J=8.1 Hz, 1H) 7.57 (d, J=1.4 Hz, 1H) 7.65 (dd, J=3.7, 1.4 Hz, 1H) 7.94 (dd, J=5.1, 1.4 Hz, 1H) 7.98 (t, J=5.9 Hz, 1H) 11.20 (s, 1H) 11.98 (s, 1H) MS (ESI(+)) m/e 454.0 (M+H)$^+$.

Example 237

N-(4-{3-amino-7-[3-(diethylamino)propoxy]-1H-indazol-4-yl}phenyl)-N'-(2-fluoro-5-methylphenyl)urea

Example 237A

3-[3-(diethylamino)propoxy]-2-fluoro-6-iodobenzonitrile

The desired product was prepared by substituting 3-(diethylamino)-propan-1-ol for 2-(4-morpholinyl)ethanol in Example 75A.

Example 237B 4-(4-aminophenyl)-7-[3-(diethylamino)propoxy]-1H-indazol-3-amine The desired product was prepared by substituting Example 237A for Example 15E in Examples 15F-G. MS (ESI(+)) m/e 354 (M+H)$^+$.

Example 237C

N-(4-{3-amino-7-[3-(diethylamino)propoxy]-1H-indazol-4-yl}phenyl)-N'-(2-fluoro-5-methylphenyl)urea The desired product was prepared by substituting Example 237B and 1-fluoro-2-isocyanato-4-methylbenzene for Example 15G and 1-fluoro-3-isocyanatobenzene, respectively, in Example 15H. $^1$H NMR (300 MHz, DMSO-D$_6$) δ ppm 1.25 (t, J=7.3 Hz, 6H) 2.11-2.20 (m, 2H) 2.28 (s, 3H) 3.16-2.35 (m, 4H) 3.31-3.41 (m, 2H) 4.24 (t, J=5.8 Hz, 2H) 6.71 (d, J=7.5 Hz, 1H) 6.79-6.84 (m, 2H) 7.11 (dd, J=11.4, 8.3 Hz, 1H) 7.36 (d, J=8.5 Hz, 2H) 7.57 (d, J=8.5 Hz, 2H) 8.00 (dd, J=7.8, 2.0 Hz, 1H) 8.52 (d, J=2.4 Hz, 1H) 9.07 (s, 1H) 9.18 (s, 1H) 11.93 (s, 1H) MS (APCI(+)) m/e 505.4 (M+H)$^+$.

Example 238

N-(4-{3-amino-7-[3-(diethylamino)propoxy]-1H-indazol-4-yl}phenyl)-N'-(3-chlorophenyl)urea The desired product was prepared by substituting Example 237B and 1-chloro-3-isocyanatobenzene for Example 15G and 1-fluoro-3-isocyanatobenzene, respectively, in Example 15H. $^1$H NMR (300 MHz, DMSO-D$_6$) δ ppm 1.25 (t, J=7.29 Hz, 6H) 2.11-2.20 (m, 2H) 3.16-3.25 (m, 4H) 3.34-3.14 (m, 2H) 4.24 (t, J=5.8 Hz, 2H) 6.71 (d, J=7.8 Hz, 1H) 6.81 (d, J=7.8 Hz, 1H) 7.03 (dt, J=6.4, 2.4 Hz, 1H) 7.26-7.32 (m, 2H) 7.36 (d, J=8.8 Hz, 2H) 7.57 (d, J=8.8 Hz, 2H) 7.73-7.74 (m, 1H) 8.92 (s, 1H) 8.98 (s, 1H) 9.05 (s, 1H) 11.92 (s, 1H) MS (ESI(+)) m/e 506.9 (M+H)$^+$.

Example 239

N-(4-{3-amino-7-[3-(diethylamino)propoxy]-1H-indazol-4-yl}phenyl)-N'-[3-(trifluoromethyl)phenyl]urea The desired product was prepared by substituting Example 237B and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 1.24 (t, J=7.3 Hz, 6H) 2.11-2.20 (m, 2H) 3.16-3.25 (m, 4H) 3.31-3.37 (m, 2H) 4.24 (t, J=5.6 Hz, 2H) 6.71 (d, J=7.8 Hz, 1H) 6.81 (m, J=7.8 Hz, 1H) 7.32 (d, J=7.1 Hz, 1H) 7.36 (d, J=8.5 Hz, 2H) 7.50-7.61 (m, 4H) 8.04 (s, 1H) 8.95 (s, 1H) 9.04 (s, 1H) 9.13 (s, 1H) 11.92 (s, 1H) MS (ESI(+)) m/e 541.2 (M+H)$^+$.

Example 240

N-(4-{3-amino-7-[3-(diethylamino)propoxy]-1H-indazol-4-yl}phenyl)-N'-(3-fluorophenyl)urea The desired product was prepared by substituting Example 237B for Example 15G in Example 15H. $^1$H NMR (300 MHz, DMSO-D$_6$) δ ppm 1.25 (t, J=7.3 Hz, 6H) 2.11-2.20 (m, 2H) 3.16-3.24 (m, 4H) 3.34-3.43 (m, 2H) 4.24 (t, J=5.6 Hz, 2H) 6.72 (d, J=7.8 Hz, 1H) 6.76-6.82 (m, 1H) 6.81 (d, J=7.8 Hz, 1H) 7.14 (ddd, J=8.1, 2.0, 0.7 Hz, 1H) 7.28-7.35 (m, 1H) 7.36 (d, J=8.8 Hz, 2H) 7.52 (dt, J=12.0, 2.3 Hz, 1H) 7.57 (d, J=8.8 Hz, 2H) 8.92 (s, 1H) 9.01 (s, 1H) 9.06 (s, 1H) 11.94 (s, 1H) MS (APCI(−)) m/e 489.3 (M−H)$^−$.

Example 241

N-[4-(3-amino-1H-indazol-4-yl)-2-fluorophenyl]-N'-[3-(trifluoromethyl)phenyl]urea The desired product was prepared by substituting 1-isocyanato-3-(trifluoromethyl)benzene for 1-isocyanato-3-methylbenzene in Examples 44A-B. $^1$H NMR (300 MHz, DMSO-D$_6$) δ ppm 4.37 (s, 2H) 6.80-6.86 (m, 1H) 7.26-7.35 (m, 4H) 7.39 (dd, J=12.2, 1.7 Hz, 1H) 7.54-7.56 (m, 2H) 8.06 (s, 1H)

8.26 (t, J=8.5 Hz, 1H) 8.76 (d, J=2.4 Hz, 1H) 9.47 (s, 1H) 11.77 (s, 1H) MS (ESI(+)) m/e 430.0 (M+H)+.

Example 242

N-[4-(3-amino-1H-indazol-4-yl)-2-fluorophenyl]-N'-[4-fluoro-3-(trifluoromethyl)phenyl]urea The desired product was prepared by substituting 1-fluoro-4-isocyanato-2-(trifluoromethyl)benzene for 1-isocyanato-3-methylbenzene in Examples 44A-B. $^1$H NMR (300 MHz, DMSO-D$_6$) δ ppm 4.37 (s, 2H) 6.83 (dd, J=4.4, 3.7 Hz, 1H) 7.25-7.29 (m, 3H) 7.38 (dd, J=12.0, 1.9 Hz, 1H) 7.46 (t, J=9.8 Hz, 1H) 7.61-7.66 (m, 1H) 8.05 (dd, J=6.4, 2.7 Hz, 1H) 8.23 (t, J=8.5 Hz, 1H) 8.75 (d, J=1.7 Hz, 1H) 9.45 (s, 1H) 11.77 (s, 1H) MS (ESI(+)) m/e 448.0 (M+H)+.

Example 243

N-[4-(3-amino-7-pyridin-3-yl-1H-indazol-4-yl)phenyl]-N'-(4-fluoro-3-methylphenyl)urea Example 243A 3-fluoro-1,1'-biphenyl-2-carbonitrile The desired product was prepared by substituting 2-fluoro-6-iodobenzonitrile for Example 1A and phenylboronic acid for Example 1B in Example 1C. Additionally, toluene/EtOH/H$_2$O (3:2:1) was substituted for DME/H$_2$O as the solvent.

Example 243B 3-fluoro-4-iodo-1,1'-biphenyl-2-carbonitrile

A solution of Example 243A (6.8 g, 34.5 mmol) in THF (110 mL) at −78° C. under nitrogen atmosphere was treated dropwise with LDA (2.0 M solution in THF) and stirred for 1 h, then a solution of iodine in THF (30 mL) was added via cannula over about 10 min. The thick mixture was allowed to warm to rt and stirred for 1 h, then treated with saturated aqueous Na2SO3 solution (10 mL). The mixture was concentrated to remove the THF, then H2O was added and the mixture was extracted with EtOAc. The extracts were washed with brine, dried (MgSO4) and concentrated. The residue was purified by flash chromatography on silica gel, eluting with EtOAc/hexanes (1:7), and the resulting solid was triturated with hexanes and EtOAc to give the desired product (6.8 g). R$_f$=0.44 (7:1 hexane:EtOAc)

Example 243C 3-fluoro-4-iodo-4'-nitro-1,1'-biphenyl-2-carbonitrile

A solution of Example 243B (2.77 g, 8.6 mmol) in 1,2-dichloroethane (50 mL) under nitrogen atmosphere was treated with nitronium tetrafluoroborate (85% technical grade, 2.0 g, 12.9 mmol) and the mixture was stirred for 3.5 h, at which time an additional portion of nitronium tetrafluoroborate (700 mg, 5.3 mmol) was added. The reaction was stirred for another 2 h, then poured over ice, and once melted the mixture was neutralized with sat. NaHCO3 solution. The mixture was extracted with EtOAc, and the extracts were washed with brine, dried (MgSO4) and concentrated. The residue was purified by flash chromatography on silica gel, eluting with hexanes/EtOAc (4:1) to give the desired product (1.84 g). MS (ESI(−)) m/e 367.9 (M−H)−.

Example 243D 3-fluoro-4'-nitro-4-pyridin-3-yl-1,1'-biphenyl-2-carbonitrile

The desired product was prepared by substituting Example 243C and pyridine-3-boronic acid for Examples 1A and 1B, respectively, in Example 1C. Additionally, PdCl2(dppf) was used in place of Pd(PPh3)4. MS (ESI(+)) m/e 320.0 (M+H)+.

Example 243E 4-(4-aminophenyl)-7-pyridin-3-yl-1H-indazol-3-amine

The desired product was prepared by substituting Example 243D for 2-fluoro-6-iodobenzonitrile in Example 1A. In addition to pyrazole cyclization, nitro reduction was also accomplished in this reaction. MS (ESI(+)) m/e 302.0 (M+H)+.

Example 243F

N-[4-(3-amino-1H-indazol-4-yl)-2-fluorophenyl]-N'-[4-fluoro-3-(trifluoromethyl)phenyl]urea The desired product was prepared by substituting Example 243E and 1-fluoro-4-isocyanato-2-methylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.23 (d, J=1.7 Hz, 3H) 6.97 (d, J=7.5 Hz, 1H) 7.06 (t, J=9.2 Hz, 1H) 7.29 (ddd, J=8.7, 4.5, 3.1 Hz, 1H) 7.39 (dd, J=6.8, 2.8 Hz, 1H) 7.43-7.47 (m, 3H) 7.62 (d, J=8.5 Hz, 2H) 7.69-7.80 (m, 1H) 8.32 (d, J=7.8 Hz, 1H) 8.67-8.80 (m, 1H) 8.71 (s, 1H) 8.87 (s, 1H) 8.90-9.15 (m, 1H) 11.81-12.42 (br. s., 1H) MS (ESI(+)) m/e 453.1 (M+H)+.

Example 244

N-[4-(3-amino-7-pyridin-3-yl-1H-indazol-4-yl)phenyl]-N'-(3-chlorophenyl)urea

The desired product was prepared by substituting Example 243E and 1-chloro-3-isocyanatobenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 6.96 (d, J=7.5 Hz, 1H) 7.02-7.05 (m, 1H) 7.28-7.35 (m, 2H) 7.44-7.47 (m, 3H) 7.63 (d, J=8.8 Hz, 2H) 7.66-7.72 (m, 1H) 7.74-7.75 (m, 1H) 8.27 (d, J=7.5 Hz, 1H) 8.61-8.85 (m, 1H) 8.93-9.04 (m, 3H) 11.73-12.36 (br. s., 1H) MS (ESI(+)) m/e 455.1 (M+H)+.

Example 245

N-[4-(3-amino-7-pyridin-3-yl-1H-indazol-4-yl)phenyl]-N'-[3-(trifluoromethyl)phenyl]urea The desired product was prepared by substituting Example 243E and 1-isocyanato-3-(trifluoromethyl)benzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 6.97 (d, J=7.1 Hz, 1H) 7.33 (d, J=7.5 Hz, 1H) 7.44-7.47 (m, 3H) 7.53

(t, J=7.8 Hz, 1H) 7.60-7.70 (m, 4H) 8.05 (s, 1H) 8.26 (d, J=8.1 Hz, 1H) 8.61-8.81 (m, 1H) 8.89-9.08 (m, 2H) 9.15 (s, 1H) 11.79-12.29 (br. s., 1H) MS (ESI(+)) e 489.1 (M+H)$^+$.

Example 246

N-[4-(3-amino-7-pyridin-3-yl-1H-indazol-4-yl)phenyl]-N'-(2-fluoro-5-methylphenyl)urea The desired product was prepared by substituting Example 243E and 1-fluoro-2-isocyanato-4-methylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 2.29 (s, 3H) 6.79-6.84 (m, 1H) 6.96 (d, J=7.5 Hz, 1H) 7.12 (dd, J=11.4, 8.3 Hz, 1H) 7.44-7.47 (m, 3H) 7.63 (d, J=8.8 Hz, 2H) 7.65-7.73 (m, 1H) 8.01 (dd, J=8.0, 1.9 Hz, 1H) 8.26 (d, J=7.8 Hz, 1H) 8.55 (d, J=2.4 Hz, 1H) 8.63-8.82 (m, 1H) 8.88-9.11 (m, 1H) 9.24 (s, 1H) 11.79-12.33 (br. s., 1H) MS (ESI(+)) m/e 453.1 (M+H)$^+$.

Example 247

N-[4-(3-amino-7-pyridin-3-yl-1H-indazol-4-yl)phenyl]-N'-[4-fluoro-3-(trifluoromethyl)phenyl]urea The desired product was prepared by substituting Example 243E and 1-fluoro-4-isocyanato-2-(trifluoromethyl)benzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) δ ppm 6.95 (d, J=7.5 Hz, 1H) 7.40-7.49 (m, 4H) 7.61-7.70 (m, 4H) 8.04 (dd, J=6.4, 2.7 Hz, 1H) 8.19-8.23 (m, 1H) 8.67 (dd, J=4.8, 1.4 Hz, 1H) 8.94-8.97 (m, 1H) 9.00 (s, 1H) 9.12 (s, 1H) 12.02 (s, 1H) MS (ESI(+)) m/e 507.1 (M+H)$^+$.

Example 248

N-(4-{3-amino-7-[3-(dimethylamino)propoxy]-1H-indazol-4-yl}phenyl)-N'-(3-methylphenyl)urea

Example 248A

3-[3-(dimethylamino)propoxy]-2-fluoro-6-iodobenzonitrile

The desired product was prepared by substituting 3-(dimethylamino)-propan-1-ol for 2-(4-morpholinyl)ethanol in Example 75A. MS (ESI(+)) m/e 349 (M+H)$^+$.

Example 248B 4-(4-aminophenyl)-7-[3-(dimethylamino)propoxy]-1H-indazol-3-amine The desired product was prepared by substituting Example 248A for Example 15E in Examples 15F-G. MS (ESI(+)) m/e 326 (M+H)$^+$.

Example 248C

N-(4-{3-amino-7-[3-(dimethylamino)propoxy]-1H-indazol-4-yl}phenyl)-N'-(3-methylphenyl)urea The desired product was prepared by substituting Example 248B and 1-isocyanato-3-methylbenzene for Example 15G and 1-fluoro-3-isocyanatobenzene, respectively, in Example 15H. $^1$H NMR (300 MHz, DMSO-D$_6$) δ ppm 2.13-2.22 (m, 2H) 2.28 (s, 3H) 2.86 (d, J=5.1 Hz, 6H) 3.34-3.41 (m, 2H) 4.22 (t, J=5.8 Hz, 2H) 6.72 (d, J=7.8 Hz, 1H) 6.80 (d, J=7.1 Hz, 1H) 6.82 (d, J=7.8 Hz, 1H) 7.16 (t, J=7.8 Hz, 1H) 7.25 (d, J=8.5 Hz, 1H) 7.32 (s, 1H) 7.34 (d, J=8.5 Hz, 2H) 7.57 (d, J=8.5 Hz, 2H) 8.68 (s, 1H) 8.83 (s, 1H) 9.40 (s, 1H) 11.94 (s, 1H) MS (ESI(+)) m/e 459.2 (M+H)$^+$.

Example 249

N-(4-{3-amino-7-[3-(dimethylamino)propoxy]-1H-indazol-4-yl}phenyl)-N'-(2-fluoro-5-methylphenyl)urea The desired product was prepared by substituting Example 248B and 1-fluoro-2-isocyanato-4-methylbenzene for Example 15G and 1-fluoro-3-isocyanatobenzene, respectively, in Example 15H. $^1$H NMR (300 MHz, DMSO-D$_6$) δ ppm 2.13-2.22 (m, 2H) 2.28 (s, 3H) 2.86 (d, J=4.8 Hz, 6H) 3.34-3.42 (m, 2H) 4.22 (t, J=5.9 Hz, 2H) 6.72 (d, J=7.8 Hz, 1H) 6.79-6.83 (m, 2H) 7.12 (dd, J=11.2, 8.5 Hz, 1H) 7.36 (d, J=8.5 Hz, 2H) 7.57 (d, J=8.5 Hz, 2H) 8.00 (dd, J=8.0, 1.9 Hz, 1H) 8.53 (d, J=2.4 Hz, 1H) 9.19 (s, 1H) 9.41 (s, 1H) 11.94 (s, 1H) MS (ESI(+)) m/e 477.1 (M+H)$^+$.

Example 250

N-(4-{3-amino-7-[3-(dimethylamino)propoxy]-1H-indazol-4-yl}phenyl)-N'-(3-fluorophenyl)urea The desired product was prepared by substituting Example 248B for Example 15G in Example 15H. $^1$H NMR (300 MHz, DMSO-D$_6$) δ ppm 2.13-2.22 (m, 2H) 2.86 (d, J=4.8 Hz, 6H) 3.34-3.41 (m, 2H) 4.22 (t, J=5.9 Hz, 2H) 6.73 (d, J=7.5 Hz, 1H) 6.79 (td, J=8.6, 2.5 Hz, 1H) 6.83 (d, J=7.8 Hz, 1H) 7.14 (ddd, J=8.1, 2.0, 1.0 Hz, 1H) 7.26-7.37 (m, 1H) 7.36 (d, J=8.5 Hz, 2H) 7.52 (dt, J=12.0, 2.3 Hz, 1H) 7.58 (d, J=8.5 Hz, 2H) 8.98 (s, 1H) 9.07 (s, 1H) 9.44 (s, 1H) 11.99 (s, 1H) MS (ESI(+)) m/e 463.2 (M+H)$^+$.

Example 251

N-(4-{3-amino-7-[3-(dimethylamino)propoxy]-1H-indazol-4-yl}phenyl)-N'-(3-chlorophenyl)urea The desired product was prepared by substituting Example 248 and 1-chloro-3-isocyanatobenzene for Example 15G and 1-fluoro-3-isocyanatobenzene, respectively, in Example 15H. $^1$H NMR (300 MHz, DMSO-D$_6$) δ ppm 2.13-2.22 (m, 2H) 2.86 (d, J=4.8 Hz, 6H) 3.34-3.41 (m, 2H) 4.22 (t, J=5.8 Hz, 2H) 6.73 (d, J=7.8 Hz, 1H) 6.82 (d, J=7.8 Hz, 1H) 7.03 (ddd, J=6.1, 3.1, 2.4 Hz, 1H) 7.27-7.32 (m, 2H) 7.36 (d, J=8.5 Hz, 2H) 7.58 (d, J=8.5 Hz, 2H) 7.73-7.75 (m, 1H) 8.98 (s, 1H) 9.04 (s, 1H) 9.41 (s, 1H) 11.96 (s, 1H) MS (ESI(+)) m/e 479.1 (M+H)$^+$.

Example 252

N-(4-{3-amino-7-[3-(dimethylamino)propoxy]-1H-indazol-4-yl}phenyl)-N'-[3-(trifluoromethyl)phenyl]urea The desired product was prepared by substituting Example 248B and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 2.13-2.22 (m, 2H) 2.86 (d, J=4.8 Hz, 6H) 3.34-3.41 (m, 2H) 4.22 (t, J=5.9 Hz, 2H) 6.72 (d, J=7.8 Hz, 1H) 6.82 (d, J=7.8 Hz, 1H) 7.32 (d, J=7.5 Hz, 1H) 7.36 (d, J=8.8 Hz, 2H) 7.50-7.61 (m, 4H) 8.05 (s, 1H) 8.98 (s, 1H) 9.16 (s, 1H) 9.38 (s, 1H) 11.92 (s, 1H) MS (ESI(+)) m/e 513.1 (M+H)$^+$.

Example 253

N-(4-{3-amino-7-[3-(dimethylamino)propoxy]-1H-indazol-4-yl}phenyl)-N'-(4-fluoro-3-methylphenyl)urea The desired product was prepared by substituting Example 248B and 1-fluoro-4-isocyanato-2-methylbenzene for Example 15G and 1-fluoro-3-isocyanatobenzene, respectively, in Example 15H. $^1$H NMR (300 MHz, DMSO-D$_6$) δ ppm 2.13-2.19 (m, 2H) 2.22 (d, J=1.7 Hz, 3H) 2.86 (d, J=5.1 Hz, 6H) 3.34-3.41 (m, 2H) 4.22 (t, J=5.9 Hz, 2H) 6.72 (d, J=7.8 Hz, 1H) 6.81 (d, J=7.8 Hz, 1H) 7.05 (t, J=9.2 Hz, 1H) 7.28 (ddd, J=8.8, 4.1, 2.7 Hz, 1H) 7.33-7.39 (m, 3H) 7.56 (d, J=8.5 Hz, 2H) 8.72 (s, 1H) 8.83 (s, 1H) 9.41 (s, 1H) 11.95 (s, 1H) MS (ESI(+)) m/e 477.2 (M+H)$^+$.

Example 254

N-{4-[3-amino-7-(3-morpholin-4-ylpropoxy)-1H-indazol-4-yl]phenyl}-N'-(3-bromophenyl)urea The desired product was prepared by substituting Example 207B and 1-bromo-3-isocyanatobenzene for Example 15G and 1-fluoro-3-isocyanatobenzene, respectively, in Example 15H. $^1$H NMR (500 MHz, DMSO-D$_6$) δ ppm 2.18-2.23 (m, 2H) 3.06-3.19 (m, 4H) 3.42-3.46 (m, 2H) 3.65-3.70 (m, 2H) 4.00-4.07 (m, 2H) 4.24 (t, J=5.8 Hz, 2H) 6.73 (d, J=7.8 Hz, 1H) 6.83 (d, J=7.8 Hz, 1H) 7.16 (ddd, J=8.1, 1.9, 0.9 Hz, 1H) 7.25 (t, J=8.1 Hz, 1H) 7.32-7.38 (m, 3H) 7.58 (d, J=8.7 Hz, 2H) 7.88 (t, J=1.9 Hz, 1H) 8.99 (s, 1H) 9.04 (s, 1H) 9.73 (s, 1H) 11.91 (s, 1H) MS (ESI(+)) m/e 565.1, 567.1 (M+H)$^+$.

Example 255

N-[4-(3-amino-1H-indazol-4-yl)-3-fluorophenyl]-N'-(3-methylphenyl)urea

Example 255A 3-fluoro-4-(4,4,5,5-tetramethyl-1,3,2-dioxaborolan-2-yl)phenylamine The desired product was prepared by substituting 4-bromo-3-fluoro-phenylamine for Example 149A in Example 149B. The mixture was heated at 85° C. overnight and the desired product was purified by flash chromatography using 30% ethyl acetate in hexanes. MS (ESI(+) m/e 238 (M+H)$^+$.

Example 255B

N-[3-fluoro-4-(4,4,5,5-tetramethyl-1,3,2-dioxaborolan-2-yl)phenyl]-N'-(3-methylphenyl)urea The desired product was prepared by substituting Example 255A and 1-isocyanato-3-methylbenzene for 4-bromo-2-ethylaniline and 1-fluoro-2-isocyanato-4-methylbenzene, respectively, in Example 149A. MS (ESI(+) m/e 371 (M+H)$^+$.

Example 255C

N-[4-(3-amino-1H-indazol-4-yl)-3-fluorophenyl]-N'-(3-methylphenyl)urea

The desired product was prepared by substituting Example 255B for Example 1B in Example 1C. $^1$H NMR (400 MHz, DMSO-D$_6$) δ ppm 2.29 (s, 3H), 6.81-6.85 (m, 2H), 7.18 (t, J=7.83 Hz, 1H), 7.25 (d, J=1.84 Hz, 1H), 7.27 (d, J=1.84 Hz, 1H), 7.30-7.34 (m, 4H), 7.64 (dd, J=12.73, 1.99 Hz, 1H), 8.74 (s, 1H), 9.04 (s, 1H); MS (ESI(+) m/e 376 (M+H)$^+$.

Example 256

N-[4-(3-amino-1H-indazol-4-yl)-3-fluorophenyl]-N'-(2-fluoro-5-methylphenyl)urea

The desired product was prepared by substituting Example 255A for 4-bromo-2-ethylaniline in Example 149A and then substituting the product for Example 1B in Example 1C. $^1$H NMR (400 MHz, DMSO-D$_6$) δ ppm 2.49 (s, 3H), 7.02-7.05 (m, 1H), 7.08 (t, J=3.84 Hz, 1H), 7.32 (dd, J=11.20, 8.44 Hz, 1H), 7.43-7.45 (m, 1H), 7.52-7.57 (m, 3H), 7.85 (dd, J=12.43, 1.69 Hz, 1H), 8.17 (d, J=7.98 Hz, 1H), 8.80 (d, J=2.15 Hz, 1H), 9.61 (s, 1H); MS (ESI(+) m/e 394 (M+H)$^+$.

Example 257

N-[4-(3-amino-1H-indazol-4-yl)-3-fluorophenyl]-N'-(3-chlorophenyl)urea

The desired product was prepared by substituting Example 255A and 1-chloro-3-isocyanatobenzene for 4-bromo-2-ethylaniline and 1-fluoro-2-isocyanato-4-methylbenzene, respectively, in Example 149A and then substituting the product for Example 1B in Example 1C. $^1$H NMR (400 MHz, DMSO-D$_6$) δ ppm 6.81 (dd, J=4.91, 2.46 Hz, 1H), 7.03-7.06 (m, 1H), 7.27-7.35 (m, 6H), 7.62 (dd, J=12.43, 1.99 Hz, 1H), 7.72 (t, J=1.99 Hz, 1H), 9.02 (s, 1H), 9.12 (s, 1H); MS (ESI(+) m/e 396 (M+H)$^+$.

Example 258

N-[4-(3-amino-1H-indazol-4-yl)-3-fluorophenyl]-N'-(4-fluoro-3-methylphenyl)urea

The desired product was prepared by substituting Example 255A and 1-fluoro-4-isocyanato-2-methylbenzene for 4-bromo-2-ethylaniline and 1-fluoro-2-isocyanato-4-methylbenzene, respectively, in Example 149A and then substituting the product for Example 1B in Example 1C. $^1$H NMR (400 MHz, DMSO-D$_6$) δ ppm 2.22 (s, 3H), 6.87 (t, J=3.84 Hz, 1H), 7.06 (t, J=9.05 Hz, 1H), 7.27-7.38 (m, 6H), 7.63 (dd, J=12.58, 1.53 Hz, 1H), 8.79 (s, 1H), 9.07 (s, 1H); MS (ESI(+) m/e 394 (M+H)$^+$.

Example 259

N-[4-(3-amino-1H-indazol-4-yl)-3-fluorophenyl]-N'-[2-fluoro-5-(trifluoromethyl)phenyl]urea The desired product was prepared by substituting Example 255A and 1-fluoro-2-isocyanato-4-(trifluoromethyl)benzene for 4-bromo-2-ethylaniline and 1-fluoro-2-isocyanato-4-methylbenzene, respectively, in Example 149A and then substituting the product for Example 1B in Example 1C. $^1$H NMR (400 MHz, DMSO-D$_6$) δ ppm 6.89 (t, J=3.84 Hz, 1H), 7.28 (dd, J=8.44, 1.99 Hz, 1H), 7.34-7.38 (m, 3H), 7.42-7.45 (m, 1H), 7.50-7.54 (m, 1H), 7.66 (dd, J=12.43, 1.99 Hz, 1H), 8.61 (dd, J=7.21, 1.99 Hz, 1H), 9.03 (d, J=2.15 Hz, 1H), 9.54 (s, 1H); MS (ESI(+) m/e 448 (M+H)$^+$.

Example 260

N-[4-(3-amino-1H-indazol-4-yl)-3-fluorophenyl]-N'-[4-fluoro-3-(trifluoromethyl)phenyl]urea The desired product was prepared by substituting Example 255A and 1-fluoro-4-isocyanato-2-(trifluoromethyl)benzene for 4-bromo-2-ethylaniline and 1-fluoro-2-isocyanato-4-methylbenzene, respectively, in Example 149A and then substituting the product for Example 1B in Example 1C. $^1$H NMR (400 MHz, DMSO-D$_6$) δ ppm 6.84 (t, J=3.99 Hz, 1H), 7.29-7.36 (m, 4H), 7.46 (t, J=9.82 Hz, 1H), 7.62 (dd, J=12.73, 1.69 Hz, 1H), 7.68 (m, 1H), 8.02 (dd, J=6.60, 2.92 Hz, 1H), 9.21 (s, 2H); MS (ESI(+) m/e 448 (M+H)$^+$.

Example 261

N-[4-(3-amino-1,2-benzisoxazol-4-yl)phenyl]-N'-(3,5-dimethylphenyl)urea

Example 261A 4-(4-aminophenyl)-1,2-benzisoxazol-3-amine

The desired product was prepared by substituting Example 95A and 4-(4,4,5,5-tetramethyl-1,3,2-dioxaborolan-2-yl)aniline for Examples 1A and 1B, respectively, in Example 1C. MS (ESI(+)) m/e 226 (M+H)$^+$.

Example 261B

N-[4-(3-amino-1,2-benzisoxazol-4-yl)phenyl]-N'-(3,5-dimethylphenyl)urea

The desired product was prepared by substituting Example 261A and 1-isocyanato-3,5-dimethylbenzene for Example 15G and 1-fluoro-3-isocyanatobenzene, respectively, in Example 15H. $^1$H NMR (300 MHz, DMSO-D$_6$) δ ppm 2.24 (s, 6H) 5.22 (s, 2H) 6.63 (s, 1H) 7.10 (s, 2H) 7.14 (d, J=6.8 Hz, 1H) 7.43 (d, J=8.5 Hz, 2H) 7.48 (d, J=8.1 Hz, 1H) 7.56-7.64 (m, 3H) 8.57 (s, 1H) 8.83 (s, 1H) MS (ESI(+)) m/e 373.1 (M+H)$^+$.

Example 262

N-[4-(3-amino-1,2-benzisoxazol-4-yl)phenyl]-N'-phenylurea

The desired product was prepared by substituting Example 261A and isocyanatobenzene for Example 15G and 1-fluoro-3-isocyanatobenzene, respectively, in Example 15H. $^1$H NMR (300 MHz, DMSO-D$_6$) δ ppm 5.22 (s, 2H) 6.99 (t, J=7.5 Hz, 1H) 7.14 (d, J=7.1 Hz, 1H) 7.30 (t, J=8.0 Hz, 2H) 7.44 (d, J=8.5 Hz, 2H) 7.46-7.50 (m, 3H) 7.58 (dd, J=8.3, 7.3 Hz, 1H) 7.63 (d, J=8.5 Hz, 2H) 8.74 (s, 1H) 8.87 (s, 1H) MS (ESI(+)) m/e 345.0 (M+H)$^+$.

Example 263

N-[4-(3-amino-1,2-benzisoxazol-4-yl)phenyl]-N'-(4-methylphenyl)urea

The desired product was prepared by substituting Example 261A and 1-isocyanato-4-methylbenzene for Example 15G and 1-fluoro-3-isocyanatobenzene, respectively, in Example 15H. $^1$H NMR (300 MHz, DMSO-D$_6$) δ ppm 2.25 (s, 3H) 5.22 (s, 2H) 7.10 (d, J=8.5 Hz, 2H) 7.13 (d, J=6.8 Hz, 1H) 7.36 (d, J=8.5 Hz, 2H) 7.43 (d, J=8.5 Hz, 2H) 7.48 (d, J=8.1 Hz, 1H) 7.55-7.63 (m, 3H) 8.62 (s, 1H) 8.83 (s, 1H) MS (ESI(+)) m/e 359.0 (M+H)$^+$.

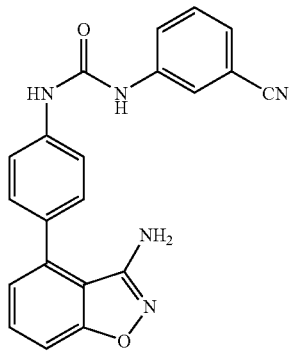

Example 264

N-[4-(3-amino-1,2-benzisoxazol-4-yl)phenyl]-N'-(3-cyanophenyl)urea

The desired product was prepared by substituting Example 261A and 3-isocyanatobenzonitrile for Example 15G and 1-fluoro-3-isocyanatobenzene, respectively, in Example 15H. $^1$H NMR (300 MHz, DMSO-D$_6$) δ ppm 5.22 (s, 2H) 7.14 (dd, J=7.1, 0.7 Hz, 1H) 7.42-7.50 (m, 4H) 7.51 (t, J=8.0 Hz, 1H) 7.59 (dd, J=8.5, 7.5 Hz, 1H) 7.64 (d, J=8.5 Hz, 2H) 7.71 (ddd, J=8.2, 2.1, 1.2 Hz, 1H) 8.00 (t, J=1.9 Hz, 1H) 9.05 (s, 1H) 9.09 (s, 1H) MS (ESI(+)) m/e 370.0 (M+H)$^+$.

Example 265

5 N-[4-(3-amino-1,2-benzisoxazol-4-yl)phenyl]-N'-[4-fluoro-3-(trifluoromethyl)phenyl]urea The desired product was prepared by substituting Example 261A and 1-fluoro-4-isocyanato-2-(trifluoromethyl)benzene for Example 15G and 1-fluoro-3-isocyanatobenzene, respectively, in Example 15H. $^1$H NMR (300 MHz, DMSO-D$_6$) δ ppm 5.22 (s, 2H) 7.14 (d, J=7.1 Hz, 1H) 7.45 (d, J=8.5 Hz, 2H) 7.45 (t, J=9.7 Hz, 1H) 7.49 (dd, J=8.1, 0.7 Hz, 1H) 7.59 (dd, J=8.5, 7.5 Hz, 1H) 7.62-7.70 (m, 3H) 8.03 (dd, J=6.4, 2.7 Hz, 1H) 9.01 (s, 1H) 9.11 (s, 1H) MS (ESI(+)) m/e 431.0 (M+H)$^+$.

Example 266

N-[4-(3-amino-1,2-benzisoxazol-4-yl)phenyl]-N'-(3-bromophenyl)urea

The desired product was prepared by substituting Example 261A and 1-bromo-3-isocyanatobenzene for Example 15G and 1-fluoro-3-isocyanatobenzene, respectively, in Example 15H. $^1$H NMR (300 MHz, DMSO-D$_6$) δ ppm 5.22 (s, 2H) 7.13-7.18 (m, 2H) 7.26 (t, J=8.0 Hz, 1H) 7.34 (ddd, J=8.1, 2.0, 1.4 Hz, 1H) 7.44 (d, J=8.5 Hz, 2H) 7.49 (dd, J=8.5, 0.9 Hz, 1H) 7.59 (dd, J=8.5, 7.1 Hz, 1H) 7.63 (d, J=8.5 Hz, 2H) 7.88 (t, J=1.9 Hz, 1H) 8.95 (s, 1H) 8.96 (s, 1H) MS (ESI(+)) m/e 422.9, 424.8 (M+H)$^+$.

Example 267

N-[4-(3-amino-1,2-benzisoxazol-4-yl)phenyl]-N'-(3-chlorophenyl)urea

The desired product was prepared by substituting Example 261A and 1-chloro-3-isocyanatobenzene for Example 15G and 1-fluoro-3-isocyanatobenzene, respectively, in Example 15H. $^1$H NMR (300 MHz, DMSO-D$_6$) δ ppm 5.75 (s, 2H) 7.03 (dt, J=6.4, 2.7 Hz, 1H) 7.14 (dd, J=7.1, 0.7 Hz, 1H) 7.28-7.35 (m, 2H) 7.44 (d, J=8.5 Hz, 2H) 7.48 (d, J=8.1 Hz, 1H) 7.59 (dd, J=8.1, 7.5 Hz, 1H) 7.63 (d, J=8.5 Hz, 2H) 7.73 (t, J=2.0 Hz, 1H) 8.96 (app. s., 2H) MS (ESI(+)) m/e 379.0 (M+H)$^+$.

Example 268

N-[4-(3-amino-1,2-benzisoxazol-4-yl)phenyl]-N'-(3-ethylphenyl)urea

The desired product was prepared by substituting Example 261A and 3-ethyl-1-isocyanatobenzene for Example 15G and 1-fluoro-3-isocyanatobenzene, respectively, in Example 15H. $^1$H NMR (300 MHz, DMSO-D$_6$) δ ppm 1.19 (t, J=7.5 Hz, 3H) 2.59 (q, J=7.5 Hz, 2H) 5.22 (s, 2H) 6.84 (d, J=7.5 Hz, 1H) 7.14 (d, J=7.1 Hz, 1H) 7.19 (t, J=7.6 Hz, 1H) 7.27 (d, J=7.8 Hz, 1H) 7.34 (s, 1H) 7.43 (d, J=8.5 Hz, 2H) 7.48 (d, J=8.1 Hz, 1H) 7.56-7.64 (m, 3H) 8.67 (s, 1H) 8.84 (s, 1H) MS (ESI(+)) m/e 373.0 (M+H)$^+$.

Example 269

N-[4-(3-amino-1,2-benzisoxazol-4-yl)phenyl]-N'-[4-(trifluoromethyl)phenyl]urea

The desired product was prepared by substituting Example 261A and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 5.22 (s, 2H) 7.15 (d, J=7.1 Hz, 1H) 7.44-7.50 (m, 3H) 7.59 (dd, J=8.5, 7.1 Hz, 1H) 7.63-7.71 (m, 6H) 9.02 (s, 1H) 9.18 (s, 1H) MS (ESI(+)) m/e 413.0 (M+H)$^+$.

Example 270

N-[4-(3-amino-1,2-benzisoxazol-4-yl)phenyl]-N'-(3-fluoro-4-methylphenyl)urea

The desired product was prepared by substituting Example 261A and 1-fluoro-5-isocyanato-2-methylbenzene for Example 15G and 1-fluoro-3-isocyanatobenzene, respectively, in Example 15H. $^1$H NMR (300 MHz, DMSO-D$_6$) δ ppm 2.17 (d, J=1.4 Hz, 3H) 5.22 (s, 2H) 7.05 (dd, J=8.3, 2.2 Hz, 1H) 7.12-7.21 (m, 2H) 7.42-7.50 (m, 4H) 7.56-7.64 (m, 3H) 8.84 (s, 1H) 8.90 (s, 1H) MS (ESI(+)) m/e 377.1 (M+H)$^+$.

Example 271

N-[4-(3-amino-1,2-benzisoxazol-4-yl)phenyl]-N'-(3-fluorophenyl)urea

The desired product was prepared by substituting Example 261A for Example 15G in Example 15H. $^1$H NMR (300 MHz, DMSO-D$_6$) δ ppm 5.22 (s, 2H) 6.77-6.83 (m, 1H) 7.13-7.18 (m, 2H) 7.32 (td, J=8.1, 7.1 Hz, 1H) 7.44 (d, J=8.8 Hz, 2H) 7.48 (dd, J=8.5, 1.0 Hz, 1H) 7.52 (dt, J=11.9, 2.4 Hz, 1H) 7.59 (dd, J=8.1, 7.5 Hz, 1H) 7.63 (d, J=8.8 Hz, 2H) 8.94 (s, 1H) 8.98 (s, 1H) MS (ESI(+)) m/e 363.0 (M+H)$^+$.

Example 272

N-[4-(3-amino-1,2-b enzisoxazol-4-yl)phenyl]-N'-(3,5-difluorophenyl)urea

The desired product was prepared by substituting Example 261A and 1,3-difluoro-5-isocyanatobenzene for Example 15G and 1-fluoro-3-isocyanatobenzene, respectively, in Example 15H. $^1$H NMR (300 MHz, DMSO-D$_6$) δ ppm 5.21 (s, 2H) 6.81 (tt, J=9.4, 2.3 Hz, 1H) 7.14 (dd, J=7.1, 0.7 Hz, 1H) 7.22 (dd, J=10.0, 2.3 Hz, 2H) 7.45 (d, J=8.5 Hz, 2H) 7.49 (dd, J=8.5, 0.7 Hz, 1H) 7.59 (dd, J=8.5, 7.1 Hz, 1H) 7.63 (d, J=8.5 Hz, 2H) 9.05 (s, 1H) 9.16 (s, 1H) MS (ESI(+)) m/e 381.0 (M+H)$^+$.

Example 273

N-[4-(3-amino-1,2-benzisoxazol-4-yl)phenyl]-N'-(3-methoxyphenyl)urea

The desired product was prepared by substituting Example 261A and 3-isocyanato-1-methoxybenzene for Example 15G and 1-fluoro-3-isocyanatobenzene, respectively, in Example 15H. $^1$H NMR (300 MHz, DMSO-D$_6$) δ ppm 3.74 (s, 3H) 5.22 (s, 2H) 6.57 (dd, J=8.0, 2.2 Hz, 1H) 6.96 (dd, J=8.1, 1.4 Hz, 1H) 7.14 (d, J=6.8 Hz, 1H) 7.19 (t, J=8.1 Hz, 1H) 7.21 (t, J=2.2 Hz, 1H) 7.43 (d, J=8.5 Hz, 2H) 7.48 (d, J=7.8 Hz, 1H) 7.58 (dd, J=8.1, 7.1 Hz, 1H) 7.62 (d, J=8.5 Hz, 2H) 8.75 (s, 1H) 8.86 (s, 1H) MS (ESI(+)) m/e 375.1 (M+H)$^+$.

Example 274

N-[4-(3-amino-1,2-benzisoxazol-4-yl)phenyl]-N'-(4-methoxyphenyl)urea

The desired product was prepared by substituting Example 261A and 4-isocyanato-1-methoxybenzene for Example 15G and 1-fluoro-3-isocyanatobenzene, respectively, in Example 15H. $^1$H NMR (300 MHz, DMSO-D$_6$) δ ppm 3.72 (s, 3H) 5.22 (s, 2H) 6.88 (d, J=8.8 Hz, 2H) 7.13 (dd, J=7.1, 0.7 Hz, 1H) 7.38 (d, J=8.8 Hz, 2H) 7.42 (d, J=8.5 Hz, 2H) 7.48 (dd, J=8.5, 0.7 Hz, 1H) 7.58 (dd, J=8.5, 7.5 Hz, 1H) 7.62 (d, J=8.5 Hz, 2H) 8.54 (s, 1H) 8.79 (s, 1H) MS (ESI(+)) m/e 375.1 (M+H)$^+$.

Example 275

N-[4-(3-amino-1,2-benzisoxazol-4-yl)phenyl]urea

A solution of Example 261A (45 mg, 0.2 mmol) and sodium isocyanate (26 mg, 0.4 mmol) in HOAc (0.5 mL) and H$_2$O (0.5 mL) was stirred overnight at rt, then diluted with water. The precipitated solid was collected by filtration and recrystallized from THF/hexanes to give an offwhite solid (35 mg, 65%). $^1$H NMR (300 MHz, DMSO-D$_6$) δ ppm 5.20 (s, 2H) 5.92 (s, 2H) 7.11 (dd, J=7.3, 0.9 Hz, 1H) 7.37 (d, J=8.5 Hz, 2H) 7.46 (dd, J=8.5, 1.0 Hz, 1H) 7.57 (d, J=8.5 Hz, 2H) 7.57 (dd, J=8.1, 7.1 Hz, 1H) 8.72 (s, 1H) MS (ESI(+)) m/e 269.0 (M+H)$^+$.

Example 276

N-[4-(3-amino-1,2-benzisoxazol-4-yl)phenyl]-N'-(3-nitrophenyl)urea

The desired product was prepared by substituting Example 261A and 1-nitro-3-isocyanatobenzene for Example 15G and 1-fluoro-3-isocyanatobenzene, respectively, in Example 15H. $^1$H NMR (300 MHz, DMSO-D$_6$) δ ppm 5.21 (s, 2H) 7.15 (d, J=6.8 Hz, 1H) 7.45-7.50 (m, 3H) 7.57-7.62 (m, 2H) 7.66 (d, J=8.5 Hz, 2H) 7.75 (dd, J=7.8, 1.7 Hz, 1H) 7.84 (dd, J=8.1, 2.4 Hz, 1H) 8.59 (t, J=2.2 Hz, 1H) 9.09 (s, 1H) 9.34 (s, 1H) MS (ESI(+)) m/e 390.0 (M+H)$^+$.

Example 277

N-[4-(3-amino-1,2-benzisoxazol-4-yl)phenyl]-N'-(4-fluorophenyl)urea

The desired product was prepared by substituting Example 261A and 1-fluoro-4-isocyanatobenzene for Example 15G and 1-fluoro-3-isocyanatobenzene, respectively, in Example 15H. $^1$H NMR (300 MHz, DMSO-D$_6$) δ ppm 5.21 (s, 2H) 7.11-7.17 (m, 3H) 7.40-7.51 (m, 5H) 7.58 (dd, J=8.1, 7.1 Hz, 1H) 7.63 (d, J=8.8 Hz, 2H) 8.80 (s, 1H) 8.90 (s, 1H) MS (ESI(+)) m/e 363.0 (M+H)$^+$.

Example 278

N-[4-(3-amino-1,2-benzisoxazol-4-yl)phenyl]-N'-(2-fluorophenyl)urea

The desired product was prepared by substituting Example 261A and 1-fluoro-2-isocyanatobenzene for Example 15G and 1-fluoro-3-isocyanatobenzene, respectively, in Example 15H. $^1$H NMR (300 MHz, DMSO-D$_6$) δ ppm 5.22 (s, 2H) 6.99-7.06 (m, 1H) 7.13-7.19 (m, 2H) 7.25 (ddd, J=11.7, 8.1, 1.5 Hz, 1H) 7.45 (d, J=8.8 Hz, 2H) 7.49 (dd, J=8.5, 1.0 Hz, 1H) 7.59 (dd, J=8.5, 7.5 Hz, 1H) 7.63 (d, J=8.5 Hz, 2H) 8.17 (td, J=8.3, 1.7 Hz, 1H) 8.62 (d, J=2.4 Hz, 1H) 9.27 (s, 1H) MS (ESI(+)) m/e 363.0 (M+H)$^+$.

Example 279

N-[4-(3-amino-1,2-benzisoxazol-4-yl)phenyl]-N'-(3-chloro-4-fluorophenyl)urea

The desired product was prepared by substituting Example 261A and 1-chloro-2-fluoro-5-isocyanatobenzene for Example 15G and 1-fluoro-3-isocyanatobenzene, respectively, in Example 15H. $^1$H NMR (300 MHz, DMSO-D$_6$) δ ppm 5.22 (s, 2H) 7.14 (dd, J=7.3, 0.9 Hz, 1H) 7.34 (m, 2H) 7.44 (d, J=8.5 Hz, 2H) 7.48 (dd, J=8.3, 0.9 Hz, 1H) 7.58 (dd, J=8.5, 7.1 Hz, 1H) 7.63 (d, J=8.5 Hz, 2H) 7.81-7.84 (m, 1H) 8.95 (s, 1H) 8.97 (s, 1H) MS (ESI(+)) m/e 397.0 (M+H)$^+$.

Example 280

N-[4-(3-amino-1,2-benzisoxazol-4-yl)phenyl]-N'-(3-chloro-4-methoxyphenyl)urea

The desired product was prepared by substituting Example 261A and 1-chloro-5-isocyanato-2-methoxybenzene for Example 15G and 1-fluoro-3-isocyanatobenzene, respectively, in Example 15H. $^1$H NMR (300 MHz, DMSO-D$_6$) δ ppm 3.82 (s, 3H) 5.22 (s, 2H) 7.10 (d, J=9.2 Hz, 1H) 7.14 (dd, J=7.1, 1.0 Hz, 1H) 7.29 (dd, J=9.2, 2.5 Hz, 1H) 7.43 (d, J=8.5 Hz, 2H) 7.48 (dd, J=8.3, 1.0 Hz, 1H) 7.58 (dd, J=8.1, 7.1 Hz, 1H) 7.62 (d, J=8.5 Hz, 2H) 7.68 (d, J=2.5 Hz, 1H) 8.71 (s, 1H) 8.87 (s, 1H) MS (ESI(+)) m/e 409.0 (M+H)$^+$.

Example 281

N-[4-(3-amino-1,2-benzisoxazol-4-yl)phenyl]-N'-[4-(dimethylamino)phenyl]urea

The desired product was prepared by substituting Example 261A and 4-dimethylamino-1-isocyanatobenzene for Example 15G and 1-fluoro-3-isocyanatobenzene, respectively, in Example 15H. $^1$H NMR (300 MHz, DMSO-D$_6$) δ ppm 2.84 (s, 6H) 5.21 (s, 2H) 6.71 (d, J=9.2 Hz, 2H) 7.13 (dd, J=7.1, 1.0 Hz, 1H) 7.28 (d, J=9.2 Hz, 2H) 7.41 (d, J=8.5 Hz, 2H) 7.47 (dd, J=8.5, 1.0 Hz, 1H) 7.58 (dd, J=8.5, 7.1 Hz, 1H) 7.61 (d, J=8.5 Hz, 2H) 8.36 (s, 1H) 8.73 (s, 1H) MS (ESI(+)) m/e 388.1 (M+H)$^+$.

Example 282

N-[4-(3-amino-1,2-benzisoxazol-4-yl)phenyl]-N'-1,3-benzodioxol-5-ylurea

The desired product was prepared by substituting Example 261A and 5-isocyanato-benzo[1,3]dioxole for Example 15G and 1-fluoro-3-isocyanatobenzene, respectively, in Example 15H. $^1$H NMR (300 MHz, DMSO-D$_6$) δ ppm 5.21 (s, 2H) 5.98 (s, 2H) 6.78 (dd, J=8.5, 2.0 Hz, 1H) 6.84 (d, J=8.5 Hz, 1H) 7.13 (dd, J=7.1, 1.0 Hz, 1H) 7.22 (d, J=2.0 Hz, 1H) 7.42 (d, J=8.5 Hz, 2H) 7.48 (dd, J=8.1, 1.0 Hz, 1H) 7.58 (dd, J=8.1, 7.5 Hz, 1H) 7.61 (d, J=8.5 Hz, 2H) 8.62 (s, 1H) 8.80 (s, 1H) MS (ESI(+)) m/e 389.0 (M+H)$^+$.

Example 283

N-[4-(3-amino-1,2-benzisoxazol-4-yl)phenyl]-N'-[4-(trifluoromethoxy)phenyl]urea

The desired product was prepared by substituting Example 261A and 4-isocyanato-1-(trifluoromethoxy)benzene for Example 15G and 1-fluoro-3-isocyanatobenzene, respectively, in Example 15H. $^1$H NMR (300 MHz, DMSO-D$_6$) δ ppm 5.22 (s, 2H) 7.14 (dd, J=7.1, 1.0 Hz, 1H) 7.30 (d, J=8.8 Hz, 2H) 7.44 (d, J=8.5 Hz, 2H) 7.48 (dd, J=8.5, 0.7 Hz, 1H) 7.59 (dd, J=8.3, 7.3 Hz, 1H) 7.59 (d, J=8.8 Hz, 2H) 7.63 (d, J=8.5 Hz, 2H) 8.93 (s, 1H) 8.96 (s, 1H) MS (ESI(−)) m/e 426.9 (M−H)$^−$.

Example 284

N-[4-(3-amino-1,2-benzisoxazol-4-yl)phenyl]-N'-[2-(trifluoromethoxy)phenyl]urea

The desired product was prepared by substituting Example 261A and 2-isocyanato-1-(trifluoromethoxy)benzene for Example 15G and 1-fluoro-3-isocyanatobenzene, respectively, in Example 15H. $^1$H NMR (300 MHz, DMSO-D$_6$) δ ppm 5.23 (s, 2H) 7.11 (td, J=7.6, 2.0 Hz, 1H) 7.15 (d, J=7.1 Hz, 1H) 7.36 (td, J=8.1, 1.4 Hz, 1H) 7.39 (ddd, J=6.6, 3.1, 1.5 Hz, 1H) 7.44-7.50 (m, 3H) 7.59 (dd, J=8.5, 7.1 Hz, 1H) 7.65

Example 285

N-[4-(3-amino-1,2-benzisoxazol-4-yl)phenyl]-N'-[3,5-bis(trifluoromethyl)phenyl]urea The desired product was prepared by substituting Example 261A and 1-isocyanato-3,5-bis(trifluoromethyl)benzene for Example 15G and 1-fluoro-3-isocyanatobenzene, respectively, in Example 15H. $^1$H NMR (300 MHz, DMSO-$D_6$) δ ppm 5.22 (s, 2H) 7.15 (dd, J=7.1, 1.0 Hz, 1H) 7.45-7.51 (m, 3H) 7.59 (dd, J=8.5, 7.1 Hz, 1H) 7.65-7.69 (m, 3H) 8.16 (s, 2H) 9.20 (s, 1H) 9.47 (s, 1H) MS (ESI(+)) m/e 481.0 (M+H)$^+$.

Example 286

N-[4-(3-amino-1,2-benzisoxazol-4-yl)phenyl]-N'-(3-chloro-4-methylphenyl)urea

The desired product was prepared by substituting Example 261A and 1-chloro-5-isocyanato-2-methylbenzene for Example 15G and 1-fluoro-3-isocyanatobenzene, respectively, in Example 15H. $^1$H NMR (300 MHz, DMSO-$D_6$) δ ppm 2.27 (s, 3H) 5.22 (s, 2H) 7.14 (dd, J=7.1, 1.0 Hz, 1H) 7.21 (dd, J=8.5, 2.0 Hz, 1H) 7.26 (d, J=8.5 Hz, 1H) 7.44 (d, J=8.8 Hz, 2H) 7.48 (dd, J=8.5, 0.7 Hz, 1H) 7.58 (dd, J=8.5, 7.5 Hz, 1H) 7.63 (d, J=8.8 Hz, 2H) 7.71 (d, J=2.0 Hz, 1H) 8.84 (s, 1H) 8.91 (s, 1H) MS (ESI(+)) m/e 393.1 (M+H)$^+$.

Example 287

N-[4-(3-amino-7-methoxy-1,2-benzisoxazol-4-yl)phenyl]-N'-[3,5-bis(trifluoromethyl)phenyl]urea The desired product was prepared by substituting Example 100C and 1-isocyanato-3,5-bis(trifluoromethyl)benzene for Example 15G and 1-fluoro-3-isocyanatobenzene, respectively, in Example 15H. $^1$H NMR (300 MHz, DMSO-$D_6$) δ ppm 3.97 (s, 3H) 5.21 (s, 2H) 7.06 (d, J=8.1 Hz, 1H) 7.17 (d, J=8.1 Hz, 1H) 7.41 (d, J=8.5 Hz, 2H) 7.63 (d, J=8.5 Hz, 2H) 7.66 (s, 1H) 8.16 (s, 2H) 9.16 (s, 1H) 9.45 (s, 1H) MS (ESI(+)) m/e 511.0 (M+H)$^+$.

Example 288

N-[4-(3-amino-7-methoxy-1,2-benzisoxazol-4-yl)phenyl]-N'-[4-(trifluoromethoxy)phenyl]urea The desired product was prepared by substituting Example 100C and 4-isocyanato-1-(trifluoromethoxy)benzene for Example 15G and 1-fluoro-3-isocyanatobenzene, respectively, in Example 15H. $^1$H NMR (300 MHz, DMSO-$D_6$) δ ppm 3.96 (s, 3H) 5.20 (s, 2H) 7.04 (d, J=8.1 Hz, 1H) 7.16 (d, J=8.1 Hz, 1H) 7.30 (d, J=8.8 Hz, 2H) 7.39 (d, J=8.5 Hz, 2H) 7.58 (d, J=8.8 Hz, 2H) 7.60 (d, J=8.5 Hz, 2H) 8.89 (s, 1H) 8.94 (s, 1H) MS (ESI(+)) m/e 459.0 (M+H)$^+$.

Example 289

N-[4-(3-amino-7-methoxy-1,2-benzisoxazol-4-yl)phenyl]-N'-(3-fluorophenyl)urea

The desired product was prepared by substituting Example 100C for Example 15G in Example 15H. $^1$H NMR (300 MHz, DMSO-$D_6$) δ ppm 3.96 (s, 3H) 5.21 (s, 2H) 6.80 (td, J=8.5, 2.4 Hz, 1H) 7.05 (d, J=7.8 Hz, 1H) 7.12-7.18 (m, 2H) 7.28-7.36 (m, 1H) 7.39 (d, J=8.5 Hz, 2H) 7.51 (dt, J=11.9, 2.2 Hz, 1H) 7.60 (d, J=8.5 Hz, 2H) 8.91 (s, 1H) 8.96 (s, 1H) MS (ESI(+)) m/e 393.0 (M+H)$^+$.

Example 290

N-[4-(3-amino-7-methoxy-1,2-benzisoxazol-4-yl)phenyl]-N'-(3-methoxyphenyl)urea

The desired product was prepared by substituting Example 100C and 3-isocyanato-1-methoxybenzene for Example 15G and 1-fluoro-3-isocyanatobenzene, respectively, in Example 15H. $^1$H NMR (300 MHz, DMSO-$D_6$) δ ppm 3.74 (s, 3H) 3.96 (s, 3H) 5.21 (s, 2H) 6.57 (dd, J=8.3, 2.5 Hz, 1H) 6.95 (dd, J=7.8, 1.5 Hz, 1H) 7.04 (d, J=7.8 Hz, 1H) 7.15-7.22 (m, 3H) 7.38 (d, J=8.5 Hz, 2H) 7.59 (d, J=8.5 Hz, 2H) 8.73 (s, 1H) 8.82 (s, 1H) MS (ESI(+)) m/e 405.0 (M+H)$^+$.

Example 291

N-[4-(3-amino-7-methoxy-1,2-benzisoxazol-4-yl)phenyl]-N'-(3,5-difluorophenyl)urea The desired product was prepared by substituting Example 100C and 1,3-difluoro-5-isocyanatobenzene for Example 15G and 1-fluoro-3-isocyanatobenzene, respectively, in Example 15H. $^1$H NMR (300 MHz, DMSO-$D_6$) δ ppm 3.96 (s, 3H) 5.20 (s, 2H) 6.80 (tt, J=9.3, 2.4 Hz, 1H) 7.05 (d, J=8.1 Hz, 1H) 7.17 (d, J=8.1 Hz, 1H) 7.19-7.26 (m, 2H) 7.40 (d, J=8.5 Hz, 2H) 7.60 (d, J=8.5 Hz, 2H) 9.01 (s, 1H) 9.14 (s, 1H) MS (ESI(+)) m/e 411.1 (M+H)$^+$.

Example 292

N-[4-(3-amino-7-methoxy-1,2-benzisoxazol-4-yl)phenyl]-N'-(4-methylphenyl)urea

The desired product was prepared by substituting Example 100C and 1-isocyanato-4-methylbenzene for Example 15G and 1-fluoro-3-isocyanatobenzene, respectively, in Example 15H. $^1$H NMR (300 MHz, DMSO-$D_6$) δ ppm 2.25 (s, 3H) 3.96 (s, 3H) 5.20 (s, 2H) 7.04 (d, J=8.1 Hz, 1H) 7.09 (d, J=8.1 Hz, 2H) 7.16 (d, J=8.1 Hz, 1H) 7.35 (d, J=8.1 Hz, 2H) 7.37 (d, J=8.5 Hz, 2H) 7.58 (d, J=8.5 Hz, 2H) 8.60 (s, 1H) 8.78 (s, 1H) MS (ESI(+)) m/e 389.1 (M+H)$^+$.

Example 293

N-[4-(3-amino-7-methoxy-1,2-benzisoxazol-4-yl)phenyl]-N'-(3-bromophenyl)urea

The desired product was prepared by substituting Example 100C and 1-bromo-3-isocyanatobenzene for Example 15G and 1-fluoro-3-isocyanatobenzene, respectively, in Example 15H. $^1$H NMR (300 MHz, DMSO-$D_6$) δ ppm 3.96 (s, 3H) 5.20 (s, 2H) 7.05 (d, J=7.8 Hz, 1H) 7.14-7.18 (m, 2H) 7.25 (t, J=8.0 Hz, 1H) 7.33 (ddd, J=8.0, 2.0, 1.2 Hz, 1H) 7.39 (d, J=8.5 Hz, 2H) 7.60 (d, J=8.5 Hz, 2H) 7.88 (t, J=1.9 Hz, 1H) 8.91 (s, 1H) 8.92 (s, 1H) MS (ESI(+)) m/e 451.0, 453.0 (M+H)$^+$.

Example 294

N-[4-(3-amino-7-methoxy-1,2-benzisoxazol-4-yl)phenyl]-N'-(3,5-dimethylphenyl)urea The desired product was prepared by substituting Example 100C and 1-isocyanato-3,5-dimethylbenzene for Example 15G and 1-fluoro-3-isocyanatobenzene, respectively, in Example 15H. $^1$H NMR (300 MHz, DMSO-D$_6$) δ ppm 2.24 (s, 6H) 3.96 (s, 3H) 5.20 (s, 2H) 6.63 (s, 1H) 7.04 (d, J=8.1 Hz, 1H) 7.09 (s, 2H) 7.16 (d, J=8.1 Hz, 1H) 7.37 (d, J=8.5 Hz, 2H) 7.59 (d, J=8.5 Hz, 2H) 8.55 (s, 1H) 8.79 (s, 1H) MS (ESI(+)) m/e 403.1 (M+H)$^+$.

Example 295

N-[4-(3-amino-7-methoxy-1,2-benzisoxazol-4-yl) phenyl]-N'-[4-(dimethylamino)phenyl]urea The desired product was prepared by substituting Example 100C and 4-dimethylamino-1-isocyanatobenzene for Example 15G and 1-fluoro-3-isocyanatobenzene, respectively, in Example 15H. $^1$H NMR (300 MHz, DMSO-D$_6$) δ ppm 2.84 (s, 6H) 3.96 (s, 3H) 5.20 (s, 2H) 6.71 (d, J=9.2 Hz, 2H) 7.03 (d, J=8.1 Hz, 1H) 7.16 (d, J=8.1 Hz, 1H) 7.28 (d, J=9.2 Hz, 2H) 7.35 (d, J=8.5 Hz, 2H) 7.57 (d, J=8.5 Hz, 2H) 8.35 (s, 1H) 8.68 (s, 1H) MS (ESI(+)) m/e 418.1 (M+H)$^+$.

Example 296

N-[4-(3-amino-7-methoxy-1,2-benzisoxazol-4-yl) phenyl]-N'-1,3-benzodioxol-5-ylurea The desired product was prepared by substituting Example 100C and 5-isocyanato-benzo[1,3]dioxole for Example 15G and 1-fluoro-3-isocyanatobenzene, respectively, in Example 15H. $^1$H NMR (300 MHz, DMSO-D$_6$) δ ppm 3.96 (s, 3H) 5.20 (s, 2H) 5.97 (s, 2H) 6.78 (dd, J=8.5, 2.0 Hz, 1H) 6.84 (d, J=8.5 Hz, 1H) 7.04 (d, J=8.1 Hz, 1H) 7.16 (d, J=8.1 Hz, 1H) 7.22 (d, J=2.0 Hz, 1H) 7.37 (d, J=8.5 Hz, 2H) 7.57 (d, J=8.5 Hz, 2H) 8.60 (s, 1H) 8.76 (s, 1H) MS (ESI(+)) m/e 419.1 (M+H)$^+$.

Example 297

N-[4-(3-amino-7-methyl-1,2-benzisoxazol-4-yl)phenyl]-N'-(3-methylphenyl)urea

Example 297A 4-iodo-7-methyl-1,2-benzisoxazol-3-amine

The desired product was prepared by substituting Example 15C for 2-bromo-6-fluorobenzonitrile in Example 95A. MS (ESI(+)) m/e 274.8 (M+H)$^+$.

Example 297B 4-(4-aminophenyl)-7-methyl-1,2-benzisoxazol-3-amine

The desired product was prepared by substituting Example 297A and 4-(4,4,5,5-tetramethyl-1,3,2-dioxaborolan-2-yl) aniline for Examples 1A and 1B, respectively, in Example 1C. MS (ESI(+)) m/e 240.0 (M+H)$^+$.

Example 297C

N-[4-(3-amino-7-methyl-1,2-benzisoxazol-4-yl)phenyl]-N'-(3-methylphenyl)urea

The desired product was prepared by substituting Example 297B and 1-isocyanato-3-methylbenzene for Example 15G and 1-fluoro-3-isocyanatobenzene, respectively, in Example 15H. $^1$H NMR (300 MHz, DMSO-D$_6$) δ ppm 2.29 (s, 3H) 2.45 (s, 3H) 5.20 (s, 2H) 6.80 (d, J=7.5 Hz, 1H) 7.03 (d, J=7.1 Hz, 1H) 7.17 (t, J=7.8 Hz, 1H) 7.25 (d, J=8.5 Hz, 1H) 7.31 (s, 1H) 7.38 (dd, J=7.5, 1.0 Hz, 1H) 7.40 (d, J=8.5 Hz, 2H) 7.61 (d, J=8.5 Hz, 2H) 8.64 (s, 1H) 8.83 (s, 1H) MS (ESI(+)) m/e 373.1 (M+H)$^+$.

Example 298

N-[4-(3-amino-7-methyl-1,2-benzisoxazol-4-yl)phenyl]-N'-(3-chlorophenyl)urea

The desired product was prepared by substituting Example 297B and 1-chloro-3-isocyanatobenzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 7.02-7.05 (m, 2H) 7.27-7.32 (m, 2H) 7.37-7.44 (m, 3H) 7.62 (d, J=8.8 Hz, 2H) 7.73-7.74 (m, 1H) 8.94 (s, 1H) 8.95 (s, 1H) MS (ESI(+)) m/e 393.0 (M+H)$^+$.

Example 299

N-[4-(3-amino-7-methyl-1,2-benzisoxazol-4-yl)phenyl]-N'-(2-fluoro-5-methylphenyl)urea The desired product was prepared by substituting Example 297B and 1-fluoro-2-isocyanato-4-methylbenzene for Example 15G and 1-fluoro-3-isocyanatobenzene, respectively, in Example 15H. $^1$H NMR (300 MHz, DMSO-D$_6$) δ ppm 2.28 (s, 3H) 2.45 (s, 3H) 5.20 (s, 2H) 6.79-6.84 (m, 1H) 7.04 (d, J=7.1 Hz, 1H) 7.11 (dd, J=11.4, 8.3 Hz, 1H) 7.37-7.43 (m, 3H) 7.61 (d, J=8.5 Hz, 2H) 8.00 (dd, J=7.6, 1.9 Hz, 1H) 8.54 (d, J=2.4 Hz, 1H) 9.24 (s, 1H) MS (ESI(+)) m/e 391.1 (M+H)$^+$.

Example 300

N-[4-(3-amino-7-methyl-1,2-benzisoxazol-4-yl)phenyl]-N'-[2-fluoro-5-(trifluoromethyl)phenyl]urea The desired product was prepared by substituting Example 297B and 1-fluoro-2-isocyanato-4-(trifluoromethyl)benzene for Example 15G and 1-fluoro-3-isocyanatobenzene, respectively, in Example 15H. $^1$H NMR (300 MHz, DMSO-D$_6$) δ ppm 2.46 (s, 3H) 5.20 (s, 2H) 7.05 (d, J=7.5 Hz, 1H) 7.38-7.45 (m, 4H) 7.48-7.55 (m, 1H) 7.63 (d, J=8.5 Hz, 2H) 8.64 (dd, J=7.3, 2.2 Hz, 1H) 8.97 (s, 1H) 9.37 (s, 1H) MS (ESI(+)) m/e 445.0 (M+H)$^+$.

Example 301

N-[4-(3-amino-7-methyl-1,2-benzisoxazol-4-yl)phenyl]-N'-[3-(trifluoromethyl)phenyl]urea The desired product was prepared by substituting Example 297B and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 7.04 (d, J=7.1 Hz, 1H) 7.32 (d, J=7.8 Hz, 1H) 7.38 (dd, J=7.3, 0.9 Hz, 1H) 7.42 (d, J=8.5 Hz, 2H) 7.53 (t, J=8.0 Hz, 1H) 7.59-7.64 (m, 3H) 8.04 (s, 1H) 9.00 (s, 1H) 9.13 (s, 1H) MS (ESI(+)) m/e 427.0 (M+H)$^+$.

Example 302

N-[4-(3-amino-7-methyl-1,2-benzisoxazol-4-yl)phenyl]-N'-(3,5-dimethylphenyl)urea The desired product was prepared by substituting Example 297B and 1-isocyanato-3,5-dimethylbenzene for Example 15G and 1-fluoro-3-isocyanatobenzene, respectively, in Example 15H. $^1$H NMR (300 MHz, DMSO-D$_6$) δ ppm 2.24 (s, 6H) 2.45 (s, 3H) 5.20 (s, 2H) 6.63 (s, 1H) 7.04 (d, J=7.5 Hz, 1H) 7.09 (s, 2H) 7.38 (dd, J=7.3, 0.9 Hz, 1H) 7.40 (d, J=8.5 Hz, 2H) 7.60 (d, J=8.5 Hz, 2H) 8.56 (s, 1H) 8.81 (s, 1H) MS (ESI(+)) m/e 387.1 (M+H)$^+$.

Example 303

N-[4-(3-amino-7-methyl-1,2-benzisoxazol-4-yl)phenyl]-N'-(3-ethylphenyl)urea

The desired product was prepared by substituting Example 297B and 3-ethyl-1-isocyanatobenzene for Example 15G and 1-fluoro-3-isocyanatobenzene, respectively, in Example 15H. $^1$H NMR (300 MHz, DMSO-D$_6$) δ ppm 1.19 (t, J=7.5 Hz, 3H) 2.45 (s, 3H) 2.58 (q, J=7.6 Hz, 2H) 5.20 (s, 2H) 6.84 (d, J=7.5 Hz, 1H) 7.04 (d, J=7.5 Hz, 1H) 7.19 (t, J=7.8 Hz, 1H) 7.27 (ddd, J=8.1, 2.0, 1.4 Hz, 1H) 7.33-7.35 (m, 1H) 7.38 (dd, J=7.3, 0.9 Hz, 1H) 7.40 (d, J=8.5 Hz, 2H) 7.61 (d, J=8.5 Hz, 2H) 8.66 (s, 1H) 8.82 (s, 1H) MS (ESI(+)) m/e 387.1 (M+H)$^+$.

Example 304

N-[4-(3-amino-7-methyl-1,2-benzisoxazol-4-yl)phenyl]-N'-(4-methylphenyl)urea

The desired product was prepared by substituting Example 297B and 1-isocyanato-4-methylbenzene for Example 15G and 1-fluoro-3-isocyanatobenzene, respectively, in Example 15H. $^1$H NMR (300 MHz, DMSO-D$_6$) δ ppm 2.25 (s, 3H) 2.45 (s, 3H) 5.19 (s, 2H) 7.03 (d, J=7.5 Hz, 1H) 7.10 (d, J=8.5 Hz, 2H) 7.34-7.41 (m, 5H) 7.60 (d, J=8.5 Hz, 2H) 8.61 (s, 1H) 8.80 (s, 1H) MS (ESI(+)) m/e 373.1 (M+H)$^+$.

Example 305

N-[4-(3-amino-7-methyl-1,2-benzisoxazol-4-yl)phenyl]-N'-[4-(trifluoromethoxy)phenyl]urea The desired product was prepared by substituting Example 297B and 1-trifluoromethoxy-4-isocyanatobenzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 7.04 (d, J=7.5 Hz, 1H) 7.30 (d, J=8.5 Hz, 2H) 7.37-7.42 (m, 3H) 7.57-7.63 (m, 4H) 8.91 (s, 1H) 8.95 (s, 1H) MS (ESI(+)) m/e 443.0 (M+H)$^+$.

Example 306

N-[4-(3-amino-7-methyl-1,2-benzisoxazol-4-yl)phenyl]-N'-(3-fluoro-4-methylphenyl)urea The desired product was prepared by substituting Example 297B and 1-fluoro-5-isocyanato-2-methylbenzene for Example 15G and 1-fluoro-3-isocyanatobenzene, respectively, in Example 15H. $^1$H NMR (300 MHz, DMSO-D$_6$) δ ppm 2.17 (s, 3H) 2.45 (s, 3H) 5.20 (s, 2H) 7.04 (d, J=7.5 Hz, 1H) 7.05 (dd, J=8.1, 2.0 Hz, 1H) 7.18 (t, J=8.7 Hz, 1H) 7.37-7.39 (m, 1H) 7.41 (d, J=8.5 Hz, 2H) 7.46 (dd, J=12.6, 2.0 Hz, 1H) 7.60 (d, J=8.5 Hz, 2H) 8.84 (s, 1H) 8.88 (s, 1H) MS (ESI(+)) m/e 391.1 (M+H)$^+$.

Example 307

N-[4-(3-amino-7-methyl-1,2-benzisoxazol-4-yl)phenyl]-N'-(3-methoxyphenyl)urea

The desired product was prepared by substituting Example 297B and 1-methoxy-3-isocyanatobenzene for Example 15G and 1-fluoro-3-isocyanatobenzene, respectively, in Example 15H. $^1$H NMR (300 MHz, DMSO-D$_6$) δ ppm 2.45 (s, 3H) 3.74 (s, 3H) 5.20 (s, 2H) 6.57 (dd, J=8.1, 2.4 Hz, 1H) 6.95 (dd, J=7.6, 1.5 Hz, 1H) 7.04 (d, J=7.5 Hz, 1H) 7.16-7.22 (m, 2H) 7.37-7.43 (m, 3H) 7.61 (d, J=8.5 Hz, 2H) 8.74 (s, 1H) 8.84 (s, 1H) MS (ESI(+)) m/e 389.0 (M+H)$^+$.

Example 308

N-[4-(3-amino-7-methyl-1,2-benzisoxazol-4-yl)phenyl]-N'-phenylurea

The desired product was prepared by substituting Example 297B and isocyanatobenzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 6.98 (tt, J=7.1, 1.4 Hz, 1H) 7.04 (d, J=7.5 Hz, 1H) 7.27-7.32 (m, 2H) 7.38 (dd, J=7.5, 1.0 Hz, 1H) 7.40 (d, J=8.8 Hz, 2H) 7.48 (dd, J=8.8, 1.0 Hz, 2H) 7.61 (d, J=8.8 Hz, 2H) 8.72 (s, 1H) 8.85 (s, 1H) MS (ESI(+)) m/e 359.0 (M+H)$^+$.

Example 309

N-[4-(3-amino-7-methyl-1,2-benzisoxazol-4-yl)phenyl]-N'-[3,5-bis(trifluoromethyl)phenyl]urea The desired product was prepared by substituting Example 297B and 1-isocyanato-3,5-bis(trifluoromethyl)benzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 7.05 (d, J=7.1 Hz, 1H) 7.39 (dd, J=7.5, 0.7 Hz, 1H) 7.43 (d, J=8.5 Hz, 2H) 7.63-7.66 (m, 3H) 8.16 (s, 2H) 9.18 (s, 1H) 9.45 (s, 1H) MS (ESI(+)) m/e 495.0 (M+H)$^+$.

Example 310

N-[4-(3-amino-7-methyl-1,2-benzisoxazol-4-yl)phenyl]-N'-(3-bromophenyl)urea

The desired product was prepared by substituting Example 297B and 1-bromo-3-isocyanatobenzene for Example 15G and 1-fluoro-3-isocyanatobenzene, respectively, in Example 15H. $^1$H NMR (300 MHz, DMSO-D$_6$) δ ppm 2.45 (s, 3H) 5.20 (s, 2H) 7.04 (d, J=7.1 Hz, 1H) 7.16 (ddd, J=7.8, 1.9, 1.2 Hz, 1H) 7.25 (t, J=8.0 Hz, 1H) 7.33 (ddd, J=8.0, 2.0, 1.2 Hz, 1H) 7.38 (m, J=7.5, 1.0 Hz, 1H) 7.41 (d, J=8.5 Hz, 2H) 7.61 (d, J=8.5 Hz, 2H) 7.88 (t, J=1.9 Hz, 1H) 8.93 (app. s., 2H) MS (ESI(+)) m/e 436.9, 438.9 (M+H)$^+$.

Example 311

N-[4-(3-amino-7-methyl-1,2-benzisoxazol-4-yl)phenyl]-N'-(3-fluorophenyl)urea

The desired product was prepared by substituting Example 297B for Example 15G in Example 15H. $^1$H NMR (300 MHz, DMSO-D$_6$) δ ppm 2.45 (s, 3H) 5.19 (s, 2H) 6.80 (tdd, J=8.5, 2.7, 1.0 Hz, 1H) 7.04 (d, J=7.5 Hz, 1H) 7.14 (ddd, J=8.2, 2.0, 0.7 Hz, 1H) 7.32 (td, J=8.2, 7.0 Hz, 1H) 7.37-7.44 (m, 3H) 7.51 (dt, J=12.0, 2.3 Hz, 1H) 7.61 (d, J=8.5 Hz, 2H) 8.92 (s, 1H) 8.96 (s, 1H) MS (ESI(+)) m/e 377.1 (M+H)$^+$.

Example 312

N-[4-(3-amino-7-methoxy-1,2-benzisoxazol-4-yl)phenyl]-N'-[4-fluoro-3-(trifluoromethyl)phenyl]urea The desired product was prepared by substituting Example 100C and 1-fluoro-4-isocyanato-2-(trifluoromethyl)benzene for Example 15G and 1-fluoro-3-isocyanatobenzene, respectively, in Example 15H. ¹H NMR (300 MHz, DMSO-D₆) δ ppm 3.96 (s, 3H) 5.20 (s, 2H) 7.05 (d, J=8.1 Hz, 1H) 7.16 (d, J=8.1 Hz, 1H) 7.39 (d, J=8.5 Hz, 2H) 7.45 (t, J=9.8 Hz, 1H) 7.61 (d, J=8.5 Hz, 2H) 7.64-7.69 (m, 1H) 8.02 (dd, J=6.4, 2.7 Hz, 1H) 8.97 (s, 1H) 9.09 (s, 1H) MS (ESI(+)) m/e 461.0 (M+H)⁺.

Example 313

N-[4-(3-amino-7-methoxy-1,2-benzisoxazol-4-yl)phenyl]-N'-(4-fluoro-3-methylphenyl)urea The desired product was prepared by substituting Example 100C and 1-fluoro-4-isocyanato-2-methylbenzene for Example 15G and 1-fluoro-3-isocyanatobenzene, respectively, in Example 15H. ¹H NMR (300 MHz, DMSO-D₆) δ ppm 2.22 (d, J=2.0 Hz, 3H) 3.96 (s, 3H) 5.20 (s, 2H) 7.03-7.09 (m, 2H) 7.16 (d, J=8.1 Hz, 1H) 7.27 (ddd, J=8.5, 4.1, 3.0 Hz, 1H) 7.35-7.39 (m, 3H) 7.59 (d, J=8.5 Hz, 2H) 8.66 (s, 1H) 8.81 (s, 1H) MS (ESI(+)) m/e 407.1 (M+H)⁺.

Example 314

N-[4-(3-amino-7-fluoro-1,2-benzisoxazol-4-yl)phenyl]-N'-[3-(trifluoromethyl)phenyl]urea Example 314A 7-fluoro-4-iodo-1,2-benzisoxazol-3-amine The desired product was prepared by substituting Example 26A for 2-bromo-6-fluorobenzonitrile in Example 95A. MS (ESI(+)) m/e 278.8 (M+H)⁺.

Example 314B 4-(4-aminophenyl)-7-fluoro-1,2-benzisoxazol-3-amine

The desired product was prepared by substituting Example 314A and 4-(4,4,5,5-tetramethyl-1,3,2-dioxaborolan-2-yl)aniline for Examples 1A and 1B, respectively, in Example 1C. MS (ESI(+)) m/e 244.0 (M+H)⁺.

Example 314C

N-[4-(3-amino-7-fluoro-1,2-benzisoxazol-4-yl)phenyl]-N'-[3-(trifluoromethyl)phenyl]urea The desired product was prepared by substituting Example 314B and 1-isocyanato-3-(trifluoromethyl)benzene for Example 15G and 1-fluoro-3-isocyanatobenzene, respectively, in Example 15H. ¹H NMR (300 MHz, DMSO-D₆) δ ppm 5.38 (s, 2H) 7.12 (dd, J=8.3, 3.9 Hz, 1H) 7.33 (d, J=7.8 Hz, 1H) 7.43 (d, J=8.8 Hz, 2H) 7.52 (dd, J=10.9, 8.1 Hz, 1H) 7.53 (t, J=7.8 Hz, 1H) 7.59-7.65 (m, 3H) 8.04 (s, 1H) 9.00 (s, 1H) 9.12 (s, 1H) MS (ESI(+)) m/e 431.0 (M+H)⁺.

Example 315

N-[4-(3-amino-7-fluoro-1,2-benzisoxazol-4-yl)phenyl]-N'-(3-chlorophenyl)urea

The desired product was prepared by substituting Example 314B and 1-chloro-3-isocyanatobenzene for Example 15G and 1-fluoro-3-isocyanatobenzene, respectively, in Example 15H. ¹H NMR (300 MHz, DMSO-D₆) δ ppm 5.38 (s, 2H) 7.03 (dt, J=6.4, 2.2 Hz, 1H) 7.12 (dd, J=8.1, 4.1 Hz, 1H) 7.27-7.35 (m, 2H) 7.42 (d, J=8.5 Hz, 2H) 7.52 (dd, J=10.9, 8.1 Hz, 1H) 7.62 (d, J=8.5 Hz, 2H) 7.72-7.74 (m, 1H) 8.95 (s, 1H) 8.96 (s, 1H) MS (ESI(+)) m/e 397.0 (M+H)⁺.

Example 316

N-[4-(3-amino-7-fluoro-1,2-benzisoxazol-4-yl)phenyl]-N'-[4-fluoro-3-(trifluoromethyl)phenyl]urea The desired product was prepared by substituting Example 314B and 1-fluoro-4-isocyanato-2-(trifluoromethyl)benzene for Example 15G and 1-fluoro-3-isocyanatobenzene, respectively, in Example 15H. ¹H NMR (300 MHz, DMSO-D₆) δ ppm 5.37 (s, 2H) 7.12 (dd, J=8.1, 4.1 Hz, 1H) 7.43 (d, J=8.5 Hz, 2H) 7.43 (d, J=9.2 Hz, 1H) 7.52 (dd, J=10.9, 8.1 Hz, 1H) 7.63 (d, J=8.5 Hz, 2H) 7.64-7.69 (m, 1H) 8.02 (dd, J=6.4, 2.7 Hz, 1H) 9.01 (s, 1H) 9.10 (s, 1H) MS (ESI(+)) m/e 449.0 (M+H)⁺.

Example 317

N-[4-(3-amino-7-fluoro-1,2-benzisoxazol-4-yl)phenyl]-N'-(3-methylphenyl)urea

The desired product was prepared by substituting Example 314B and 1-isocyanato-3-methylbenzene for Example 15G and 1-fluoro-3-isocyanatobenzene, respectively, in Example 15H. ¹H NMR (300 MHz, DMSO-D₆) δ ppm 2.29 (s, 3H) 5.38 (s, 2H) 6.81 (d, J=7.5 Hz, 1H) 7.11 (dd, J=8.1, 4.1 Hz, 1H) 7.17 (t, J=7.8 Hz, 1H) 7.25 (d, J=8.5 Hz, 1H) 7.32 (s, 1H) 7.41 (d, J=8.5 Hz, 2H) 7.51 (dd, J=10.9, 8.1 Hz, 1H) 7.62 (d, J=8.5 Hz, 2H) 8.65 (s, 1H) 8.85 (s, 1H) MS (ESI(+)) m/e 377.1 (M+H)⁺.

Example 318

N-[4-(3-amino-7-fluoro-1,2-benzisoxazol-4-yl)phenyl]-N'-[2-fluoro-5-(trifluoromethyl)phenyl]urea The desired product was prepared by substituting Example 314B and 1-fluoro-2-isocyanato-4-(trifluoromethyl)benzene for Example 15G and 1-fluoro-3-isocyanatobenzene, respectively, in Example 15H. ¹H NMR (300 MHz, DMSO-D₆) δ ppm 5.38 (s, 2H) 7.12 (dd, J=8.3, 3.9 Hz, 1H) 7.38-7.55 (m, 5H) 7.64 (d, J=8.8 Hz, 2H) 8.64 (dd, J=7.3, 2.2 Hz, 1H) 8.97 (d, J=3.1 Hz, 1H) 9.37 (s, 1H) MS (ESI(+)) m/e 449.0 (M+H)⁺.

Example 319

N-[4-(3-amino-7-fluoro-1,2-benzisoxazol-4-yl)phenyl]-N'-(2-fluoro-5-methylphenyl)urea The desired product was prepared by substituting Example 314B and 1-fluoro-2-isocyanato-4-methylbenzene for Example 15G and 1-fluoro-3-isocyanatobenzene, respectively, in Example 15H. ¹H NMR (300 MHz, DMSO-D₆) δ ppm 2.28 (s, 3H) 5.38 (s, 2H) 6.79-6.84 (m, 1H) 7.08-7.15 (m, 2H) 7.43 (d, J=8.5 Hz, 2H) 7.52 (dd, J=10.9, 8.1 Hz, 1H) 7.62 (d, J=8.5 Hz, 2H) 8.00 (dd, J=7.6, 1.9 Hz, 1H) 8.55 (d, J=2.4 Hz, 1H) 9.25 (s, 1H) MS (ESI(+)) m/e 395.0 (M+H)⁺.

Example 320

N-{4-[3-amino-7-(trifluoromethoxy)-1,2-benzisoxazol-4-yl]phenyl}-N'-[2-fluoro-5-(trifluoromethyl)phenyl]urea

Example 320A 6-bromo-2-fluoro-3-(trifluoromethoxy)benzonitrile

The desired product was prepared by substituting 4-bromo-2-fluoro-1-trifluoromethoxy-benzene for 2-fluoro-4-iodo-1-methylbenzene in Examples 15A-C. MS (ESI(−)) m/e 282 (M−H)−.

Example 320B 4-bromo-7-(trifluoromethoxy)-1,2-benzisoxazol-3-amine

A solution of propan-2-one oxime (810 mg, 1.1 mmol) in THF (50 mL) was treated with potassium tert-butoxide (1.23 g) stirred at r.t for 30 min, then treated with example 320A (2.84 g, 10 mmol). The reaction mixture was stirred at r.t. for 30 min, then partitioned between EtOAc and water. The organic extract was washed with brine, dried (MgSO$_4$) and concentrated. The residue was dissolved in ethanol (20 mL), treated with 5% HCl (20 mL) and heated at reflux for 2 h. The reaction was allowed to cool to r.t the concentrated to half its volume resulting in a precipitate which was collected via filtration. The crude solid was purified via silica gel chromatography eluting with 0 to 10% EtOAc-hexanes to give 0.95 g of example 320B. MS (ESI(+)) m/e 297, 299 (M+H)+.

Example 320C 4-(4-aminophenyl)-7-(trifluoromethoxy)-1,2-benzisoxazol-3-amine The desired product was prepared by substituting Example 320B for Example 15H in Example 15G. MS (ESI(+)) m/e 310 (M+H)+.

Example 320D

N-{4-[3-amino-7-(trifluoromethoxy)-1,2-benzisoxazol-4-yl]phenyl}-N'-[2-fluoro-5-(trifluoromethyl)phenyl]urea The desired product was prepared by substituting Example 320C and 1-fluoro-2-isocyanato-4-(trifluoromethyl)benzene for Example 15G and 1-fluoro-3-isocyanatobenzene, respectively, in Example 15H. $^1$H NMR (300 MHz, DMSO-D$_6$) δ ppm 5.44 (s, 2H), 7.22 (d, J=7.80 Hz, 1H), 7.35-7.46 (m, 1H), 7.46-7.52 (m, 3H), 7.62-7.72 (m, 3H), 8.64 (dd, J=7.29, 2.20 Hz, 1H), 8.98 (d, J=2.71 Hz, 1H), 9.40 (s, 1H); MS (ESI(+)) m/e 515 (M+H)+.

Example 321

N-{4-[3-amino-7-(trifluoromethoxy)-1,2-benzisoxazol-4-yl]phenyl}-N'-[3-(trifluoromethyl)phenyl]urea The desired product was prepared by substituting Example 320C and 1-isocyanato-3-(trifluoromethyl)benzene for Example 15G and 1-fluoro-3-isocyanatobenzene, respectively, in Example 15H. $^1$H NMR (300 MHz, DMSO-D$_6$) δ ppm 5.44 (s, 2H), 7.22 (d, J=8.14 Hz, 1H), 7.33 (d, J=7.80 Hz, 1H), 7.45-7.72 (m, 7H), 8.04 (s, 1H), 9.03 (s, 1H), 9.13 (s, 1H); MS (ESI(+)) m/e 497 (M+H)+.

Example 322

N-{4-[3-amino-7-(trifluoromethoxy)-1,2-benzisoxazol-4-yl]phenyl}-N'-(2-fluoro-5-methylphenyl)urea The desired product was prepared by substituting Example 320C and 1-fluoro-2-isocyanato-4-methylbenzene for Example 15G and 1-fluoro-3-isocyanatobenzene, respectively, in Example 15H. $^1$H NMR (300 MHz, DMSO-D$_6$) δ ppm 2.28 (s, 3H), 5.44 (s, 2H), 6.75-6.90 (m, 1H), 7.12 (dd, J=11.36, 8.31 Hz, 1H), 7.21 (d, J=8.14 Hz, 1H), 7.47 (d, J=8.82 Hz, 2H), 7.55-7.75 (m, 3H), 8.00 (dd, J=7.97, 1.86 Hz, 1H), 8.56 (d, J=2.71 Hz, 1H), 9.28 (s, 1H); MS (ESI(+)) m/e 461 (M+H)+.

Example 323

N-{4-[3-amino-7-(trifluoromethoxy)-1,2-benzisoxazol-4-yl]phenyl}-N'-(3-chlorophenyl)urea The desired product was prepared by substituting Example 320C and 3-chloro-1-isocyanatobenzene for Example 15G and 1-fluoro-3-isocyanatobenzene, respectively, in Example 15H. $^1$H NMR (300 MHz, DMSO-D$_6$) δ ppm 5.43 (s, 2H), 7.95-7.06 (m, 1H), 7.21 (d, J=8.14 Hz, 1H), 7.25-7.35 (m, 2H), 7.47 (d, J=8.48 Hz, 2H), 7.6-7.9 (m, 4H), 8.97 (s, 1H), 8.99 (s, 1H); MS (ESI(+)) m/e 463 (M+H)+.

Example 324

N-{4-[3-amino-7-(trifluoromethoxy)-1,2-benzisoxazol-4-yl]phenyl}-N'-(3-bromophenyl)urea The desired product was prepared by substituting Example 320C and 3-bromo-1-isocyanatobenzene for Example 15G and 1-fluoro-3-isocyanatobenzene, respectively, in Example 15H. $^1$H NMR (300 MHz, DMSO-D$_6$) δ ppm 5.43 (s, 2H), 7.10-7.37 (m, 4H), 7.47 (d, J=8.82 Hz, 2H), 7.60-7.72 (m, 3H), 7.88 (t, J=2.03 Hz, 1H), 8.96 (s, 1H), 8.99 (s, 1H); MS (ESI(+)) m/e 507 (M+H)+.

Example 325

N-{4-[3-amino-7-(trifluoromethoxy)-1,2-benzisoxazol-4-yl]phenyl}-N'-[4-fluoro-3-(trifluoromethyl)phenyl]urea The desired product was prepared by substituting Example 320C and 1-fluoro-4-isocyanato-2-(trifluoromethyl)benzene for Example 15G and 1-fluoro-3-isocyanatobenzene, respectively, in Example 15H. $^1$H NMR (300 MHz, DMSO-D$_6$) δ ppm 5.43 (s, 2H), 7.21 (d, J=8.14 Hz, 1H), 7.40-7.52 (m, J=9.15, 9.15 Hz, 3H), 7.60-7.75 (m, 4H), 7.90-8.10 (dd, J=6.44, 2.71 Hz, 1H), 9.04 (s, 1H), 9.12 (s, 1H); MS (ESI(+)) m/e 515 (M+H)+.

Example 326

N-{4-[3-amino-7-(trifluoromethoxy)-1,2-benzisoxazol-4-yl]phenyl}-N'-(4-fluoro-3-methylphenyl)urea The desired product was prepared by substituting Example 320C and 1-fluoro-4-isocyanato-2-methylbenzene for Example 15G and 1-fluoro-3-isocyanatobenzene, respectively, in Example 15H. $^1$H NMR (300 MHz, DMSO-D$_6$) δ ppm 2.23 (s, 3H), 5.43 (s, 2H), 7.06 (t, J=9.16 Hz, 1H), 7.21 (d, J=8.14 Hz, 1H), 7.25-7.40 (m, 2H), 7.45 (d, J=8.48 Hz, 2H), 7.58-7.78 (m, 3H), 8.69 (s, 1H), 8.88 (s, 1H); MS (ESI (+)) m/e 461 (M+H)$^+$.

Example 327

N-[4-(3-amino-1,2-benzisothiazol-4-yl)phenyl]-N'-(3,5-dimethylphenyl)urea

Example 327A 2-(benzylthio)-6-iodobenzonitrile

A suspension of potassium tert-butoxide (1.12 g, 10.0 mmol) and phenyl-methanethiol (1.24 g, 10 mmol) in THF (30 mL) at room temperature was stirred for 10 minutes before treating with 2-fluoro-6-iodo-benzonitrile (2.47 g, 10 mmol). The solution was stirred for 1 hour at room temperature, poured into a saturated ammonium chloride solution and filtered. The filter cake was recrystallized from hexanes to provide 2.41 g (53% yield) of the desired product. MS (ESI (−)) m/e 350.0 (M−H)$^-$.

Example 327B 4-iodo-1,2-benzisothiazol-3-amine

Example 327A (2.5 g, 7.1 mmol) was treated with sulfuryl chloride (1.0 M in dichloromethane, 3.5 mL, 35.5 mmol), stirred at room temperature for 2 hours and concentrated. The residue was dissolved in minimal THF, treated with ammonia (7.0 M in methanol, 10 mL), stirred at room temperature for 1 hour, diluted with water and extracted with ethyl acetate. The combine organic layers were washed with brine, dried (MgSO$_4$), filtered and concentrated. The residue was triturated from ethyl acetate/hexanes to provide 1.2 g (61% yield) of the desired product. MS (ESI(−)) m/e 274.8, 276.7 (M−H)$^-$.

Example 327C

N-[4-(3-amino-1,2-benzisothiazol-4-yl)phenyl]-N'-(3,5-dimethylphenyl)urea

The desired product was prepared by substituting 1-isocyanato-3,5-dimethylbenzene for 1-isocyanato-3-methylbenzene, in example 1B and Example 327B for example 1A in example 1C. In addition PdCl$_2$.dppf.CH$_2$Cl$_2$ was used in place of Pd(PPh$_3$)$_4$. $^1$H NMR (300 MHz, DMSO-D$_6$) δ ppm 2.24 (s, 6H), 5.45 (s, 2H), 6.63 (s, 1H), 7.09 (s, 2H), 7.35 (d, J=8.48 Hz, 2H), 7.50-7.70 (m, 3H), 7.97 (d, J=8.14 Hz, 1H), 8.59 (s, 1H), 8.85 (s, 2H); MS (ESI(+)) m/e 389.0 (M+H)$^+$.

Example 328

N-[4-(3-amino-1,2-benzisothiazol-4-yl)phenyl]-N'-(3-chlorophenyl)urea

The desired product was prepared by substituting 3-chloro-1-isocyanatobenzene for 1-isocyanato-3-methylbenzene, in example 1B and Example 327B for example 1A in example 1C. In addition PdCl$_2$.dppf.CH$_2$Cl$_2$ was used in place of Pd(PPh$_3$)$_4$. $^1$H NMR (300 MHz, DMSO-D$_6$) δ ppm 5.45 (s, 2H), 7.01-7.10 (m, 1H), 7.17 (d, J=7.80 Hz, 1H), 7.30-7.40 (m, 3H), 7.50-7.65 (m, 4H), 7.70-7.80 (m, 1H), 7.97 (dd, J=7.97, 0.85 Hz, 1H), 9.00 (s, 2H); MS (ESI(+)) m/e 395.0 (M+H)$^+$.

Example 329

N-[4-(3-amino-1,2-benzisothiazol-4-yl)phenyl]-N'-(2-fluoro-5-methylphenyl)urea

The desired product was prepared by substituting 1-fluoro-2-isocyanato-4-methylbenzen for 1-isocyanato-3-methylbenzene, in example 1B and Example 327B for example 1A in example 1C. In addition PdCl$_2$.dppf.CH$_2$Cl$_2$ was used in place of Pd(PPh$_3$)$_4$. $^1$H NMR (300 MHz, DMSO-D$_6$) δ ppm 2.28 (s, 3H), 5.45 (s, 2H) 6.78-6.88 (m, 1H) 7.05-7.25 (m, 2H), 7.37 (d, J=8.48 Hz, 2H), 7.50-7.70 (m, 3H), 7.90-8.10 (m, 2H), 8.56 (d, J=2.37 Hz, 1H), 9.28 (s, 1H); MS (ESI(+)) m/e 393.0 (M+H)$^+$.

Example 330

N-[4-(3-amino-1,2-benzisothiazol-4-yl)phenyl]-N'-(3-methylphenyl)urea

The desired product was prepared by substituting Example 327B for example 1A in example 1C. In addition PdCl$_2$.dppf.CH$_2$Cl$_2$ was used in place of Pd(PPh$_3$)$_4$. $^1$H NMR (300 MHz, DMSO-D$_6$) δ ppm 2.29 (s, 3H), 5.45 (s, 2H), 6.81 (d, J=7.46 Hz, 1H), 7.20-7.40 (m, 3H), 7.48-7.56 (m, 6H), 7.97 (d, J=8.14 Hz, 1H), 8.67 (s, 1H), 8.87 (s, 1H); MS (ESI(+)) m/e 375.0 (M+H)$^+$.

Example 331

N-[4-(3-amino-1,2-benzisothiazol-4-yl)phenyl]-N'-[3-(trifluoromethyl)phenyl]urea The desired product was prepared by substituting 1-isocyanato-3-(trifluoromethyl)benzene for 1-isocyanato-3-methylbenzene, in example 1B and Example 327B for example 1A in example 1C. In addition PdCl$_2$.dppf.CH$_2$Cl$_2$ was used in place of Pd(PPh$_3$)$_4$. $^1$H NMR (300 MHz, DMSO-D$_6$) δ ppm 5.45 (s, 2H), 7.17 (d, J=7.12 Hz, 1H), 7.25-7.45 (m, 3H), 7.50-7.60 (m, 5H), 7.97 (d, J=7.46 Hz, 1H), 8.04 (s, 1H), 9.02 (s, 1H), 9.14 (s, 1H); MS (ESI(+)) m/e 429 (M+H)$^+$.

Example 332

N-[4-(3-amino-7-fluoro-1H-indazol-4-yl)-2-fluorophenyl]-N'-(2-fluoro-5-methylphenyl)urea Example 332A 2-fluoro-4-(4,4,5,5-tetramethyl-1,3,2-dioxaborolan-2-yl)phenylamine The desired product was prepared by substituting 4-bromo-2-fluoro-phenylamine for Example 149A in Example 149B. $^1$H NMR (300 MHz, DMSO-D$_6$) δ ppm 3.32 (s, 12H) 5.56 (s, 2H) 6.72 (dd, J=8.82, 7.80 Hz, 1H) 7.13 (m, 1H) 7.18 (dd, J=7.97, 1.19 Hz, 1H).

Example 332B

N-(2-fluoro-5-methylphenyl)-N'-[2-fluoro-4-(4,4,5,5-tetramethyl-1,3,2-dioxaborolan-2-yl)phenyl]urea The desired product was prepared by substituting Example 332A for 4-bromo-2-ethylaniline in Example 149A. MS (ESI(+)) m/e 389 (M+H)$^+$.

Example 332C 7-fluoro-4-iodo-1H-indazol-3-amine

The desired product was prepared by substituting Example 26A for Example 15E in Example 15F. MS (ESI(+)) m/e 278 (M+H)$^+$.

Example 332D

N-[4-(3-amino-7-fluoro-1H-indazol-4-yl)-2-fluorophenyl]-N'-(2-fluoro-5-methylphenyl)urea The desired product was prepared by substituting Example 332B and Example 332C for Example 1B and Example 1A, respectively, in Example 1C. $^1$H NMR (300 MHz, DMSO-D$_6$) δ ppm 2.28 (s, 3H), 6.77-6.81 (m, 2H), 7.09-7.17 (m, 2H), 7.24 (dd, J=8.48, 2.03 Hz, 1H), 7.36 (dd, J=12.21, 2.03 Hz, 1H), 8.03 (dd, J=7.97, 2.20 Hz, 1H), 8.31 (t, J=8.48 Hz, 1H), 9.03 (d, J=2.37 Hz, 1H), 9.15 (d, J=2.37 Hz, 1H); MS (ESI(+) m/e 412 (M+H)$^+$.

Example 333

N-[4-(3-amino-7-fluoro-1H-indazol-4-yl)-2-fluorophenyl]-N'-(3-chlorophenyl)urea

Example 333A

N-(3-chlorophenyl)-N'-[3-fluoro-4-(4,4,5,5-tetramethyl-1,3,2-dioxaborolan-2-yl)phenyl]urea The desired product was prepared by substituting Example 332A and 1-chloro-3-isocyanato-benzene for 4-bromo-2-ethylaniline and 1-fluoro-2-isocyanato-4-methylbenzene, respectively, in Example 149A. MS (ESI(+)) m/e 391 (M+H)$^+$.

Example 333B

N-[4-(3-amino-7-fluoro-1H-indazol-4-yl)-2-fluorophenyl]-N'-(3-chlorophenyl)urea

The desired product was prepared by substituting Example 333A and Example 332C for Example 1B and Example 1A, respectively, in Example 1C. $^1$H NMR (300 MHz, DMSO-D$_6$) δ ppm 6.79 (dd, J=7.80, 4.07 Hz, 1H), 7.03-7.07 (m, 1H), 7.14 (dd, J=11.36, 7.97 Hz, 1H), 7.24-7.39 (m, 4H), 7.75 (t, J=2.03 Hz, 1H), 8.25 (t, J=8.48 Hz, 1H), 8.73 (d, J=2.37 Hz, 1H), 9.31 (s, 1H); MS (ESI(+) m/e 414 (M+H)$^+$.

Example 334

N-(4-{3-amino-7-[(1-methylpiperidin-4-yl)methoxy]-1H-indazol-4-yl}-2-fluorophenyl)-N'-(2-fluoro-5-methylphenyl)urea

Example 334A 2-fluoro-6-iodo-3-[(1-methylpiperidin-4-yl)methoxy]benzonitrile The desired product was prepared by substituting 1-methyl-4-piperidinemethanol for 2-(4-morpholinyl)ethanol in Example 75A. MS (ESI(+)) m/e 375 (M+H)$^+$.

Example 334B 4-iodo-7-[(1-methylpiperidin-4-yl)methoxy]-1H-indazol-3-amine

The desired product was prepared by substituting Example 334A for Example 15E in Example 15F. MS (ESI(+)) m/e 387 (M+H)$^+$.

Example 334C

N-(4-{3-amino-7-[(1-methylpiperidin-4-yl)methoxy]-1H-indazol-4-yl}-2-fluorophenyl)-N'-(2-fluoro-5-methylphenyl)urea The desired product was prepared by substituting Example 334B and Example 5A for Example 1A and Example 1B in Example 1C. $^1$H NMR (300 MHz, DMSO-D$_6$) δ ppm 1.42-1.58 (m, 2H), 2.08-2.18 (m, 3H), 2.28 (s, 3H), 2.79 (d, J=4.75 Hz, 3H), 2.91-3.11 (m, 2H), 3.51 (d, J=12.21 Hz, 2H), 4.03 (d, J=6.44 Hz, 2H), 6.71 (d, J=7.80 Hz, 1H), 6.81-6.83 (m, 2H), 7.11 (dd, J=11.36, 8.31 Hz, 1H), 7.36 (d, J=8.48 Hz, 2H), 7.57 (d, J=8.81 Hz, 2H), 8.00 (dd, J=7.97, 2.20 Hz, 1H), 8.53 (d, J=2.71 Hz, 1H), 9.19 (s, 1H); MS (ESI(+) m/e 503 (M+H)$^+$.

Example 335

N-(4-{3-amino-7-[(1-methylpiperidin-4-yl)methoxy]-1H-indazol-4-yl}phenyl)-N'-(3-methylphenyl)urea The desired product was prepared by substituting Example 334B for Example 1A in Example 1C. $^1$H NMR (300 MHz, DMSO-D$_6$) δ ppm 1.41-1.53 (m, 2H), 2.07-2.18 (m, 3H), 2.29 (s, 3H), 2.79 (d, J=4.75 Hz, 3H), 2.92-3.05 (m, 2H), 3.51 (d, J=12.55 Hz, 2H), 4.03 (d, J=6.44 Hz, 2H), 6.71 (d, J=7.46 Hz, 1H), 6.81 (m, 2H), 7.16 (m, 1H), 7.25 (d, J=8.14 Hz, 1H), 7.32 (s, 1H), 7.34 (d, J=8.48 Hz, 2H), 7.57 (d, J=8.48 Hz, 2H), 8.69 (s, 1H), 8.83 (s, 1H); MS (ESI(+) m/e 485 (M+H)$^+$.

Example 336

N-(4-{3-amino-7-[(1-methylpiperidin-4-yl)methoxy]-1H-indazol-4-yl}phenyl)-N'-(3-chlorophenyl)urea The desired product was prepared by substituting Example 334B and 1-chloro-3-isocyanatobenzene for Example 1A and 1-isocyanato-3-methylbenzene, respectively, in Examples 1B-C. ¹H NMR (300 MHz, DMSO-D₆) δ ppm 1.41-1.53 (m, 2H), 2.07-2.18 (m, 3H), 2.79 (d, J=4.75 Hz, 3H), 2.92-3.05 (m, 2H), 3.51 (d, J=12.55 Hz, 2H), 4.03 (d, J=6.44 Hz, 2H), 6.72 (d, J=7.80 Hz, 1H), 6.82 (d, J=7.80 Hz, 1H), 7.01-7.04 (m, 1H), 7.30-7.32 (m, 2H), 7.36 (d, J=8.48 Hz, 2H), 7.57 (d, J=8.48 Hz, 2H), 7.74 (m, 1H), 8.98 (s, 1H), 9.04 (s, 1H); MS (ESI(+) m/e 505 (M+H)⁺.

Example 337

N-(4-{3-amino-7-[(1-methylpiperidin-4-yl)methoxy]-1H-indazol-4-yl}phenyl)-N'-(4-fluoro-3-methylphenyl)urea The desired product was prepared by substituting Example 334B and 1-fluoro-2-methyl-4-isocyanatobenzene for Example 1A and 1-isocyanato-3-methylbenzene, respectively, in Examples 1B-C. ¹H NMR (300 MHz, DMSO-D₆) δ ppm 1.41-1.53 (m, 2H), 2.07-2.18 (m, 3H), 2.22 (s, 3H) 2.79 (d, J=4.75 Hz, 3H), 2.92-3.05 (m, 2H), 3.51 (d, J=12.55 Hz, 2H), 4.03 (d, J=6.44 Hz, 2H), 6.72 (d, J=7.46 Hz, 1H), 6.82 (d, J=7.80 Hz, 1H), 7.05 (t, J=9.16 Hz, 1H), 7.25-7.40 (m, 2H), 7.34 (d, J=8.48 Hz, 2H), 7.56 (d, J=8.82 Hz, 2H), 8.73 (s, 1H), 8.85 (s, 1H); MS (ESI(+) m/e 503 (M+H)⁺.

Example 338

N-{4-[3-amino-7-(3-pyridin-3-ylpropoxy)-1H-indazol-4-yl]phenyl}-N'-(3-chlorophenyl)urea

Example 338A 2-fluoro-6-iodo-3-(3-pyridin-3-ylpropoxy)benzonitrile

The desired product was prepared by 3-pyridinepropanol for 2-(4-morpholinyl)ethanol in Example 75A. MS (ESI(+)) m/e 383 (M+H)⁺.

Example 338B 4-iodo-7-(3-pyridin-3-ylpropoxy)-1H-indazol-3-amine

The desired product was prepared by substituting Example 338A for Example 15E in Example 15F. MS (ESI(+)) m/e 395 (M+H)⁺.

Example 338C

N-{4-[3-amino-7-(3-pyridin-3-ylpropoxy)-1H-indazol-4-yl]phenyl}-N'-(3-chlorophenyl)urea The desired product was prepared by substituting Example 338B and 1-chloro-3-isocyanatobenzene for Example 1A and 1-isocyanato-3-methylbenzene, respectively, in Examples 1B-C. ¹H NMR (300 MHz, DMSO-D₆) δ ppm 2.13-2.22 (m, 2H), 3.05 (t, J=7.12 Hz, 2H), 4.16 (t, J=5.93 Hz, 2H), 6.73 (d, J=7.80 Hz, 1H), 6.81 (d, J=7.80 Hz, 1H), 7.01-7.04 (m, 1H), 7.27-7.32 (m, 2H), 7.37 (d, J=8.81 Hz, 2H), 7.58 (d, J=8.81 Hz, 2H), 7.74 (t, J=2.03 Hz, 1H), 7.83 (dd, J=7.80, 5.42 Hz, 1H), 8.32 (d, J=7.80 Hz, 1H), 8.69 (d, J=4.07 Hz, 1H), 8.77 (d, J=2.03 Hz, 1H), 8.97 (s, 1H), 9.03 (s, 1H); MS (ESI(+) m/e 513 (M+H)⁺.

Example 339

N-{4-[3-amino-7-(3-pyridin-3-ylpropoxy)-1H-indazol-4-yl]phenyl}-N'-(3-methylphenyl)urea The desired product was prepared by substituting Example 338B for Example 1A in Example 1C. ¹H NMR (300 MHz, DMSO-D₆) δ ppm 2.15-2.22 (m, 2H), 2.29 (s, 3H), 3.05 (t, J=7.12 Hz, 2H), 4.16 (t, J=5.93 Hz, 2H), 6.72 (d, J=7.80 Hz, 1H), 6.79-6.82 (m, 2H), 7.16 (m, 1H), 7.25 (m, 1H), 7.32 (s, 1H), 7.35 (d, J=8.81 Hz, 2H), 7.57 (d, J=8.81 Hz, 2H), 7.83 (dd, J=7.80, 5.42 Hz, 1H), 8.31 (d, J=8.14 Hz, 1H), 8.69 (m, 2H), 8.77 (d, J=1.69 Hz, 1H), 8.82 (s, 1H); MS (ESI(+) m/e 493 (M+H)⁺.

Example 340

N-{4-[3-amino-7-(3-pyridin-3-ylpropoxy)-1H-indazol-4-yl]phenyl}-N'-[4-fluoro-3-(trifluoromethyl)phenyl]urea The desired product was prepared by substituting Example 338B and 1-fluoro-4-isocyanato)-2-(trifluoromethyl)benzene for Example 1A and 1-isocyanato-3-methylbenzene, respectively, in Examples 1B-C. ¹H NMR (300 MHz, DMSO-D₆) δ ppm 2.07-2.19 (m, 2H), 3.05 (t, J=7.12 Hz, 2H), 4.15 (t, J=5.93 Hz, 2H), 6.71 (d, J=7.80 Hz, 1H), 6.80 (d, J=7.80 Hz, 1H), 7.37 (d, J=8.82 Hz, 2H), 7.45 (t, J=9.16 Hz, 1H), 7.58 (d, J=8.48 Hz, 2H), 7.66 (m, 1H), 7.78 (dd, J=7.80, 5.42 Hz, 1H), 8.04 (dd, J=6.78, 2.71 Hz, 1H), 8.25 (d, J=8.14 Hz, 1H), 8.66 (d, J=4.41 Hz, 1H), 8.74 (d, J=1.70 Hz, 1H), 9.00 (s, 1H), 9.16 (s, 1H); MS (ESI(+) m/e 565 (M+H)⁺.

Example 341

N-{4-[3-amino-7-(3-pyridin-3-ylpropoxy)-1H-indazol-4-yl]phenyl}-N'-(4-fluoro-3-methylphenyl)urea The desired product was prepared by substituting Example 338B and 1-fluoro-4-isocyanato-2-methylbenzene for Example 1A and 1-isocyanato-3-methylbenzene, respectively, in Examples 1B-C. ¹H NMR (300 MHz, DMSO-D₆) δ ppm 2.15-2.22 (m, 2H), 2.22 (s, 3H), 3.05 (t, J=7.12 Hz, 2H), 4.15 (t, J=6.10 Hz, 2H), 6.72 (d, J=7.80 Hz, 1H), 6.82 (d, J=7.80 Hz, 1H), 7.05 (t, J=9.16 Hz, 1H), 7.19-7.40 (m, 4H), 7.56 (d, J=8.48 Hz, 2H), 7.82 (dd, J=7.97, 5.26 Hz, 1H), 8.30 (d, J=7.12 Hz, 1H), 8.69 (dd, J=5.43, 1.36 Hz, 1H), 8.73 (s, 1H), 8.76 (d, J=1.70 Hz, 1H), 8.85 (s, 1H); MS (ESI(+) m/e 511 (M+H)⁺.

Example 342

N-{4-[3-amino-7-(3-pyridin-3-ylpropoxy)-1H-indazol-4-yl]phenyl}-N'-(3-chloro-4-fluorophenyl)urea The desired product was prepared by substituting Example 338B and 1-fluoro-2-chloro-4-isocyanatobenzene for Example 1A and 1-isocyanato-3-methylbenzene, respectively, in Examples 1B-C. ¹H NMR (300 MHz, DMSO-D₆) δ ppm 2.13-2.22 (m, 2H), 3.05 (t, J=7.12 Hz, 2H), 4.15 (t, J=5.93 Hz, 2H), 6.71 (d, J=7.80 Hz, 1H), 6.80 (d, J=7.80 Hz, 1H), 7.33-7.38 (m, 4H), 7.57 (d, J=8.48 Hz, 2H), 7.77-7.84

(m, 2H), 8.27 (d, J=7.80 Hz, 1H), 8.67 (dd, J=5.42, 1.36 Hz, 1H), 8.75 (d, J=1.70 Hz, 1H), 8.97 (s, 1H), 9.01 (s, 1H); MS (ESI(+) m/e 531 (M+H)⁺.

Example 343

N-{4-[3-amino-7-(3-pyridin-3-ylpropoxy)-1H-indazol-4-yl]phenyl}-N'-[3-(trifluoromethyl)phenyl]urea The desired product was prepared by substituting Example 338B and 1-isocyanato-3-(trifluoromethyl)benzene for Example 1A and 1-isocyanato-3-methylbenzene, respectively, in Examples 1B-C. ¹H NMR (300 MHz, DMSO-D₆) δ ppm 2.13-2.22 (m, 2H), 3.05 (t, J=7.12 Hz, 2H), 4.15 (t, J=6.10 Hz, 2H), 6.72 (d, J=7.80 Hz, 1H), 6.81 (m, 1H), 7.32 (d, J=7.46 Hz, 1H), 7.37 (d, J=8.48 Hz, 2H), 7.53 (t, J=7.97 Hz, 1H), 7.60 (m, 3H), 7.81 (dd, J=8.14, 5.42 Hz, 1H), 8.05 (s, 1H), 8.28 (d, J=8.14 Hz, 1H), 8.68 (dd, J=5.26, 1.19 Hz, 1H), 8.76 (d, J=1.70 Hz, 1H), 9.01 (s, 1H), 9.19 (s, 1H); MS (ESI(+) m/e 547 (M+H)⁺.

Example 344

N-{4-[3-amino-7-(3-pyridin-4-ylpropoxy)-1H-indazol-4-yl]phenyl}-N'-(2-fluoro-5-methylphenyl)urea Example 344A 2-fluoro-6-iodo-3-(3-pyridin-4-ylpropoxy)benzonitrile The desired product was prepared by 4-pyridinepropanol for 2-(4-morpholinyl)ethanol in Example 75A. MS (ESI(+) m/e 382.9 (M+H)⁺.

Example 344B 4-iodo-7-(3-pyridin-4-ylpropoxy)-1H-indazol-3-amine

The desired product was prepared by substituting Example 344A for Example 15E in Example 15F. MS (ESI(+) m/e 395 (M+H)⁺.

Example 344C

N-{4-[3-amino-7-(3-pyridin-4-ylpropoxy)-1H-indazol-4-yl]phenyl}-N'-(2-fluoro-5-methylphenyl)urea The desired product was prepared by substituting Example 344B and 1-fluoro-2-isocyanato-4-methylbenzene for Example 1A and 1-isocyanato-3-methylbenzene, respectively, in Examples 1B-C. ¹H NMR (300 MHz, DMSO-D₆) δ ppm 2.09-2.15 (m, 2H), 2.28 (s, 3H), 2.90 (t, J=7.12 Hz, 2H), 4.13 (t, J=6.10 Hz, 2H), 4.32 (s, 2H), 6.67 (d, J=7.80 Hz, 1H), 6.75 (d, J=7.80 Hz, 1H), 6.78-6.82 (m, 1H), 7.11 (dd, J=11.36, 8.31 Hz, 1H), 7.31 (d, J=6.10 Hz, 2H), 7.36 (d, J=8.48 Hz, 2H), 7.56 (d, J=8.48 Hz, 2H), 8.01 (dd, J=7.97, 2.20 Hz, 1H), 8.47 (d, J=5.76 Hz, 2H), 8.53 (d, J=2.71 Hz, 1H), 9.18 (s, 1H), 11.90 (s, 1H); MS (ESI(+) m/e 511 (M+H)⁺.

Example 345

N-{4-[3-amino-7-(3-pyridin-4-ylpropoxy)-1H-indazol-4-yl]phenyl}-N'-(3-methylphenyl)urea The desired product was prepared by substituting Example 344B for Example 1A in Example 1C. ¹H NMR (300 MHz, DMSO-D₆) δ ppm 2.07-2.16 (m, 2H), 2.29 (s, 3H), 2.90 (m, 2H), 4.13 (t, J=5.93 Hz, 2H), 4.32 (s, 2H), 6.67 (d, J=7.46 Hz, 1H), 6.75 (d, J=7.80 Hz, 1H), 6.80 (d, J=7.12 Hz, 1H), 7.16 (t, J=7.80 Hz, 1H), 7.25 (d, J=8.14 Hz, 1H), 7.31 (dd, J=4.07, 1.70 Hz, 3H), 7.35 (d, J=8.48 Hz, 2H), 7.56 (d, J=8.48 Hz, 2H), 8.47 (d, J=6.10 Hz, 2H), 8.64 (s, 1H), 8.77 (s, 1H), 11.90 (s, 1H); MS (ESI+) m/e 493 (M+H)⁺.

Example 346

N-{4-[3-amino-7-(3-pyridin-4-ylpropoxy)-1H-indazol-4-yl]phenyl}-N'-(3-chlorophenyl)urea The desired product was prepared by substituting Example 344B and 1-chloro-3-isocyanatobenzene for Example 1A and 1-isocyanato-3-methylbenzene, respectively, in Examples 1B-C. ¹H NMR (300 MHz, DMSO-D₆) δ ppm 2.13 (m, 2H), 4.13 (t, J=6.10 Hz, 2H), 4.32 (s, 2H), 6.67 (d, J=7.80 Hz, 1H), 6.75 (m, 1H), 7.02 (m, 1H), 7.31 (m, J=6.10, 2.03 Hz, 5H), 7.36 (d, J=8.81 Hz, 2H), 7.56 (m, J=8.48 Hz, 3H), 7.73 (s, 1H), 8.47 (m, 2H), 8.90 (s, 1H), 8.97 (s, 1H), 11.90 (s, 1H); MS (ESI(+) m/e 513 (M+H)⁺.

Example 347

N-[4-(3-amino-1H-indazol-4-yl)-2-(methoxymethoxy)phenyl]-N'-(2-fluoro-5-methylphenyl)urea Example 347A N-(4-bromo-2-hydroxyphenyl)-N'-(2-fluoro-5-methylphenyl)urea The desired product was prepared by substituting 2-Amino-5-bromo-phenol for 4-bromo-2-ethylaniline in example 149A. MS (ESI(+)) m/e 339 and 341 (M+H)⁺.

Example 347B

N-[4-bromo-2-(methoxymethoxy)phenyl]-N'-(2-fluoro-5-methylphenyl)urea

A solution of example 347A (68 mg, 0.2 mmol) in acetone (2 mL) was treated with K2CO3 (41 mg, 0.3 mmol) and MOM-Cl (0.023 mL, 0.3 mmol), stirred at reflux for 2 h, then allowed to cool to room temperature and treated with water. The resulting suspension was filtered and the filter cake was dried to give 58 mg of example 347B. ¹H NMR (300 MHz, DMSO-D₆) δ ppm 2.27 (s, 3H) 3.45 (s, 3H) 5.32 (s, 2H) 6.78-6.83 (m, 1H) 7.12-7.15 (m, 2H) 7.29 (d, J=2.37 Hz, 1H) 7.98 (dd, J=7.97, 1.86 Hz, 1H) 8.13 (d, J=8.82 Hz, 1H) 8.82 (s, 1H) 9.22 (d, J=1.70 Hz, 1H).

Example 347C

N-[4-(3-amino-1H-indazol-4-yl)-2-(methoxymethoxy)phenyl]-N'-(2-fluoro-5-methylphenyl)urea The desired product was prepared substituting example 347B for example 44A in example 44B. ¹H NMR (300 MHz, DMSO-D₆) d ppm 2.28 (s, 3H) 3.47 (s, 3H) 4.42 (s, 2H) 5.37 (s, 2H) 6.78-6.83 (m, 2H) 7.08 (dd, J=8.3, 1.9 Hz, 1H) 7.11 (dd, J=11.4, 8.3 Hz, 1H) 7.24 (d, J=2.0 Hz, 1H) 7.26 (s, 1H) 7.27 (d, J=2.7 Hz, 1H) 8.04 (dd, J=8.1, 2.0 Hz, 1H) 8.29 (d, J=8.5 Hz, 1H) 8.89 (s, 1H) 9.26 (d, J=1.7 Hz, 1H) 11.72 (s, 1H); MS (ESI(+)) m/e 436.2 (M+H)+.

Example 348

N-[4-(3-amino-1H-indazol-4-yl)-2-hydroxyphenyl]-N'-(2-fluoro-5-methylphenyl)urea

Example 348A

N-(4-bromo-2-tetrahydro-2H-pyran-2-ylphenyl)-N'-(2-fluoro-5-methylphenyl)urea

A solution of example 347A (150 mg, 0.44 mmol) and dihydropyran (0.24 mL, 2.4 mmol) in $CH_2Cl_2$ (2 mL) was treated with TsOH (1 mg) stirred at room temperature for 1 h then partitioned between EtOAc and sat. aq. $NaHCO_3$ solution. The organic extract was washed with brine, dried ($MgSO_4$), concentrated and purified via silica gel chromatography eluting with 20% EtOAc-hexanes to give 190 mg of 348A.

Example 348B

N-[4-(3-amino-1H-indazol-4-yl)-2-hydroxyphenyl]-N'-(2-fluoro-5-methylphenyl)urea The desired product was prepared by substituting example 348A (190 mg, 0.4 mmol) for 44A in example 44B, then dissolving the crude product in methanol treating with one drop of 1N HCl and stirring at r.t for 12 h. Purification via silica gel chromatography eluting with 5% methanol-methylene chloride gave 14 mg of 348B. $^1H$ NMR (500 MHz, DMSO-$D_6$) d ppm 2.28 (s, 3H) 6.77-6.81 (m, 2H) 6.85 (dd, J=8.4, 1.9 Hz, 1H) 6.94 (d, J=2.2 Hz, 1H) 7.09 (dd, J=11.2, 8.4 Hz, 1H) 7.24-7.29 (m, 2H) 8.02 (dd, J=7.8, 1.3 Hz, 1H) 8.17 (d, J=8.4 Hz, 1H) 8.81 (s, 1H) 9.19 (d, J=1.9 Hz, 1H) 10.14 (s, 1H) 11.74 (s, 1H); MS (ESI(+)) m/e 391.7 (M+H)+.

Example 349

N-[4-(3-amino-1H-indazol-4-yl)phenyl]-N'-[2-fluoro-5-(hydroxymethyl)phenyl]urea

Example 349A

N-(4-bromophenyl)-N'-[2-fluoro-5-(hydroxymethyl)phenyl]urea

A solution of (3-amino-4-fluoro-phenyl)-methanol (0.61 g, 4.3 mmol) in $CH_2Cl_2$ (20 mL) was treated with 1-isocyanato-4-bromobenzene (0.85 g, 4.3 mmol) stirred at room temperature overnight resulting in a thick suspension which was filtered to give 1.43 g of 349 as a off white solid. MS (ESI(−)) m/e 336.9, 338.9 (M−H)+.

Example 349B

N-[4-(3-amino-1H-indazol-4-yl)phenyl]-N'-[2-fluoro-5-(hydroxymethyl)phenyl]urea

The desired product was prepared by substituting example 349A for 149A in examples 149B-C. $^1H$ NMR (300 MHz, DMSO-$D_6$) d ppm 4.33 (s, 2H) 4.46 (d, J=5.8 Hz, 2H) 5.22 (t, J=5.8 Hz, 1H) 6.79 (dd, J=5.4, 2.4 Hz, 1H) 6.95 (ddd, J=8.1, 4.8, 2.0 Hz, 1H) 7.11-7.30 (m, 3H) 7.41 (d, J=8.5 Hz, 2H) 7.60 (d, J=8.5 Hz, 2H) 8.16 (dd, J=7.8, 2.0 Hz, 1H) 8.58 (d, J=2.4 Hz, 1H) 9.21 (s, 1H) 11.71 (s, 1H); MS (ESI(+)) m/e 392.0 (M+H)+.

Example 350

N-[4-(3-amino-7-thien-3-yl-1H-indazol-4-yl)phenyl]-N'-[3-(trifluoromethyl)phenyl]urea

Example 350A 4-(4-aminophenyl)-7-thien-3-yl-1H-indazol-3-amine

The desired product was prepared substituting thiophene-3-boronic acid for pyridine-3-boronic acid in examples 243D-E, then following the procedure of example 352B. $R_f$=0.24 (EtOAc).

Example 350B

N-[4-(3-amino-7-thien-3-yl-1H-indazol-4-yl)phenyl]-N'-[3-(trifluoromethyl)phenyl]urea The desired product was prepared by substituting Example 350A and 1-isocyanato-3-trifluoromethylbenzene for Example 15G and 1-fluoro-3-isocyanatobenzene, respectively, in Example 15H. $^1H$ NMR (300 MHz, DMSO-$D_6$) d ppm 6.92 (d, J=7.1 Hz, 1H) 7.33 (d, J=7.5 Hz, 1H) 7.44 (d, J=8.8 Hz, 2H) 7.48-7.68 (m, 6H) 7.73 (dd, J=4.8, 2.7 Hz, 1H) 7.96 (d, J=2.4 Hz, 1H) 8.05 (s, 1H) 9.01 (s, 1H) 9.15 (s, 1H) 11.96 (s, 1H); MS (ESI(+)) m/e 494.0 (M+H)+.

Example 351

N-[4-(3-amino-7-thien-3-yl-1H-indazol-4-yl)phenyl]-N'-(2-fluoro-5-methylphenyl)urea The desired product was prepared by substituting Example 350A and 1-fluoro-2-isocyanato-4-methylbenzene for Example 15G and 1-fluoro-3-isocyanatobenzene, respectively, in Example 15H. $^1H$ NMR (300 MHz, DMSO-$D_6$) d ppm 2.29 (s, 3H) 6.79-6.84 (m, 1H) 6.89 (d, J=7.5 Hz, 1H) 7.12 (dd, J=11.4, 8.3 Hz, 1H) 7.44 (d, J=8.5 Hz, 2H) 7.54 (d, J=7.1 Hz, 1H) 7.57-7.64 (m, 3H) 7.72 (dd, J=4.9, 2.9 Hz, 1H) 7.95 (s, 1H) 8.02 (d, J=6.8 Hz, 1H) 8.55 (d, J=2.0 Hz, 1H) 9.23 (s, 1H) 11.84 (s, 1H); MS (ESI(+)) m/e 458.1 (M+H)+.

Example 352

N-[4-(3-amino-7-pyridin-4-yl-1H-indazol-4-yl)phenyl]-N'-(4-fluoro-3-methylphenyl)urea

Example 352A 4-(4-nitrophenyl)-7-pyridin-4-yl-1H-indazol-3-amine

The desired product was prepared by substituting pyridine-4-boronic acid for pyridine-3-boronic acid in examples 243D-E. Unlike example 243E only a small amount (ca. 20%) of the reduced product 352A was obtained. MS (ESI(+)) m/e 332 (M+H)+.

Example 352B 4-(4-aminophenyl)-7-pyridin-4-yl-1H-indazol-3-amine

A mixture of 352A (370 mg, 1.1 mmol), iron (374 mg) and NH4Cl (60 mg, 1.1 mmol) in ethanol (20 mL), THF (10 mL)

and water (4 mL) was heated at reflux for 5 h, diluted with THF (20 mL), filtered through a pad of celite, washing with ethanol. The filtrate was concentrated and the residue was triturated from water to give 313 mg of 352A as a light yellow solid. MS (ESI(+)) m/e 302 (M+H)+.

Example 352C

N-[4-(3-amino-7-pyridin-4-yl-1H-indazol-4-yl)phenyl]-N'-(4-fluoro-3-methylphenyl)urea The desired product was prepared by substituting Example 352B and 1-fluoro-4-isocyanato-2-methylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 2.23 (d, J=2.0 Hz, 3H) 7.02 (d, J=7.5 Hz, 1H) 7.06 (t, J=9.2 Hz, 1H) 7.29 (ddd, J=8.7, 4.3, 2.9 Hz, 1H) 7.39 (dd, J=7.1, 2.4 Hz, 1H) 7.46 (d, J=8.8 Hz, 2H) 7.64 (d, J=8.8 Hz, 2H) 7.72 (d, J=7.5 Hz, 1H) 8.22 (d, J=3.7 Hz, 2H) 8.78 (s, 1H) 8.85-8.92 (m, 2H) 8.96 (s, 1H); MS (ESI(+)) m/e 453.3 (M+H)+.

Example 353

N-[4-(3-amino-7-pyridin-4-yl-1H-indazol-4-yl)phenyl]-N'-[3-(trifluoromethyl)phenyl]urea The desired product was prepared by substituting Example 352B and 1-isocyanato-3-trifluoromethylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 7.02 (d, J=7.1 Hz, 1H) 7.33 (d, J=7.5 Hz, 1H) 7.48 (d, J=8.5 Hz, 2H) 7.53 (t, J=8.0 Hz, 1H) 7.62 (d, J=8.5 Hz, 1H) 7.67 (d, J=8.5 Hz, 2H) 7.71 (d, J=7.8 Hz, 1H) 8.05 (s, 1H) 8.19 (d, J=2.4 Hz, 2H) 8.87 (d, J=2.4 Hz, 2H) 9.11 (s, 1H) 9.23 (s, 1H); MS (ESI(+)) m/e 489.1 (M+H)+.

Example 354

N-[4-(3-amino-7-pyridin-4-yl-1H-indazol-4-yl)phenyl]-N'-(3-chlorophenyl)urea

The desired product was prepared by substituting Example 352B and 1-chloro-3-isocyanatobenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 7.00-7.05 (m, 2H) 7.29-7.33 (m, 2H) 7.47 (d, J=8.8 Hz, 2H) 7.65 (d, J=8.8 Hz, 2H) 7.70 (d, J=7.5 Hz, 1H) 7.75 (dd, J=2.5, 1.2 Hz, 1H) 8.17 (d, J=3.7 Hz, 2H) 8.86 (d, J=3.7 Hz, 2H) 9.08 (app. s, 2H); MS (ESI(+)) m/e 455.2 (M+H)+.

Example 355

N-[4-(3-amino-7-pyridin-4-yl-1H-indazol-4-yl)phenyl]-N'-(2-fluoro-5-methylphenyl)urea The desired product was prepared by substituting Example 352B and 1-fluoro-2-isocyanato-4-methylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 2.29 (s, 3H) 6.80-6.85 (m, 1H) 7.01 (d, J=7.5 Hz, 1H) 7.12 (dd, J=11.4, 8.3 Hz, 1H) 7.47 (d, J=8.8 Hz, 2H) 7.64 (d, J=8.8 Hz, 2H) 7.69 (d, J=7.5 Hz, 1H) 8.01 (dd, J=8.0, 1.9 Hz, 1H) 8.14-8.19 (m, 2H) 8.57 (d, J=2.7 Hz, 1H) 8.82-8.89 (m, 2H) 9.28 (s, 1H); MS (ESI(+)) m/e 453.3 (M+H)+.

Example 356

N-[4-(3-amino-7-pyridin-4-yl-1H-indazol-4-yl)phenyl]-N'-[4-fluoro-3-(trifluoromethyl)phenyl]urea The desired product was prepared by substituting Example 352B and 1-fluoro-4-isocyanato-2-trifluoromethylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 4.45 (s, 2H) 6.95 (d, J=7.5 Hz, 1H) 7.42-7.47 (m, 1H) 7.45 (d, J=8.5 Hz, 2H) 7.50 (d, J=7.5 Hz, 1H) 7.64 (d, J=8.5 Hz, 2H) 7.64-7.69 (m, 1H) 7.71 (d, J=6.1 Hz, 2H) 8.03 (dd, J=6.6, 2.6 Hz, 1H) 8.68 (d, J=6.1 Hz, 2H) 8.99 (s, 1H) 9.11 (s, 1H) 11.98 (s, 1H); MS (ESI(+)) m/e 507.2 (M+H)+.

Example 357

N-[4-(3-amino-7-pyridin-4-yl-1H-indazol-4-yl)phenyl]-N'-[2-fluoro-5-(trifluoromethyl)phenyl]urea The desired product was prepared by substituting Example 352B and 1-fluoro-2-isocyanato-4-trifluoromethylbenzene for Example 15G and 1-fluoro-3-isocyanatobenzene, respectively, in Example 15H. Additionally, DMF was used in place of CH$_2$Cl$_2$. $^1$H NMR (300 MHz, DMSO-D$_6$) d ppm 7.01 (d, J=7.5 Hz, 1H) 7.42-7.49 (m, 3H) 7.65-7.71 (m, 4H) 8.04 (dd, J=6.4, 2.7 Hz, 1H) 8.14-8.21 (m, 2H) 8.82-8.90 (m, 2H) 9.12 (s, 1H) 9.23 (s, 1H); MS (ESI(+)) m/e 507.7 (M+H)+.

Example 358

N-[4-(3-amino-5-fluoro-1H-indazol-4-yl)phenyl]-N'-(3-bromophenyl)urea

Example 358A 5-fluoro-4-iodo-1H-indazol-3-amine

The desired product was prepared by substituting 2,5-difluoro-benzonitrile for example 243A in example 243B, then substituting the product for 2-fluoro-6-iodo-benzonitrile in example 1A. MS (ESI(+) m/e 278 (M+H)+.

Example 358B

N-[4-(3-amino-5-fluoro-1H-indazol-4-yl)phenyl]-N'-(3-bromophenyl)urea

The desired product was prepared by substituting 1-bromo-3-isocyanatobenzene for 1-isocyanato-3-methylbenzene and Example 358B for 1A, respectively and in Examples 1B-C and purifying as in example 3. $^1$H NMR (300 MHz, DMSO-D$_6$) d ppm 7.15-7.38 (m, 7H) 7.61 (d, J=8.8 Hz, 2H) 7.88 (t, J=1.9 Hz, 1H) 8.95 (s, 1H) 8.95 (s, 1H) 11.82 (s, 1H); MS (ESI(+)) m/e 439.9, 441.9 (M+H)+.

Example 359

N-[4-(3-amino-5-fluoro-1H-indazol-4-yl)phenyl]-N'-(3-methylphenyl)urea

The desired product was prepared by substituting Example 358B for 1A in Examples 1C and purifying as in example 3.

¹H NMR (300 MHz, DMSO-D₆) d ppm 2.29 (s, 3H) 4.19 (s, 2H) 6.80 (d, J=7.5 Hz, 1H) 7.14-7.30 (m, 4H) 7.32 (s, 1H) 7.35 (d, J=8.5 Hz, 2H) 7.61 (d, J=8.5 Hz, 2H) 8.65 (s, 1H) 8.83 (s, 1H) 11.74 (s, 1H); MS (ESI(+)) m/e 376.1 (M+H)⁺.

Example 360

N-[4-(3-amino-5-fluoro-1H-indazol-4-yl)phenyl]-N'-phenylurea

The desired product was prepared by substituting 1-isocyanatobenzene for 1-isocyanato-3-methylbenzene and Example 358B for 1A, respectively and in Examples 1B-C and purifying as in example 3. ¹H NMR (300 MHz, DMSO-D₆) d ppm 6.98 (t, J=7.3 Hz, 1H) 7.21 (t, J=9.3 Hz, 1H) 7.27-7.32 (m, 3H) 7.36 (d, J=8.1 Hz, 2H) 7.48 (d, J=7.8 Hz, 2H) 7.61 (d, J=8.5 Hz, 2H) 8.74 (s, 1H) 8.86 (s, 1H) 11.81 (s, 1H).

Example 361

N-[4-(3-amino-5-fluoro-1H-indazol-4-yl)phenyl]-N'-[2-fluoro-3-(trifluoromethyl)phenyl]urea The desired product was prepared by substituting 1-fluoro-2-isocyanato-4-trifluoromethylbenzene for 1-isocyanato-3-methylbenzene and Example 358B for 1A, respectively and in Examples 1B-C. ¹H NMR (300 MHz, DMSO-D₆) d ppm 7.21 (t, J=9.2 Hz, 1H) 7.29 (dd, J=9.2, 4.1 Hz, 1H) 7.37-3.40 (m, 4H) 7.63 (d, J=8.5 Hz, 2H) 8.45-8.50 (m, 1H) 8.90 (d, J=2.4 Hz, 1H) 9.32 (s, 1H) 11.81 (br. s, 1H); MS (ESI(+)) m/e 448.1 (M+H)⁺.

Example 362

N-[4-(3-amino-5-fluoro-1H-indazol-4-yl)phenyl]-N'-(2-fluoro-5-methylphenyl)urea

The desired product was prepared by substituting Example 358B and 5A for 1A and 1B, respectively in Examples 1C and purifying as in example 3. ¹H NMR (300 MHz, DMSO-D₆) d ppm 2.28 (s, 3H) 6.82 (ddd, J=8.5, 4.8, 2.0 Hz, 1H) 7.12 (dd, J=11.5, 8.1 Hz, 1H) 7.25 (t, J=9.3 Hz, 1H) 7.33 (dd, J=9.2, 4.1 Hz, 1H) 7.38 (d, J=8.5 Hz, 2H) 7.62 (d, J=8.5 Hz, 2H) 8.01 (dd, J=7.8, 2.0 Hz, 1H) 8.55 (d, J=2.4 Hz, 1H) 9.26 (s, 1H) 12.01 (br. s, 1H); MS (ESI(+)) m/e 394.0 (M+H)⁺.

Example 363

N-[4-(3-amino-5-fluoro-1H-indazol-4-yl)phenyl]-N'-[3-(trifluoromethyl)phenyl]urea The desired product was prepared by substituting 1-isocyanato-3-trifluoromethylbenzene for 1-isocyanato-3-methylbenzene and Example 358B for 1A, respectively in Examples 1B-C and purifying as in example 3. ¹H NMR (300 MHz, DMSO-D₆) d ppm 7.22 (t, J=9.5 Hz, 1H) 7.28-7.34 (m, 2H) 7.38 (d, J=8.1 Hz, 2H) 7.53 (t, J=8.0 Hz, 1H) 7.59-7.65 (m, 3H) 8.04 (s, 1H) 9.01 (s, 1H) 9.14 (s, 1H) 11.85 (br. s, 1H); MS (ESI(+)) m/e 430.0 (M+H)⁺.

Example 364

N-[4-(3-amino-5-fluoro-1H-indazol-4-yl)phenyl]-N'-[4-fluoro-3-(trifluoromethyl)phenyl]urea The desired product was prepared by substituting 1-fluoro-4-isocyanato-3-trifluoromethylbenzene for 1-isocyanato-3-methylbenzene and Example 358B for 1A, respectively in Examples 1B-C and purifying as in example 3. ¹H NMR (300 MHz, DMSO-D₆) d ppm 7.23 (t, J=9.5 Hz, 1H) 7.32 (dd, J=9.2, 4.1 Hz, 1H) 7.38 (d, J=8.1 Hz, 2H) 7.45 (t, J=9.5 Hz, 1H) 7.66 (m, 3H) 8.03 (dd, J=6.4, 2.7 Hz, 1H) 9.04 (s, 1H) 9.15 (s, 1H) 11.94 (br. s, 1H); MS (ESI(+)) m/e 448.0 (M+H)⁺.

Example 365

N-[4-(3-amino-5-fluoro-1H-indazol-4-yl)phenyl]-N'-(3-chlorophenyl)urea

The desired product was prepared by substituting 1-chloro-3-isocyanatobenzene for 1-isocyanato-3-methylbenzene and Example 358B for 1A, respectively in Examples 1B-C and purifying as in example 3. ¹H NMR (300 MHz, DMSO-D₆) d ppm 7.02-7.05 (m, 1H) 7.25 (t, J=9.5 Hz, 1H) 7.29-7.35 (m, 3H) 7.38 (d, J=8.5 Hz, 2H) 7.62 (d, J=8.5 Hz, 2H) 7.73-7.75 (m, 1H) 9.00 (s, 1H) 9.01 (s, 1H) 12.01 (br. s, 1H); MS (ESI(+)) m/e 396.0 (M+H)⁺.

Example 366

N-[4-(3-amino-5-fluoro-1H-indazol-4-yl)phenyl]-N'-(4-fluoro-3-methylphenyl)urea

The desired product was prepared by substituting 1-fluoro-4-isocyanato-3-methylbenzene for 1-isocyanato-3-methylbenzene and Example 358B for 1A, respectively in Examples 1B-C and purifying as in example 3. ¹H NMR (300 MHz, DMSO-D₆) d ppm 2.22 (d, J=1.7 Hz, 3H) 7.06 (t, J=9.2 Hz, 1H) 7.21-7.40 (m, 6H) 7.61 (d, J=8.5 Hz, 2H) 8.71 (s, 1H) 8.88 (s, 1H) 12.01 (br. s, 1H); MS (ESI(+)) m/e 396.0 (M+H)⁺.

Example 367

N-[4-(3-amino-5-fluoro-1H-indazol-4-yl)phenyl]-N'-(3-chloro-4-fluorophenyl)urea

The desired product was prepared by substituting 1-fluoro-2-chloro-4-isocyanatobenzene for 1-isocyanato-3-methylbenzene and Example 358B for 1A, respectively in Examples 1B-C and purifying as in example 3. ¹H NMR (300 MHz, DMSO-D₆) d ppm 7.24 (t, J=9.5 Hz, 1H) 7.30-7.39 (m, 5H) 7.62 (d, J=8.8 Hz, 2H) 7.82-7.85 (m, 1H) 9.00 (s, 1H) 9.01 (s, 1H) 11.99 (br. s, 1H); MS (ESI(+)) m/e 414.0 (M+H)⁺.

Example 368

N-[4-(3-amino-7-bromo-1H-indazol-4-yl)phenyl]-N'-(2-fluoro-5-methylphenyl)urea

The desired product was prepared by substituting 3-bromo-2-fluoro-6-iodobenzonitrile for 2-fluoro-6-iodobenzonitrile and 1-fluoro-2-isocyanato-4-methylbenzene for 1-isocyanato-3-methylbenzene in Examples 1A-C. ¹H NMR (300 MHz, DMSO-D₆) d ppm 2.28 (s, 3H) 6.73 (d, J=7.5 Hz, 1H) 6.79-6.84 (m, 1H) 7.11 (dd, J=11.4, 8.3 Hz, 1H) 7.40 (d, J=8.8 Hz, 2H) 7.51 (d, J=7.80 Hz, 1H) 7.60 (d, J=8.8 Hz, 2H) 8.01 (dd, J=7.5, 2.0 Hz, 1H) 8.54 (d, J=2.4 Hz, 1H) 9.22 (s, 1H) 12.08 (br. s, 1H); MS (ESI(+)) m/e 453.9, 455.9 (M+H)⁺.

Example 369

3-[({[4-(3-amino-1H-indazol-4-yl)phenyl]amino}carbonyl)amino]-4-fluorobenzoic acid

Example 369A 4-(4-aminophenyl)-1H-indazol-3-amine

The desired product was prepared by substituting 2-fluoro-6-benzonitrile for 15F in example 15G, then substituting the product for 2-fluoro-6-benzonitrile in example 1A. MS (ESI(+)) m/e 225 (M+H)$^+$.

Example 369B tert-butyl 3-amino-4-(4-aminophenyl)-1H-indazole-1-carboxylate

A −78 C solution of 369A (100 mg, 0.45 mmol) in THF (6 mL) was treated with LDA (0.245 mL, 2M solution in heptane, 0.49 mmol), stirred at −50 for 15 minutes, treated with solid (Boc)$_2$O (98 mg, 0.45 mmol). The reaction was allowed to gradually warm up to room temperature over 2 h, concentrated in vacuo and purified via silica gel chromatography eluting first with 75% EtOAc: hexanes then with 8% methanol: CH$_2$Cl$_2$ to give 62 mg of 369B. MS (ESI(+)) m/e 325 (M+H)$^+$.

Example 369C methyl 3-[({[4-(3-amino-1H-indazol-4-yl)phenyl]amino}carbonyl)amino]-4-fluorobenzoate A 0 C solution of 3-Amino-4-fluoro-benzoic acid methyl ester (29 mg, 0.17 mmol) in THF (4 mL) was treated with triethyl amine (0.026 mL) and 4-nitrophenyl chloroformate (38 mg), stirred at 0 C for 45 min, then treated with a solution of example 396B (56 mg, 0.17 mmol) in THF (3 mL) followed by an additional 0.026 mL of Et3N. The resulting mixture was allowed to warm up to room temperature slowly, stirred overnight, diluted with water and extracted twice with EtOAc. The combined organics were washed with brine, dried (MgSO4), concentrated and purified via silica gel chromatography eluting with EtOAc to give 98 mg of 3-Amino-4-{4-[3-(2-fluoro-5-methoxycarbonyl-phenyl)-ureido]-phenyl}-indazole-1-carboxylic acid tert-butyl ester. This compound was dissolved in CH$_2$Cl$_2$ (2 mL), cooled to 0 C, treated with TFA (1 mL), stirred at 0 for 45 min then at room temperature for 1 h. The reaction was quenched with sat. aq. NaHCO3 adjusting the pH to 8-9 then extracted with EtOAc (3×). The combined organics were washed with brine, dried (MgSO4), concentrated and purified via silica gel chromatography eluting with first EtOAc then 12% methanol: CH$_2$Cl$_2$ to give 30 mg of 369C as a white solid. MS (ESI(+)) m/e 420 (M+H)$^+$.

Example 369D

3-[({[4-(3-amino-1H-indazol-4-yl)phenyl]amino}carbonyl)amino]-4-fluorobenzoic acid A solution of 369C (20 mg, 0.05 mmol) in methanol (1 mL) was treated with a solution of NaOH 911 mg) in water (1 mL), stirred at reflux for 7 h and concentrated. The residue was diluted with water, the pH was adjusted to pH of 3 with 1 N HCl, and the resulting solid was collected via filtration to give 17 mg of 369D. H NMR (300 MHz, DMSO-D$_6$) d ppm 4.34 (br. s, 2H) 6.79 (dd, J=5.3, 2.5 Hz, 1H) 7.24-7.28 (m, 2H) 7.34-7.43 (m, 3H) 7.60-7.64 (m, 3H) 8.77 (d, J=2.7 Hz, 1H) 8.85 (dd, J=8.1, 2.0 Hz, 1H) 9.27 (s, 1H) 11.72 (br. s, 1H) 13.00 (br. s, 1H).

Example 370

N-[4-(3-amino-1H-indazol-6-yl)phenyl]-N'-(2-fluoro-5-methylphenyl)urea

The desired product was prepared by substituting Example 182A for 1A in Example 5B. MS (ESI(+)Q1MS m/z 376 (M+H)$^+$; $^1$H NMR (300 MHz, DMSO-D$_6$) δ ppm 2.28 (s, 3H) 6.78-6.84 (m, 1H) 7.11 (dd, J=11.36, 8.31 Hz, 1H) 7.33 (dd, J=8.65, 1.19 Hz, 1H) 7.48 (s, 1H) 7.57 (d, J=8.82 Hz, 2H) 7.67 (d, J=8.82 Hz, 2H) 7.84 (d, J=8.48 Hz, 1H) 8.00 (dd, J=7.80, 2.37 Hz, 1H) 8.51 (d, J=2.71 Hz, 1H) 9.19 (s, 1H)

Example 371

N-[2-({3-amino-4-[4-({[(3-fluorophenyl)amino]carbonyl}amino)phenyl]-1H-indazol-7-yl}oxy)ethyl]methanesulfonamide The desired product was prepared by substituting Example 178A for Example 15G in Example 15H. MS (ESI(+)Q1MS m/z 499 (M+H)$^+$; $^1$H NMR (500 MHz, DMSO-D$_6$) δ ppm 2.99 (s, 3H) 3.44 (q, J=5.61 Hz, 2H) 4.23 (t, J=5.61 Hz, 2H) 6.72 (d, J=7.49 Hz, 1H) 6.79 (td, J=8.58, 2.18 Hz, 1H) 6.83 (d, J=7.80 Hz, 1H) 7.13-7.17 (m, 2H) 7.29-7.34 (m, 1H) 7.37 (d, J=8.42 Hz, 2H) 7.51 (dt, J=11.93, 2.30 Hz, 1H) 7.57 (d, J=8.73 Hz, 2H) 8.85 (s, 1H) 8.94 (s, 1H)

Example 372

N-(4-{3-amino-7-[3-(dimethylamino)propoxy]-1H-indazol-4-yl}phenyl)-N'-[4-fluoro-3-(trifluoromethyl)phenyl]urea The desired product was prepared by substituting Example 248B and 1-fluoro-4-isocyanato-2-(trifluoromethyl)benzene for Example 15G and 1-fluoro-3-isocyanatobenzene, respectively, in Example 15H. MS (ESI(+)Q1MS m/z 531 (M+H)$^+$; $^1$H NMR (300 MHz, DMSO-D$_6$) δ ppm 2.15-2.20 (m, 2H) 2.86 (d, J=5.09 Hz, 6H) 3.34-3.41 (m, 2H) 4.22 (t, J=5.76 Hz, 2H) 6.72 (d, J=7.46 Hz, 1H) 6.81 (d, J=7.80 Hz, 1H) 7.36 (d, J=8.48 Hz, 2H) 7.45 (t, J=9.83 Hz, 1H) 7.58 (d, J=8.48 Hz, 2H) 7.63-7.69 (m, 1H) 8.04 (dd, J=6.44, 2.71 Hz, 1H) 9.02 (s, 1H) 9.18 (s, 1H)

Example 373

N-[4-(1-acetyl-3-amino-1H-indazol-4-yl)phenyl]-N'-(2-fluoro-5-methylphenyl)urea

Example 373A 1-acetyl-4-iodo-1H-indazol-3-amine

A solution of example 1A (215 mg, 0.83 mmol), acetic anhydride (0.086 mL) and 18-crown-6 (438 mg) in CH$_2$Cl$_2$ (5 mL) was stirred at room temperature overnight, then partitioned between EtOAc and water. The organic extract was dried (MgSO4), concentrated and purified via silica gel chromatography eluting with 1 to 1 hexane:EtOAc to give 110 mg of 373A. ¹H NMR (300 MHz, DMSO-D₆) δ ppm 2.53 (s, 3H) 6.01 (s, 2H) 7.26 (t, J=7.46 Hz, 1H) 7.77 (d, J=7.46 Hz, 1H) 8.31 (d, J=8.48 Hz, 1H).

Example 373B

N-[4-(1-acetyl-3-amino-1H-indazol-4-yl)phenyl]-N'-(2-fluoro-5-methylphenyl)urea

The desired product was prepared by substituting Example 373A for 1A in Example 5B. MS (ESI(−)Q1MS m/z 416 (M−H)⁻; ¹H NMR (300 MHz, DMSO-D₆) δ ppm 2.28 (s, 3H) 2.55 (s, 3H) 5.20 (s, 2H) 6.79-6.84 (m, 1H) 7.12 (dd, J=11.53, 8.48 Hz, 1H) 7.18 (d, J=7.46 Hz, 1H) 7.42 (d, J=8.48 Hz, 2H) 7.57-7.64 (m, 3H) 8.00 (dd, J=7.63, 1.87 Hz, 1H) 8.29 (d, J=8.14 Hz, 1H) 8.56 (d, J=2.71 Hz, 1H) 9.26 (s, 1H)

Example 374

N-[4-(3-amino-7-fluoro-1H-indazol-4-yl)phenyl]-N'-(4-bromo-3-methylphenyl)urea

The desired product was prepared as the trifluoroacetate salt by substituting Example 26B and 1-bromo-4-isocyanato-2-methylbenzene for Example 15G and 1-fluoro-3-isocyanatobenzene, respectively, in Example 15H. MS (ESI (+)): m/e 456 (M+H); ¹H NMR (300 MHz, DMSO-D₆) δ ppm 2.32 (s, 3H) 6.74 (dd, J=7.80, 4.41 Hz, 1H) 7.13 (dd, J=11.19, 7.80 Hz, 1H) 7.27 (dd, J=8.65, 2.54 Hz, 1H) 7.37 (d, J=8.48 Hz, 2H) 7.44-7.49 (m, 2H) 7.58 (d, J=8.48 Hz, 2H) 8.80 (s, 1H) 8.87 (s, 1H).

Example 375

N-[4-(3-amino-1-phenyl-1H-indazol-4-yl)phenyl]-N'-(2-fluoro-5-methylphenyl)urea

Example 375A 2-(4-iodo-1-phenyl-1H-indazol-3-yl)-1H-isoindole-1,3(2H)-dione

A mixture of 162A (940 mg), phenyl boronic acid (590 mg), cupric acetate (440 mg), triethylamine (0.674 mL) in CH₂Cl₂ (20 mL) was stirred at room temperature overnight, then concentrated. The residue was purified via silica gel chromatography eluting with 20% EtOAc in hexane to give 770 mg of 375A. MS (ESI(+)) m/e 466.1 (M+H)⁺.

Example 375B 4-iodo-1-phenyl-1H-indazol-3-amine

The desired product was prepared by substituting 375A for 162B in example 162C. MS (ESI(+)) m/e 336.1 (M+H)⁺.

Example 375C

N-[4-(3-amino-1-phenyl-1H-indazol-4-yl)phenyl]-N'-(2-fluoro-5-methylphenyl)urea

The desired product was prepared by substituting Example 375B for 1A in Example 5B. MS (ESI(+)Q1MS m/z 452 (M+H)⁺; ¹H NMR (300 MHz, DMSO-D₆) δ ppm 2.29 (s, 3H) 4.75 (s, 1H) 6.83 (m, 1H) 6.97 (d, J=6.44 Hz, 1H) 7.12 (dd, J=11.53, 8.48 Hz, 1H) 7.26 (t, J=7.29 Hz, 1H) 7.43-7.47 (m, 3H) 7.50-7.55 (m, 2H) 7.61-7.74 (m, 5H) 8.01 (dd, J=7.97, 2.20 Hz, 1H) 8.57 (d, J=2.37 Hz, 1H) 9.26 (s, 1H)

Example 376

N-{4-[3-amino-7-(3-pyridin-3-ylpropoxy)-1H-indazol-4-yl]phenyl}-N'-(2-fluoro-5-methylphenyl)urea The desired product was prepared by substituting Example 338B and 1-fluoro-2-isocyanato-4-methylbenzene for Example 1A and 1-isocyanato-3-methylbenzene, respectively, in Examples 1B-C. MS (ESI(+)Q1MS m/z 511 (M+H); ¹H NMR (300 MHz, DMSO-D₆) δ ppm 2.14-2.18 (m, 2H) 2.28 (s, 3H) 3.01 (t, J=7.4 Hz, 2H) 4.14 (t, J=6.10 Hz, 2H) 6.70 (d, J=7.80 Hz, 1H) 6.77-6.84 (m, 2H) 7.11 (dd, J=11.36, 8.31 Hz, 1H) 7.37 (d, J=8.82 Hz, 2H) 7.56 (d, J=8.48 Hz, 2H) 7.70-7.73 (m, 1H) 8.01 (dd, J=7.97, 2.20 Hz, 1H) 8.17 (d, J=9.49 Hz, 1H) 8.52 (d, J=3.05 Hz, 1H) 8.62 (d, J=5.09 Hz, 1H) 8.70 (s, 1H) 9.17 (s, 1H).

Example 377

N-[4-(3-amino-1H-indazol-6-yl)phenyl]-N'-phenylurea

The desired product was prepared by substituting Example 182A and N-phenyl)N'-[4-(4,4,5,5-tetramethyl-1,3,2-dioxaborolan-2-yl)phenyl]urea for 1A and 5A respectively, in Example 5B. MS (ESI(+)Q1MS m/z 344 (M+H)⁺; ¹H NMR (300 MHz, DMSO-D₆) δ ppm 5.33 (s, 2H) 6.97 (t, J=7.29 Hz, 1H) 7.19 (dd, J=8.31, 1.19 Hz, 1H) 7.28 (t, J=7.97 Hz, 2H) 7.38 (s, 1H) 7.48 (d, J=7.46 Hz, 2H) 7.59 (m, 4H) 7.72 (d, J=8.48 Hz, 1H) 8.90 (s, 1H) 8.96 (s, 1H) 11.38 (s, 1H)

Example 378

N-[4-(3-amino-1H-indazol-6-yl)phenyl]-N'-[3-(trifluoromethyl)phenyl]urea

The desired product was prepared by substituting Example 182A and N-(3-trifluoromethylphenyl)-N'-[4-(4,4,5,5-tetramethyl-1,3,2-dioxaborolan-2-yl)phenyl]urea for 1A and 5A respectively, in Example 5B. MS (ESI(+)Q1MS m/z 412 (M+H)⁺; ¹H NMR (300 MHz, DMSO-D₆) δ ppm 7.33 (dd, J=7.97, 4.58 Hz, 2H) 7.55-7.58 (m, 3H) 7.58 (d, J=8.82 Hz, 2H) 7.67 (d, J=8.82 Hz, 2H) 7.85 (d, J=8.48 Hz, 1H) 8.04 (s, 1H) 8.95 (s, 1H) 9.11 (s, 1H).

Example 379

N-[4-(3-amino-1H-indazol-4-yl)phenyl]-N'-thien-3-ylurea

The desired product was prepared by substituting 3-isocyanato-thiophene for 1-isocyanato-3-methylbenzene in Examples 5A-B. ¹H NMR (300 MHz, DMSO-D₆) δ ppm 4.33 (s, 2H) 6.78 (dd, J=5.59, 2.20 Hz, 1H) 7.07 (dd, J=5.09, 1.36 Hz, 1H) 7.24-7.28 (m, 2H) 7.29-7.33 (m, 1H) 7.39 (d, J=8.48 Hz, 2H) 7.45 (dd, J=5.09, 3.39 Hz, 1H) 7.59 (d, J=8.48 Hz, 2H) 8.78 (s, 1H) 8.99 (s, 1H) 11.70 (s, 1H); MS (ESI (+)) m/e 350 (M+H)⁺.

Example 380

N-[4-(3-amino-1H-indazol-4-yl)phenyl]-N'-cyclopentylurea

The desired product was prepared by substituting isocyanato-cyclopentane for 1-isocyanato-3-methylbenzene in Examples 5A-B. $^1$H NMR (300 MHz, DMSO-$D_6$) δ ppm 1.31-1.45 (m, 2H) 1.47-1.71 (m, 4H) 1.77-1.93 (m, 2H) 3.89-4.00 (m, 1H) 4.31 (s, 2H) 6.21 (d, J=7.12 Hz, 1H) 6.75 (dd, J=5.59, 2.20 Hz, 1H) 7.22-7.27 (m, 2H) 7.32 (d, J=8.48 Hz, 2H) 7.50 (d, J=8.48 Hz, 2H) 8.39 (s, 1H) 11.68 (s, 1H). MS (ESI (+)) m/e 336 (M+H)$^+$.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

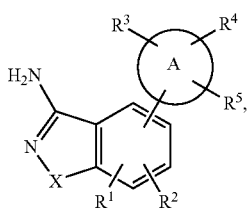

(I)

or a therapeutically acceptable salt thereof, wherein
A is phenyl;
X is NR$^9$;
R$^1$ and R$^2$ are independently selected from the group consisting of hydrogen, alkoxy, alkoxyalkoxy, alkoxyalkyl, alkyl, aryl, arylalkyl, aryloxy, aryloxyalkyl, halo, haloalkoxy, haloalkyl, hydroxy, hydroxyalkoxy, hydroxyalkyl, (NR$^a$R$^b$)alkoxy, (NR$^a$R$^b$)alkenyl, (NR$^a$R$^b$)alkyl, (NR$^a$R$^b$)alkynyl, (NR$^a$R$^b$)carbonylalkenyl, and (NR$^a$R$^b$)carbonylalkyl;
R$^3$ and R$^4$ are each independently selected from the group consisting of hydrogen, alkoxy, alkoxyalkoxy, alkyl, halo, haloalkoxy, haloalkyl, and hydroxy;
R$^5$ is LR$^6$;
L is selected from the group consisting of (CH$_2$)$_m$N(R$^7$)C(O)N(R$^8$)(CH$_2$)$_n$ and CH$_2$C(O)NR$^7$, wherein m is 0 and n is 0, and wherein each group is drawn with its left end attached to A;
R$^6$ is selected from the group consisting of hydrogen, aryl, cycloalkyl, heterocyclyl, and 1,3-benzodioxolyl wherein the 1,3-benzodioxolyl can be optionally substituted with one, two, or three substituents independently selected from the group consisting of alkenyl, alkoxy, alkoxyalkyl, alkoxycarbonyl, alkyl, alkylcarbonyl, aryl, arylalkoxy, arylalkyl, aryloxy, carboxy, cyano, cycloalkyl, halo, haloalkoxy, haloalkyl, a second heterocyclyl group, heterocyclylalkyl, hydroxy, hydroxyalkyl, nitro, —NR$^c$R$^d$, and (NR$^c$R$^d$)alkyl;
R$^7$ and R$^8$ are independently selected from the group consisting of hydrogen and alkyl;
R$^9$ is selected from the group consisting of hydrogen, alkenyl, alkoxyalkyl, alkyl, alkylcarbonyl, aryl, heterocyclylalkyl, hydroxyalkyl, and (NR$^a$R$^b$)alkyl;
R$^a$ and R$^b$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, and cycloalkyl; and R$^c$ and R$^d$ are independently selected from the group consisting of hydrogen, alkyl, alkylcarbonyl, aryl, arylalkyl, cycloalkyl, cycloalkylalkyl, heterocyclyalkyl and heterocyclyl.

2. The compound of claim 1 of formula (II)

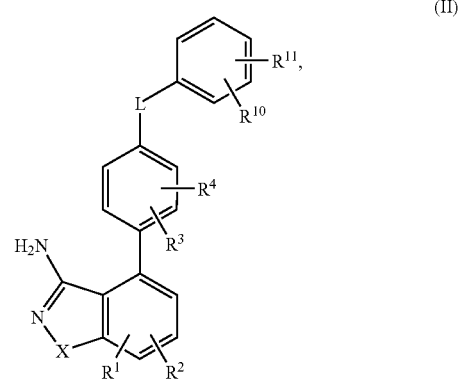

(II)

or a therapeutically acceptable salt thereof, wherein
R$^1$ and R$^2$ are independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, (NR$^a$R$^b$)alkoxy, (NR$^a$R$^b$)alkenyl, (NR$^a$R$^b$)alkyl, (NR$^a$R$^b$)carbonylalkenyl, and (NR$^a$R$^b$)carbonylalkyl;
R$^3$ and R$^4$ are independently selected from the group consisting of hydrogen, alkoxy, alkyl, halo, haloalkoxy, haloalkyl, and hydroxy;
L is selected from the group consisting of (CH$_2$)$_m$N(R$^7$)C(O)N(R$^8$)(CH$_2$)$_n$ and CH$_2$C(O)NR$^7$, wherein m is 0 and n is 0, and wherein each group is drawn with its left end attached to the ring substituted with R$^3$ and R$^4$;
R$^7$ and R$^8$ are independently selected from the group consisting of hydrogen and alkyl;
R$^9$ is selected from the group consisting of hydrogen, alkenyl, alkoxyalkyl, alkyl, alkylcarbonyl, aryl, heterocyclylalkyl, hydroxyalkyl, and (NR$^a$R$^b$)alkyl;
R$^{10}$ and R$^{11}$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —NR$^c$R$^d$;
R$^a$ and R$^b$ are independently selected from the group consisting of hydrogen, alkyl, alkylcarbonyl, alkylsulfonyl, arylsulfonyl, and haloalkylsulfonyl; and
R$^c$ and R$^d$ are independently selected from the group consisting of hydrogen, alkyl, alkylcarbonyl, aryl, arylalkyl, cycloalkyl, cycloalkylalkyl, heterocyclyl, and heterocyclylalkyl.

3. The compound of claim 2 wherein L is CH$_2$C(O)NR$^7$.

4. The compound of claim 3 selected from the group consisting of
2-[4-(3-amino-1H-indazol-4-yl)phenyl]-N-(3-chlorophenyl)acetamide;
2-[4-(3-amino-1H-indazol-4-yl)phenyl]-N-(4-fluoro-3-methylphenyl)acetamide;
2-[4-(3-amino-1H-indazol-4-yl)phenyl]-N-[3-(trifluoromethyl)phenyl]acetamide;
2-[4-(3-amino-1H-indazol-4-yl)phenyl]-N-(3-methylphenyl)acetamide; and
2-[4-(3-amino-1-methyl-1H-indazol-4-yl)phenyl]-N-(3-methylphenyl)acetamide.

5. The compound of claim 2 wherein L is $(CH_2)_m N(R^7)C(O)N(R^8)(CH_2)_n$.

6. The compound of claim 5 wherein $R^7$ and $R^8$ are hydrogen, and $R^9$ is selected from the group consisting of alkoxyalkyl, alkyl, alkylcarbonyl, aryl, heterocyclylalkyl, hydroxyalkyl, and $(NR^aR^b)$alkyl.

7. The compound of claim 6 selected from the group consisting of
N-[4-(3-amino-1-methyl-1H-indazol-4-yl)phenyl]-N'-(3-methylphenyl)urea;
N-[4-(3-amino-1-methyl-1H-indazol-4-yl)phenyl]-N'-phenyl urea;
N-[4-(3-amino-1-methyl-1H-indazol-4-yl)phenyl]-N'-(2-methylphenyl)urea;
N-[4-(3-amino-1-methyl-1H-indazol-4-yl)phenyl]-N'-(4-methylphenyl)urea;
N-[4-(3-amino-1-methyl-1H-indazol-4-yl)phenyl]-N'-(3-methoxyphenyl)urea;
N-[4-(3-amino-1-methyl-1H-indazol-4-yl)phenyl]-N'-(3-fluorophenyl)urea;
N-[4-(3-amino-1-methyl-1H-indazol-4-yl)phenyl]-N'-(3-chlorophenyl)urea;
N-[4-(3-amino-1-methyl-1H-indazol-4-yl)phenyl]-N'-(3-bromophenyl)urea;
N-[4-(3-amino-1-methyl-1H-indazol-4-yl)phenyl]-N'-[3-(trifluoromethyl)phenyl]urea;
N-[4-(3-amino-1-methyl-1H-indazol-4-yl)phenyl]-N'-(2-fluoro-5-methylphenyl)urea;
N-{4-[3-amino-1-(2-hydroxyethyl)-1H-indazol-4-yl]phenyl}-N'-(3-methylphenyl)urea;
N-(4-{3-amino-1-[2-(4-morpholinyl)ethyl]-1H-indazol-4-yl}phenyl)-N'-(2-fluoro-5-methylphenyl)urea;
N-(4-{3-amino-1-[2-(4-morpholinyl)ethyl]-1H-indazol-4-yl}phenyl)-N'-(3-fluorophenyl)urea;
N-(4-{3-amino-1-[2-(4-morpholinyl)ethyl]-1H-indazol-4-yl}phenyl)-N'-(3-chlorophenyl)urea;
N-(4-{3-amino-1-[2-(4-morpholinyl)ethyl]-1H-indazol-4-yl}phenyl)-N'-[3-(trifluoromethyl)phenyl]urea;
N-[4-(3-amino-1-methyl-1H-indazol-4-yl)phenyl]-N'-(3-methylphenyl)urea;
N-(4-{3-amino-1-[2-(dimethylamino)ethyl]-1H-indazol-4-yl}phenyl)-N'-(2-fluoro-5-methylphenyl)urea;
N-(4-{3-amino-1-[2-(dimethylamino)ethyl]-1H-indazol-4-yl}phenyl)-N'-(3-chlorophenyl)urea;
N-{4-[3-amino-1-(2-methoxyethyl)-1H-indazol-4-yl]phenyl}-N'-(2-fluoro-5-methylphenyl)urea;
N-[4-(1-acetyl-3-amino-1H-indazol-4-yl)phenyl]-N'-(2-fluoro-5-methylphenyl)urea; and
N-[4-(3-amino-1-phenyl-1H-indazol-4-yl)phenyl]-N'-(2-fluoro-5-methylphenyl)urea.

8. The compound of claim 5 wherein $R^7$ and $R^8$ are hydrogen, and $R^9$ is hydrogen.

9. The compound of claim 8 selected from the group consisting of
N-(4-{3-amino-7-[(dimethylamino)methyl]-1H-indazol-4-yl}phenyl)-N'-(2-fluoro-5-methylphenyl)urea;
N-(4-{3-amino-7-[(dimethylamino)methyl]-1H-indazol-4-yl}phenyl)-N'-(3-chlorophenyl)urea;
N-(4-{3-amino-7-[(dimethylamino)methyl]-1H-indazol-4-yl}phenyl)-N'-[3-(trifluoromethyl)phenyl]urea;
N-[4-(3-amino-7-hydroxy-1H-indazol-4-yl)phenyl]-N'-(2-fluoro-5-methylphenyl)urea;
N-[4-(3-amino-7-hydroxy-1H-indazol-4-yl)phenyl]-N'-(3-fluorophenyl)urea;
N-[4-(3-amino-7-hydroxy-1H-indazol-4-yl)phenyl]-N'-(3-bromophenyl)urea;
N-[4-(3-amino-7-hydroxy-1H-indazol-4-yl)phenyl]-N'-[2-fluoro-5-(trifluoromethyl)phenyl]urea;
N-[4-(3-amino-7-hydroxy-1H-indazol-4-yl)phenyl]-N'-[4-fluoro-3-(trifluoromethyl)phenyl]urea;
N-[4-(3-amino-7-hydroxy-1H-indazol-4-yl)phenyl]-N'-(3-chlorophenyl)urea;
N-[4-(3-amino-7-hydroxy-1H-indazol-4-yl)phenyl]-N'-[3-(trifluoromethyl)phenyl]urea;
N-{4-[3-amino-7-fluoro-6-(hydroxymethyl)-1H-indazol-4-yl]phenyl}-N'-(2-fluoro-5-methylphenyl)urea;
N-{4-[3-amino-7-fluoro-6-(hydroxymethyl)-1H-indazol-4-yl]phenyl}-N'-[3-(trifluoromethyl)phenyl]urea;
N-{4-[3-amino-7-fluoro-6-(hydroxymethyl)-1H-indazol-4-yl]phenyl}-N'-(3-chlorophenyl)urea;
N-{4-[3-amino-7-fluoro-6-(hydroxymethyl)-1H-indazol-4-yl]phenyl}-N'-(3-methylphenyl)urea;
N-{4-[3-amino-7-fluoro-6-(hydroxymethyl)-1H-indazol-4-yl]phenyl}-N'-(3-fluorophenyl)urea;
N-(4-{3-amino-6-[(diethylamino)methyl]-7-fluoro-1H-indazol-4-yl}phenyl)-N'-(2-fluoro-5-methylphenyl)urea;
N-(4-{3-amino-6-[(diethylamino)methyl]-7-fluoro-1H-indazol-4-yl}phenyl)-N'-[3-(trifluoromethyl)phenyl]urea;
N-(4-{3-amino-6-[(diethylamino)methyl]-7-fluoro-1H-indazol-4-yl}phenyl)-N'-(3-chlorophenyl)urea;
N-(4-{3-amino-6-[(diethylamino)methyl]-7-fluoro-1H-indazol-4-yl}phenyl)-N'-(3-methylphenyl)urea;
N-(4-{3-amino-7-[(isopropylamino)methyl]-1H-indazol-4-yl}phenyl)-N'-(2-fluoro-5-methylphenyl)urea;
N-(4-{3-amino-7-[(isopropylamino)methyl]-1H-indazol-4-yl}phenyl)-N'-(3-chlorophenyl)urea;
N-(4-{3-amino-7-[(isopropylamino)methyl]-1H-indazol-4-yl}phenyl)-N'-[3-(trifluoromethyl)phenyl]urea;
N-(4-{3-amino-7-[(isopropylamino)methyl]-1H-indazol-4-yl}phenyl)-N'-(3-methylphenyl)urea; and
N-(4-{3-amino-7-[(isopropylamino)methyl]-1H-indazol-4-yl}phenyl)-N'-(4-fluoro-3-methylphenyl)urea.

10. The compound of claim 8 selected from the group consisting of
N-[4-(3-amino-7-fluoro-1H-indazol-4-yl)phenyl]-N'-(3-bromophenyl)urea;
N-[4-(3-amino-7-fluoro-1H-indazol-4-yl)phenyl]-N'-(3-chlorophenyl)urea;
N-[4-(3-amino-7-fluoro-1H-indazol-4-yl)phenyl]-N'-[3-(trifluoromethyl)phenyl]urea;
N-[4-(3-amino-7-fluoro-1H-indazol-4-yl)phenyl]-N'-(3-methylphenyl)urea;
N-[4-(3-amino-7-bromo-1H-indazol-4-yl)phenyl]-N'-(3-methylphenyl)urea;
N-[4-(3-amino-7-fluoro-1H-indazol-4-yl)phenyl]-N'-(2-fluoro-5-methylphenyl)urea;
N-[4-(3-amino-6-bromo-1H-indazol-4-yl)phenyl]-N'-(3-methylphenyl)urea;
N-[4-(3-amino-7-fluoro-1H-indazol-4-yl)phenyl]-N'-[2-fluoro-5-(trifluoromethyl)phenyl]urea;
N-[4-(3-amino-7-fluoro-1H-indazol-4-yl)phenyl]-N'-(4-fluorophenyl)urea;
N-[4-(3-amino-7-fluoro-1H-indazol-4-yl)phenyl]-N'-(2-fluorophenyl)urea;
N-[4-(3-amino-7-fluoro-1H-indazol-4-yl)phenyl]-N'-(3-fluoro-4-methylphenyl)urea;
N-[4-(3-amino-7-fluoro-1H-indazol-4-yl)-2-fluorophenyl]-N'-(2-fluoro-5-methylphenyl)urea;
N-[4-(3-amino-7-fluoro-1H-indazol-4-yl)-2-fluorophenyl]-N'-(3-chlorophenyl)urea;

N-[4-(3-amino-5-fluoro-1H-indazol-4-yl)phenyl]-N'-(3-bromophenyl)urea;
N-[4-(3-amino-5-fluoro-1H-indazol-4-yl)phenyl]-N'-(3-methylphenyl)urea;
N-[4-(3-amino-5-fluoro-1H-indazol-4-yl)phenyl]-N'-phenylurea;
N-[4-(3-amino-5-fluoro-1H-indazol-4-yl)phenyl]-N'-[2-fluoro-3-(trifluoromethyl)phenyl]urea;
N-[4-(3-amino-5-fluoro-1H-indazol-4-yl)phenyl]-N'-(2-fluoro-5-methylphenyl)urea;
N-[4-(3-amino-5-fluoro-1H-indazol-4-yl)phenyl]-N'-[3-(trifluoromethyl)phenyl]urea;
N-[4-(3-amino-5-fluoro-1H-indazol-4-yl)phenyl]-N'-[4-fluoro-3-(trifluoromethyl)phenyl]urea;
N-[4-(3-amino-5-fluoro-1H-indazol-4-yl)phenyl]-N'-(3-chlorophenyl)urea;
N-[4-(3-amino-5-fluoro-1H-indazol-4-yl)phenyl]-N'-(4-fluoro-3-methylphenyl)urea;
N-[4-(3-amino-5-fluoro-1H-indazol-4-yl)phenyl]-N'-(3-chloro-4-fluorophenyl)urea;
N-[4-(3-amino-7-bromo-1H-indazol-4-yl)phenyl]-N'-(2-fluoro-5-methylphenyl)urea; and
N-[4-(3-amino-7-fluoro-1H-indazol-4-yl)phenyl]-N'-(4-bromo-3-methylphenyl)urea.

11. The compound of claim 1 wherein one of $R^1$ and $R^2$ is hydrogen and the other is selected from the group consisting of $(NR^aR^b)$carbonylalkenyl and $(NR^aR^b)$alkoxy.

12. The compound of claim 11 selected from the group consisting of
N-(4-{3-amino-7-[2-(dimethylamino)ethoxy]-1H-indazol-4-yl}phenyl)-N'-phenylurea;
N-(4-{3-amino-7-[2-(dimethylamino)ethoxy]-1H-indazol-4-yl}phenyl)-N'-3-bromophenyl)urea;
N-(4-{3-amino-7-[2-(dimethylamino)ethoxy]-1H-indazol-4-yl}phenyl)-N'-(3-methylphenyl)urea;
N-(4-{3-amino-7-[2-(dimethylamino)ethoxy]-1H-indazol-4-yl}phenyl)-N'-(3-chlorophenyl)urea;
N-(4-{3-amino-7-[2-(diethylamino)ethoxy]-1H-indazol-4-yl}phenyl)-N'-phenylurea;
N-(4-{3-amino-7-[2-(diethylamino)ethoxy]-1H-indazol-4-yl}phenyl)-N'-(3-fluorophenyl)urea;
N-(4-{3-amino-7-[2-(diethylamino)ethoxy]-1H-indazol-4-yl}phenyl)-N'-(2-fluoro-5-methylphenyl)urea;
N-(4-{3-amino-7-[2-(diethylamino)ethoxy]-1H-indazol-4-yl}phenyl)-N'-(3-methylphenyl)urea;
N-(4-{3-amino-7-[2-(diethylamino)ethoxy]-1H-indazol-4-yl}phenyl)-N'-(3-bromophenyl)urea;
N-(4-{3-amino-7-[2-(diethylamino)ethoxy]-1H-indazol-4-yl}phenyl)-N'-[2-fluoro-5-(trifluoromethyl)phenyl]urea;
N-(4-{3-amino-7-[2-(diethylamino)ethoxy]-1H-indazol-4-yl}phenyl)-N'-(3-chlorophenyl)urea;
N-(4-{3-amino-7-[2-(diethylamino)ethoxy]-1H-indazol-4-yl}phenyl)-N'-[3-(trifluoromethyl)phenyl]urea;
N-[2-({3-amino-4-[4-({[(2-fluoro-5-methylphenyl)amino]carbonyl}amino)phenyl]-1H-indazol-7-yl}oxy)ethyl]methanesulfonamide;
N-[2-({3-amino-4-[4-({[(3-methylphenyl)amino]carbonyl}amino)phenyl]-1H-indazol-7-yl}oxy)ethyl]methanesulfonamide;
N-{2-[(3-amino-4-{4-[({[2-fluoro-5-(trifluoromethyl)phenyl]amino}carbonyl)amino]phenyl}-1H-indazol-7-yl)oxy]ethyl}methanesulfonamide;
N-[2-({3-amino-4-[4-({[(3-chlorophenyl)amino]carbonyl}amino)phenyl]-1H-indazol-7-yl}oxy)ethyl]methanesulfonamide;
N-{2-[(3-amino-4-{4-[({[3-(trifluoromethyl)phenyl]amino}carbonyl)amino]phenyl}-1H-indazol-7-yl)oxy]ethyl}methanesulfonamide,
N-[2-({3-amino-4-[4-({[(3-methylphenyl)amino]carbonyl}amino)phenyl]-1H-indazol-7-yl}oxy)ethyl]-1,1,1-trifluoromethanesulfonamide;
N-[2-({3-amino-4-[4-({[(2-fluoro-5-methylphenyl)amino]carbonyl}amino)phenyl]-1H-indazol-7-yl}oxy)ethyl]-1,1,1-trifluoromethanesulfonamide;
N-[2-({3-amino-4-[4-({[(3-fluorophenyl)amino]carbonyl}amino)phenyl]-1H-indazol-7-yl}oxy)ethyl]-1,1,1-trifluoromethanesulfonamide;
N-[2-({3-amino-4-[4-({[(2-fluoro-5-methylphenyl)amino]carbonyl}amino)phenyl]-1H-indazol-7-yl}oxy)ethyl]benzenesulfonamide;
N-{2-[(3-amino-4-{4-[({[3-(trifluoromethyl)phenyl]amino}carbonyl)amino]phenyl}-1H-indazol-7-yl)oxy]ethyl}benzenesulfonamide;
N-[2-({3-amino-4-[4-({[(3-fluorophenyl)amino]carbonyl}amino)phenyl]-1H-indazol-7-yl}oxy)ethyl]benzenesulfonamide;
N-[2-({3-amino-4-[4-({[(3-chlorophenyl)amino]carbonyl}amino)phenyl]-1H-indazol-7-yl}oxy)ethyl]benzenesulfonamide;
N-[2-({3-amino-4-[4-({[(2-fluoro-5-methylphenyl)amino]carbonyl}amino)phenyl]-1H-indazol-7-yl}oxy)ethyl]thiophene-2-sulfonamide;
N-[2-({3-amino-4-[4-({[(3-methylphenyl)amino]carbonyl}amino)phenyl]-1H-indazol-7-yl}oxy)ethyl]thiophene-2-sulfonamide;
N-(4-{3-amino-7-[3-(diethylamino)propoxy]-1H-indazol-4-yl}phenyl)-N'-(2-fluoro-5-methylphenyl)urea;
N-{4-(3-amino-7-[3-(diethylamino)propoxy]-1H-indazol-4-yl}phenyl)-N'-(3-chlorophenyl)urea;
N-(4-{3-amino-7-[3-(diethylamino)propoxy]-1H-indazol-4-yl}phenyl)-N'-[3-(trifluoromethyl)phenyl]urea;
N-(4-{3-amino-7-[3-(diethylamino)propoxy]-1H-indazol-4-yl}phenyl)-N'-(3-fluorophenyl)urea;
N-(4-{3-amino-7-[3-(dimethylamino)propoxy]-1H-indazol-4-yl}phenyl)-N'-(3-methylphenyl)urea;
N-(4-{3-amino-7-[3-(dimethylamino)propoxy]-1H-indazol-4-yl}phenyl)-N'-(2-fluoro-5-methylphenyl)urea;
N-(4-{3-amino-7-[3-(dimethylamino)propoxy]-1H-indazol-4-yl}phenyl)-N'-(3-fluorophenyl)urea;
N-(4-{3-amino-7-[3-(dimethylamino)propoxy]-1H-indazol-4-yl}phenyl)-N'-(3-chlorophenyl)urea;
N-(4-{3-amino-7-[3-(dimethylamino)propoxy]-1H-indazol-4-yl}phenyl)-N'-[3-(trifluoromethyl)phenyl]urea;
N-(4-{3-amino-7-[3-(dimethylamino)propoxy]-1H-indazol-4-yl}phenyl)-N'-(4-fluoro-3-methylphenyl)urea;
N-[2-({3-amino-4-[4-({[(3-fluorophenyl)amino]carbonyl}amino)phenyl]-1H-indazol-7-yl}oxy)ethyl]methanesulfonamide; and
N-(4-{3-amino-7-[3-(dimethylamino)propoxy]-1H-indazol-4-yl}phenyl)-N'-[4-fluoro-3-(trifluoromethyl)phenyl]urea.

13. The compound of claim 1 wherein one of $R^1$ and $R^2$ is hydrogen and the other is selected from the group consisting of alkoxy, alkoxyalkoxy, and alkyl.

14. The compound of claim 1 wherein one of $R^3$ and $R^4$ is hydrogen and the other is selected from the group consisting of alkoxyalkoxy, alkyl, halo, haloalkoxy, and hydroxy.

15. The compound of claim 14 selected from the group consisting of
N-[4-(3-amino-1H-indazol-4-yl)-2-fluorophenyl]-N'-(3-methylphenyl)urea;

N-[4-(3-amino-1H-indazol-4-yl)-2-fluorophenyl]-N'-(3-fluorophenyl)urea;
N-[4-(3-amino-1H-indazol-4-yl)-2-fluorophenyl]-N'-(3,5-dimethylphenyl)urea;
N-[4-(3-amino-1H-indazol-4-yl)-2-fluorophenyl]-N'-(3-ethylphenyl)urea;
N-[4-(3-amino-1H-indazol-4-yl)-2-fluorophenyl]-N'-(3-chloro-4-fluorophenyl)urea;
N-[4-(3-amino-1H-indazol-4-yl)-2-fluorophenyl]-N'-(3-fluoro-4-methylphenyl)urea;
N-[4-(3-amino-1H-indazol-4-yl)-2-fluorophenyl]-N'-(3-chlorophenyl)urea;
N-[4-(3-amino-1H-indazol-4-yl)-2-methylphenyl]-N'-(3-methylphenyl)urea;
N-[4-(3-amino-1H-indazol-4-yl)-2-ethylphenyl]-N'-(2-fluoro-5-methylphenyl)urea;
N-[4-(3-amino-1H-indazol-4-yl)-2-ethylphenyl]-N'-[3-(trifluoromethyl)phenyl]urea;
N-[4-(3-amino-1H-indazol-4-yl)-2-fluorophenyl]-N'-[3-(trifluoromethyl)phenyl]urea;
N-[4-(3-amino-1H-indazol-4-yl)-2-fluorophenyl]-N'-[4-fluoro-3-(trifluoromethyl)phenyl]urea;
N-[4-(3-amino-1H-indazol-4-yl)-3-fluorophenyl]-N'-(3-methylphenyl)urea;
N-[4-(3-amino-1H-indazol-4-yl)-3-fluorophenyl]-N'-(2-fluoro-5-methylphenyl)urea;
N-[4-(3-amino-1H-indazol-4-yl)-3-fluorophenyl]-N'-(3-chlorophenyl)urea;
N-[4-(3-amino-1H-indazol-4-yl)-3-fluorophenyl]-N'-(4-fluoro-3-methylphenyl)urea;
N-[4-(3-amino-1H-indazol-4-yl)-2-hydroxyphenyl]-N'-(2-fluoro-5-methylphenyl)urea;
N-[4-(3-amino-1H-indazol-4-yl)-2-(trifluoromethoxy)phenyl]-N'-(2-fluoro-5-methylphenyl)urea and
N-[4-(3-amino-1H-indazol-4-yl)-2-fluorophenyl]-N'-(2-fluoro-5-methylphenyl)urea.

16. The compound of claim 1 wherein $R^3$ and $R^4$ are hydrogen.

17. The compound of claim 16 selected from the group consisting of
N-[4-(3-amino-1H-indazol-4-yl)phenyl]-N'-(3-methylphenyl)urea;
N-[4-(3-amino-1H-indazol-4-yl)phenyl]-N'-3,5-dimethoxyphenyl)urea;
N-[4-(3-amino-1H-indazol-4-yl)phenyl]-N'-[3-(trifluoromethyl)phenyl]urea;
N-[4-(3-amino-1H-indazol-4-yl)phenyl]-N'-(3-bromophenyl)urea;
N-[4-(3-amino-1H-indazol-4-yl)phenyl]-N'-(3-bromo-4-methylphenyl)urea;
N-[4-(3-amino-1H-indazol-4-yl)phenyl]-N'-(3-ethylphenyl)urea;
N-[4-(3-amino-1H-indazol-4-yl)phenyl]-N'-phenylurea;
N-[4-(3-amino-1H-indazol-4-yl)phenyl]-N'-(3-fluoro-4-methylphenyl)urea;
N-[4-(3-amino-1H-indazol-4-yl)phenyl]-N'-(2-fluorophenyl)urea;
N-[4-(3-amino-1H-indazol-4-yl)phenyl]-N'-(4-fluorophenyl)urea;
N-[4-(3-amino-1H-indazol-4-yl)phenyl]-N'-(3-fluorophenyl)urea;
N-[4-(3-amino-1H-indazol-4-yl)phenyl]-N'-(3-hydroxyphenyl)urea;
N-[3-(3-amino-1H-indazol-4-yl)phenyl]-N'-(3-methylphenyl)urea;
N-[4-(3-amino-1H-indazol-4-yl)phenyl]-N'-[4-fluoro-3-(trifluoromethyl)phenyl]urea;
N-[4-(3-amino-1H-indazol-4-yl)phenyl]-N'-[2-fluoro-3-(trifluoromethyl)phenyl]urea;
N-[4-(3-amino-1H-indazol-4-yl)phenyl]-N'-(4-bromo-2-fluorophenyl)urea;
N-[4-(3-amino-1H-indazol-4-yl)phenyl]-N'-(5-fluoro-2-methylphenyl)urea;
N-[4-(3-amino-1H-indazol-4-yl)phenyl]-N'-(4-fluoro-3-methylphenyl)urea; and
N-[4-(3-amino-1H-indazol-4-yl)phenyl]-N'-[2-fluoro-5-(hydroxymethyl)phenyl]urea.

18. The compound of claim 2 wherein $R^1$ and $R^2$ are independently selected from the group consisting of hydrogen, alkoxy, alkoxyalkoxy, alkoxyalkyl, aryloxy, aryloxyalkyl, halo, haloalkoxy, haloalkyl, hydroxy, hydroxyalkoxy, hydroxyalkyl, $(NR^aR^b)$alkoxy, $(NR^aR^b)$alkenyl, $(NR^aR^b)$alkyl, $(NR^aR^b)$carbonylalkenyl, and $(NR^aR^b)$carbonylalkyl.

19. A pharmaceutical composition comprising a compound of claim 1 or a therapeutically acceptable salt thereof, in combination with a therapeutically acceptable carrier.

20. The compound of claim 8 wherein one of $R^1$ and $R^2$ is hydrogen and the other is aryloxyalkyl.

21. The compound of claim 1 selected from the group consisting of N-(4-{3-amino-7-[(4-chlorophenoxy)methyl]-1H-indazol-4-yl}phenyl)-N'-(2-fluoro-5-methylpheny)urea;
N-(4-{3-amino-7-[(4-chlorophenoxy)methyl]-1H-indazol-4-yl}phenyl)-N'-(3-chloropheny)urea;
N-(4-{3-amino-7-[(4-chlorophenoxy)methyl]-1H-indazol-4-yl}phenyl)-N'-[3-(trifluoromethyl)phenyl]urea;
N-(4-{3-amino-7-[(4-chlorophenoxy)methyl]-1H-indazol-4-yl}phenyl)-N'-(3-methylphenOurea; and
N-(4-{3-amino-7-[(4-chlorophenoxy)methyl]-1H-indazol-4-yl}phenyl)-N'-(4-fluoro-3-methylpheny)urea.

* * * * *

UNITED STATES PATENT AND TRADEMARK OFFICE
CERTIFICATE OF CORRECTION

PATENT NO. : 8,063,091 B2
APPLICATION NO. : 12/507575
DATED : November 22, 2011
INVENTOR(S) : Yujia Dai et al.

It is certified that error appears in the above-identified patent and that said Letters Patent is hereby corrected as shown below:

Column 159, part of Claim 7, Line 12 revise "phenyl urea" to read as --phenylurea--

Column 161, part of Claim 12, Line 34 revise "zol-4-yl}phenyl)-N'-3-bromophenyl)urea;" to read as --zol-4-yl}phenyl)-N'-(3-bromophenyl)urea;--

Column 162, part of Claim 12, Line 3 revise "ethyl}methanesulfonamide," to read as --ethyl}methanesulfonamide;--

Column 162, part of Claim 12, Line 17, remove space "N-{2-[(3-amino-4-{4-[({[3-    (trifluoromethyl)phenyl]" to read as --N-{2-[(3-amino-4-{4-[({[3-(trifluoromethyl)phenyl]--

Column 162, part of Claim 12, Line 34, revise "N-{4-(3-amino-7-[3-(diethylamino)propoxy]-1H-inda-" to read as --N-(4-{3-amino-7-[3-(diethylamino)propoxy]-1H-inda- --

Column 163, part of Claim 17, Line 17, revise "N-[4-(3-amino-1H-indazol-4-yl)phenyl]-N"-3,5-" to read as --N-[4-(3-amino-1H-indazol-4-yl)phenyl-N'-(3,5- --

Column 164, part of Claim 21, Lines 42-43, revise "N-(4- {3-amino-7-[(4-chlorophenoxy)methyl]-1H-indazol-4-yl}phenyl)-N'-(3-chloropheny)urea;" to read as --N-(4-{3-amino-7-[(4-chlorophenoxy)methyl]-1H-indazol-4-yl}phenyl)-N'-(3-chlorophenyl)urea;--

Column 164, part of Claim 21, Line 47, revise "zol-4-yl}phenyl)-N'-(3-methylphenyOurea; and" to read as --zol-4-yl}phenyl)-N'-(3-methylphenyl)urea; and--

Signed and Sealed this
Eighth Day of January, 2013

David J. Kappos
*Director of the United States Patent and Trademark Office*